US009127053B2

(12) United States Patent
West et al.

(10) Patent No.: US 9,127,053 B2
(45) Date of Patent: Sep. 8, 2015

(54) ANTI-JAGGED 1/JAGGED 2 CROSS-REACTIVE ANTIBODIES, ACTIVATABLE ANTI-JAGGED ANTIBODIES AND METHODS OF USE THEREOF

(71) Applicant: CYTOMX THERAPEUTICS, INC., South San Francisco, CA (US)

(72) Inventors: James William West, San Mateo, CA (US); Jason Gary Sagert, San Mateo, CA (US); Paul H. Bessette, Camarillo, CA (US); Henry Bernard Lowman, El Granada, CA (US); Nancy E. Stagliano, San Francisco, CA (US); Olga Vasiljeva, Cupertino, CA (US); Elizabeth-Edna Mary Menendez, San Mateo, CA (US)

(73) Assignee: CYTOMX THERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 13/923,935

(22) Filed: Jun. 21, 2013

(65) Prior Publication Data
US 2014/0010810 A1 Jan. 9, 2014

Related U.S. Application Data

(60) Provisional application No. 61/663,307, filed on Jun. 22, 2012, provisional application No. 61/749,212, filed on Jan. 4, 2013, provisional application No. 61/749,486, filed on Jan. 7, 2013, provisional application No. 61/755,810, filed on Jan. 23, 2013.

(51) Int. Cl.
*A61K 39/00* (2006.01)
*A61K 39/395* (2006.01)
*C07K 16/18* (2006.01)
*C07K 16/28* (2006.01)

(52) U.S. Cl.
CPC ............. *C07K 16/18* (2013.01); *C07K 16/28* (2013.01); *C07K 16/2896* (2013.01); *A61K 2039/505* (2013.01); *C07K 2317/21* (2013.01); *C07K 2317/33* (2013.01); *C07K 2317/55* (2013.01); *C07K 2317/622* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,562,958 B1 | 5/2003 | Breton et al. | |
| 6,696,245 B2 | 2/2004 | Winter et al. | |
| 6,703,489 B1 | 3/2004 | Ish-Horowicz et al. | |
| 7,282,203 B2 | 10/2007 | Coignet | |
| 7,449,303 B2 | 11/2008 | Coignet | |
| 7,504,490 B1 | 3/2009 | Weinstock et al. | |
| 8,809,504 B2 | 8/2014 | Lauermann | |
| 2003/0032781 A1 | 2/2003 | Sakano et al. | |
| 2008/0317760 A1 | 12/2008 | Gurney et al. | |
| 2009/0060916 A1 | 3/2009 | De Silva et al. | |
| 2009/0117038 A1 | 5/2009 | Sukumar et al. | |
| 2009/0304719 A1 | 12/2009 | Daugherty et al. | |
| 2010/0189651 A1 | 7/2010 | Stagliano et al. | |
| 2011/0178279 A1* | 7/2011 | Williams et al. | 530/388.22 |
| 2012/0301489 A1* | 11/2012 | Gurney et al. | 424/174.1 |

FOREIGN PATENT DOCUMENTS

| | | |
|---|---|---|
| WO | WO 96/27610 A1 | 12/1996 |
| WO | WO 97/45143 A1 | 4/1997 |
| WO | WO 03/006990 A1 | 1/2003 |
| WO | WO 2009/014726 A1 | 1/2009 |
| WO | WO 2009/025846 A2 | 2/2009 |
| WO | WO 2009/091518 A2 | 7/2009 |
| WO | WO 2010/081173 A2 | 7/2010 |
| WO | WO 2010/129609 A2 | 11/2010 |
| WO | WO 2011/063237 A2 | 5/2011 |
| WO | WO 2013/147793 A1 | 10/2013 |
| WO | WO 2014/028446 A1 | 2/2014 |

OTHER PUBLICATIONS

Lobry et al. 2011. J. Exp Med. 208:1931-1935.*
Sethi et al. 2011. Cancer Cell. 19:1-22.*
Alley et al 2010. Curr. Opin in Chem Biol. 14:529-537.*
Abd-Elgaliel, W. R., Cruz-Monserrate Z, Logdon, C., and Tung, C-H, Molecular imaging of Cathepsin E-positive tumors in mice using a novel protease-activatable fluorescent probe. *Mol. Biosyst.* 7(12):3207-13 (2011); Epub Sep. 20, 2011 (2011).
Fanger et al., Production and use of anti-FcR bispecific antibodies. *Immunomethods* 4:72-81 (1994).
Geller, A. I. et al., Long-term increases in neurotransmitter release from neuronal cells expressing a constitutively active adenylate cyclase from a herpes simplex virus type 1 vector. *Proc Natl Acad Sci USA* 90:7603 (1993).
Gostring L et al, Quantification of internalization of EGFR-binding Affibody molecules: Methodological aspects. *Int J Oncol* 36, 757-763 (2010).

(Continued)

*Primary Examiner* — Shulamith H Shafer
(74) *Attorney, Agent, or Firm* — Cooley LLP; Ivor R. Elrifi

(57) ABSTRACT

This invention relates generally to the generation of antibodies, e.g., monoclonal antibodies including fully human monoclonal antibodies, that recognize Jagged 1 and/or Jagged 2, to antibodies, e.g., monoclonal antibodies including fully human antibodies that recognize Jagged 1 and/or Jagged 2, and nucleic acid molecules that encode antibodies, e.g., nucleic acid molecules that encode monoclonal antibodies including fully human cross-reactive antibodies that recognize both Jagged 1 and Jagged 2, and to methods of making the anti-Jagged antibodies and methods of using the anti-Jagged antibodies as therapeutics, prophylactics, and diagnostics. The invention also relates generally to activatable antibodies that include a masking moiety (MM), a cleavable moiety (CM), and an antibody (AB) that specifically bind to Jagged 1 and Jagged 2, and to methods of making and using these activatable anti-Jagged antibodies in a variety of therapeutic, diagnostic and prophylactic indications.

33 Claims, 26 Drawing Sheets

(56) References Cited

OTHER PUBLICATIONS

Greenberg NM et al, Prostate cancer in a transgenic mouse. *Proc Natl Acad Sci USA* 92, 3439-3443 (1995).

Jabaiah, Abeer and Daugherty, Patrick, Directed evolution of protease beacons that enable sensitive detection of endogenous MT1-MMP activity in tumor cell lines. *Chem. Biol.* 18, 392-401 (2011).

Kunkel TA, Rapid and efficient site-specific mutagenesis without phenotypic selection. *Proc Natl Aced Sci USA* 82, 488-492 (1985).

La Rocca et al., Zymographic detection and clinical correlations of MMP-2 and MMP-9 in breast cancer sera. *British J. of Cancer* 90(7): 1414-1421 (2004).

Shimizu K et al., Binding of Delta1, Jagged 1, and Jagged 2 to Notch2 rapidly induces cleavage, nuclear translocation, and hyperphosphorylation of Notch2. *Molecular Cellular Biology* 20(18): 6913-6922 (2000).

Shimizu K et al., Physical interaction of Delta1, Jagged 1, and Jagged 2 with Notch1 and Notch3 receptors. *Biochemical and Biophysical Research Communications* 276(1): 385-389 (2000).

Siegel PM et al., Elevated expression of activated forms of Neu/ErbB-2 and ErbB-3 are involved in the induction of mammary tumors in transgenic mice: implications for human breast cancer. *The EMBO Journal* 18, 2149-2164 (1999).

Uyttendaele H1, Closson V, Wu G, Roux F, Weinmaster G, Kitajewski J., Notch4 and Jagged-1 induce microvessel differentiation of rat brain endothelial cells. *Microvasc Res.* 60(2):91-103 (2000).

Zhu L et al., Real-time video imaging of protease expression in vivo. *Theranostics* 1:18-27 (2011).

\* cited by examiner

Days post 1st dose

Days

On cell 4D11 FAB binding

FIGURE 22
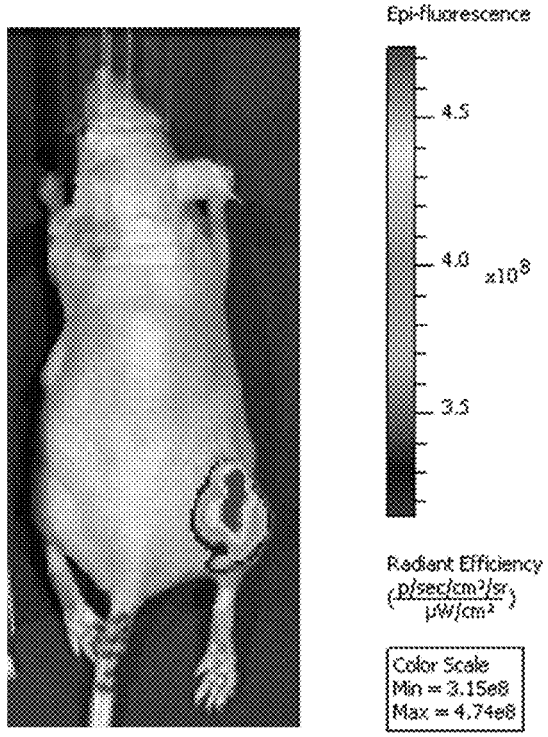
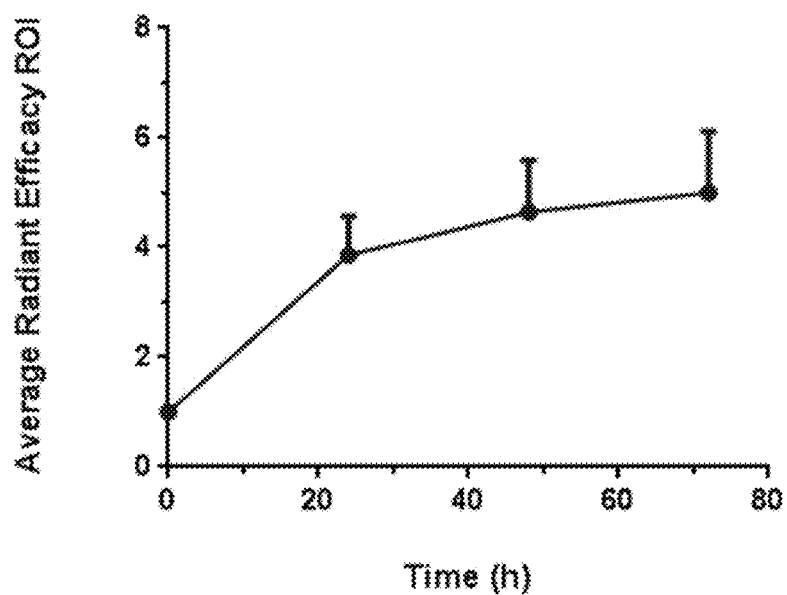

FIGURE 27A

| Clone | hJag1 | hJag2 |
|---|---|---|
| 125.14 | | +++ |
| 125.15 | ++ | |
| 346.4 | ++ | |
| 346.5 | ++ | |
| 346.7 | +++ | +++ |
| 346.8 | + | |
| 346.13 | | ++ |
| 346.16 | +++ | + |
| 346.19 | + | |
| 346.21 | + | |
| 346.24 | + | + |

| Clone | hJag1 | hJag2 |
|---|---|---|
| 346.26 | ++ | |
| 346.27 | ++ | |
| 346.28 | +++ | +++ |
| 346.30 | | ++ |
| 346.31 | ++ | |
| 346.32 | | + |
| 346.37 | + | |
| 346.39 | + | +++ |
| 346.40 | +++ | ++ |
| 346.47 | | +++ |

FIGURE 27B

| Fab | Kd (nM) | | | |
|---|---|---|---|---|
| | hJAG1 | hJAG2 | rJAG1 | rJAG2 |
| Parental | 63 | 35 | 53 | ND |
| Matured | <1 | <1 | <1 | <1 |

Tramp Model Mouse #2

ANTI-JAGGED 1/JAGGED 2 CROSS-REACTIVE ANTIBODIES, ACTIVATABLE ANTI-JAGGED ANTIBODIES AND METHODS OF USE THEREOF

RELATED APPLICATIONS

This application claims the benefit of U.S. Provisional Application No. 61/663,307, filed Jun. 22, 2012; U.S. Provisional Application No. 61/749,212, filed Jan. 4, 2013; U.S. Provisional Application No. 61/749,486, filed Jan. 7, 2013; and U.S. Provisional Application No. 61/755,810, filed Jan. 23, 2013; each of which is incorporated herein by reference in its entirety.

INCORPORATION OF SEQUENCE LISTING

The contents of the text file named "42652519001US.txt", which was created on Jul. 29, 2013 and is 179 KB in size, are hereby incorporated by reference in their entirety.

FIELD OF THE INVENTION

This invention relates generally to the generation of antibodies, e.g., monoclonal antibodies including fully human monoclonal antibodies, that recognize Jagged 1 and/or Jagged 2, to antibodies, e.g., monoclonal antibodies including fully human antibodies that recognize Jagged 1 and/or Jagged 2, and nucleic acid molecules that encode antibodies, e.g., nucleic acid molecules that encode monoclonal antibodies including fully human cross-reactive antibodies that recognize both Jagged 1 and Jagged 2, and to methods of making the anti-Jagged antibodies and methods of using the anti-Jagged antibodies as therapeutics, prophylactics, and diagnostics. The invention also relates generally to activatable antibodies that specifically bind to Jagged 1 and Jagged 2, and methods of making and using these activatable anti-Jagged antibodies in a variety of therapeutic, diagnostic and prophylactic indications.

BACKGROUND OF THE INVENTION

The Notch signaling pathway regulates a wide variety of cell types and cellular processes. The Notch signaling pathway is regulated by ligand binding, including ligands such as Jagged 1 and Jagged 2. Accordingly, there exists a need for therapeutics and diagnostics that target the Notch signaling pathway, including Jagged 1 and/or Jagged 2.

SUMMARY OF THE INVENTION

The present invention describes compositions for the diagnosis and/or treatment of cancer or fibrotic disease. Specifically, this invention provides antibodies that bind both Jagged 1 and Jagged 2 and inhibit their binding to and signaling through Notch receptors. The invention provides monoclonal antibodies that specifically bind to Jagged 1 and Jagged 2. The antibodies of the invention modulate, e.g., block, inhibit, reduce, antagonize, neutralize or otherwise interfere with binding of Jagged 1 to Notch receptors, binding of Jagged 2 to Notch receptors, binding of Jagged 1 and Jagged 2 to Notch Receptors, signaling through the interaction between Jagged 1 and Notch receptors, signaling through the interaction between Jagged 2 and Notch receptors, and/or signaling through the interaction among both Jagged 1, Jagged 2 and Notch receptors. These antibodies are referred to herein as "anti-Jagged antibodies." The anti-Jagged antibodies of the invention include monoclonal antibodies, such as, for example, fully human monoclonal antibodies, as well as humanized monoclonal antibodies and chimeric antibodies. In some embodiments, the antibodies are IgG isotype. In some embodiments, the antibodies are IgG1 isotype. In some embodiments, the antibodies have one of any of the isotypes disclosed herein.

Jagged 1, initially identified as Jagged and also referred to as JAG1, JAGL1 and/or HJ1, has been shown to be a transmembrane ligand for Notch. Jagged 2 is another ligand of Notch that is related to Jagged 1. Both Jagged 1 and Jagged 2 are ligands for Notch-1, Notch-2, Notch-3 and Notch-4 receptors. (See e.g., Shimizu K et al., "Binding of Delta1, Jagged 1, and Jagged 2 to Notch2 rapidly induces cleavage, nuclear translocation, and hyperphosphorylation of Notch2." Molecular Cellular Biology 20(18): 6913-6922 (2000); Shimizu K et al., "Physical interaction of Delta1, Jagged 1, and Jagged 2 with Notch1 and Notch3 receptors. Biochemical and Biophysical Research Communications 276(1): 385-389 (2000); Microvasc Res. 60(2):91-103 (2000)). Jagged proteins were originally referred to as Serrate proteins.

Exemplary monoclonal antibodies of the invention include, for example, the 4D11 antibody, the 4B2 antibody, the 4E7 antibody, the 4E11 antibody, the 6B7 antibody, and the 6F8 antibody. Other suitable antibodies include an antibody that binds to the same epitope as the 4D11 antibody, the 4B2 antibody, the 4E7 antibody, the 4E11 antibody, the 6B7 antibody, and/or the 6F8 antibody.

These antibodies show specificity for human Jagged 1 and human Jagged 2, and they have been shown to inhibit or otherwise interfere with Jagged 1 and/or Jagged 2 mediated signaling through Notch receptors. These antibodies also show specificity for mouse and rat Jagged 1. In some embodiments, these antibodies also show specificity for mouse and/or rat Jagged 2.

In some embodiments, anti-Jagged antibodies of the disclosure can be internalized upon binding to Jagged 1 and/or Jagged 2 expressed on a diseased cell, e.g., on a cancer cell or a cell involved in a fibrotic disorder.

The anti-Jagged antibodies of the invention include antibodies that contain a combination of a VH CDR1 sequence, a VH CDR2 sequence, a VH CDR3 sequence, a VL CDR1 sequence, a VL CDR2 sequence, and a VL CDR3 sequence selected from the combinations shown in Table 2. The anti-Jagged antibodies of the invention include antibodies that contain a combination of a VH CDR1 sequence, a VH CDR2 sequence, a VH CDR3 sequence, a VL CDR1 sequence, a VL CDR2 sequence, and a VL CDR3 sequence that are at least 90%, 91%, 92%, 93%, 94%, 95%, 96%, 97%, 98%, 99% or more identical to the sequences shown in Table 2.

The anti-Jagged antibodies of the invention include antibodies that contain a combination of a VH CDR1 sequence, a VH CDR2 sequence, a VH CDR3 sequence, a VL CDR1 sequence, a VL CDR2 sequence, and a VL CDR3 sequence of at least one antibody selected from the group consisting of the 4D11 antibody, the 4B2 antibody, the 4E7 antibody, the 4E11 antibody, the 6B7 antibody, and the 6F8 antibody. The anti-Jagged antibodies of the invention include antibodies that contain a combination of a VH CDR1 sequence, a VH CDR2 sequence, a VH CDR3 sequence, a VL CDR1 sequence, a VL CDR2 sequence, and a VL CDR3 sequence that are at least 90%, 91%, 92%, 93%, 94%, 95%, 96%, 97%, 98%, 99% or more identical to the respective CDR sequences of at least one antibody selected from the group consisting of the 4D11 antibody, the 4B2 antibody, the 4E7 antibody, the 4E11 antibody, the 6B7 antibody, and the 6F8 antibody.

The anti-Jagged antibodies of the invention include antibodies that contain a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes at least the amino acid sequence SYAMS (SEQ ID NO: 200); a VH CD2 sequence that includes at least the amino acid sequence SIDPEGRQTYYADSVKG (SEQ ID NO: 208); a VH CDR3 sequence that includes at least the amino acid sequence DIGGRSAFDY (SEQ ID NO: 209); a VL CDR1 sequence that includes at least the amino acid sequence RASQSISSY (SEQ ID NO: 210); a VL CDR2 sequence that includes at least the amino acid sequence AASSLQS (SEQ ID NO: 211); and a VL CDR3 sequence that includes at least the amino acid sequence QQTVVAPPL (SEQ ID NO: 212).

The anti-Jagged antibodies of the invention include antibodies that contain a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 93%, 94%, 95%, 96%, 97%, 98%, 99% or more identical to the amino acid sequence SYAMS (SEQ ID NO: 200); a VH CD2 sequence that includes a sequence that is at least 90%, 91%, 92%, 93%, 94%, 95%, 96%, 97%, 98%, 99% or more identical to the amino acid sequence SIDPEGRQTYYADSVKG (SEQ ID NO: 208); a VH CDR3 sequence that includes a sequence that is at least 90%, 91%, 92%, 93%, 94%, 95%, 96%, 97%, 98%, 99% or more identical to the amino acid sequence DIGGRSAFDY (SEQ ID NO: 209); a VL CDR1 sequence that includes a sequence that is at least 90%, 91%, 92%, 93%, 94%, 95%, 96%, 97%, 98%, 99% or more identical to the amino acid sequence RASQSISSY (SEQ ID NO: 210); a VL CDR2 sequence that includes a sequence that is at least 90%, 91%, 92%, 93%, 94%, 95%, 96%, 97%, 98%, 99% or more identical to the amino acid sequence AASSLQS (SEQ ID NO: 211); and a VL CDR3 sequence that includes a sequence that is at least 90%, 91%, 92%, 93%, 94%, 95%, 96%, 97%, 98%, 99% or more identical to the amino acid sequence QQTVVAPPL (SEQ ID NO: 212).

The anti-Jagged antibodies of the invention include antibodies that contain a VH CDR1 sequence that includes at least the amino acid sequence SYAMS (SEQ ID NO: 200); a VH CD2 sequence that includes at least the amino acid sequence SIDPEGRQTYYADSVKG (SEQ ID NO: 208); a VH CDR3 sequence that includes at least the amino acid sequence DIGGRSAFDY (SEQ ID NO: 209); a VL CDR1 sequence that includes at least the amino acid sequence RASQSISSY (SEQ ID NO: 210); a VL CDR2 sequence that includes at least the amino acid sequence AASSLQS (SEQ ID NO: 211); and a VL CDR3 sequence that includes at least the amino acid sequence QQTVVAPPL (SEQ ID NO: 212).

The anti-Jagged antibodies of the invention include antibodies that contain a VH CDR1 sequence that includes a sequence that is at least 90%, 91%, 92%, 93%, 94%, 95%, 96%, 97%, 98%, 99% or more identical to the amino acid sequence SYAMS (SEQ ID NO: 200); a VH CD2 sequence that includes a sequence that is at least 90%, 91%, 92%, 93%, 94%, 95%, 96%, 97%, 98%, 99% or more identical to the amino acid sequence SIDPEGRQTYYADSVKG (SEQ ID NO: 208); a VH CDR3 sequence that includes a sequence that is at least 90%, 91%, 92%, 93%, 94%, 95%, 96%, 97%, 98%, 99% or more identical to the amino acid sequence DIGGRSAFDY (SEQ ID NO: 209); a VL CDR1 sequence that includes a sequence that is at least 90%, 91%, 92%, 93%, 94%, 95%, 96%, 97%, 98%, 99% or more identical to the amino acid sequence RASQSISSY (SEQ ID NO: 210); a VL CDR2 sequence that includes a sequence that is at least 90%, 91%, 92%, 93%, 94%, 95%, 96%, 97%, 98%, 99% or more identical to the amino acid sequence AASSLQS (SEQ ID NO: 211); and a VL CDR3 sequence that includes a sequence that is at least 90%, 91%, 92%, 93%, 94%, 95%, 96%, 97%, 98%, 99% or more identical to the amino acid sequence QQTVVAPPL (SEQ ID NO: 212).

The anti-Jagged antibodies of the invention include antibodies that contain a combination of a variable heavy chain region and a variable light chain region selected from the combinations listed in Table 4. The anti-Jagged antibodies of the invention include antibodies that contain a combination of a variable heavy chain region and a variable light chain region that are at least 90%, 91%, 92%, 93%, 94%, 95%, 96%, 97%, 98%, 99% or more identical to the combinations listed in Table 4.

In some embodiments, the anti-Jagged antibody includes a light chain sequence that includes SEQ ID NO: 74. In some embodiments, the anti-Jagged antibody includes a light chain sequence that includes an amino acid sequence that is at least 90%, 91%, 92%, 93%, 94%, 95%, 96%, 97%, 98%, 99% or more identical to the amino acid sequence of SEQ ID NO: 74. In some embodiments, the anti-Jagged antibody includes a heavy chain sequence that includes SEQ ID NO: 76. In some embodiments, the anti-Jagged antibody includes a heavy chain sequence that includes an amino acid sequence that is at least 90%, 91%, 92%, 93%, 94%, 95%, 96%, 97%, 98%, 99% or more identical to the amino acid sequence of SEQ ID NO: 76. In some embodiments, the anti-Jagged antibody includes a light chain sequence that includes SEQ ID NO: 74 a heavy chain sequence that includes SEQ ID NO: 76. In some embodiments, the anti-Jagged antibody includes a light chain sequence that includes an amino acid sequence that is at least 90%, 91%, 92%, 93%, 94%, 95%, 96%, 97%, 98%, 99% or more identical to the amino acid sequence of SEQ ID NO: 74 and a heavy chain sequence that includes an amino acid sequence that is at least 90%, 91%, 92%, 93%, 94%, 95%, 96%, 97%, 98%, 99% or more identical to the amino acid sequence of SEQ ID NO: 76.

In some embodiments, the anti-Jagged antibody includes a light chain sequence that includes SEQ ID NO: 54. In some embodiments, the anti-Jagged antibody includes a light chain sequence that includes an amino acid sequence that is at least 90%, 91%, 92%, 93%, 94%, 95%, 96%, 97%, 98%, 99% or more identical to the amino acid sequence of SEQ ID NO: 54. In some embodiments, the anti-Jagged antibody includes a heavy chain sequence that includes SEQ ID NO: 56. In some embodiments, the anti-Jagged antibody includes a heavy chain sequence that includes an amino acid sequence that is at least 90%, 91%, 92%, 93%, 94%, 95%, 96%, 97%, 98%, 99% or more identical to the amino acid sequence of SEQ ID NO: 56. In some embodiments, the anti-Jagged antibody includes a light chain sequence that includes SEQ ID NO: 54 a heavy chain sequence that includes SEQ ID NO: 56. In some embodiments, the anti-Jagged antibody includes a light chain sequence that includes an amino acid sequence that is at least 90%, 91%, 92%, 93%, 94%, 95%, 96%, 97%, 98%, 99% or more identical to the amino acid sequence of SEQ ID NO: 54 and a heavy chain sequence that includes an amino acid sequence that is at least 90%, 91%, 92%, 93%, 94%, 95%, 96%, 97%, 98%, 99% or more identical to the amino acid sequence of SEQ ID NO: 56.

In some embodiments, the anti-Jagged antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the anti-Jagged antibody via a linker. In some embodiments, the linker is a cleavable linker. In some embodiments, the agent is an agent selected from the group listed in Table 30. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof.

In some embodiments, the anti-Jagged antibody also includes a detectable moiety. In some embodiments, the detectable moiety is a diagnostic agent.

In some embodiments, the anti-Jagged antibody naturally contains one or more disulfide bonds. In some embodiments, the anti-Jagged antibody can be engineered to include one or more disulfide bonds.

The invention also provides an isolated nucleic acid molecule encoding an anti-Jagged antibody described herein, as well as vectors that include these isolated nucleic acid sequences. The invention provides methods of producing an anti-Jagged antibody by culturing a cell under conditions that lead to expression of the anti-Jagged antibody, wherein the cell comprises such a nucleic acid molecule. In some embodiments, the cell comprises such a vector.

The invention also provides activatable antibodies and activatable antibody compositions that include an antibody or antigen-binding fragment thereof that specifically binds Jagged 1 and Jagged 2 coupled or otherwise attached to a masking moiety (MM), such that coupling of the MM reduces the ability of the antibody or antigen-binding fragment thereof to bind Jagged 1 and Jagged 2. These activatable antibodies are collectively referred to herein as activatable anti-Jagged antibodies, also referred to herein as anti-Jagged activatable antibodies or Jagged activatable antibodies. In some embodiments, the MM is coupled via a sequence that includes a substrate for a protease, for example, a protease that is co-localized with Jagged 1 and/or Jagged 2 at a treatment site or a diagnostic site in a subject. The activatable anti-Jagged antibodies provided herein are stable in circulation, activated at intended sites of therapy and/or diagnosis but not in normal, i.e., healthy tissue, and, when activated, exhibit binding to Jagged 1 and Jagged 2 that is at least comparable to the corresponding, unmodified antibody.

The activatable anti-Jagged antibodies of the invention include antibodies that contain a combination of a VH CDR1 sequence, a VH CDR2 sequence, a VH CDR3 sequence, a VL CDR1 sequence, a VL CDR2 sequence, and a VL CDR3 sequence selected from the combinations shown in Table 2. The anti-Jagged antibodies of the invention include antibodies that contain a combination of a VH CDR1 sequence, a VH CDR2 sequence, a VH CDR3 sequence, a VL CDR1 sequence, a VL CDR2 sequence, and a VL CDR3 sequence that are at least 90%, 91%, 92%, 93%, 94%, 95%, 96%, 97%, 98%, 99% or more identical to the sequences shown in Table 2.

The activatable anti-Jagged antibodies of the invention include antibodies that contain a combination of a VH CDR1 sequence, a VH CDR2 sequence, a VH CDR3 sequence, a VL CDR1 sequence, a VL CDR2 sequence, and a VL CDR3 sequence of at least one antibody selected from the group consisting of the 4D11 antibody, the 4B2 antibody, the 4E7 antibody, the 4E11 antibody, the 6B7 antibody, and the 6F8 antibody. The anti-Jagged antibodies of the invention include antibodies that contain a combination of a VH CDR1 sequence, a VH CDR2 sequence, a VH CDR3 sequence, a VL CDR1 sequence, a VL CDR2 sequence, and a VL CDR3 sequence that are at least 90%, 91%, 92%, 93%, 94%, 95%, 96%, 97%, 98%, 99% or more identical to the respective CDR sequences of at least one antibody selected from the group consisting of the 4D11 antibody, the 4B2 antibody, the 4E7 antibody, the 4E11 antibody, the 6B7 antibody, and the 6F8 antibody.

The anti-Jagged antibodies of the invention include antibodies that contain a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes at least the amino acid sequence SYAMS (SEQ ID NO: 200); a VH CD2 sequence that includes at least the amino acid sequence SIDPEGRQTYYADSVKG (SEQ ID NO: 208); a VH CDR3 sequence that includes at least the amino acid sequence DIGGRSAFDY (SEQ ID NO: 209); a VL CDR1 sequence that includes at least the amino acid sequence RASQSISSY (SEQ ID NO: 210); a VL CDR2 sequence that includes at least the amino acid sequence AASSLQS (SEQ ID NO: 211); and a VL CDR3 sequence that includes at least the amino acid sequence QQTVVAPPL (SEQ ID NO: 212).

The anti-Jagged antibodies of the invention include antibodies that contain a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 93%, 94%, 95%, 96%, 97%, 98%, 99% or more identical to the amino acid sequence SYAMS (SEQ ID NO: 200); a VH CD2 sequence that includes a sequence that is at least 90%, 91%, 92%, 93%, 94%, 95%, 96%, 97%, 98%, 99% or more identical to the amino acid sequence SIDPEGRQTYYADSVKG (SEQ ID NO: 208); a VH CDR3 sequence that includes a sequence that is at least 90%, 91%, 92%, 93%, 94%, 95%, 96%, 97%, 98%, 99% or more identical to the amino acid sequence DIGGRSAFDY (SEQ ID NO: 209); a VL CDR1 sequence that includes a sequence that is at least 90%, 91%, 92%, 93%, 94%, 95%, 96%, 97%, 98%, 99% or more identical to the amino acid sequence RASQSISSY (SEQ ID NO: 210); a VL CDR2 sequence that includes a sequence that is at least 90%, 91%, 92%, 93%, 94%, 95%, 96%, 97%, 98%, 99% or more identical to the amino acid sequence AASSLQS (SEQ ID NO: 211); and a VL CDR3 sequence that includes a sequence that is at least 90%, 91%, 92%, 93%, 94%, 95%, 96%, 97%, 98%, 99% or more identical to the amino acid sequence QQTVVAPPL (SEQ ID NO: 212).

The anti-Jagged antibodies of the invention include antibodies that contain a VH CDR1 sequence that includes at least the amino acid sequence SYAMS (SEQ ID NO: 200); a VH CD2 sequence that includes at least the amino acid sequence SIDPEGRQTYYADSVKG (SEQ ID NO: 208); a VH CDR3 sequence that includes at least the amino acid sequence DIGGRSAFDY (SEQ ID NO: 209); a VL CDR1 sequence that includes at least the amino acid sequence RASQSISSY (SEQ ID NO: 210); a VL CDR2 sequence that includes at least the amino acid sequence AASSLQS (SEQ ID NO: 211); and a VL CDR3 sequence that includes at least the amino acid sequence QQTVVAPPL (SEQ ID NO: 212).

The anti-Jagged antibodies of the invention include antibodies that contain a VH CDR1 sequence that includes a sequence that is at least 90%, 91%, 92%, 93%, 94%, 95%, 96%, 97%, 98%, 99% or more identical to the amino acid sequence SYAMS (SEQ ID NO: 200); a VH CD2 sequence that includes a sequence that is at least 90%, 91%, 92%, 93%, 94%, 95%, 96%, 97%, 98%, 99% or more identical to the amino acid sequence SIDPEGRQTYYADSVKG (SEQ ID NO: 208); a VH CDR3 sequence that includes a sequence that is at least 90%, 91%, 92%, 93%, 94%, 95%, 96%, 97%, 98%, 99% or more identical to the amino acid sequence DIGGR-SAFDY (SEQ ID NO: 209); a VL CDR1 sequence that includes a sequence that is at least 90%, 91%, 92%, 93%, 94%, 95%, 96%, 97%, 98%, 99% or more identical to the amino acid sequence RASQSISSY (SEQ ID NO: 210); a VL CDR2 sequence that includes a sequence that is at least 90%, 91%, 92%, 93%, 94%, 95%, 96%, 97%, 98%, 99% or more identical to the amino acid sequence AASSLQS (SEQ ID NO: 211); and a VL CDR3 sequence that includes a sequence that is at least 90%, 91%, 92%, 93%, 94%, 95%, 96%, 97%, 98%, 99% or more identical to the amino acid sequence QQTVVAPPL (SEQ ID NO: 212).

The activatable anti-Jagged antibodies of the invention include antibodies that contain a combination of a variable heavy chain region and a variable light chain region selected from the combinations listed in Table 4. The anti-Jagged antibodies of the invention include antibodies that contain a combination of a variable heavy chain region and a variable light chain region that are at least 90%, 91%, 92%, 93%, 94%, 95%, 96%, 97%, 98%, 99% or more identical to the combinations listed in Table 4.

In some embodiments, the anti-Jagged antibody of the activatable antibody includes a light chain sequence that includes SEQ ID NO: 74. In some embodiments, the anti-Jagged antibody includes a light chain sequence that includes an amino acid sequence that is at least 90%, 91%, 92%, 93%, 94%, 95%, 96%, 97%, 98%, 99% or more identical to the amino acid sequence of SEQ ID NO: 74. In some embodiments, the anti-Jagged antibody includes a heavy chain sequence that includes SEQ ID NO: 76. In some embodiments, the anti-Jagged antibody includes a heavy chain sequence that includes an amino acid sequence that is at least 90%, 91%, 92%, 93%, 94%, 95%, 96%, 97%, 98%, 99% or more identical to the amino acid sequence of SEQ ID NO: 76. In some embodiments, the anti-Jagged antibody includes a light chain sequence that includes SEQ ID NO: 74 and a heavy chain sequence that includes SEQ ID NO: 76. In some embodiments, the anti-Jagged antibody includes a light chain sequence that includes an amino acid sequence that is at least 90%, 91%, 92%, 93%, 94%, 95%, 96%, 97%, 98%, 99% or more identical to the amino acid sequence of SEQ ID NO: 74 and a heavy chain sequence that includes an amino acid sequence that is at least 90%, 91%, 92%, 93%, 94%, 95%, 96%, 97%, 98%, 99% or more identical to the amino acid sequence of SEQ ID NO: 76.

In some embodiments, the anti-Jagged antibody includes a light chain sequence that includes an amino acid sequence selected from the group consisting of SEQ ID NO: 74, 132, 134, 136, 138, 140, 142, 144 and 146. In some embodiments, the anti-Jagged antibody includes a light chain sequence that includes an amino acid sequence that is at least 90%, 91%, 92%, 93%, 94%, 95%, 96%, 97%, 98%, 99% or more identical to an amino acid sequence selected from the group consisting of SEQ ID NO: 74, 132, 134, 136, 138, 140, 142, 144 and 146. In some embodiments, the anti-Jagged antibody includes a heavy chain sequence that includes SEQ ID NO: 76 or SEQ ID NO: 148. In some embodiments, the anti-Jagged antibody includes a heavy chain sequence that includes an amino acid sequence that is at least 90%, 91%, 92%, 93%, 94%, 95%, 96%, 97%, 98%, 99% or more identical to an amino acid sequence selected from the group consisting of SEQ ID NO: 74, 132, 134, 136, 138, 140, 142, 144 and 146. In some embodiments, the anti-Jagged antibody includes a light chain sequence that includes an amino acid sequence selected from the group consisting of SEQ ID NO: 74, 132, 134, 136, 138, 140, 142, 144 and 146 and a heavy chain sequence that includes SEQ ID NO: 76 or SEQ ID NO: 148. In some embodiments, the anti-Jagged antibody includes a light chain sequence that includes an amino acid sequence that is at least 90%, 91%, 92%, 93%, 94%, 95%, 96%, 97%, 98%, 99% or more identical to an amino acid sequence selected from the group consisting of SEQ ID NO: 74, 132, 134, 136, 138, 140, 142, 144 and 146 and a heavy chain sequence that includes an amino acid sequence that is at least 90%, 91%, 92%, 93%, 94%, 95%, 96%, 97%, 98%, 99% or more identical to the amino acid sequence of SEQ ID NO: 76 or SEQ ID NO: 148.

The activatable antibodies described herein in an activated state bind Jagged 1 and Jagged 2 and include (i) an antibody or an antigen binding fragment thereof (AB) that specifically binds to Jagged 1 and Jagged 2; (ii) a masking moiety (MM) that inhibits the binding of the AB to Jagged 1 and Jagged 2 when the activatable antibody is in an uncleaved state; and (c) a cleavable moiety (CM) coupled to the AB, wherein the CM is a polypeptide that functions as a substrate for a protease. In some embodiments, the MM is coupled to the AB via the CM.

In some embodiments, the activatable antibody has the structural arrangement from N-terminus to C-terminus as follows in the uncleaved state: MM-CM-AB or AB-CM-MM.

In some embodiments, the activatable antibody comprises a linking peptide between the MM and the CM.

In some embodiments, the activatable antibody comprises a linking peptide between the CM and the AB.

In some embodiments, the activatable antibody comprises a first linking peptide (LP1) and a second linking peptide (LP2), and wherein the activatable antibody has the structural arrangement from N-terminus to C-terminus as follows in the uncleaved state: MM-LP1-CM-LP2-AB or AB-LP2-CM-LP1-MM. In some embodiments, the two linking peptides need not be identical to each other.

In some embodiments, at least one of LP1 or LP2 includes an amino acid sequence selected from the group consisting of $(GS)_n$, $(GGS)_n$, $(GSGGS)_n$ (SEQ ID NO: 123) and $(GGGS)_n$ (SEQ ID NO: 124), where n is an integer of at least one. In some embodiments, at least one of LP1 or LP2 includes an amino acid sequence selected from the group consisting of GGSG (SEQ ID NO: 125), GGSGG (SEQ ID NO: 126), GSGSG (SEQ ID NO: 127), GSGGG (SEQ ID NO: 128), GGGSG (SEQ ID NO: 129), and GSSSG (SEQ ID NO: 130).

In some embodiments, the activatable antibody includes an antibody or antigen-binding fragment thereof that specifically binds Jagged 1 and Jagged 2. In some embodiments, the antibody or immunologically active fragment thereof that binds Jagged 1 and Jagged 2 is a monoclonal antibody, domain antibody, single chain, Fab fragment, a F(ab')$_2$ fragment, a scFv, a scAb, a dAb, a single domain heavy chain antibody, or a single domain light chain antibody. In some embodiments, such an antibody or immunologically active fragment thereof that binds Jagged 1 and Jagged 2 is a rodent (e.g., mouse or rat), chimeric, humanized or fully human monoclonal antibody.

In some embodiments, activated anti-Jagged antibodies of the disclosure (i.e., in a cleaved state) can be internalized upon binding to Jagged 1 and/or Jagged 2 expressed on a diseased cell, e.g., on a cancer cell or a cell involved in a fibrotic disorder.

In some embodiments, the AB has an equilibrium dissociation constant of about 100 nM or less for binding to Jagged 1 and Jagged 2.

In some embodiments, the MM has an equilibrium dissociation constant for binding to the AB that is greater than the equilibrium dissociation constant of the AB to Jagged 1 and Jagged 2.

In some embodiments, the MM has an equilibrium dissociation constant for binding to the AB that is no more than the equilibrium dissociation constant of the AB to Jagged 1 and Jagged 2.

In some embodiments, the MM does not interfere or compete with the AB for binding to Jagged 1 and Jagged 2 when the activatable antibody is in a cleaved state.

In some embodiments, the MM is a polypeptide of about 2 to 40 amino acids in length. In some embodiments, the MM is a polypeptide of no more than 40 amino acids in length.

In some embodiments, the MM polypeptide sequence is different from that of Jagged 1 and Jagged 2 and wherein the MM polypeptide sequence is no more than 50% identical to any natural binding partner of the AB. In some embodiments, the MM polypeptide sequence is different from that of Jagged 1 and Jagged 2 and wherein the MM polypeptide sequence is no more than 25% identical to any natural binding partner of the AB. In some embodiments, the MM polypeptide sequence is different from that of Jagged 1 and Jagged 2 and wherein the MM polypeptide sequence is no more than 10% identical to any natural binding partner of the AB.

In some embodiments, the coupling of the MM reduces the ability of the AB to bind Jagged 1 and Jagged 2 such that the dissociation constant ($K_d$) of the AB when coupled to the MM towards Jagged 1 and Jagged 2 is at least 20 times greater than the $K_d$ of the AB when not coupled to the MM towards Jagged 1 and Jagged 2.

In some embodiments, the coupling of the MM reduces the ability of the AB to bind Jagged 1 and Jagged 2 such that the dissociation constant ($K_d$) of the AB when coupled to the MM towards Jagged 1 and Jagged 2 is at least 40 times greater than the $K_d$ of the AB when not coupled to the MM towards Jagged 1 and Jagged 2.

In some embodiments, the coupling of the MM reduces the ability of the AB to bind Jagged 1 and Jagged 2 such that the dissociation constant ($K_d$) of the AB when coupled to the MM towards Jagged 1 and Jagged 2 is at least 100 times greater than the $K_d$ of the AB when not coupled to the MM towards Jagged 1 and Jagged 2.

In some embodiments, the coupling of the MM reduces the ability of the AB to bind Jagged 1 and Jagged 2 such that the dissociation constant ($K_d$) of the AB when coupled to the MM towards Jagged 1 and Jagged 2 is at least 1000 times greater than the $K_d$ of the AB when not coupled to the MM towards Jagged 1 and Jagged 2.

In some embodiments, the coupling of the MM reduces the ability of the AB to bind Jagged 1 and Jagged 2 such that the dissociation constant ($K_d$) of the AB when coupled to the MM towards Jagged 1 and Jagged 2 is at least 10,000 times greater than the $K_d$ of the AB when not coupled to the MM towards Jagged 1 and Jagged 2.

In some embodiments, in the presence of Jagged 1 and Jagged 2, the MM reduces the ability of the AB to bind Jagged 1 and Jagged 2 by at least 90% when the CM is uncleaved, as compared to when the CM is cleaved when assayed in vitro using a target displacement assay such as, for example, the assay described in PCT Publication Nos. WO 2009/025846 and WO 2010/081173, the contents of each of which are hereby incorporated by reference in their entirety.

In some embodiments, the MM does not interfere or compete with the AB of the activatable antibody in a cleaved state for binding to the Jagged target.

In some embodiments, the MM is an amino acid sequence selected from the group of those listed in Tables 9, 11-14, and 20-23.

In some embodiments, the protease is co-localized with Jagged 1 and/or Jagged 2 in a tissue, and the protease cleaves the CM in the activatable antibody when the activatable antibody is exposed to the protease.

In some embodiments, the CM is positioned in the activatable antibody such that in the uncleaved state, binding of the activatable antibody to Jagged 1 and Jagged 2 is reduced to occur with an equilibrium dissociation constant that is at least 20-fold greater than the equilibrium dissociation constant of an unmodified AB binding to Jagged 1 and Jagged 2, and whereas in the cleaved state, the AB binds Jagged 1 and Jagged 2.

In some embodiments, the CM is positioned in the activatable antibody such that in the uncleaved state, binding of the activatable antibody to Jagged 1 and Jagged 2 is reduced to occur with an equilibrium dissociation constant that is at least 40-fold greater than the equilibrium dissociation constant of an unmodified AB binding to Jagged 1 and Jagged 2, and whereas in the cleaved state, the AB binds Jagged 1 and Jagged 2.

In some embodiments, the CM is positioned in the activatable antibody such that in the uncleaved state, binding of the activatable antibody to Jagged 1 and Jagged 2 is reduced to occur with an equilibrium dissociation constant that is at least 50-fold greater than the equilibrium dissociation constant of an unmodified AB binding to Jagged 1 and Jagged 2, and whereas in the cleaved state, the AB binds Jagged 1 and Jagged 2.

In some embodiments, the CM is positioned in the activatable antibody such that in the uncleaved state, binding of the activatable antibody to Jagged 1 and Jagged 2 is reduced to occur with an equilibrium dissociation constant that is at least 100-fold greater than the equilibrium dissociation constant of an unmodified AB binding to Jagged 1 and Jagged 2, and whereas in the cleaved state, the AB binds Jagged 1 and Jagged 2.

In some embodiments, the CM is positioned in the activatable antibody such that in the uncleaved state, binding of the activatable antibody to Jagged 1 and Jagged 2 is reduced to occur with an equilibrium dissociation constant that is at least 200-fold greater than the equilibrium dissociation constant of an unmodified AB binding to Jagged 1 and Jagged 2, and whereas in the cleaved state, the AB binds Jagged 1 and Jagged 2.

In some embodiments, the CM is a polypeptide of up to 15 amino acids in length.

In some embodiments, the CM includes the amino acid sequence LSGRSDNH (SEQ ID NO: 213). In some embodiments, the cleavable moiety is selected for use with a specific protease, for example a protease that is known to be co-localized with the target of the activatable antibody. For example, suitable cleavable moieties for use in the activatable anti-Jagged antibodies of the disclosure are cleaved by at least a protease such as urokinase, legumain, and/or MT-SP1 (matriptase) and include the sequence TGRGPSWV (SEQ ID NO: 214); SARGPSRW (SEQ ID NO: 215); TARGPSFK (SEQ ID NO: 216); LSGRSDNH (SEQ ID NO: 213); GGWHTGRN (SEQ ID NO: 217); HTGRSGAL (SEQ ID NO: 218); PLTGRSGG (SEQ ID NO: 219); AARGPAIH (SEQ ID NO: 220); RGPAFNPM (SEQ ID NO: 221); SSRGPAYL (SEQ ID NO: 222); RGPATPIM (SEQ ID NO: 223);

RGPA (SEQ ID NO: 224); GGQPSGMWGW (SEQ ID NO: 225); FPRPLGITGL (SEQ ID NO: 226); VHMPLGFLGP (SEQ ID NO: 227); SPLTGRSG (SEQ ID NO: 228); SAGF-SLPA (SEQ ID NO: 229); LAPLGLQRR (SEQ ID NO: 230); SGGPLGVR (SEQ ID NO: 231); and/or PLGL (SEQ ID NO: 232).

In some embodiments, the CM is a substrate for a protease selected from the group consisting of those shown in Table 33. In some embodiments, the protease is selected from the group consisting of uPA, legumain, MT-SP1, ADAM17, BMP-1, TMPRSS3, TMPRSS4, MMP-9, MMP-12, MMP-13, and MMP-14. In some embodiments, the protease is a cathepsin. In some embodiments, the CM is a substrate for a protease selected from the group consisting of uPA (urokinase plasminogen activator), legumain and MT-SP1 (matriptase). In some embodiments, the protease comprises uPA. In some embodiments, the protease comprises legumain. In some embodiments, the protease comprises MT-SP1. In some embodiments, the protease comprises a matrix metalloproteinase (MMP).

In some embodiments, the CM is a substrate for at least two proteases. In some embodiments, each protease is selected from the group consisting of those shown in Table 33. In some embodiments, the CM is a substrate for at least two proteases, wherein one of the proteases is selected from the group consisting of uPA, legumain and MT-SP1 and the other protease is selected from the group consisting of those shown in Table 33. In some embodiments, the CM is a substrate for at least two proteases selected from the group consisting of uPA, legumain and MT-SP1.

In some embodiments, the activatable antibody includes at least a first CM and a second CM. In some embodiments, the first CM and the second CM are each polypeptides of no more than 15 amino acids long. In some embodiments, the first CM and the second CM in the activatable antibody have the structural arrangement from N-terminus to C-terminus as follows in the uncleaved state: MM-CM1-CM2-AB or AB-CM2-CM1-MM. In some embodiments, at least one of the first CM and the second CM is a polypeptide that functions as a substrate for a protease selected from the group consisting of uPA, legumain, and MT-SP1. In some embodiments, the first CM is cleaved by a first cleaving agent selected from the group consisting of uPA, legumain, and MT-SP1 in a target tissue and the second CM is cleaved by a second cleaving agent in a target tissue. In some embodiments, the other protease is selected from the group consisting of those shown in Table 33. In some embodiments, the first cleaving agent and the second cleaving agent are the same protease selected from the group consisting of uPA, legumain, and MT-SP1, and the first CM and the second CM are different substrates for the enzyme. In some embodiments, the first cleaving agent and the second cleaving agent are the same protease selected from the group consisting of those shown in Table 33. In some embodiments, the first cleaving agent and the second cleaving agent are different proteases. In some embodiments, the first cleaving agent and the second cleaving agent are co-localized in the target tissue. In some embodiments, the first CM and the second CM are cleaved by at least one cleaving agent in the target tissue.

In some embodiments, the activatable antibody is exposed to and cleaved by a protease such that, in the activated or cleaved state, the activated antibody includes a light chain amino acid sequence that includes at least a portion of LP2 and/or CM sequence after the protease has cleaved the CM.

In some embodiments, the MM and the CM include an amino acid sequence selected from the group consisting of SEQ ID NO: 182, 184, 186, 188, 190, 192, 194, and 196.

In some embodiments, the activatable antibody also includes a signal peptide. In some embodiments, the signal peptide is conjugated to the activatable antibody via a spacer. In some embodiments, the spacer is conjugated to the activatable antibody in the absence of a signal peptide. In some embodiments, the spacer is joined directly to the MM of the activatable antibody.

In some embodiments, the activatable antibody in an uncleaved state comprises a spacer that is joined directly to the MM and has the structural arrangement from N-terminus to C-terminus of spacer-MM-CM-AB. In some embodiments, the spacer includes at least the amino acid sequence QGQSGQ (SEQ ID NO: 233). In some embodiments, the MM and spacer include the amino acid sequence of SEQ ID NO: 180. In some embodiments, the MM and spacer include the amino acid sequence QGQSGQCNIWLVGGDCRG-WQG (SEQ ID NO: 234).

In some embodiments, the activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the AB via a linker. In some embodiments, the linker is a cleavable linker. In some embodiments, the agent is an agent selected from the group listed in Table 30. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof.

In some embodiments, the activatable antibody also includes a detectable moiety. In some embodiments, the detectable moiety is a diagnostic agent.

In some embodiments, the AB of the activatable antibody naturally contains one or more disulfide bonds. In some embodiments, the AB can be engineered to include one or more disulfide bonds.

In some embodiments, the serum half-life of the activatable antibody is at least 5 days when administered to an organism. In some embodiments, the serum half-life of the activatable antibody is at least 4 days when administered to an organism. In some embodiments, the serum half-life of the activatable antibody is at least 3 days when administered to an organism. In some embodiments, the serum half-life of the activatable antibody is at least 2 days when administered to an organism. In some embodiments, the serum half-life of the activatable antibody is at least 24 hours when administered to an organism. In some embodiments, the serum half-life of the activatable antibody is at least 20 hours when administered to an organism. In some embodiments, the serum half-life of the activatable antibody is at least 18 hours when administered to an organism. In some embodiments, the serum half-life of the activatable antibody is at least 16 hours when administered to an organism. In some embodiments, the serum half-life of the activatable antibody is at least 14 hours when administered to an organism. In some embodiments, the serum half-life of the activatable antibody is at least 12 hours when administered to an organism. In some embodiments, the serum half-life of the activatable antibody is at least 10 hours when administered to an organism. In some embodiments, the serum half-life of the activatable antibody is at least 8 hours when administered to an organism. In some embodiments, the serum half-life of the activatable antibody is at least 6 hours when administered to an organism. In some embodiments, the serum half-life of the activatable antibody is at least 4 hours when administered to an organism. In some embodiments, the serum half-life of the activatable antibody is at least 3 hours when administered to an organism.

In some embodiments, the activatable anti-Jagged antibody and/or conjugated activatable anti-Jagged antibody is monospecific. In some embodiments, the activatable anti-Jagged antibody and/or conjugated activatable anti-Jagged antibody is multispecific, e.g., by way of non-limiting example, bispecific or trifunctional. In some embodiments, the activatable anti-Jagged antibody and/or conjugated activatable anti-Jagged antibody is formulated as part of a pro-Bispecific T Cell Engager (BITE) molecule. In some embodiments, the activatable anti-Jagged antibody and/or conjugated activatable anti-Jagged antibody is formulated as part of a pro-Chimeric Antigen Receptor (CAR) modified T cell or other engineered receptor.

The disclosure also provides compositions and methods that include an activatable anti-Jagged antibody that includes an antibody or antibody fragment (AB) that specifically binds a Jagged target (e.g., Jagged 1 and/or Jagged 2), where the AB is coupled to a masking moiety (MM) that decreases the ability of the AB to bind its target. In some embodiments, the activatable anti-Jagged antibody further includes a cleavable moiety (CM) that is a substrate for a protease. The compositions and methods provided herein enable the attachment of one or more agents to one or more cysteine residues in the AB without compromising the activity (e.g., the masking, activating or binding activity) of the activatable anti-Jagged antibody. In some embodiments, the compositions and methods provided herein enable the attachment of one or more agents to one or more cysteine residues in the AB without reducing or otherwise disturbing one or more disulfide bonds within the MM. The compositions and methods provided herein produce an activatable anti-Jagged antibody that is conjugated to one or more agents, e.g., any of a variety of therapeutic, diagnostic and/or prophylactic agents, preferably without any of the agent(s) being conjugated to the MM of the activatable anti-Jagged antibody. The compositions and methods provided herein produce conjugated activatable anti-Jagged antibodies in which the MM retains the ability to effectively and efficiently mask the AB of the activatable antibody in an uncleaved state. The compositions and methods provided herein produce conjugated activatable anti-Jagged antibodies in which the activatable antibody is still activated, i.e., cleaved, in the presence of a protease that can cleave the CM.

The activatable anti-Jagged antibodies have at least one point of conjugation for an agent, but in the methods and compositions provided herein less than all possible points of conjugation are available for conjugation to an agent. In some embodiments, the one or more points of conjugation are sulfur atoms involved in disulfide bonds. In some embodiments, the one or more points of conjugation are sulfur atoms involved in interchain disulfide bonds. In some embodiments, the one or more points of conjugation are sulfur atoms involved in interchain sulfide bonds, but not sulfur atoms involved in intrachain disulfide bonds. In some embodiments, the one or more points of conjugation are sulfur atoms of cysteine or other amino acid residues containing a sulfur atom. Such residues may occur naturally in the antibody structure or may be incorporated into the antibody by site-directed mutagenesis, chemical conversion, or mis-incorporation of non-natural amino acids.

Also provided are methods of preparing a conjugate of an activatable anti-Jagged antibody having one or more interchain disulfide bonds in the AB and one or more intrachain disulfide bonds in the MM, and a drug reactive with free thiols is provided. The method generally includes partially reducing interchain disulfide bonds in the activatable antibody with a reducing agent, such as, for example, TCEP; and conjugating the drug reactive with free thiols to the partially reduced activatable antibody. As used herein, the term partial reduction refers to situations where an activatable anti-Jagged antibody is contacted with a reducing agent and less than all disulfide bonds, e.g., less than all possible sites of conjugation are reduced. In some embodiments, less than 99%, 98%, 97%, 96%, 95%, 90%, 85%, 80%, 75%, 70%, 65%, 60%, 55%, 50%, 45%, 40%, 35%, 30%, 25%, 20%, 15%, 10% or less than 5% of all possible sites of conjugation are reduced.

In yet other embodiments, a method of reducing and conjugating an agent, e.g., a drug, to an activatable anti-Jagged antibody resulting in selectivity in the placement of the agent is provided. The method generally includes partially reducing the activatable anti-Jagged antibody with a reducing agent such that any conjugation sites in the masking moiety or other non-AB portion of the activatable antibody are not reduced, and conjugating the agent to interchain thiols in the AB. The conjugation site(s) are selected so as to allow desired placement of an agent to allow conjugation to occur at a desired site. The reducing agent is, for example, TCEP. The reduction reaction conditions such as, for example, the ratio of reducing agent to activatable antibody, the length of incubation, the temperature during the incubation, the pH of the reducing reaction solution, etc., are determined by identifying the conditions that produce a conjugated activatable antibody in which the MM retains the ability to effectively and efficiently mask the AB of the activatable antibody in an uncleaved state. The ratio of reduction agent to activatable anti-Jagged antibody will vary depending on the activatable antibody. In some embodiments, the ratio of reducing agent to activatable anti-Jagged antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1.

In some embodiments, a method of reducing interchain disulfide bonds in the AB of an activatable anti-Jagged antibody and conjugating an agent, e.g., a thiol-containing agent such as a drug, to the resulting interchain thiols to selectively locate agent(s) on the AB is provided. The method generally includes partially reducing the AB with a reducing agent to form at least two interchain thiols without forming all possible interchain thiols in the activatable antibody; and conjugating the agent to the interchain thiols of the partially reduced AB. For example, the AB of the activatable antibody is partially reduced for about 1 hour at about 37° C. at a desired ratio of reducing agent:activatable antibody. In some embodiments, the ratio of reducing agent to activatable antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1.

The thiol-containing reagent can be, for example, cysteine or N-acetyl cysteine. The reducing agent can be, for example, TCEP. In some embodiments, the reduced activatable antibody can be purified prior to conjugation, using for example, column chromatography, dialysis, or diafiltration. Alternatively, the reduced antibody is not purified after partial reduction and prior to conjugation.

The invention also provides partially reduced activatable anti-Jagged antibodies in which at least one interchain disulfide bond in the activatable antibody has been reduced with a reducing agent without disturbing any intrachain disulfide bonds in the activatable antibody, wherein the activatable antibody includes an antibody or an antigen binding fragment thereof (AB) that specifically binds to a Jagged target (e.g., Jagged 1 and/or Jagged 2), a masking moiety (MM) that inhibits the binding of the AB of the activatable antibody in an uncleaved state to the Jagged target, and a cleavable moiety (CM) coupled to the AB, wherein the CM is a polypeptide that functions as a substrate for a protease. In some embodiments the MM is coupled to the AB via the CM. In some embodiments, one or more intrachain disulfide bond(s) of the activatable antibody is not disturbed by the reducing agent. In some embodiments, one or more intrachain disulfide bond(s) of the MM within the activatable antibody is not disturbed by the reducing agent. In some embodiments, the activatable antibody in the uncleaved state has the structural arrangement from N-terminus to C-terminus as follows: MM-CM-AB or AB-CM-MM. In some embodiments, reducing agent is TCEP.

In some embodiments, the anti-Jagged antibodies and/or the activatable anti-Jagged antibodies described herein are used in conjunction with one or more additional agents or a combination of additional agents. Suitable additional agents include current pharmaceutical and/or surgical therapies for an intended application, such as, for example, cancer. For example, the anti-Jagged antibodies and/or activatable anti-Jagged antibodies can be used in conjunction with an additional chemotherapeutic or anti-neoplastic agent. For example, in some embodiments, the additional chemotherapeutic agent is gemcitabine.

In some embodiments, the anti-Jagged antibody and/or activatable anti-Jagged antibody and additional agent are formulated into a single therapeutic composition, and the anti-Jagged antibody and/or activatable anti-Jagged antibody and additional agent are administered simultaneously. Alternatively, the anti-Jagged antibody and/or activatable anti-Jagged antibody and additional agent are separate from each other, e.g., each is formulated into a separate therapeutic composition, and the anti-Jagged antibody and/or activatable anti-Jagged antibody and the additional agent are administered simultaneously, or the anti-Jagged antibody and/or activatable anti-Jagged antibody and the additional agent are administered at different times during a treatment regimen. For example, the anti-Jagged antibody and/or activatable anti-Jagged antibody is administered prior to the administration of the additional agent, the anti-Jagged antibody and/or activatable anti-Jagged antibody is administered subsequent to the administration of the additional agent, or the anti-Jagged antibody and/or activatable anti-Jagged antibody and the additional agent are administered in an alternating fashion. As described herein, the anti-Jagged antibody and/or activatable anti-Jagged antibody and additional agent are administered in single doses or in multiple doses.

The invention also provides an isolated nucleic acid molecule encoding an activatable anti-Jagged antibody described herein, as well as vectors that include these isolated nucleic acid sequences. The invention provides methods of producing an activatable antibody by culturing a cell under conditions that lead to expression of the activatable antibody, wherein the cell comprises such a nucleic acid molecule. In some embodiments, the cell comprises such a vector.

The invention also provides a method of manufacturing activatable antibodies that binds Jagged 1 and Jagged 2 in an activated state by (a) culturing a cell comprising a nucleic acid construct that encodes the activatable antibody under conditions that lead to expression of the activatable antibody, wherein the activatable antibody comprises a masking moiety (MM), a cleavable moiety (CM), and an antibody or an antigen binding fragment thereof (AB) that specifically binds Jagged 1 and Jagged 2, and (b) recovering the activatable antibody.

The invention also provides a method of manufacturing activatable antibodies that binds Jagged 1 and Jagged 2 in an activated state by (a) culturing a cell comprising a nucleic acid construct that encodes the activatable antibody under conditions that lead to expression of the activatable antibody, wherein the activatable antibody comprises a masking moiety (MM), a cleavable moiety (CM), and an antibody or an antigen binding fragment thereof (AB) that specifically binds Jagged 1 and Jagged 2, (i) wherein the CM is a polypeptide that includes an amino acid sequence that functions as a substrate for a protease; and (ii) wherein the CM is positioned in the activatable antibody such that, in an uncleaved state, the MM interferes with specific binding of the AB to Jagged 1 and Jagged 2 and in a cleaved state the MM does not interfere or compete with specific binding of the AB to Jagged 1 and Jagged 2; and (b) recovering the activatable antibody.

The present invention also provides methods of treating, preventing, delaying the progression of or otherwise ameliorating a symptom of pathologies associated with aberrant Jagged 1 and/or Jagged 2 activity (e.g., aberrant signaling, including aberrant signaling through Notch receptors), or alleviating a symptom associated with such pathologies, by administering an antibody and/or an activatable antibody of the invention to a subject in which such treatment or prevention is desired. The invention also provides methods of reducing, inhibiting or otherwise modulating angiogenesis in a subject using the anti-Jagged antibodies and/or activatable anti-Jagged antibodies described herein. The subject to be treated is, e.g., human or other mammal. In some embodiments, the subject is a non-human mammal, such as a non-human primate, companion animal (e.g., cat, dog, horse), farm animal, work animal, or zoo animal. In some embodiments, the subject is a rodent.

The anti-Jagged antibody and/or activatable anti-Jagged antibody is administered in an amount sufficient to treat, prevent or alleviate a symptom associated with the pathology. The amount of antibody and/or an activatable antibody sufficient to treat or prevent the pathology in the subject is, for example, an amount that is sufficient to reduce Jagged 1 and/or Jagged 2 signaling (e.g., Jagged 1 mediated signaling through Notch receptors and/or Jagged 2 mediated signaling through Notch receptors). As used herein, the term "reduced"

refers to a decreased signaling through one or more Notch receptors in the presence of a monoclonal antibody and/or an activatable antibody of the invention. Jagged 1 and/or Jagged 2 mediated signaling is decreased when the level of signaling through one or more Notch receptors in the presence of an anti-Jagged antibody and/or an activatable antibody of the invention is greater than or equal to 5%, 10%, 20%, 25%, 30%, 40%, 50%, 60%, 70%, 75%, 80%, 90%, 95%, 99%, or 100% lower than a control level of signaling through one or more Notch receptors (i.e., the level of signaling through one or more Notch receptors in the absence of the monoclonal antibody). Level of signaling through one or more Notch receptors is measured using any of a variety of standard techniques, such as, by way of non-limiting example, measurement of downstream gene activation, such as Hey and Hes, and/or luciferase reporter assays responsive to Notch receptor activation. Those skilled in the art will appreciate that the level of signaling through one or more Notch receptors can be measured using a variety of assays, including, for example, commercially available kits.

Pathologies treated and/or prevented and/or for which the progression is delayed and/or for which a symptom is ameliorated using the anti-Jagged antibodies, activatable anti-Jagged antibodies and/or conjugated activatable anti-Jagged antibodies of the invention include, for example, cancer. In some embodiments, the anti-Jagged antibodies, activatable anti-Jagged antibodies and/or conjugated activatable anti-Jagged antibodies of the invention are used to treat, prevent, delay the progression of, and/or ameliorate a symptom of a pathology such as, for example, leukemias, including T-cell acute lymphoblastic leukemia (T-ALL), lymphoblastic diseases including multiple myeloma, and solid tumors, including lung, colorectal, prostate, pancreatic and breast, including triple negative breast cancer. In addition, since notch signaling is important for the survival and growth of cancer stem cells, inhibition of Jagged dependent notch signaling would impact stem cell growth and survival.

In some embodiments, the anti-Jagged antibodies, activatable anti-Jagged antibodies and/or conjugated activatable anti-Jagged antibodies of the invention are used to treat, prevent, delay the progression of, and/or ameliorate a symptom of a pathology such as, for example, bone disease or metastasis in cancer, regardless of primary tumor origin.

In some embodiments, the anti-Jagged antibodies, activatable anti-Jagged antibodies and/or conjugated activatable anti-Jagged antibodies of the invention are used to treat, prevent, delay the progression of, and/or ameliorate a symptom of a pathology such as, for example, breast cancer, including by way of non-limiting example, ER/PR+ breast cancer, Her2+ breast cancer, triple-negative breast cancer.

In some embodiments, the anti-Jagged antibodies, activatable anti-Jagged antibodies and/or conjugated activatable anti-Jagged antibodies of the invention are used to treat, prevent, delay the progression of, and/or ameliorate a symptom of a pathology such as, for example, colorectal cancer.

In some embodiments, the anti-Jagged antibodies, activatable anti-Jagged antibodies and/or conjugated activatable anti-Jagged antibodies of the invention are used to treat, prevent, delay the progression of, and/or ameliorate a symptom of a pathology such as, for example, gastric cancer.

In some embodiments, the anti-Jagged antibodies, activatable anti-Jagged antibodies and/or conjugated activatable anti-Jagged antibodies of the invention are used to treat, prevent, delay the progression of, and/or ameliorate a symptom of a pathology such as, for example, glioblastoma.

In some embodiments, the anti-Jagged antibodies, activatable anti-Jagged antibodies and/or conjugated activatable anti-Jagged antibodies of the invention are used to treat, prevent, delay the progression of, and/or ameliorate a symptom of a pathology such as, for example, head and neck cancer.

In some embodiments, the anti-Jagged antibodies, activatable anti-Jagged antibodies and/or conjugated activatable anti-Jagged antibodies of the invention are used to treat, prevent, delay the progression of, and/or ameliorate a symptom of a pathology such as, for example, lung cancer, such as by way of non-limiting example, non-small cell lung cancer.

In some embodiments, the anti-Jagged antibodies, activatable anti-Jagged antibodies and/or conjugated activatable anti-Jagged antibodies of the invention are used to treat, prevent, delay the progression of, and/or ameliorate a symptom of a pathology such as, for example, multiple myeloma.

In some embodiments, the anti-Jagged antibodies, activatable anti-Jagged antibodies and/or conjugated activatable anti-Jagged antibodies of the invention are used to treat, prevent, delay the progression of, and/or ameliorate a symptom of a pathology such as, for example, ovarian cancer.

In some embodiments, the anti-Jagged antibodies, activatable anti-Jagged antibodies and/or conjugated activatable anti-Jagged antibodies of the invention are used to treat, prevent, delay the progression of, and/or ameliorate a symptom of a pathology such as, for example, pancreatic cancer.

In some embodiments, the anti-Jagged antibodies, activatable anti-Jagged antibodies and/or conjugated activatable anti-Jagged antibodies of the invention are used to treat, prevent, delay the progression of, and/or ameliorate a symptom of a pathology such as, for example, prostate cancer.

In some embodiments, the anti-Jagged antibodies, activatable anti-Jagged antibodies and/or conjugated activatable anti-Jagged antibodies of the invention are used to treat, prevent, delay the progression of, and/or ameliorate a symptom of a pathology such as, for example, sarcoma.

In some embodiments, the anti-Jagged antibodies, activatable anti-Jagged antibodies and/or conjugated activatable anti-Jagged antibodies of the invention are used to treat, prevent, delay the progression of, and/or ameliorate a symptom of a pathology such as, for example, renal cancer, such as by way of nonlimiting example, renal cell carcinoma.

In some embodiments, the anti-Jagged antibodies, activatable anti-Jagged antibodies and/or conjugated activatable anti-Jagged antibodies of the invention are used to treat, prevent, delay the progression of, and/or ameliorate a symptom of a pathology such as, for example, skin cancer, such as by way of nonlimiting example, squamous cell cancer, basal cell carcinoma, melanoma.

In addition to cancer, Jagged-dependent notch signaling is critical to epithelial and fibroblast differentiation to myofibroblasts, cells with a central role in the development of fibrotic disease. Inhibition of Jagged dependent notch signaling, and therefore inhibition of the emergence of myofibroblasts, would be an effective treatment for fibrotic diseases of the kidney, liver, lung, and skin. In some embodiments, the anti-Jagged antibodies, activatable anti-Jagged antibodies and/or conjugated activatable anti-Jagged antibodies are used to treat a fibrotic disorder, such as idiopathic pulmonary fibrosis (IPF).

In some embodiments, the anti-Jagged antibodies, activatable anti-Jagged antibodies and/or conjugated activatable anti-Jagged antibodies of the invention are used to treat, prevent, delay the progression of, and/or ameliorate a symptom of a pathology such as, for example, fibrotic disease.

In some embodiments, the anti-Jagged antibodies, activatable anti-Jagged antibodies and/or conjugated activatable anti-Jagged antibodies of the invention are used to treat, prevent, delay the progression of, and/or ameliorate a symptom of a pathology such as, for example, idiopathic pulmonary fibrosis, kidney fibrotic disease, liver fibrotic disease, peritoneal dialysis-induced fibrosis, scleroderma.

In some embodiments, the anti-Jagged antibodies, activatable anti-Jagged antibodies and/or conjugated activatable anti-Jagged antibodies of the invention are used to treat, prevent, delay the progression of, and/or ameliorate a symptom of a pathology such as, for example, hearing loss.

An anti-Jagged antibody, activatable anti-Jagged antibody and/or conjugated activatable anti-Jagged antibody used in any of the embodiments of these methods and uses can be administered at any stage of the disease. For example, such an anti-Jagged antibody, activatable anti-Jagged antibody and/or conjugated activatable anti-Jagged antibody can be administered to a patient suffering cancer of any stage, from early to metastatic. The terms subject and patient are used interchangeably herein.

An anti-Jagged antibody, activatable anti-Jagged antibody and/or conjugated activatable anti-Jagged antibody used in any of the embodiments of these methods and uses can be used in a treatment regimen comprising neoadjuvant therapy.

An anti-Jagged antibody, activatable anti-Jagged antibody and/or conjugated activatable anti-Jagged antibody used in any of the embodiments of these methods and uses can be administered either alone or in combination with one or more chemotherapeutic agents or other biologics.

The invention also provides methods and kits for using the anti-Jagged antibodies and/or activatable anti-Jagged antibodies in a variety of diagnostic and/or prophylactic indications. For example, the invention provides methods and kits for detecting presence or absence of a cleaving agent and a target of interest in a subject or a sample by (i) contacting a subject or sample with an activatable anti-Jagged antibody, wherein the activatable anti-Jagged antibody comprises a masking moiety (MM), a cleavable moiety (CM) that is cleaved by the cleaving agent, and an antigen binding domain or fragment thereof (AB) that specifically binds the target of interest, wherein the activatable anti-Jagged antibody in an uncleaved, non-activated state comprises a structural arrangement from N-terminus to C-terminus as follows: MM-CM-AB or AB-CM-MM; (a) wherein the MM is a peptide that inhibits binding of the AB to the Jagged target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the Jagged target, and in a cleaved, activated state the MM does not interfere or compete with specific binding of the AB to the Jagged target; and (ii) measuring a level of activated activatable anti-Jagged antibody in the subject or sample, wherein a detectable level of activated activatable anti-Jagged antibody in the subject or sample indicates that the cleaving agent and a Jagged target are present in the subject or sample and wherein no detectable level of activated activatable anti-Jagged antibody in the subject or sample indicates that the cleaving agent, a Jagged target or both the cleaving agent and a Jagged target are absent and/or not sufficiently present in the subject or sample.

In some embodiments, the activatable anti-Jagged antibody is an activatable anti-Jagged antibody to which a therapeutic agent is conjugated. In some embodiments, the activatable anti-Jagged antibody is not conjugated to an agent. In some embodiments, the activatable anti-Jagged antibody comprises a detectable label. In some embodiments, the detectable label is positioned on the AB. In some embodiments, measuring the level of activatable anti-Jagged antibody in the subject or sample is accomplished using a secondary reagent that specifically binds to the activated antibody, wherein the reagent comprises a detectable label. In some embodiments, the secondary reagent is an antibody comprising a detectable label.

In some embodiments of these methods and kits, the activatable anti-Jagged antibody includes a detectable label. In some embodiments of these methods and kits, the detectable label includes an imaging agent, a contrasting agent, an enzyme, a fluorescent label, a chromophore, a dye, one or more metal ions, or a ligand-based label. In some embodiments of these methods and kits, the imaging agent comprises a radioisotope. In some embodiments of these methods and kits, the radioisotope is indium or technetium. In some embodiments of these methods and kits, the contrasting agent comprises iodine, gadolinium or iron oxide. In some embodiments of these methods and kits, the enzyme comprises horseradish peroxidase, alkaline phosphatase, or β-galactosidase. In some embodiments of these methods and kits, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods and kits, the luminescent label comprises an N-methylacrydium derivative. In some embodiments of these methods, the label comprises an Alexa Fluor® label, such as Alex Fluor® 680 or Alexa Fluor® 750. In some embodiments of these methods and kits, the ligand-based label comprises biotin, avidin, streptavidin or one or more haptens.

In some embodiments of these methods and kits, the subject is a mammal. In some embodiments of these methods and kits, the subject is a human. In some embodiments, the subject is a non-human mammal, such as a non-human primate, companion animal (e.g., cat, dog, horse), farm animal, work animal, or zoo animal. In some embodiments, the subject is a rodent.

In some embodiments of these methods, the method is an in vivo method. In some embodiments of these methods, the method is an in situ method. In some embodiments of these methods, the method is an ex vivo method. In some embodiments of these methods, the method is an in vitro method.

In some embodiments of the methods and kits, the method or kit is used to identify or otherwise refine a patient population suitable for treatment with an activatable anti-Jagged antibody of the disclosure. For example, patients that test positive for both the target (e.g., Jagged 1 and/or Jagged 2) and a protease that cleaves the substrate in the cleavable moiety (CM) of the activatable anti-Jagged antibody being tested in these methods are identified as suitable candidates for treatment with such an activatable anti-Jagged antibody comprising such a CM. Likewise, patients that test negative for both of the targets (e.g., Jagged 1 and Jagged 2) and the protease that cleaves the substrate in the CM in the activatable antibody being tested using these methods might be identified as suitable candidates for another form of therapy.

In some embodiments, a method or kit is used to identify or otherwise refine a patient population suitable for treatment with an anti-Jagged activatable antibody and/or conjugated activatable anti-Jagged antibody (e.g., activatable antibody to which a therapeutic agent is conjugated) of the disclosure, followed by treatment by administering that activatable anti-Jagged antibody and/or conjugated activatable anti-Jagged antibody to a subject in need thereof. For example, patients that test positive for both the targets (e.g., Jagged 1 and Jagged 2) and a protease that cleaves the substrate in the cleavable moiety (CM) of the activatable anti-Jagged antibody and/or conjugated activatable anti-Jagged antibody being tested in these methods are identified as suitable candidates for treatment with such antibody and/or such a conjugated activatable anti-Jagged antibody comprising such a CM, and the patient is then administered a therapeutically effective amount of the activatable anti-Jagged antibody and/or conjugated activatable anti-Jagged antibody that was tested. Likewise, patients that test negative for either or both of the target (e.g., Jagged 1 and/or Jagged 2) and the protease that cleaves the substrate in the CM in the activatable anti-Jagged antibody being tested using these methods might be identified as suitable candidates for another form of therapy.

In some embodiments, such patients can be tested with other antibody and/or conjugated activatable anti-Jagged antibody until a suitable antibody and/or conjugated activatable anti-Jagged antibody for treatment is identified (e.g., an activatable anti-Jagged antibody and/or conjugated activatable anti-Jagged antibody comprising a CM that is cleaved by the patient at the site of disease). In some embodiments, the patient is then administered a therapeutically effective amount of the activatable anti-Jagged antibody and/or conjugated for which the patient tested positive.

In some embodiments of these methods and kits, the MM is a peptide having a length from about 4 to 40 amino acids. In some embodiments of these methods and kits, the activatable anti-Jagged antibody comprises a linker peptide, wherein the linker peptide is positioned between the MM and the CM. In some embodiments of these methods and kits, the activatable anti-Jagged antibody comprises a linker peptide, where the linker peptide is positioned between the AB and the CM. In some embodiments of these methods and kits, the activatable anti-Jagged antibody comprises a first linker peptide (L1) and a second linker peptide (L2), wherein the first linker peptide is positioned between the MM and the CM and the second linker peptide is positioned between the AB and the CM. In some embodiments of these methods and kits, each of L1 and L2 is a peptide of about 1 to 20 amino acids in length, and wherein each of L1 and L2 need not be the same linker. In some embodiments of these methods and kits, one or both of L1 and L2 comprises a glycine-serine polymer. In some embodiments of these methods and kits, at least one of L1 and L2 comprises an amino acid sequence selected from the group consisting of (GS)n, (GSGGS)n (SEQ ID NO: 123) and (GGGS)n (SEQ ID NO: 124), where n is an integer of at least one. In some embodiments of these methods and kits, at least one of L1 and L2 comprises an amino acid sequence having the formula (GGS)n, where n is an integer of at least one. In some embodiments of these methods and kits, at least one of L1 and L2 comprises an amino acid sequence selected from the group consisting of Gly-Gly-Ser-Gly (SEQ ID NO: 125), Gly-Gly-Ser-Gly-Gly (SEQ ID NO: 126), Gly-Ser-Gly-Ser-Gly (SEQ ID NO: 127), Gly-Ser-Gly-Gly-Gly (SEQ ID NO: 128), Gly-Gly-Gly-Ser-Gly (SEQ ID NO: 129), and Gly-Ser-Ser-Ser-Gly (SEQ ID NO: 130).

In some embodiments of these methods and kits, the AB comprises an antibody or antibody fragment sequence selected from the cross-reactive anti-Jagged antibody sequences presented herein. In some embodiments of these methods and kits, the AB comprises a Fab fragment, a scFv or a single chain antibody (scAb).

In some embodiments of these methods and kits, the cleaving agent is a protease that is co-localized in the subject or sample with the Jagged target and the CM is a polypeptide that functions as a substrate for the protease, wherein the protease cleaves the CM in the activatable anti-Jagged antibody when the activatable anti-Jagged antibody is exposed to the protease. In some embodiments of these methods and kits, the CM is a polypeptide of up to 15 amino acids in length. In some embodiments of these methods and kits, the CM is coupled to the N-terminus of the AB. In some embodiments of these methods and kits, the CM is coupled to the C-terminus of the AB. In some embodiments of these methods and kits, the CM is coupled to the N-terminus of a VL chain of the AB.

In some embodiments of these methods and kits, the cleaving agent is an enzyme and the CM is a substrate for the enzyme. In some embodiments of these methods and kits, the enzyme is a protease disclosed herein. In some embodiments of these methods and kits, the protease is one of the proteases disclosed herein. In some embodiments of these methods and kits, the protease is selected from the group consisting of uPA, legumain, MT-SP1, ADAM17, BMP-1, TMPRSS3, TMPRSS4, MMP-9, MMP-12, MMP-13, and MMP-14. In some embodiments, the protease is a cathepsin.

Pharmaceutical compositions according to the invention can include an antibody and/or an activatable antibody of the invention and a carrier. These pharmaceutical compositions can be included in kits, such as, for example, diagnostic kits.

One skilled in the art will appreciate that the antibodies of the invention have a variety of uses. For example, the proteins of the invention are used as therapeutic agents to prevent the activation of Jagged-mediated signaling through Notch receptors in a variety of disorders. The antibodies of the invention are also used as reagents in diagnostic kits or as diagnostic tools, or these antibodies can be used in competition assays to generate therapeutic reagents.

BRIEF DESCRIPTION OF DRAWINGS

FIG. 9A demonstrates that cultures of NRK-F49 retain a characteristic monolayer when cultured in the presence of 100 nM anti-Jagged 4D11. FIG. 9B demonstrates characteristic foci formation for NRK-F49 cultured in the presence of 10 ng/mL TGFβ1. FIG. 9C demonstrates that TGFβ1-stimulated, fibrotic foci formation is completely inhibited by 100 nM anti-Jagged 4D11 in cultures treated with 10 ng/mL TGFβ1.

FIG. 22 is an image and a graph depicting the in vivo imaging of an anti-Jagged antibody. FIG. 22A is an image that provides a representation of the labeled 4D11 antibody fluorescence signal 48 hours post-injection in the BxPC3 tumor xenograft mouse model. FIG. 22B is a graph showing the mean T/N ratio of average radiant efficacy for the antibody 4D11 dose group±SD.

FIGS. 27A-27C are a series of tables and graphs depicting that anti-Jagged antibodies of the disclosure bind Jagged 1 and Jagged 2 with high affinity and with human/rodent cross-reactivity. The table in FIG. 27A demonstrates the diversity of specificities among anti-Jagged clones. The table in FIG. 27B demonstrates that the anti-Jagged antibody 4D11 has a high affinity for all four Jagged ligands: human Jagged 1 (hJAG1), human Jagged 2 (hJAG2), rat Jagged 1 (rJAG1) and rat Jagged 2 (rJAG2). The graphs in FIG. 27C demonstrate that both matured anti-Jagged Fab fragments of the disclosure (top panel) and matured IgG molecules of the disclosure (bottom panel) inhibit Notch signaling.

DETAILED DESCRIPTION

Figure 1:
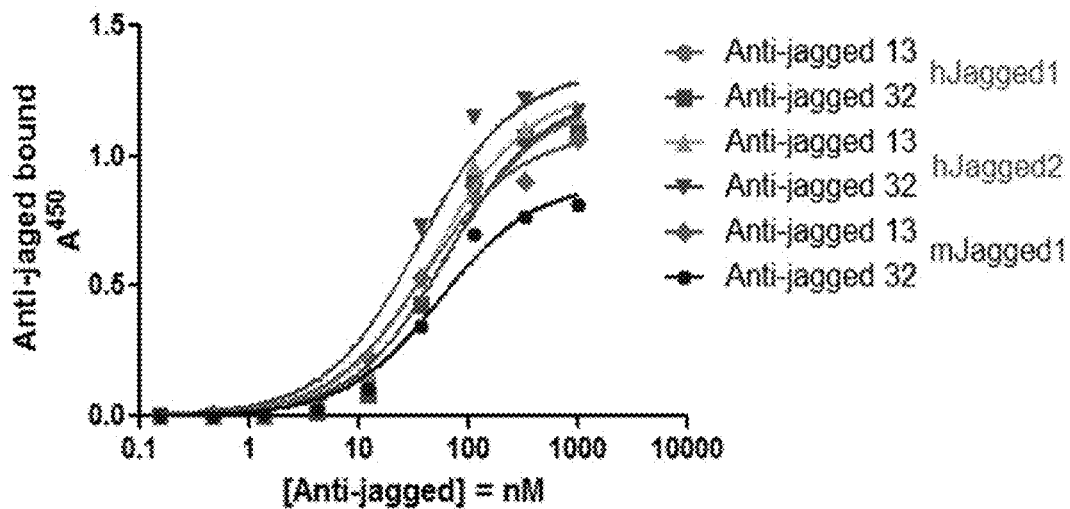
FIG. 1 is a graph depicting the binding of Anti-Jagged antibodies referred to herein as Anti-Jagged 13 and Anti-Jagged 32 to human and mouse Jagged 1 and human Jagged 2.

The present invention describes novel compositions for the diagnosis and treatment of cancer. Specifically this invention provides antibodies that bind Jagged 1 and Jagged 2 and inhibit their binding to and signaling through Notch receptors. The present invention provides monoclonal antibodies that specifically bind Jagged 1 and Jagged 2 (i.e., cross-reactive monoclonal antibodies). These antibodies are collectively referred to herein as "anti-Jagged antibodies."

Indications that would benefit from Jagged inhibition would include cancers. For example, indications would include leukemias, including T-cell acute lymphoblastic leukemia (T-ALL), lymphoblastic diseases including multiple myeloma, and solid tumors, including lung, colorectal, prostate, pancreatic and breast, including triple negative breast cancer. In addition, since notch signaling is important for the survival and growth of cancer stem cells, inhibition of Jagged dependent notch signaling would impact stem cell growth and survival. For example, indications include bone disease or metastasis in cancer, regardless of primary tumor origin; breast cancer, including by way of non-limiting example, ER/PR+ breast cancer, Her2+ breast cancer, triple-negative breast cancer; colorectal cancer; gastric cancer; glioblastoma; head and neck cancer; lung cancer, such as by way of non-limiting example, non-small cell lung cancer; multiple myeloma ovarian cancer; pancreatic cancer; prostate cancer; sarcoma; renal cancer, such as by way of nonlimiting example, renal cell carcinoma; and/or skin cancer, such as by way of nonlimiting example, squamous cell cancer, basal cell carcinoma, melanoma.

In addition to cancer, Jagged-dependent notch signaling is critical to epithelial and fibroblast differentiation to myofibroblasts, cells with a central role in the development of fibrotic disease. Inhibition of Jagged dependent notch signaling, and therefore inhibition of the emergence of myofibroblasts, would be an effective treatment for fibrotic diseases of the kidney, liver, lung, and skin. For example, indications would include a fibrotic disorder, such as idiopathic pulmonary fibrosis (IPF); kidney fibrotic disease, liver fibrotic disease, peritoneal dialysis-induced fibrosis, and/or scleroderma.

Other suitable indications include, for example, a pathology such as, for example, hearing loss.

The antibodies of the present invention bind to a Jagged 1 epitope and/or a Jagged 2 epitope with an equilibrium binding constant ($K_d$) of ≤1 µM. In some embodiments, antibodies of the present invention bind to a Jagged 1 epitope and/or a Jagged 2 epitope with a $K_d$ of ≤100 nM, ≤10 nM, or ≤1 nM. In some embodiments, the anti-Jagged antibodies provided herein exhibit a $K_d$ in the range approximately between ≤1 nM to about 1 pM. In some embodiments, antibodies of the present invention bind to a Jagged 1 epitope and/or a Jagged 2 epitope with an "off rate constant" ($K_{off}$) of $<10^{-2}$, $<10^{-3}$, $<10^{-4}$, or $<10^{-5}$. In some embodiments, anti-Jagged antibodies provided herein exhibit a $K_{off}$ of $<10^{-4}$. In some embodiments, anti-Jagged antibodies provided herein exhibit a $K_{off}$ of $<10^{-5}$. In some embodiments, an antibody of the present invention binds to an EGF domain of Jagged 1 and of Jagged 2. In some embodiments, an antibody of the present invention binds to a DSL domain of Jagged 1 and of Jagged 2.

The anti-Jagged antibodies and/or an activatable antibody of the invention serve to modulate, block, inhibit, reduce, antagonize, neutralize or otherwise interfere with the biological activity of Jagged 1 and/or Jagged 2. Biological activities of Jagged 1 and/or Jagged 2 include, for example, signaling through one or more Notch receptors. For example, the anti-Jagged antibodies completely or partially inhibit Jagged 1 and/or Jagged 2 biological activity by partially or completely modulating, blocking, inhibiting, reducing antagonizing, neutralizing, or otherwise interfering with the binding of Jagged 1 and/or Jagged to one or more Notch receptors, or otherwise partially or completely modulating, blocking, inhibiting, reducing, antagonizing, neutralizing Jagged 1 and/or Jagged 2 mediated signaling activity.

The anti-Jagged antibodies are considered to completely modulate, block, inhibit, reduce, antagonize, neutralize or otherwise interfere with Jagged 1 and/or Jagged 2 biological activity when the level Jagged 1 and/or Jagged 2 activity in the presence of the anti-Jagged antibody is decreased by at least 95%, e.g., by 96%, 97%, 98%, 99% or 100% as compared to the level of activity in the absence of an anti-Jagged antibody described herein. The anti-Jagged antibodies are considered to partially modulate, block, inhibit, reduce, antagonize, neutralize or otherwise interfere with Jagged 1 and/or Jagged 2 activity when the level Jagged 1 and/or Jagged 2 activity in the presence of the anti-Jagged antibody is decreased by less than 95%, e.g., 10%, 20%, 25%, 30%, 40%, 50%, 60%, 75%, 80%, 85% or 90% as compared to the level of activity in the absence of an anti-Jagged antibody described herein. Examples of Jagged activity include, but are not limited to, cell division and differentiation, cell survival/apoptosis, epithelial-mesenchymal transition (EMT) and invasion, angiogenesis, self-renewal of cancer stem cells, and osteolytic bone lesions. While not being bound by theory, it is thought that Jagged's role in angiogenesis is different from that of VEGF.

DEFINITIONS

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, domain antibody, single chain, Fab, and F(ab')$_2$ fragments, scFvs, and an Fab expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as IgG$_1$, IgG$_2$, IgG$_3$, IgG$_4$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences that are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is ≤1 µM; for example, in some embodiments ≤100 nM and in some embodiments ≤10 nM.

As used herein, the terms "specific binding," "immunological binding," and "immunological binding properties" refer to the non-covalent interactions of the type that occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361: 186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to EGFR, when the equilibrium binding constant ($K_d$) is ≤1 µM, for example in some embodiments ≤100 nM, in some embodiments ≤10 nM, and in some embodiments ≤100 pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide that it is not linked to in nature, or (3) does not occur in nature as part of a larger sequence. Polynucleotides in accordance with the invention include the nucleic acid molecules encoding the heavy chain immunoglobulin molecules shown herein, and nucleic acid molecules encoding the light chain immunoglobulin molecules shown herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of murine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecules shown herein, and the light chain immunoglobulin molecules shown herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and that has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences that are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. In some embodiments, oligonucleotides are 10 to 60 bases in length, for example in some embodiments 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the invention are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotide linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

As used herein, the twenty conventional amino acids and their abbreviations follow conventional usage. See Immunology—A Synthesis (2nd Edition, E. S. Golub and D. R. Gren, Eds., Sinauer Associates, Sunderland7 Mass. (1991)). Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and that are 5' to the 5' end of the RNA transcript are referred to as "upstream sequences", sequence regions on the DNA strand having the same sequence as the RNA and that are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, for example in some embodiments, at least 90 percent sequence identity, in some embodiments at least 95 percent sequence identity, and in some embodiments at least 99 percent sequence identity.

In some embodiments, residue positions that are not identical differ by conservative amino acid substitutions.

As discussed herein, minor variations in the amino acid sequences of antibodies or immunoglobulin molecules are contemplated as being encompassed by the present invention, providing that the variations in the amino acid sequence maintain at least 75%, for example in some embodiments at least 80%, 90%, 95%, and in some embodiments 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. In some embodiments, amino- and carboxy-termini of fragments or analogs occur near boundaries of functional domains. Structural and functional domains can be identified by comparison of the nucleotide and/or amino acid sequence data to public or proprietary sequence databases. Computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

In some embodiments, amino acid substitutions are those that: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (for example, conservative amino acid substitutions) may be made in the naturally-occurring sequence (for example, in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion and/or one or more internal deletion(s), but where the remaining amino acid sequence is identical to the corresponding positions in the naturally-occurring sequence deduced, for example, from a full length cDNA sequence. Fragments typically are at least 5, 6, 8 or 10 amino acids long, for example in some embodiments at least 14 amino acids long, in some embodiments at least 20 amino acids long, usually at least 50 amino acids long, and in some embodiments at least 70 amino acids long. The term "analog" as used herein refers to polypeptides that are comprised of a segment of at least 25 amino acids that has substantial identity to a portion of a deduced amino acid sequence and that has specific binding to EGFR, under suitable binding conditions. Typically, polypeptide analogs comprise a conservative amino acid substitution (or addition or deletion) with respect to the naturally-occurring sequence. Analogs typically are at least 20 amino acids long, for example in some embodiments at least 50 amino acids long or longer, and can often be as long as a full-length naturally-occurring polypeptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3H$, $^{14}C$, $^{15}N$, $^{35}S$, $^{90}Y$, $^{99}Tc$, $^{111}In$, $^{125}I$, $^{131}I$), fluorescent labels (e.g., a fluorophore, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and a substantially purified fraction is a composition wherein the object species comprises at least about 50 percent (on a molar basis) of all macromolecular species present.

Generally, a substantially pure composition will comprise more than about 80 percent of all macromolecular species present in the composition, for example in some embodiments more than about 85%, 90%, 95%, and 99%. In some embodiments, the object species is purified to essential homogeneity (contaminant species cannot be detected in the composition by conventional detection methods) wherein the composition consists essentially of a single macromolecular species.

The term patient includes human and veterinary subjects.

Indications that would benefit from Jagged inhibition include leukemias, including T-cell acute lymphoblastic leukemia (T-ALL), lymphoblastic diseases including multiple myeloma, and solid tumors, including lung, colorectal, prostate, pancreatic and breast, including triple negative breast cancer. In addition, since notch signaling is important for the survival and growth of cancer stem cells, inhibition of Jagged dependent notch signaling would impact stem cell growth and survival. In addition to cancer, Jagged dependent notch signaling is critical to epithelial and fibroblast differentiation to myofibroblasts, cells with a central role in the development of fibrotic disease. Inhibition of Jagged dependent notch signaling, and therefore inhibition of the emergence of myofibroblasts, would be an effective treatment for fibrotic diseases of the kidney, liver, lung, and skin.

Anti-Jagged Antibodies and Activatable Anti-Jagged Antibodies

Monoclonal antibodies and/or an activatable antibody of the invention have the ability to inhibit Jagged 1 and/or Jagged 2 mediated signaling through Notch receptors. Inhibition is determined using any of a variety of art-recognized techniques, including the assays described in the examples provided herein.

Anti-Jagged antibodies and/or activatable anti-Jagged antibodies of the invention additionally include, for example, the combinations of heavy chain complementarity determining regions (VH CDRs) and light chain complementarity determining regions (VL CDRs). Examples of such CDRs are shown in Table 2 below or are the CDRs of antibodies disclosed herein, including, but not limited to, those in Table 3 and Table 4. In some embodiments, anti-Jagged antibodies of the invention include antibodies that contain a combination of a VH CDR1 sequence, a VH CDR2 sequence, a VH CDR3 sequence, a VL CDR1 sequence, a VL CDR2 sequence, and a VL CDR3 sequence of at least one antibody selected from the group consisting of the 4D11 antibody, the 4B2 antibody, the 4E7 antibody, the 4E11 antibody, the 6B7 antibody, and the 6F8 antibody. In some embodiments, anti-Jagged antibodies of the invention include antibodies that contain a combination of a VH CDR1 sequence, a VH CDR2 sequence, a VH CDR3 sequence, a VL CDR1 sequence, a VL CDR2 sequence, and a VL CDR3 sequence that are at least 90%, 91%, 92%, 93%, 94%, 95%, 96%, 97%, 98%, 99% or more identical to the sequences of at least one antibody selected from the group consisting of the 4D11 antibody, the 4B2 antibody, the 4E7 antibody, the 4E11 antibody, the 6B7 antibody, and the 6F8 antibody.

The anti-Jagged antibodies of the invention include antibodies that contain a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes at least the amino acid sequence SYAMS (SEQ ID NO: 200); a VH CD2 sequence that includes at least the amino acid sequence SIDPEGRQTYYADSVKG (SEQ ID NO: 208); a VH CDR3 sequence that includes at least the amino acid sequence DIG-GRSAFDY (SEQ ID NO: 209); a VL CDR1 sequence that includes at least the amino acid sequence RASQSISSY (SEQ ID NO: 210); a VL CDR2 sequence that includes at least the amino acid sequence AASSLQS (SEQ ID NO: 211); and a VL CDR3 sequence that includes at least the amino acid sequence QQTVVAPPL (SEQ ID NO: 212).

The anti-Jagged antibodies of the invention include antibodies that contain a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 93%, 94%, 95%, 96%, 97%, 98%, 99% or more identical to the amino acid sequence SYAMS (SEQ ID NO: 200); a VH CD2 sequence that includes a sequence that is at least 90%, 91%, 92%, 93%, 94%, 95%, 96%, 97%, 98%, 99% or more identical to the amino acid sequence SIDPEGRQTYYADSVKG (SEQ ID NO: 208); a VH CDR3 sequence that includes a sequence that is at least 90%, 91%, 92%, 93%, 94%, 95%, 96%, 97%, 98%, 99% or more identical to the amino acid sequence DIGGR-SAFDY (SEQ ID NO: 209); a VL CDR1 sequence that includes a sequence that is at least 90%, 91%, 92%, 93%, 94%, 95%, 96%, 97%, 98%, 99% or more identical to the amino acid sequence RASQSISSY (SEQ ID NO: 210); a VL CDR2 sequence that includes a sequence that is at least 90%, 91%, 92%, 93%, 94%, 95%, 96%, 97%, 98%, 99% or more identical to the amino acid sequence AASSLQS (SEQ ID NO: 211); and a VL CDR3 sequence that includes a sequence that is at least 90%, 91%, 92%, 93%, 94%, 95%, 96%, 97%, 98%, 99% or more identical to the amino acid sequence QQTVVAPPL (SEQ ID NO: 212).

The anti-Jagged antibodies of the invention include antibodies that contain a VH CDR1 sequence that includes at least the amino acid sequence SYAMS (SEQ ID NO: 200); a VH CD2 sequence that includes at least the amino acid sequence SIDPEGRQTYYADSVKG (SEQ ID NO: 208); a VH CDR3 sequence that includes at least the amino acid sequence DIG-GRSAFDY (SEQ ID NO: 209); a VL CDR1 sequence that includes at least the amino acid sequence RASQSISSY (SEQ ID NO: 210); a VL CDR2 sequence that includes at least the amino acid sequence AASSLQS (SEQ ID NO: 211); and a VL CDR3 sequence that includes at least the amino acid sequence QQTVVAPPL (SEQ ID NO: 212).

The anti-Jagged antibodies of the invention include antibodies that contain a VH CDR1 sequence that includes a sequence that is at least 90%, 91%, 92%, 93%, 94%, 95%, 96%, 97%, 98%, 99% or more identical to the amino acid sequence SYAMS (SEQ ID NO: 200); a VH CD2 sequence that includes a sequence that is at least 90%, 91%, 92%, 93%, 94%, 95%, 96%, 97%, 98%, 99% or more identical to the amino acid sequence SIDPEGRQTYYADSVKG (SEQ ID NO: 208); a VH CDR3 sequence that includes a sequence that is at least 90%, 91%, 92%, 93%, 94%, 95%, 96%, 97%, 98%, 99% or more identical to the amino acid sequence DIGGR-SAFDY (SEQ ID NO: 209); a VL CDR1 sequence that includes a sequence that is at least 90%, 91%, 92%, 93%, 94%, 95%, 96%, 97%, 98%, 99% or more identical to the amino acid sequence RASQSISSY (SEQ ID NO: 210); a VL CDR2 sequence that includes a sequence that is at least 90%, 91%, 92%, 93%, 94%, 95%, 96%, 97%, 98%, 99% or more identical to the amino acid sequence AASSLQS (SEQ ID NO: 211); and a VL CDR3 sequence that includes a sequence that is at least 90%, 91%, 92%, 93%, 94%, 95%, 96%, 97%, 98%, 99% or more identical to the amino acid sequence QQTVVAPPL (SEQ ID NO: 212).

Exemplary antibodies and/or activatable antibodies of the invention include, for example, the 4D11 antibody, the 4B2 antibody, the 4E7 antibody, the 4E11 antibody, the 6B7 antibody, and the 6F8 antibody, and variants thereof. These antibodies show specificity for human Jagged 1 and Jagged 2, and they have been shown to inhibit human Jagged 1 and/or human Jagged 2 mediated signaling through Notch receptors. These antibodies include the combinations of a heavy chain variable region (VH) and a light chain variable region (VL), as shown in the amino acid and corresponding nucleic acid sequences listed in Table 4 and shown in Example 5.

Also included in the invention are antibodies and/or activatable antibodies that bind to the same epitope as the antibodies described herein. For example, antibodies and/or an activatable antibody of the invention specifically bind to human Jagged 1, wherein the antibody binds to an epitope that includes one or more amino acid residues on human Jagged 1 (shown, for example, in Accession Nos. AAC52020.1; AAB84053.1; NP_000205.1; P78504.3; AAB39007.1; EAX10341.1; AAI26208.1; AAI26206.1; AAH98393.1; CAC07198.1 and/or BAG35596.1). Antibodies and/or activatable antibodies of the invention specifically bind to human Jagged 2, wherein the antibody binds to an epitope that includes one or more amino acid residues on human Jagged 2 (see e.g., Accession Nos. AAB61285, AAB71189.1, EAW81901.1, NP_002217.3, and/or Q9Y219.3). Antibodies of the invention specifically bind both human Jagged 1 and human Jagged 2, wherein the antibody binds to an epitope that includes one or more amino acid residues on human Jagged 1 and an epitope that includes one or more amino acid residues on human Jagged 2.

Those skilled in the art will recognize that it is possible to determine, without undue experimentation, if a monoclonal antibody (e.g., fully human monoclonal antibody) and/or an activatable antibody has the same or similar specificity as a monoclonal antibody and/or an activatable antibody of the invention (e.g., 4D11, 4B2, 4E7, 4E11, 6B7, and/or 6F8 antibodies and activatable antibodies that include these antibodies) by ascertaining whether the former prevents the latter from binding to Jagged 1, Jagged 2 or both Jagged 1 and Jagged 2. If the monoclonal antibody and/or an activatable antibody being tested competes with the monoclonal antibody and/or an activatable antibody of the invention, as shown by a decrease in binding by the monoclonal antibody and/or an activatable antibody of the invention, then the two monoclonal antibodies and/or activatable antibodies bind to the same, or a closely related, epitope.

One embodiment for determining whether a monoclonal antibody and/or an activatable antibody has the specificity of monoclonal antibody and/or an activatable antibody of the invention is to pre-incubate the monoclonal antibody and/or an activatable antibody of the invention with soluble Jagged 1 and/or Jagged 2 protein (with which it is normally reactive), and then add the monoclonal antibody and/or an activatable antibody being tested to determine if the monoclonal antibody and/or an activatable antibody being tested is inhibited in its ability to bind Jagged 1 and/or Jagged 2. If the monoclonal antibody and/or an activatable antibody being tested is inhibited then, in all likelihood, it has the same, or functionally equivalent, epitopic specificity as the monoclonal antibody and/or an activatable antibody of the invention.

Screening of monoclonal antibodies and/or an activatable antibody of the invention, can be also carried out, e.g., by measuring Jagged 1 and/or Jagged 2 mediated signaling through Notch receptors and determining whether the test monoclonal antibody is able to modulate, block, inhibit, reduce, antagonize, neutralize or otherwise interfere with Jagged 1 and/or Jagged 2 mediated signaling through Notch receptors. Examples of Jagged activity include, but are not limited to, cell division and differentiation, cell survival/apoptosis, epithelial-mesenchymal transition (EMT) and invasion, angiogenesis, self-renewal of cancer stem cells, and osteolytic bone lesions. Methods to measure such activities are known to those skilled in the art.

Various procedures known within the art may be used for the production of monoclonal antibodies directed against human Jagged 1 and/or human Jagged 2, or against derivatives, fragments, analogs homologs or orthologs thereof. (See, for example, Antibodies: A Laboratory Manual, Harlow E, and Lane D, 1988, Cold Spring Harbor Laboratory Press, Cold Spring Harbor, N.Y., incorporated herein by reference). Fully human antibodies are antibody molecules in which the entire sequence of both the light chain and the heavy chain, including the CDRs, arise from human genes. Such antibodies are termed "human antibodies," or "fully human antibodies" herein. Human monoclonal antibodies are prepared, for example, using the procedures described in the Examples provided below. Human monoclonal antibodies can be also prepared by using the trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

Antibodies are purified by well-known techniques, such as affinity chromatography using protein A or protein G, which provide primarily the IgG fraction of immune serum. Subsequently, or alternatively, the specific antigen that is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The antibodies of the invention are monoclonal antibodies. Monoclonal antibodies that modulate, block, inhibit, reduce, antagonize, neutralize or otherwise interfere with Jagged 1 and/or Jagged 2 mediated signaling through Notch receptors are generated, e.g., by immunizing an animal with Jagged 1 and/or Jagged 2, such as, for example, murine, rat or human Jagged 1 and/or Jagged 2 or an immunogenic fragment, derivative or variant thereof. Alternatively, the animal is immunized with cells transfected with a vector containing a nucleic acid molecule encoding Jagged 1 and/or Jagged 2 such that Jagged 1 and/or Jagged 2 is expressed and associated with the surface of the transfected cells. Alternatively, the antibodies are obtained by screening a library that contains antibody or antigen binding domain sequences for binding to Jagged 1 and/or Jagged 2. This library is prepared, e.g., in bacteriophage as protein or peptide fusions to a bacteriophage coat protein that is expressed on the surface of assembled phage particles and the encoding DNA sequences contained within the phage particles (i.e., "phage displayed library"). Hybridomas resulting from myeloma/B cell fusions are then screened for reactivity to Jagged 1 and Jagged 2.

Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that, in some embodiments, contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In some embodiments, immortalized cell lines are those that fuse efficiently, support stable high level expression of antibody by the selected antibody-producing cells, and are sensitive to a medium such as HAT medium. In some embodiments, immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. The binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. For antibodies isolated from murine hybridomas, the DNA also can be modified, for example, by substituting the coding sequence for human heavy and light chain constant domains in place of the homologous murine sequences (see U.S. Pat. No. 4,816,567; Morrison, Nature 368, 812-13 (1994)). Antibody-encoding DNA can be covalently joined to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Human Antibodies and Humanization of Antibodies

Monoclonal antibodies of the invention include fully human antibodies or humanized antibodies. These antibodies are suitable for administration to humans without engendering an immune response by the human against the administered immunoglobulin.

An anti-Jagged antibody is generated, for example, using the procedures described in the Examples provided below.

In some methods, an anti-Jagged antibody is developed, for example, using phage-display methods using antibodies containing only human sequences. Such approaches are well-known in the art, e.g., in WO92/01047 and U.S. Pat. No. 6,521,404, which are hereby incorporated by reference. In this approach, a combinatorial library of phage carrying random pairs of light and heavy chains are screened using natural or recombinant source of Jagged 1, Jagged 2 and/or both Jagged 1 and Jagged 2 or fragments thereof. In another approach, an anti-Jagged antibody can be produced by a process wherein at least one step of the process includes immunizing a transgenic, non-human animal with human Jagged 1 protein, Jagged 2 protein or both Jagged 1 and Jagged 2 protein. In this approach, some of the endogenous heavy and/or kappa light chain loci of this xenogenic non-human animal have been disabled and are incapable of the rearrangement required to generate genes encoding immunoglobulins in response to an antigen. In addition, at least one human heavy chain locus and at least one human light chain locus have been stably transfected into the animal. Thus, in response to an administered antigen, the human loci rearrange to provide genes encoding human variable regions immunospecific for the antigen. Upon immunization, therefore, the xenomouse produces B-cells that secrete fully human immunoglobulins.

A variety of techniques are well-known in the art for producing xenogenic non-human animals. For example, see U.S. Pat. No. 6,075,181 and No. 6,150,584, which is hereby incorporated by reference in its entirety. This general strategy was demonstrated in connection with generation of the first XenoMouse™ strains as published in 1994. See Green et al. Nature Genetics 7:13-21 (1994), which is hereby incorporated by reference in its entirety. See also, U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2 and European Patent No., EP 0 463 151 B1 and International Patent Applications No. WO 94/02602, WO 96/34096, WO 98/24893, WO 00/76310 and related family members.

In an alternative approach, others have utilized a "minilocus" approach in which an exogenous Ig locus is mimicked through the inclusion of pieces (individual genes) from the Ig locus. Thus, one or more VH genes, one or more $D_H$ genes, one or more $J_H$ genes, a mu constant region, and a second constant region (e.g., a gamma constant region) are formed into a construct for insertion into an animal. See e.g., U.S. Pat. Nos. 5,545,806; 5,545,807; 5,591,669; 5,612,205;5,625,825; 5,625,126; 5,633,425; 5,643,763; 5,661,016; 5,721,367; 5,770,429; 5,789,215; 5,789,650; 5,814,318; 5,877; 397; 5,874,299; 6,023,010; and 6,255,458; and European Patent No. 0 546 073 B1; and International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and related family members.

Generation of human antibodies from mice in which, through microcell fusion, large pieces of chromosomes, or entire chromosomes, have been introduced, has also been demonstrated. See European Patent Application Nos. 773 288 and 843 961.

Human anti-mouse antibody (HAMA) responses have led the industry to prepare chimeric or otherwise humanized antibodies. When chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against Jagged 1, Jagged 2 and/or both Jagged 1 and Jagged 2 in order to vitiate or otherwise mitigate concerns and/or effects of HAMA or HACA response.

The production of antibodies with reduced immunogenicity is also accomplished via humanization, chimerization and display techniques using appropriate libraries. It will be appreciated that murine antibodies or antibodies from other species can be humanized or primatized using techniques well known in the art. See e.g., Winter and Harris Immunol Today 14:43 46 (1993) and Wright et al. Crit, Reviews in Immunol. 12125-168 (1992). The antibody of interest may be engineered by recombinant DNA techniques to substitute the CH1, CH2, CH3, hinge domains, and/or the framework domain with the corresponding human sequence (See WO 92102190 and U.S. Pat. Nos. 5,530,101, 5,585,089, 5,693, 761, 5,693,792, 5,714,350, and 5,777,085). Also, the use of Ig cDNA for construction of chimeric immunoglobulin genes is known in the art (Liu et al. P.N.A.S. 84:3439 (1987) and J. Immunol. 139:3521 (1987)). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of immunological Interest, N.I.H. publication no. 91-3242. Human C region genes are readily available from known clones. The choice of isotype will be guided by the desired effecter functions, such as complement fixation, or activity in antibody-dependent cellular cytotoxicity. Suitable isotypes are $IgG_1$, $IgG_3$ and $IgG_4$. Either of the human light chain constant regions, kappa or lambda, may be used. The chimeric antibody is then expressed by conventional methods.

Antibody fragments, such as Fv, $F(ab')_2$ and Fab may be prepared by cleavage of the intact protein, e.g., by protease or chemical cleavage. Alternatively, a truncated gene is designed. For example, a chimeric gene encoding a portion of the $F(ab')_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting antibody may be joined to any strong promoter, including retroviral LTRs, e.g., SV-40 early promoter, (Okayama et al. Mol. Cell. Bio. 3:280 (1983)), Rous sarcoma virus LTR (Gorman et al. P.N.A.S. 79:6777 (1982)), and moloney murine leukemia virus LTR (Grosschedl et al. Cell 41:885 (1985)). Also, as will be appreciated, native Ig promoters and the like may be used.

Further, human antibodies or antibodies from other species can be generated through display type technologies, including, without limitation, phage display, retroviral display, ribosomal display, and other techniques, using techniques well known in the art and the resulting molecules can be subjected to additional maturation, such as affinity maturation, as such techniques are well known in the art. Wright et al. Crit, Reviews in Immunol. 12125-168 (1992), Hanes and Plückthun PNAS USA 94:4937-4942 (1997) (ribosomal display), Parmley and Smith Gene 73:305-318 (1988) (phage display), Scott, TIBS, vol. 17:241-245 (1992), Cwirla et al. PNAS USA 87:6378-6382 (1990), Russel et al. Nucl. Acids Research 21:1081-1085 (1993), Hoganboom et al. Immunol. Reviews 130:43-68 (1992), Chiswell and McCafferty TIBTECH; 10:80-8A (1992), and U.S. Pat. No. 5,733,743. If display technologies are utilized to produce antibodies that are not human, such antibodies can be humanized as described above.

Using these techniques, antibodies can be generated to Jagged 1, Jagged 2 and/or both Jagged 1 and Jagged 2 expressing cells, Jagged 1 itself, Jagged 2 itself, forms of Jagged 1 and/or Jagged 2, epitopes or peptides thereof, and expression libraries thereto (See e.g., U.S. Pat. No. 5,703, 057) that can thereafter be screened as described above for the activities described herein.

Anti-Jagged antibodies of the invention can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, that have a targeting moiety (e.g. a ligand to a cellular surface receptor), and a nucleic acid binding moiety (e.g. polylysine), viral vectors (e.g. a DNA or RNA viral vector), fusion proteins such as described in PCT/US 95/02140 (WO 95/22618) that is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Suitable vectors include viral vectors, fusion proteins and chemical conjugates. Retroviral vectors include moloney murine leukemia viruses. In some embodiments, DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cell's cytoplasm. Avipox virus vectors result in only short term expression of the nucleic acid. In some embodiments, adenovirus vectors, adeno-associated virus vectors and herpes simplex virus (HSV) vectors are preferred for introducing the nucleic acid into neural cells. The adenovirus vector results in shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266: 292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways, for example, to detect the presence of Jagged 1, Jagged 2 and/or both Jagged 1 and Jagged 2 in a sample. The antibody can also be used to try to bind to and disrupt Jagged 1, Jagged 2, and/or both Jagged 1 and Jagged 2-related signaling.

Techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

The invention also includes $F_v$, $F_{ab}$, $F_{ab'}$, and $F_{(ab')2}$ antibody fragments, single chain anti-Jagged antibodies, bispecific anti-Jagged antibodies, multispecific anti-Jagged antibodies, and heteroconjugate anti-Jagged antibodies.

Bispecific antibodies are antibodies that have binding specificities for at least two different antigens. In the present case, one of the binding specificities is for Jagged 1 and Jagged 2. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion is, in some embodiments, with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers that are recovered from recombinant cell culture. The interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')₂ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')₂ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from E. coli and chemically coupled to form bispecific antibodies. Shalaby et al., J. Exp. Med. 175:217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (scFv, or ScFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm that binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells that express a particular antigen. These antibodies possess an antigen-binding arm and an arm that binds a cytotoxic agent or a radionuclide chelator, such as EOTUBE, DPTA, DOTA, or TETA. Another bispecific antibody embodiment binds the protein antigen described herein and further binds tissue factor (TF).

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating diseases and disorders associated with Jagged 1 and/or Jagged 2 signaling. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate). Suitable cytotoxic agents include, for example, dolastatins and derivatives thereof (e.g. auristatin E, AFP, MMAF, MMAE). For example, the cytotoxic agent is monomethyl auristatin E (MMAE). In some embodiments, the agent is an agent selected from the group listed in Table 30. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof.

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{64}$Cu, $^{125}$I, $^{131}$I, $^{131}$In, $^{99m}$Tc, $^{90}$Y, $^{186}$Re, and $^{89}$Zr.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Table 30 lists some of the exemplary pharmaceutical agents that may be employed in the herein described invention but in no way is meant to be an exhaustive list.

TABLE 30

Exemplary Pharmaceutical Agents for Conjugation

CYTOTOXIC AGENTS

Auristatins
Auristatin E
Monomethyl auristatin E (MMAE)
Desmethyl auristatin E (DMAE)
Auristatin F
Monomethyl auristatin F (MMAF)
Desmethyl auristatin F (DMAF)
Auristatin derivatives, e.g., amides thereof
Auristatin tyramine
Auristatin quinoline
Dolastatins
Dolastatin derivatives
Dolastatin 16 DmJ
Dolastatin 16 Dpv
Maytansinoids, e.g. DM-1; DM-4
Maytansinoid derivatives
Duocarmycin
Duocarmycin derivatives
Alpha-amanitin
Anthracyclines
Doxorubicin
Daunorubicin
Bryostatins
Camptothecin
Camptothecin derivatives
7-substituted Camptothecin
10,11-Difluoromethylenedioxycamptothecin
Combretastatins
Debromoaplysiatoxin
Kahalalide-F
Discodermolide
Ecteinascidins

ANTIVIRALS

Acyclovir
Vira A
Symmetrel

ANTIFUNGALS

Nystatin
Turbostatin
Phenstatins
Hydroxyphenstatin
Spongistatin 5
Spongistatin 7
Halistatin 1
Halistatin 2
Halistatin 3
Modified Bryostatins
Halocomstatins
Pyrrolobenzimidazoles (PBI)
Cibrostatin6
Doxaliform
Anthracyclins analogues
Anthracyclins analogues
Cemadotin analogue (CemCH2-SH)
Pseudomonas toxin A (PE38) variant
Pseudomonas toxin A (ZZ-PE38) variant
ZJ-101
OSW-1
4-Nitrobenzyloxycarbonyl Derivatives of O6-Benzylguanine
Topoisomerase inhibitors
Hemiasterlin
Cephalotaxine

TABLE 30-continued

Exemplary Pharmaceutical Agents for Conjugation

Homoharringtonine
Pyrrolobenzodiazepine dimers (PBDs)
Functionalized pyrrolobenzodiazepenes
Calicheamicins
Podophyllotoxins
Taxanes
Vinca alkaloids

CONJUGATABLE DETECTION REAGENTS

Fluorescein and derivatives thereof
Fluorescein isothiocyanate (FITC)

ADDITIONAL ANTI-NEOPLASTICS

Adriamycin
Cerubidine
Bleomycin
Alkeran
Velban
Oncovin
Fluorouracil
Methotrexate
Thiotepa
Bisantrene
Novantrone
Thioguanine
Procarabizine
Cytarabine

ANTI-BACTERIALS

Aminoglycosides
Streptomycin
Neomycin
Kanamycin
Amikacin
Gentamicin
Tobramycin
Streptomycin B
Spectinomycin
Ampicillin
Sulfanilamide
Polymyxin
Chloramphenicol

RADIOPHARMACEUTICALS $^{125}$I
$^{131}$I
$^{89}$Zr
$^{111}$In
$^{123}$I
$^{131}$I
$^{99m}$Tc
$^{201}$Tl
$^{133}$Xe
$^{11}$C
$^{62}$Cu
$^{18}$F
$^{68}$Ga
$^{13}$N
$^{15}$O
$^{38}$K
$^{82}$Rb
$^{99}$mTc (Technetium)

HEAVY METALS

Barium
Gold
Platinum

ANTI-MYCOPLASMALS

Tylosine
Spectinomycin

Those of ordinary skill in the art will recognize that a large variety of possible moieties can be coupled to the resultant antibodies of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. In some embodiments, the preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

Suitable linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker Particularly suitable linkers include: (i) SMPT (4-succinimidyloxycarbonyl-alpha-methyl-alpha-(2-pridyl-dithio)-toluene (Pierce Chem. Co., Cat. (21558G); (ii) SPDP (succinimidyl-6 [3-(2-pyridyldithio) propionamido]hexanoate (Pierce Chem. Co., Cat #21651G); and (iii) Sulfo-LC-SPDP (sulfo-succinimidyl 6 [3-(2-pyridyldithio)-propianamide]hexanoate (Pierce Chem. Co. Cat. #2165-G.

The linkers described above contain components that have different attributes, thus leading to conjugates with differing physio-chemical properties. For example, the linker SMPT contains a sterically hindered disulfide bond, and can form conjugates with increased stability. Disulfide linkages, are in general, less stable than other linkages because the disulfide linkage is cleaved in vitro, resulting in less conjugate available.

The reagent EDC (1-ethyl-3-(3-dimethylaminopropyl)carbodiimide hydrochloride is useful to create a carboxamide starting with a carboxylic acid and a primary or secondary amine. Thus, EDC may be used to link lysine residues in an antibody with a carboxylic acid in a linker or toxin, or to link aspartate or glutamate residues in an antibody with an amine in a linker or toxin. Such conjugation reactions utilizing EDC may be enhanced by addition of NHS (N-hydroxysuccinimide) or sulfo-NHS (N-hydroxy-3-oxysulfonylsuccinimide). Addition of NHS or sulfo-NHS to such conjugation reactions may enhance the rate, completeness, selectivity, and/or reproducibility of the conjugation reactions.

In some embodiments, the linkers are cleavable. In some embodiments, the linkers are non-cleavable. In some embodiments, two or more linkers are present. The two or more linkers are all the same, e.g., cleavable or non-cleavable, or the two or more linkers are different, e.g., at least one cleavable and at least one non-cleavable.

The present invention utilizes several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB. According to the invention, ABs may be covalently attached to an agent through an intermediate linker having at least two reactive groups, one to react with AB and one to react with the agent. The linker, which may include any compatible organic compound, can be chosen such that the reaction with AB (or agent) does not adversely affect AB reactivity and selectivity. Furthermore, the attachment of linker to agent might not destroy the activity of the agent. Suitable linkers for reaction with oxidized antibodies or oxidized antibody fragments include those containing an amine selected from the group consisting of primary amine, secondary amine, hydrazine, hydrazide, hydroxylamine, phenylhydrazine, semicarbazide and thiosemicarbazide groups. Such reactive functional groups may exist as part of the structure of the linker, or may be introduced by suitable chemical modification of linkers not containing such groups.

According to the present invention, suitable linkers for attachment to reduced ABs include those having certain reactive groups capable of reaction with a sulfhydryl group of a reduced antibody or fragment. Such reactive groups include, but are not limited to: reactive haloalkyl groups (including, for example, haloacetyl groups), p-mercuribenzoate groups and groups capable of Michael-type addition reactions (including, for example, maleimides and groups of the type described by Mitra and Lawton, 1979, J. Amer. Chem. Soc. 101: 3097-3110).

According to the present invention, suitable linkers for attachment to neither oxidized nor reduced Abs include those having certain functional groups capable of reaction with the primary amino groups present in unmodified lysine residues in the Ab. Such reactive groups include, but are not limited to, NHS carboxylic or carbonic esters, sulfo-NHS carboxylic or carbonic esters, 4-nitrophenyl carboxylic or carbonic esters, pentafluorophenyl carboxylic or carbonic esters, acyl imidazoles, isocyanates, and isothiocyanates.

According to the present invention, suitable linkers for attachment to neither oxidized nor reduced Abs include those having certain functional groups capable of reaction with the carboxylic acid groups present in aspartate or glutamate residues in the Ab, which have been activated with suitable reagents. Suitable activating reagents include EDC, with or without added NHS or sulfo-NHS, and other dehydrating agents utilized for carboxamide formation. In these instances, the functional groups present in the suitable linkers would include primary and secondary amines, hydrazines, hydroxylamines, and hydrazides.

The agent may be attached to the linker before or after the linker is attached to the AB. In certain applications it may be desirable to first produce an AB-linker intermediate in which the linker is free of an associated agent. Depending upon the particular application, a specific agent may then be covalently attached to the linker. In other embodiments the AB is first attached to the MM, CM and associated linkers and then attached to the linker for conjugation purposes.

Branched Linkers:

In specific embodiments, branched linkers that have multiple sites for attachment of agents are utilized. For multiple site linkers, a single covalent attachment to an AB would result in an AB-linker intermediate capable of binding an agent at a number of sites. The sites may be aldehyde or sulfhydryl groups or any chemical site to which agents can be attached.

Alternatively, higher specific activity (or higher ratio of agents to AB) can be achieved by attachment of a single site linker at a plurality of sites on the AB. This plurality of sites may be introduced into the AB by either of two methods.

First, one may generate multiple aldehyde groups and/or sulfhydryl groups in the same AB. Second, one may attach to an aldehyde or sulfhydryl of the AB a "branched linker" having multiple functional sites for subsequent attachment to linkers. The functional sites of the branched linker or multiple site linker may be aldehyde or sulfhydryl groups, or may be any chemical site to which linkers may be attached. Still higher specific activities may be obtained by combining these two approaches, that is, attaching multiple site linkers at several sites on the AB.

Cleavable Linkers:

Peptide linkers that are susceptible to cleavage by enzymes of the complement system, such as but not limited to urokinase, tissue plasminogen activator, trypsin, plasmin, or another enzyme having proteolytic activity may be used in one embodiment of the present invention. According to one method of the present invention, an agent is attached via a linker susceptible to cleavage by complement. The antibody is selected from a class that can activate complement. The antibody-agent conjugate, thus, activates the complement cascade and releases the agent at the target site. According to another method of the present invention, an agent is attached via a linker susceptible to cleavage by enzymes having a proteolytic activity such as a urokinase, a tissue plasminogen activator, plasmin, or trypsin. These cleavable linkers are useful in conjugated activatable antibodies that include an extracellular toxin, e.g., by way of non-limiting example, any of the extracellular toxins shown in Table 30.

Non-liming examples of cleavable linker sequences are provided in Table 31.

TABLE 31

Exemplary Linker Sequences for Conjugation

| Types of Cleavable Sequences | Amino Acid Sequence |
|---|---|
| Plasmin cleavable sequences | |
| Pro-urokinase | PRFKIIGG (SEQ ID NO: 235) |
| | PRFRIIGG (SEQ ID NO: 236) |
| TGFβ | SSRHRRALD (SEQ ID NO: 237) |
| Plasminogen | RKSSIIIRMRDVVL (SEQ ID NO: 238) |
| Staphylokinase | SSSFDKGKYKKGDDA (SEQ ID NO: 239) |
| | SSSFDKGKYKRGDDA (SEQ ID NO: 240) |
| Factor Xa cleavable sequences | IEGR (SEQ ID NO: 241) |
| | IDGR (SEQ ID NO: 242) |
| | GGSIDGR (SEQ ID NO: 243) |
| MMP cleavable sequences | |
| Gelatinase A | PLGLWA (SEQ ID NO: 244) |
| Collagenase cleavable sequences | |
| Calf skin collagen (α1(I) chain) | GPQGIAGQ (SEQ ID NO: 245) |
| Calf skin collagen (α2(I) chain) | GPQGLLGA (SEQ ID NO: 246) |
| Bovine cartilage collagen (α1(II) chain) | GIAGQ (SEQ ID NO: 247) |
| Human liver collagen (α1(III) chain) | GPLGIAGI (SEQ ID NO: 248) |
| Human α$_2$M | GPEGLRVG (SEQ ID NO: 249) |
| Human PZP | YGAGLGVV (SEQ ID NO: 250) |
| | AGLGVVER (SEQ ID NO: 251) |
| | AGLGISST (SEQ ID NO: 252) |
| Rat α$_1$M | EPQALAMS (SEQ ID NO: 253) |
| | QALAMSAI (SEQ ID NO: 254) |
| Rat α$_2$M | AAYHLVSQ (SEQ ID NO: 255) |
| | MDAFLESS (SEQ ID NO: 256) |
| Rat α$_1$I$_3$(2J) | ESLPVVAV (SEQ ID NO: 257) |
| Rat α$_1$I$_3$(27J) | SAPAVESE (SEQ ID NO: 258) |
| Human fibroblast collagenase (autolytic cleavages) | DVAQFVLT (SEQ ID NO: 259) |
| | VAQFVLTE (SEQ ID NO: 260) |
| | AQFVLTEG (SEQ ID NO: 261) |
| | PVQPIGPQ (SEQ ID NO: 262) |

In addition, agents may be attached via disulfide bonds (for example, the disulfide bonds on a cysteine molecule) to the AB. Since many tumors naturally release high levels of glutathione (a reducing agent) this can reduce the disulfide bonds with subsequent release of the agent at the site of delivery. In certain specific embodiments the reducing agent that would modify a CM would also modify the linker of the conjugated activatable antibody.

Spacers and Cleavable Elements:

In still another embodiment, it may be necessary to construct the linker in such a way as to optimize the spacing between the agent and the AB of the activatable antibody. This may be accomplished by use of a linker of the general structure:

wherein
W is either —NH—CH$_2$— or —CH$_2$—;
Q is an amino acid, peptide; and
n is an integer from 0 to 20.

In still other embodiments, the linker may comprise a spacer element and a cleavable element. The spacer element serves to position the cleavable element away from the core of the AB such that the cleavable element is more accessible to the enzyme responsible for cleavage. Certain of the branched linkers described above may serve as spacer elements.

Throughout this discussion, it should be understood that the attachment of linker to agent (or of spacer element to cleavable element, or cleavable element to agent) need not be particular mode of attachment or reaction. Any reaction providing a product of suitable stability and biological compatibility is acceptable.

Serum Complement and Selection of Linkers:

According to one method of the present invention, when release of an agent is desired, an AB that is an antibody of a class that can activate complement is used. The resulting conjugate retains both the ability to bind antigen and activate the complement cascade. Thus, according to this embodiment of the present invention, an agent is joined to one end of the cleavable linker or cleavable element and the other end of the linker group is attached to a specific site on the AB. For example, if the agent has an hydroxy group or an amino group, it may be attached to the carboxy terminus of a peptide, amino acid or other suitably chosen linker via an ester or amide bond, respectively. For example, such agents may be attached to the linker peptide via a carbodimide reaction. If the agent contains functional groups that would interfere with attachment to the linker, these interfering functional groups can be blocked before attachment and deblocked once the product conjugate or intermediate is made. The opposite or amino terminus of the linker is then used either directly or after further modification for binding to an AB that is capable of activating complement.

Linkers (or spacer elements of linkers) may be of any desired length, one end of which can be covalently attached to specific sites on the AB of the activatable antibody. The other end of the linker or spacer element may be attached to an amino acid or peptide linker.

Thus when these conjugates bind to antigen in the presence of complement the amide or ester bond that attaches the agent to the linker will be cleaved, resulting in release of the agent in its active form. These conjugates, when administered to a subject, will accomplish delivery and release of the agent at the target site, and are particularly effective for the in vivo delivery of pharmaceutical agents, antibiotics, antimetabolites, antiproliferative agents and the like as presented in but not limited to those in Table 30.

Linkers for Release without Complement Activation:

In yet another application of targeted delivery, release of the agent without complement activation is desired since activation of the complement cascade will ultimately lyse the target cell. Hence, this approach is useful when delivery and release of the agent should be accomplished without killing the target cell. Such is the goal when delivery of cell mediators such as hormones, enzymes, corticosteroids, neurotransmitters, genes or enzymes to target cells is desired. These conjugates may be prepared by attaching the agent to an AB that is not capable of activating complement via a linker that is mildly susceptible to cleavage by serum proteases. When this conjugate is administered to an individual, antigen-antibody complexes will form quickly whereas cleavage of the agent will occur slowly, thus resulting in release of the compound at the target site.

Biochemical Cross Linkers:

In other embodiments, the activatable antibody may be conjugated to one or more therapeutic agents using certain biochemical cross-linkers. Cross-linking reagents form molecular bridges that tie together functional groups of two different molecules. To link two different proteins in a stepwise manner, hetero-bifunctional cross-linkers can be used that eliminate unwanted homopolymer formation.

Peptidyl linkers cleavable by lysosomal proteases are also useful, for example, Val-Cit, Val-Ala or other dipeptides. In addition, acid-labile linkers cleavable in the low-pH environment of the lysosome may be used, for example: bis-sialyl ether. Other suitable linkers include cathepsin-labile substrates, particularly those that show optimal function at an acidic pH.

Exemplary hetero-bifunctional cross-linkers are referenced in Table 32.

TABLE 32

Exemplary Hetero-Bifunctional Cross Linkers
HETERO-BIFUNCTIONAL CROSS-LINKERS

| Linker | Reactive Toward | Advantages and Applications | Spacer Arm Length after cross-linking (Angstroms) |
|---|---|---|---|
| SMPT | Primary amines Sulfhydryls | Greater stability | 11.2 Å |
| SPDP | Primary amines Sulfhydryls | Thiolation Cleavable cross-linking | 6.8 Å |
| LC-SPDP | Primary amines Sulfhydryls | Extended spacer arm | 15.6 Å |
| Sulfo-LC-SPDP | Primary amines Sulfhydryls | Extender spacer arm Water-soluble | 15.6 Å |
| SMCC | Primary amines | Stable maleimide reactive group | 11.6 Å |
| | Sulfhydryls | Enzyme-antibody conjugation Hapten-carrier protein conjugation | |
| Sulfo-SMCC | Primary amines | Stable maleimide reactive group | 11.6 Å |
| | Sulfhydryls | Water-soluble Enzyme-antibody conjugation | |
| MBS | Primary amines Sulfhydryls | Enzyme-antibody conjugation Hapten-carrier protein conjugation | 9.9 Å |
| Sulfo-MBS | Primary amines Sulfhydryls | Water-soluble | 9.9 Å |
| SIAB | Primary amines Sulfhydryls | Enzyme-antibody conjugation | 10.6 Å |
| Sulfo-SIAB | Primary amines Sulfhydryls | Water-soluble | 10.6 Å |
| SMPB | Primary amines Sulfhydryls | Extended spacer arm Enzyme-antibody conjugation | 14.5 Å |

TABLE 32-continued

Exemplary Hetero-Bifunctional Cross Linkers
HETERO-BIFUNCTIONAL CROSS-LINKERS

| Linker | Reactive Toward | Advantages and Applications | Spacer Arm Length after cross-linking (Angstroms) |
|---|---|---|---|
| Sulfo-SMPB | Primary amines Sulfhydryls | Extended spacer arm Water-soluble | 14.5 Å |
| EDE/Sulfo-NHS | Primary amines Carboxyl groups | Hapten-Carrier conjugation | 0 |
| ABH | Carbohydrates Nonselective | Reacts with sugar groups | 11.9 Å |

Non-Cleavable Linkers or Direct Attachment:

In still other embodiments of the invention, the conjugate may be designed so that the agent is delivered to the target but not released. This may be accomplished by attaching an agent to an AB either directly or via a non-cleavable linker.

These non-cleavable linkers may include amino acids, peptides, D-amino acids or other organic compounds that may be modified to include functional groups that can subsequently be utilized in attachment to ABs by the methods described herein. A-general formula for such an organic linker could be W—(CH$_2$)$_n$-Q wherein
W is either —NH—CH$_2$— or —CH$_2$—;
Q is an amino acid, peptide; and
n is an integer from 0 to 20.

Non-Cleavable Conjugates:

Alternatively, a compound may be attached to ABs that do not activate complement. When using ABs that are incapable of complement activation, this attachment may be accomplished using linkers that are susceptible to cleavage by activated complement or using linkers that are not susceptible to cleavage by activated complement.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Activatable Anti-Jagged Antibodies

The activatable antibodies and activatable antibody compositions provided herein contain at least an antibody or antibody fragment thereof (collectively referred to as AB throughout the disclosure), that specifically binds Jagged 1 and Jagged 2, wherein the AB is modified by a masking moiety (MM).

When the AB is modified with a MM and is in the presence of Jagged 1 and/or Jagged 2, specific binding of the AB to its target is reduced or inhibited, as compared to the specific binding of the AB not modified with an MM or the specific binding of the parental AB to the target.

The K$_d$ of the AB modified with a MM towards the target, i.e., Jagged 1 and Jagged 2, is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000,100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the K$_d$ of the AB not modified with an MM or the parental AB towards the target. Conversely, the binding affinity of the AB modified with a MM towards the target, i.e., Jagged 1 and Jagged 2, is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000, 000, 100-1,000, 100-10,000, 100-100,000, 100-1,000,000, 100-10,000,000, 1,000-10,000, 1,000-100,000, 1,000-1,000, 000, 1000-10,000,000, 10,000-100,000, 10,000-1,000,000, 10,000-10,000,000, 100,000-1,000,000, or 100,000-10,000, 000 times lower than the binding affinity of the AB not modified with an MM or the parental AB towards the target.

The dissociation constant (K$_d$) of the MM towards the AB is generally greater than the K$_d$ of the AB towards the target, i.e., Jagged 1 and Jagged 2. The K$_d$ of the MM towards the AB can be at least 5, 10, 25, 50, 100, 250, 500, 1,000, 2,500, 5,000, 10,000, 100,000, 1,000,000 or even 10,000,000 times greater than the K$_d$ of the AB towards the target, i.e., Jagged 1 and Jagged 2. Conversely, the binding affinity of the MM towards the AB is generally lower than the binding affinity of the AB towards the target, i.e., Jagged 1 and Jagged 2. The binding affinity of MM towards the AB can be at least 5, 10, 25, 50, 100, 250, 500, 1,000, 2,500, 5,000, 10,000, 100,000, 1,000,000 or even 10,000,000 times lower than the binding affinity of the AB towards the target, i.e., Jagged 1 and Jagged 2.

When the AB is modified with a MM and is in the presence of the target, i.e., Jagged 1 and Jagged 2, specific binding of the AB to its target is reduced or inhibited, as compared to the specific binding of the AB not modified with an MM or the specific binding of the parental AB to the target. When compared to the binding of the AB not modified with an MM or the binding of the parental AB to the target, i.e., Jagged 1 and Jagged 2, the AB's ability to bind the target when modified with an MM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or more when measured in vivo or in an in vitro assay.

The MM inhibits the binding of the AB to the target, i.e., Jagged 1 and Jagged 2. The MM binds the antigen binding domain of the AB and inhibits binding of the AB to Jagged 1 and Jagged 2. The MM can sterically inhibit the binding of the AB to the target, i.e., Jagged 1 and Jagged 2. The MM can allosterically inhibit the binding of the AB to its target. In these embodiments when the AB is modified or coupled to a MM and in the presence of target, i.e., Jagged 1 and Jagged 2, there is no binding or substantially no binding of the AB to the target, or no more than 0.001%, 0.01%, 0.1%, 1%, 2%, 3%, 4%, 5%, 6%, 7%, 8%, 9%, 10%, 15%, 20%, 25%, 30%, 35%, 40%, or 50% binding of the AB to the target, as compared to the binding of the AB not modified with an MM, the parental AB, or the AB not coupled to an MM to the target, for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

When an AB is coupled to or modified by a MM, the MM 'masks' or reduces or otherwise inhibits the specific binding of the AB to Jagged 1 and Jagged 2. When an AB is coupled to or modified by a MM, such coupling or modification can effect a structural change that reduces or inhibits the ability of the AB to specifically bind its target.

An AB coupled to or modified with an MM can be represented by the following formulae (in order from an amino (N) terminal region to carboxyl (C) terminal region:

(MM)-(AB)

(AB)-(MM)

(MM)-L-(AB)

(AB)-L-(MM)

where MM is a masking moiety, the AB is an antibody or antibody fragment thereof, and the L is a linker. In many embodiments, it may be desirable to insert one or more linkers, e.g., flexible linkers, into the composition so as to provide for flexibility.

In certain embodiments, the MM is not a natural binding partner of the AB. In some embodiments the MM contains no or substantially no homology to any natural binding partner of the AB. In other embodiments the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the AB. In some embodiments, the MM is no more than 25% identical to any natural binding partner of the AB. In some embodiments, the MM is no more than 50% identical to any natural binding partner of the AB. In some embodiments, the MM is no more than 20% identical to any natural binding partner of the AB. In some embodiments, the MM is no more than 10% identical to any natural binding partner of the AB.

In some embodiments, the activatable antibodies include an AB that is modified by an MM and also includes one or more cleavable moieties (CM). Such activatable antibodies exhibit activatable/switchable binding, to the AB's target, i.e., Jagged 1 and Jagged 2. Activatable antibodies generally include an antibody or antibody fragment (AB), modified by or coupled to a masking moiety (MM) and a modifiable or cleavable moiety (CM). In some embodiments, the CM contains an amino acid sequence that serves as a substrate for a protease of interest.

The elements of the activatable antibodies are arranged so that the MM and CM are positioned such that in a cleaved (or relatively active) state and in the presence of a target, the AB binds a target, i.e., Jagged 1 and Jagged 2, while in an uncleaved (or relatively inactive) state in the presence of the target, specific binding of the AB to its target, i.e., Jagged 1 and Jagged 2, is reduced or inhibited. The specific binding of the AB to its target can be reduced due to the inhibition or masking of the AB's ability to specifically bind its target by the MM.

The $K_d$ of the AB modified with a MM and a CM towards the target, i.e., Jagged 1 and Jagged 2, is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10, 000,000, 10,000-100,000, 10,000-1,000,000, 10,000-10,000,000, 10,000-10,000,000, 100,000-1,000,000, or 100,000-10,000,000 times greater than the $K_d$ of the AB not modified with an MM and a CM or the parental AB towards the target, i.e., Jagged 1 and Jagged 2. Conversely, the binding affinity of the AB modified with a MM and a CM towards the target, i.e., Jagged 1 and Jagged 2, is at least 5, 10, 25, 50, 100, 250, 500, 1,000, 2,500, 5,000, 10,000, 50,000, 100,000, 500,000, 1,000,000, 5,000, 000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1, 000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM and a CM or the parental AB towards the target, i.e., Jagged 1 and Jagged 2.

When the AB is modified with a MM and a CM and is in the presence of the target but not in the presence of a modifying agent (for example a protease), specific binding of the AB to its target, i.e., Jagged 1 and Jagged 2, is reduced or inhibited, as compared to the specific binding of the AB not modified with an MM and a CM or the parental AB to the target. When compared to the binding of the parental AB or the binding of an AB not modified with an MM and a CM to its target, the AB's ability to bind the target when modified with an MM and a CM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

As used herein, the term cleaved state refers to the condition of the activatable antibodies following modification of the CM by a protease. The term uncleaved state, as used herein, refers to the condition of the activatable antibodies in the absence of cleavage of the CM by a protease. As discussed above, the term "activatable antibodies" is used herein to refer to an activatable antibody in both its uncleaved (native) state, as well as in its cleaved state. It will be apparent to the ordinarily skilled artisan that in some embodiments a cleaved activatable antibody may lack an MM due to cleavage of the CM by protease, resulting in release of at least the MM (e.g., where the MM is not joined to the activatable antibodies by a covalent bond (e.g., a disulfide bond between cysteine residues).

By activatable or switchable is meant that the activatable antibody exhibits a first level of binding to a target, i.e., Jagged 1 and/or Jagged 2, when in a inhibited, masked or uncleaved state (i.e., a first conformation), and a second level of binding to the target, i.e., Jagged 1 and/or Jagged 2, in the uninhibited, unmasked and/or cleaved state (i.e., a second conformation), where the second level of target binding is greater than the first level of binding. In general, the access of target to the AB of the activatable antibody is greater in the presence of a cleaving agent capable of cleaving the CM than in the absence of such a cleaving agent. Thus, when the activatable antibody is in the uncleaved state, the AB is inhibited from target binding and can be masked from target binding (i.e., the first conformation is such the AB cannot bind the target), and in the cleaved state the AB is not inhibited or is unmasked to target binding.

The CM and AB of the activatable antibodies are selected so that the AB represents a binding moiety for Jagged 1 and Jagged 2, and the CM represents a substrate for a protease that is co-localized with Jagged 1 and Jagged 2 at a treatment site or diagnostic site in a subject. The activatable antibodies disclosed herein find particular use where, for example, a protease capable of cleaving a site in the CM is present at relatively higher levels in target-containing tissue of a treatment site or diagnostic site than in tissue of non-treatment sites (for example in healthy tissue).

In some embodiments activatable antibodies provide for reduced toxicity and/or adverse side effects that could otherwise result from binding of the AB at non-treatment sites if the AB were not masked or otherwise inhibited from binding Jagged 1 and Jagged 2.

In general, an activatable antibody can be designed by selecting an AB of interest and constructing the remainder of the activatable antibody so that, when conformationally constrained, the MM provides for masking of the AB or reduction of binding of the AB to its target. Structural design criteria can be to be taken into account to provide for this functional feature.

Activatable antibodies exhibiting a switchable phenotype of a desired dynamic range for target binding in an inhibited versus an uninhibited conformation are provided. Dynamic range generally refers to a ratio of (a) a maximum detected level of a parameter under a first set of conditions to (b) a minimum detected value of that parameter under a second set of conditions. For example, in the context of an activatable antibody, the dynamic range refers to the ratio of (a) a maximum detected level of target protein, i.e., Jagged 1 and Jagged 2, binding to an activatable antibody in the presence of protease capable of cleaving the CM of the activatable antibodies to (b) a minimum detected level of target protein, i.e., Jagged 1 and Jagged 2, binding to an activatable antibody in the absence of the protease. The dynamic range of an activatable antibody can be calculated as the ratio of the equilibrium dissociation constant of an activatable antibody cleaving agent (e.g., enzyme) treatment to the equilibrium dissociation constant of the activatable antibodies cleaving agent treatment. The greater the dynamic range of an activatable antibody, the better the switchable phenotype of the activatable antibody. Activatable antibodies having relatively higher dynamic range values (e.g., greater than 1) exhibit more desirable switching phenotypes such that target protein binding by the activatable antibodies occurs to a greater extent (e.g., predominantly occurs) in the presence of a cleaving agent (e.g., enzyme) capable of cleaving the CM of the activatable antibodies than in the absence of a cleaving agent.

Activatable antibodies can be provided in a variety of structural configurations. Exemplary formulae for activatable antibodies are provided below. It is specifically contemplated that the N- to C-terminal order of the AB, MM and CM may be reversed within an activatable antibody. It is also specifically contemplated that the CM and MM may overlap in amino acid sequence, e.g., such that the CM is contained within the MM.

For example, activatable antibodies can be represented by the following formula (in order from an amino (N) terminal region to carboxyl (C) terminal region:

(MM)-(CM)-(AB)

(AB)-(CM)-(MM)

where MM is a masking moiety, CM is a cleavable moiety, and AB is an antibody or fragment thereof. It should be noted that although MM and CM are indicated as distinct components in the formulae above, in all exemplary embodiments (including formulae) disclosed herein it is contemplated that the amino acid sequences of the MM and the CM could overlap, e.g., such that the CM is completely or partially contained within the MM. In addition, the formulae above provide for additional amino acid sequences that may be positioned N-terminal or C-terminal to the activatable antibodies elements.

In certain embodiments, the MM is not a natural binding partner of the AB. In some embodiments the MM contains no or substantially no homology to any natural binding partner of the AB. In other embodiments the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the AB. In some embodiments, the MM is no more than 50% identical to any natural binding partner of the AB. In some embodiments, the MM is no more than 25% identical to any natural binding partner of the AB. In some embodiments, the MM is no more than 20% identical to any natural binding partner of the AB. In some embodiments, the MM is no more than 10% identical to any natural binding partner of the AB.

In many embodiments it may be desirable to insert one or more linkers, e.g., flexible linkers, into the activatable antibody construct so as to provide for flexibility at one or more of the MM-CM junction, the CM-AB junction, or both. For example, the AB, MM, and/or CM may not contain a sufficient number of residues (e.g., Gly, Ser, Asp, Asn, especially Gly and Ser, particularly Gly) to provide the desired flexibility. As such, the switchable phenotype of such activatable antibody constructs may benefit from introduction of one or more amino acids to provide for a flexible linker. In addition, as described below, where the activatable antibody is provided as a conformationally constrained construct, a flexible linker can be operably inserted to facilitate formation and maintenance of a cyclic structure in the uncleaved activatable antibody.

For example, in certain embodiments an activatable antibody comprises one of the following formulae (where the formula below represent an amino acid sequence in either N- to C-terminal direction or C- to N-terminal direction):

(MM)-L1-(CM)-(AB)

(MM)-(CM)-L2-(AB)

(MM)-L1-(CM)-L2-(AB)

wherein MM, CM, and AB are as defined above; wherein L1 and L2 are each independently and optionally present or absent, are the same or different flexible linkers that include at least 1 flexible amino acid (e.g., Gly). In addition, the formulae above provide for additional amino acid sequences that may be positioned N-terminal or C-terminal to the activatable antibodies elements. Examples include, but are not limited to, targeting moieties (e.g., a ligand for a receptor of a cell present in a target tissue) and serum half-life extending moieties (e.g., polypeptides that bind serum proteins, such as immunoglobulin (e.g., IgG) or serum albumin (e.g., human serum albumin (HAS)).

In some embodiments, the cleavable moiety (CM) of the activatable antibody includes an amino acid sequence that can serve as a substrate for a protease, usually an extracellular protease. The CM may be selected based on a protease that is co-localized in tissue with the desired target of the AB of the activatable antibody. A variety of different conditions are known in which a target of interest is co-localized with a protease, where the substrate of the protease is known in the art. In the example of cancer, the target tissue can be a cancerous tissue, particularly cancerous tissue of a solid tumor. There are reports in the literature of increased levels of proteases having known substrates in a number of cancers, e.g., solid tumors. See, e.g., La Rocca et al, (2004) British J. of Cancer 90(7): 1414-1421. Non-liming examples of disease include: all types of cancers (breast, lung, colorectal, prostate, melanomas, head and neck, pancreatic, etc.), rheumatoid arthritis, Crohn's disuse, SLE, cardiovascular damage, ischemia, etc. For example, indications would include leukemias, including T-cell acute lymphoblastic leukemia (T-ALL), lymphoblastic diseases including multiple myeloma, and solid tumors, including lung, colorectal, prostate, pancreatic and breast, including triple negative breast cancer. For example, indications include bone disease or metastasis in cancer, regardless of primary tumor origin; breast cancer, including by way of non-limiting example, ER/PR+ breast cancer, Her2+ breast cancer, triple-negative breast cancer; colorectal cancer; gastric cancer; glioblastoma; head and neck cancer; lung cancer, such as by way of non-limiting example, non-small cell lung cancer; multiple myeloma ovarian cancer; pancreatic cancer; prostate cancer; sarcoma; renal cancer, such as by way of nonlimiting example, renal cell carcinoma; and/or skin cancer, such as by way of nonlimiting example, squamous cell cancer, basal cell carcinoma, melanoma. In addition to cancer, Jagged-dependent notch signaling is critical to epithelial and fibroblast differentiation to myofibroblasts, cells with a central role in the development of fibrotic disease. Inhibition of Jagged dependent notch signaling, and therefore inhibition of the emergence of myofibroblasts, would be an effective treatment for fibrotic diseases of the kidney, liver, lung, and skin. For example, indications would include a fibrotic disorder, such as idiopathic pulmonary fibrosis (IPF); kidney fibrotic disease, liver fibrotic disease, peritoneal dialysis-induced fibrosis, and/or scleroderma. Other suitable indications include, for example, a pathology such as, for example, hearing loss.

The CM is specifically cleaved by an enzyme at a rate of about $0.001\text{-}1500\times10^4 \text{ M}^{-1}\text{S}^{-1}$ or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250, or $1500\times10^4 \text{ M}^{-1}\text{S}^{-1}$.

For specific cleavage by an enzyme, contact between the enzyme and CM is made. When the activatable antibody comprising an AB coupled to a MM and a CM is in the presence of target and sufficient enzyme activity, the CM can be cleaved. Sufficient enzyme activity can refer to the ability of the enzyme to make contact with the CM and effect cleavage. It can readily be envisioned that an enzyme may be in the vicinity of the CM but unable to cleave because of other cellular factors or protein modification of the enzyme.

Exemplary substrates include but are not limited to substrates cleavable by one or more of the following enzymes or proteases in Table 33:

| ADAMS, ADAMTS, e.g. |
| --- |
| ADAM8 |
| ADAM9 |
| ADAM10 |
| ADAM12 |
| ADAM15 |
| ADAM17/TACE |
| ADAMTS1 |
| ADAMTS4 |
| ADAMTS5 |

-continued

| Aspartate proteases, e.g., |
| --- |
| BACE |
| Aspartic cathepsins, e.g., |
| Cathepsin D |
| Cathepsin E |
| Caspases, e.g., |
| Caspase 1 |
| Caspase 2 |
| Caspase 3 |
| Caspase 4 |
| Caspase 5 |
| Caspase 6 |
| Caspase 7 |
| Caspase 8 |
| Caspase 9 |
| Caspase 10 |
| Caspase 14 |
| Cysteine cathepsins, e.g., |
| Cathepsin B |
| Cathepsin C |
| Cathepsin K |
| Cathepsin L |
| Cathepsin S |
| Cathepsin V/L2 |
| Cathepsin X/Z/P |
| Cysteine proteinases, e.g., |
| Cruzipain |
| Legumain |
| KLKs, e.g., |
| KLK4 |
| KLK5 |
| KLK6 |
| KLK7 |
| KLK8 |
| KLK10 |
| KLK11 |
| KLK13 |
| KLK14 |
| Metallo proteinases, e.g., |
| Meprin |
| Neprilysin |
| PSMA |
| BMP-1 |
| MMPs, e.g., |
| MMP-1 |
| MMP-2 |
| MMP-3 |
| MMP-7 |
| MMP-8 |
| MMP-9 |
| MMP-10 |
| MMP-11 |
| MMP-12 |
| MMP-13 |
| MMP-14 |
| MMP-15 |
| MMP-19 |
| MMP-23 |
| MMP-24 |
| MMP-26 |
| MMP-27 |
| Serine proteases, e.g., |
| activated protein C |
| Cathepsin A |
| Cathepsin G |
| Chymase |
| coagulation factor proteases (e.g., FVIIa, FIXa, FXa, FXIa, |

FXIIa)

Elastase
Granzyme B
Guanidinobenzoatase
Human Neutrophil Elastase
NS3/4A
Plasmin
PSA
tPA
Thrombin
Tryptase
uPA
Type II Transmembrane
Serine Proteases (TTSPs), e.g., DESC1
DPP-4
FAP
Hepsin
Matriptase-2
MT-SP1/Matriptase
TMPRSS2
TMPRSS3
TMPRSS4

For example, in some embodiments, the substrate is cleavable by one or more of the following enzymes or proteases: uPA, legumain, MT-SP1, ADAM17, BMP-1, TMPRSS3, TMPRSS4, MMP-9, MMP-12, MMP-13, and/or MMP-14. In some embodiments, the protease is selected from the group of uPA, legumain, and MT-SP1. In some embodiments, the protease is a matrix metalloproteinase.

Linkers suitable for use in compositions described herein are generally ones that provide flexibility of the modified AB or the activatable antibodies to facilitate the inhibition of the binding of the AB to the target. Such linkers are generally referred to as flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, or 20 amino acids in length.

Exemplary flexible linkers include glycine polymers (G)n, glycine-serine polymers (including, for example, (GS)n, (GSGGS)n (SEQ ID NO: 123) and (GGGS)n (SEQ ID NO: 124), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11173-142 (1992)). Exemplary flexible linkers include, but are not limited to Gly-Gly-Ser-Gly (SEQ ID NO: 125), Gly-Gly-Ser-Gly-Gly (SEQ ID NO: 126), Gly-Ser-Gly-Ser-Gly (SEQ ID NO: 127), Gly-Ser-Gly-Gly-Gly (SEQ ID NO: 128), Gly-Gly-Gly-Ser-Gly (SEQ ID NO: 129), Gly-Ser-Ser-Ser-Gly (SEQ ID NO: 130), and the like. The ordinarily skilled artisan will recognize that design of an activatable antibodies can include linkers that are all or partially flexible, such that the linker can include a flexible linker as well as one or more portions that confer less flexible structure to provide for a desired activatable antibodies structure.

In addition to the elements described above, the activatable antibodies can contain additional elements such as, for example, amino acid sequence N- or C-terminal of the activatable antibodies. For example, activatable antibodies can include a targeting moiety to facilitate delivery to a cell or tissue of interest. Activatable antibodies can be conjugated to an agent, such as a therapeutic agent, an antineoplastic agent, a toxin or fragment thereof, a detectable moiety or a diagnostic agent. Examples of agents are disclosed herein.

The activatable antibodies can also include any of the conjugated agents, linkers and other components described herein in conjunction with an anti-Jagged antibody of the invention, including by way of non-limiting example, any of the agents listed in Table 30 and/or any of the linkers listed in Table 31 and/or Table 32.

Activatable Anti-Jagged Antibodies Having Non-Binding Steric Moieties or Binding Partners for Non-Binding Steric Moieties The invention also provides activatable anti-Jagged antibodies that include non-binding steric moieties (NB) or binding partners (BP) for non-binding steric moieties, where the BP recruits or otherwise attracts the NB to the activatable anti-Jagged antibody. The activatable anti-Jagged antibodies provided herein include, for example, an activatable anti-Jagged antibody that includes a non-binding steric moiety (NB), a cleavable linker (CL) and antibody or antibody fragment (AB) that binds Jagged 1 and Jagged 2; an activatable antibody that includes a binding partner for a non-binding steric moiety (BP), a CL and an AB; and an activatable anti-Jagged antibody that includes a BP to which an NB has been recruited, a CL and an AB that binds Jagged 1 and Jagged 2. Activatable antibodies in which the NB is covalently linked to the CL and AB of the activatable anti-Jagged antibody or is associated by interaction with a BP that is covalently linked to the CL and AB of the activatable anti-Jagged antibody are referred to herein as "NB-containing activatable anti-Jagged antibodies." By activatable or switchable is meant that the activatable antibody exhibits a first level of binding to a target, i.e., Jagged 1 and/or Jagged 2, when the activatable antibody is in an inhibited, masked or uncleaved state (i.e., a first conformation), and a second level of binding to the target when the activatable antibody is in an uninhibited, unmasked and/or cleaved state (i.e., a second conformation, i.e., activated antibody), where the second level of target binding is greater than the first level of target binding. The activatable antibody compositions can exhibit increased bioavailability and more favorable biodistribution compared to conventional antibody therapeutics.

In some embodiments, activatable antibodies provide for reduced toxicity and/or adverse side effects that could otherwise result from binding of the anti-Jagged AB at non-treatment sites and/or non-diagnostic sites if the anti-Jagged AB were not masked or otherwise inhibited from binding to such a site.

In one embodiment, the activatable antibody includes a non-binding steric moiety (NB); a cleavable linker (CL); and an antibody or antibody fragment (AB) that binds specifically to Jagged 1 and Jagged 2, wherein the NB is a polypeptide that does not bind specifically to the AB; the CL is a polypeptide that includes a substrate (S) for an enzyme; the CL is positioned such that in an uncleaved state, the NB interferes with binding of the AB to Jagged 1 and/or Jagged 2 and in a cleaved state, the NB does not interfere with binding of the AB to Jagged 1 and/or Jagged 2; and the NB does not inhibit cleavage of the CL by the enzyme. As used herein and throughout, the term polypeptide refers to any polypeptide that includes at least two amino acid residues, including larger polypeptides, full-length proteins and fragments thereof, and the term polypeptide is not limited to single-chain polypeptides and can include multi-unit, e.g., multi-chain, polypeptides. In cases where the polypeptide is of a shorter length, for example, less than 50 amino acids total, the terms peptide and polypeptide are used interchangeably herein, and in cases where the polypeptide is of a longer length, for example, 50 amino acids or greater, the terms polypeptide and protein are used interchangeably herein.

In one embodiment, the activatable antibody includes a non-binding steric moiety (NB); a cleavable linker (CL); and an antibody or antibody fragment (AB) that binds specifically to Jagged 1 and Jagged 2, wherein (i) the NB includes a polypeptide that does not bind specifically to the AB; (ii) CL is a polypeptide of up to 50 amino acids in length that includes a substrate (S) for an enzyme; (iii) the CL is positioned such that in an uncleaved state, the NB interferes with binding of the AB to Jagged 1 and/or Jagged 2 and in a cleaved state, the NB does not interfere with binding of the AB to Jagged 1 and/or Jagged 2; and (iv) the NB does not inhibit cleavage of the CL by the enzyme. For example, the CL has a length of up to 15 amino acids, a length of up to 20 amino acids, a length of up to 25 amino acids, a length of up to 30 amino acids, a length of up to 35 amino acids, a length of up to 40 amino acids, a length of up to 45 amino acids, a length of up to 50 amino acids, a length in the range of 10-50 amino acids, a length in the range of 15-50 amino acids, a length in the range of 20-50 amino acids, a length in the range of 25-50 amino acids, a length in the range of 30-50 amino acids, a length in the range of 35-50 amino acids, a length in the range of 40-50 amino acids, a length in the range of 45-50 amino acids, a length in the range of 10-40 amino acids, a length in the range of 15-40 amino acids, a length in the range of 20-40 amino acids, a length in the range of 25-40 amino acids, a length in the range of 30-40 amino acids, a length in the range of 35-40 amino acids, a length in the range of 10-30 amino acids, a length in the range of 15-30 amino acids, a length in the range of 20-30 amino acids, a length in the range of 25-30 amino acids, a length in the range of 10-20 amino acids, or a length in the range of 10-15 amino acids.

In one embodiment, the activatable antibody includes a non-binding steric moiety (NB); a cleavable linker (CL); and an antibody or antibody fragment (AB) that binds specifically to Jagged 1 and Jagged 2, wherein (i) the NB includes a polypeptide that does not bind specifically to the AB; (ii) the CL is a polypeptide that includes a substrate (S) for an enzyme; (iii) the CL is positioned such that in an uncleaved state, the NB interferes with binding of the AB to Jagged 1 and/or Jagged 2 and in a cleaved state, the NB does not interfere with binding of the AB to Jagged 1 and/or Jagged 2; (iv) the NB does not inhibit cleavage of the CL by the enzyme; and (v) the activatable antibody has the structural arrangement from N-terminus to C-terminus as follows in the uncleaved state: NB-CL-AB or AB-CL-NB.

In one embodiment, the activatable antibody includes a non-binding steric moiety (NB); a cleavable linker (CL); and an antibody or antibody fragment (AB) that binds specifically to Jagged 1 and Jagged 2, wherein (i) the NB includes a polypeptide that does not bind specifically to the AB; (ii) the CL is a polypeptide that includes a substrate (S) for an enzyme; (iii) the CL is positioned such that in an uncleaved state, the NB interferes with binding of the AB to Jagged 1 and/or Jagged 2 and in a cleaved state, the NB does not interfere with binding of the AB to Jagged 1 and/or Jagged 2, and wherein the NB in the uncleaved activatable antibody reduces the ability of the AB to bind Jagged 1 and/or Jagged 2 by at least 50%, for example, by at least 60%, by at least 70%, by at least 75%, by at least 80%, by at least 85%, by at least 90%, by at least 95%, by at least 96%, by at least 97%, by at least 98%, by at least 99%, by at least 100% as compared to the ability of the cleaved AB to bind Jagged 1 and/or Jagged 2; and (iv) the NB does not inhibit cleavage of the CL by the enzyme. The reduction in the ability of the AB to bind Jagged 1 and/or Jagged 2 is determined, for example, using an assay as described herein or an in vitro target displacement assay such as, for example, the assay described in PCT Publication Nos. WO 2009/025846 and WO 2010/081173.

In one embodiment, the activatable antibody includes a binding partner (BP) for a non-binding steric moiety (NB); a cleavable linker (CL); and an antibody or antibody fragment (AB) that binds specifically to Jagged 1 and Jagged 2, wherein the BP is a polypeptide that binds to the NB when exposed thereto; the NB does not bind specifically to the AB; the CL is a polypeptide that includes a substrate (S) for an enzyme; the CL is positioned such that in an uncleaved state in the presence of the NB, the NB interferes with binding of the AB to Jagged 1 and/or Jagged 2 and in a cleaved state, the NB does not interfere with binding of the AB to Jagged 1 and/or Jagged 2 and the BP does not interfere with binding of the AB to Jagged 1 and/or Jagged 2; and the NB and the BP do not inhibit cleavage of the CL by the enzyme. In some examples of this embodiment, the BP of the activatable antibody is optionally bound to the NB. In one embodiment, the NB is recruited by the BP of the activatable antibody in vivo.

In some examples of any of these activatable anti-Jagged antibody embodiments, the activatable anti-Jagged antibody is formulated as a composition. In some of these embodiments, the composition also includes the NB, where the NB is co-formulated with the activatable anti-Jagged antibody that includes the BP, the CL, and the AB. In some examples of this embodiment, the BP is selected from the group consisting of an albumin binding peptide, a fibrinogen binding peptide, a fibronectin binding peptide, a hemoglobin binding peptide, a transferrin binding peptide, an immunoglobulin domain binding peptide, and other serum protein binding peptides.

In some examples of any of these activatable anti-Jagged antibody embodiments, the NB is a soluble, globular protein. In some examples of any of these activatable anti-Jagged antibody embodiments, the NB is a protein that circulates in the bloodstream. In some examples of any of these activatable anti-Jagged antibody embodiments, the NB is selected from the group consisting of albumin, fibrinogen, fibronectin, hemoglobin, transferrin, an immunoglobulin domain, and other serum proteins.

In some examples of any of these activatable anti-Jagged antibody embodiments, the CL is a polypeptide that includes a substrate (S) for a protease. In some examples of any of these activatable anti-Jagged antibody embodiments, the protease is co-localized with Jagged 1 and/or Jagged 2 in a tissue, and the protease cleaves the CL in the activatable anti-Jagged antibody when the activatable antibody is exposed to the protease. In some examples of any of these activatable anti-Jagged antibody embodiments, the CL is a polypeptide of up to 50 amino acids in length. In some examples of any of these activatable anti-Jagged antibody embodiments, the CL is a polypeptide that includes a substrate (S) having a length of up to 15 amino acids, e.g., 3 amino acids long, 4 amino acids long, 5 amino acids long, 6 amino acids long, 7 amino acids long, 8 amino acids long, 9 amino acids long, 10 amino acids long, 11 amino acids long, 12 amino acids long, 13 amino acids long, 14 amino acids long, or 15 amino acids long.

In some examples of any of these activatable anti-Jagged antibody embodiments, the activatable antibody has the structural arrangement from N-terminus to C-terminus as follows in the uncleaved state: NB-CL-AB, AB-CL-NB, BP-CL-AB or AB-CL-BP. In embodiments where the activatable anti-Jagged antibody includes a BP and the activatable antibody is in the presence of the corresponding NB, the activatable antibody has a structural arrangement from N-terminus to C-terminus as follows in the uncleaved state: NB:BP-CM-AB or AB-CM-BP:NB, where ":" represents an interaction, e.g., binding, between the NB and BP.

In some examples of any of these activatable anti-Jagged antibody embodiments, the activatable antibody includes an antibody or antigen-binding fragment thereof that specifically binds Jagged 1 and Jagged 2 and is a monoclonal antibody, domain antibody, single chain, Fab fragment, a F(ab)$_2$ fragment, a scFv, a scab, a dAb, a single domain heavy chain antibody, and a single domain light chain antibody. In some embodiments, such an antibody or immunologically active fragment thereof that binds Jagged 1 and Jagged 2 is a mouse, chimeric, humanized or fully human monoclonal antibody.

In some examples of any of these activatable anti-Jagged antibody embodiments, the activatable antibody includes a combination of a VH CDR1 sequence, a VH CDR2 sequence, a VH CDR3 sequence, a VL CDR1 sequence, a VL CDR2 sequence, and a VL CDR3 sequence selected from the combinations shown in Table 2. In some embodiments, the activatable antibody includes a combination of a VH CDR1 sequence, a VH CDR2 sequence, a VH CDR3 sequence, a VL CDR1 sequence, a VL CDR2 sequence, and a VL CDR3 sequence that are at least 90%, 91%, 92%, 93%, 94%, 95%, 96%, 97%, 98%, 99% or more identical to the sequences shown in Table 2.

The anti-Jagged antibodies of the invention include antibodies that contain a combination of a VH CDR1 sequence, a VH CDR2 sequence, a VH CDR3 sequence, a VL CDR1 sequence, a VL CDR2 sequence, and a VL CDR3 sequence of at least one antibody selected from the group consisting of the 4D11 antibody, the 4B2 antibody, the 4E7 antibody, the 4E11 antibody, the 6B7 antibody, and the 6F8 antibody.

The anti-Jagged antibodies of the invention include antibodies that contain a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes at least the amino acid sequence SYAMS (SEQ ID NO: 200); a VH CD2 sequence that includes at least the amino acid sequence SIDPEGRQTYYADSVKG (SEQ ID NO: 208); a VH CDR3 sequence that includes at least the amino acid sequence DIGGRSAFDY (SEQ ID NO: 209); a VL CDR1 sequence that includes at least the amino acid sequence RASQSISSY (SEQ ID NO: 210); a VL CDR2 sequence that includes at least the amino acid sequence AASSLQS (SEQ ID NO: 211); and a VL CDR3 sequence that includes at least the amino acid sequence QQTVVAPPL (SEQ ID NO: 212).

The anti-Jagged antibodies of the invention include antibodies that contain a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 93%, 94%, 95%, 96%, 97%, 98%, 99% or more identical to the amino acid sequence SYAMS (SEQ ID NO: 200); a VH CD2 sequence that includes a sequence that is at least 90%, 91%, 92%, 93%, 94%, 95%, 96%, 97%, 98%, 99% or more identical to the amino acid sequence SIDPEGRQTYYADSVKG (SEQ ID NO: 208); a VH CDR3 sequence that includes a sequence that is at least 90%, 91%, 92%, 93%, 94%, 95%, 96%, 97%, 98%, 99% or more identical to the amino acid sequence DIGGRSAFDY (SEQ ID NO: 209); a VL CDR1 sequence that includes a sequence that is at least 90%, 91%, 92%, 93%, 94%, 95%, 96%, 97%, 98%, 99% or more identical to the amino acid sequence RASQSISSY (SEQ ID NO: 210); a VL CDR2 sequence that includes a sequence that is at least 90%, 91%, 92%, 93%, 94%, 95%, 96%, 97%, 98%, 99% or more identical to the amino acid sequence AASSLQS (SEQ ID NO: 211); and a VL CDR3 sequence that includes a sequence that is at least 90%, 91%, 92%, 93%, 94%, 95%, 96%, 97%, 98%, 99% or more identical to the amino acid sequence QQTVVAPPL (SEQ ID NO: 212).

The anti-Jagged antibodies of the invention include antibodies that contain a VH CDR1 sequence that includes at least the amino acid sequence SYAMS (SEQ ID NO: 200); a VH CD2 sequence that includes at least the amino acid sequence SIDPEGRQTYYADSVKG (SEQ ID NO: 208); a VH CDR3 sequence that includes at least the amino acid sequence DIGGRSAFDY (SEQ ID NO: 209); a VL CDR1 sequence that includes at least the amino acid sequence RASQSISSY (SEQ ID NO: 210); a VL CDR2 sequence that includes at least the amino acid sequence AASSLQS (SEQ ID NO: 211); and a VL CDR3 sequence that includes at least the amino acid sequence QQTVVAPPL (SEQ ID NO: 212).

The anti-Jagged antibodies of the invention include antibodies that contain a VH CDR1 sequence that includes a sequence that is at least 90%, 91%, 92%, 93%, 94%, 95%, 96%, 97%, 98%, 99% or more identical to the amino acid sequence SYAMS (SEQ ID NO: 200); a VH CD2 sequence that includes a sequence that is at least 90%, 91%, 92%, 93%, 94%, 95%, 96%, 97%, 98%, 99% or more identical to the amino acid sequence SIDPEGRQTYYADSVKG (SEQ ID NO: 208); a VH CDR3 sequence that includes a sequence that is at least 90%, 91%, 92%, 93%, 94%, 95%, 96%, 97%, 98%, 99% or more identical to the amino acid sequence DIGGRSAFDY (SEQ ID NO: 209); a VL CDR1 sequence that includes a sequence that is at least 90%, 91%, 92%, 93%, 94%, 95%, 96%, 97%, 98%, 99% or more identical to the amino acid sequence RASQSISSY (SEQ ID NO: 210); a VL CDR2 sequence that includes a sequence that is at least 90%, 91%, 92%, 93%, 94%, 95%, 96%, 97%, 98%, 99% or more identical to the amino acid sequence AASSLQS (SEQ ID NO: 211); and a VL CDR3 sequence that includes a sequence that is at least 90%, 91%, 92%, 93%, 94%, 95%, 96%, 97%, 98%, 99% or more identical to the amino acid sequence QQTVVAPPL (SEQ ID NO: 212).

In some examples of any of these activatable anti-Jagged antibody embodiments, the activatable antibody includes a combination of a variable heavy chain region and a variable light chain region selected from the combinations listed in Table 4. In some embodiments, the activatable antibody includes a combination of a variable heavy chain region and a variable light chain region that are at least 90%, 91%, 92%, 93%, 94%, 95%, 96%, 97%, 98%, 99% or more identical to the combinations listed in Table 4.

In some examples of any of these activatable anti-Jagged antibody embodiments, the activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the AB via a linker. In some embodiments, the linker is a cleavable linker. In some embodiments, the agent is an agent selected from the group listed in Table 30. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof.

In some examples of any of these activatable anti-Jagged antibody embodiments, the activatable antibody also includes a detectable moiety. In some embodiments, the detectable moiety is a diagnostic agent.

In some examples of any of these activatable anti-Jagged antibody embodiments, the activatable antibody also includes a spacer. In some examples of any of these activatable anti-Jagged antibody embodiments, the activatable antibody also includes a signal peptide. In some embodiments, the signal peptide is conjugated to the activatable antibody via a spacer. In some examples of any of these activatable anti-Jagged antibody embodiments, the spacer is joined directly to the MM of the activatable antibody.

In some examples of any of these activatable anti-Jagged antibody embodiments, the serum half-life of the activatable antibody is at least 5 days when administered to an organism. In some embodiments, the serum half-life of the activatable antibody is at least 4 days when administered to an organism. In some embodiments, the serum half-life of the activatable antibody is at least 3 days when administered to an organism. In some embodiments, the serum half-life of the activatable antibody is at least 2 days when administered to an organism. In some embodiments, the serum half-life of the activatable antibody is at least 24 hours when administered to an organism. In some embodiments, the serum half-life of the activatable antibody is at least 20 hours when administered to an organism. In some embodiments, the serum half-life of the activatable antibody is at least 18 hours when administered to an organism. In some embodiments, the serum half-life of the activatable antibody is at least 16 hours when administered to an organism. In some embodiments, the serum half-life of the activatable antibody is at least 14 hours when administered to an organism. In some embodiments, the serum half-life of the activatable antibody is at least 12 hours when administered to an organism. In some embodiments, the serum half-life of the activatable antibody is at least 10 hours when administered to an organism. In some embodiments, the serum half-life of the activatable antibody is at least 8 hours when administered to an organism. In some embodiments, the serum half-life of the activatable antibody is at least 6 hours when administered to an organism. In some embodiments, the serum half-life of the activatable antibody is at least 4 hours when administered to an organism. In some embodiments, the serum half-life of the activatable antibody is at least 3 hours when administered to an organism.

The invention also provides an isolated nucleic acid molecule encoding any of these activatable anti-Jagged antibodies, as well as vectors that include these isolated nucleic acid sequences. The invention provides methods of producing an activatable antibody by culturing a cell under conditions that lead to expression of the activatable antibody, wherein the cell comprises such a nucleic acid sequence. In some embodiments, the cell comprises such a vector.

The dissociation constant ($K_d$) of the NB-containing activatable antibody toward the target is greater than the $K_d$ of the AB towards the target when it is not associated with the NB or NB:BP. The dissociation constant ($K_d$) of the NB-containing activatable antibody toward the target is greater than the $K_d$ of the parental AB towards the target. For example, the $K_d$ of the NB-containing activatable antibody toward the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB when it is not associated with the NB or NB:BP or the $K_d$ of the parental AB towards the target. Conversely, the binding affinity of the NB-containing activatable antibody towards the target is lower than the binding affinity of the AB when it is not associated with the NB or NB:BP or lower than the binding affinity of the parental AB towards the target. For example, the binding affinity of the NB-containing activatable antibody toward the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB when it is not associated with the NB or NB:BP or lower than the binding affinity of the parental AB towards the target.

When the NB-containing activatable antibody is in the presence of Jagged 1 and/or Jagged 2, specific binding of the AB to Jagged 1 and/or Jagged 2 is reduced or inhibited, as compared to the specific binding of the AB when it is not associated with the NB or NB:BP. When the NB-containing activatable antibody is in the presence of Jagged 1 and/or Jagged 2, specific binding of the AB to Jagged 1 and/or Jagged 2 is reduced or inhibited, as compared to the specific binding of the parental AB to Jagged 1 and/or Jagged 2. When compared to the binding of the AB not associated with an NB or NB:BP or the binding of the parental AB to Jagged 1 and Jagged 2, the ability of the NB-containing activatable antibody to bind Jagged 1 and/or Jagged 2 is reduced, for example, by at least 50%, 60%, 70%, 80%, 90%, 92%, 93%, 94%, 95%, 96%, 97%, 98%, 99%, or even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vitro and/or in vivo.

When the NB-containing activatable antibody is in the presence of Jagged 1 and Jagged 2 but not in the presence of a modifying agent (for example a protease or other enzyme), specific binding of the AB to Jagged 1 and/or Jagged 2 is reduced or inhibited, as compared to the specific binding of the AB when it is not associated with the NB or NB:BP. When the NB-containing activatable antibody is in the presence of Jagged 1 and/or Jagged 2 but not in the presence of a modifying agent (for example a protease, other enzyme, reduction agent, or light), specific binding of the AB to Jagged 1 and/or Jagged 2 is reduced or inhibited, as compared to the specific binding of the parental AB to Jagged 1 and/or Jagged 2. When compared to the binding of the AB not associated with an NB or NB:BP or the binding of the parental AB to Jagged 1 and/or Jagged 2, the ability of the NB-containing activatable antibody to bind Jagged 1 and/or Jagged 2 is reduced, for example, by at least 50%, 60%, 70%, 80%, 90%, 92%, 93%, 94%, 95%, 96%, 97%, 98%, 99%, or even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vitro and/or in vivo.

In some examples of any of these activatable antibody embodiments, the activatable antibody includes an agent conjugated to the AB to produce an activatable antibody conjugate. In some embodiments of the activatable antibody conjugate, the agent is a therapeutic agent. In some embodiments, the agent is a diagnostic agent. In some embodiments, the agent is a detectable marker. In some embodiments of the activatable antibody conjugate, the agent is an antineoplastic agent. In some embodiments of the activatable antibody conjugate, the agent is a toxin or fragment thereof. In some embodiments of the activatable antibody conjugate, the agent is conjugated to the AB via a linker. In some embodiments of the activatable antibody conjugate, the linker is a cleavable linker. In some embodiments, the agent is an agent selected from the group listed in Table 30. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof.

In some examples of any of these activatable antibody embodiments, the activatable antibodies are dual-target binding activatable antibodies. Such dual target binding activatable antibodies contain two Abs that may bind the same or different targets. In specific embodiments, dual-targeting activatable antibodies contain bispecific antibodies or antibody fragments.

Dual target binding activatable antibodies are designed so as to have a CL cleavable by a cleaving agent that is co-localized in a target tissue with one or both of the targets capable of binding to the ABs of the activatable antibodies. Dual target binding activatable antibodies with more than one AB to the same or different targets can be designed so as to have more than one CL, wherein the first CL is cleavable by a cleaving agent in a first target tissue and wherein the second CL is cleavable by a cleaving agent in a second target tissue, with one or more of the targets binding to the ABs of the activatable antibodies. In one embodiment, the first and second target tissues are spatially separated, for example, at different sites in the organism. In one embodiment, the first and second target tissues are the same tissue temporally separated, for example the same tissue at two different points in time, for example the first time point is when the tissue is an early stage tumor, and the second time point is when the tissue is a late stage tumor.

The invention also provides nucleic acid molecules encoding the activatable antibodies described herein. The invention also provides vectors that include these nucleic acids. The activatable antibodies described herein are produced by culturing a cell under conditions that lead to expression of the activatable antibody, wherein the cell includes these nucleic acid molecules or vectors.

The invention also provides methods of manufacturing activatable antibodies. In one embodiment, the method includes the steps of (a) culturing a cell that includes a nucleic acid construct that encodes the activatable antibody under conditions that lead to expression of the activatable antibody, wherein the activatable antibody includes (i) a non-binding steric moiety (NB); (ii) a cleavable linker (CL); and (iii) an antibody or an antigen binding fragment thereof (AB) that specifically binds a target, wherein (1) the NB does not bind specifically to the AB; (2) the CL is a polypeptide that includes a substrate (S) for an enzyme; (3) the CL is positioned such that in an uncleaved state, the NB interferes with binding of the AB to the target and in a cleaved state, the NB does not interfere with binding of the AB to the target; and (4) the NB does not inhibit cleavage of the CL by the enzyme; and (b) recovering the activatable antibody.

In another embodiment, the method includes the steps of (a) culturing a cell that includes a nucleic acid construct that encodes the activatable antibody under conditions that lead to expression of the activatable antibody, wherein the activatable antibody includes (i) a binding partner (BP) for a non-binding steric moiety (NB); (ii) a cleavable linker (CL); and (iii) an antibody or an antigen binding fragment thereof (AB) that specifically binds a target, wherein (1) the NB does not bind specifically to the AB; (2) the CL is a polypeptide that includes a substrate (S) for an enzyme; (3) the CL is positioned such that in an uncleaved state in the presence of the NB, the NB interferes with binding of the AB to the target and in a cleaved state, the NB does not interfere with binding of the AB to the target and the BP does not interfere with binding of the AB to the target; and (4) the NB and the BP do not inhibit cleavage of the CL by the enzyme; and (b) recovering the activatable antibody. In some examples of this embodiment, the BP of the activatable antibody is bound to the NB.

Use of Anti-Jagged Antibodies and Activatable Anti-Jagged Antibodies

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2): 210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

In one embodiment, an antibody and/or an activatable antibody of the invention, which include a monoclonal antibody of the invention (e.g., a fully human monoclonal antibody) and/or an activatable antibody, may be used as therapeutic agents. Such agents will generally be employed to diagnose, prognose, monitor, treat, alleviate, and/or prevent a disease or pathology associated with Jagged 1 and/or Jagged 2 signaling through Notch receptors in a subject. A therapeutic regimen is carried out by identifying a subject, e.g., a human patient or other mammal suffering from (or at risk of developing) a disorder such as a cancer, including both leukemias and solid tumors, or a fibrotic disorder, using standard methods. An antibody and/or an activatable antibody preparation, for example in some embodiments, one having high specificity and high affinity for its target antigen, is administered to the subject and will generally have an effect due to its binding with the target. Administration of the antibody and/or an activatable antibody may abrogate or inhibit or interfere with the signaling function of the target (e.g., Jagged 1 and/or Jagged 2 mediated signaling through Notch receptors). Administration of the antibody and/or an activatable antibody may abrogate or inhibit or interfere with the binding of the target (e.g., Jagged 1 and/or Jagged 2) with an endogenous ligand (e.g., a Notch receptor) to which it naturally binds. For example, the antibody and/or an activatable antibody binds to the target and modulates, blocks, inhibits, reduces, antagonizes, neutralizes, or otherwise interferes with Jagged 1 and/or Jagged 2 mediated signaling through Notch receptors.

Generally, alleviation or treatment of a disease or disorder involves the lessening of one or more symptoms or medical problems associated with the disease or disorder. For example, in the case of cancer, the therapeutically effective amount of the drug can accomplish one or a combination of the following: reduce the number of cancer cells; reduce the tumor size; inhibit (i.e., to decrease to some extent and/or stop) cancer cell infiltration into peripheral organs; inhibit tumor metastasis; inhibit, to some extent, tumor growth; and/or relieve to some extent one or more of the symptoms associated with the cancer. In some embodiments, a composition of this invention can be used to prevent the onset or reoccurrence of the disease or disorder in a subject, e.g., a human or other mammal, such as a non-human primate, companion animal (e.g., cat, dog, horse), farm animal, work animal, or zoo animal. The terms subject and patient are used interchangeably herein A therapeutically effective amount of an antibody and/or an activatable antibody of the invention relates generally to the amount needed to achieve a therapeutic objective. As noted above, this may be a binding interaction between the antibody and/or an activatable antibody and its target antigen that, in certain cases, interferes with the functioning of the target. The amount required to be administered will furthermore depend on the binding affinity of the antibody and/or an activatable antibody for its specific antigen, and will also depend on the rate at which an administered antibody and/or an activatable antibody is depleted from the free volume other subject to which it is administered. Common ranges for therapeutically effective dosing of an antibody and/or antibody fragment and/or an activatable antibody of the invention may be, by way of nonlimiting example, from about 0.1 mg/kg body weight to about 50 mg/kg body weight. Common dosing frequencies may range, for example, from twice daily to once a week.

Efficaciousness of treatment is determined in association with any known method for diagnosing or treating the particular inflammatory-related disorder. Alleviation of one or more symptoms of the cancer or fibrotic disorder indicates that the antibody and/or an activatable antibody confers a clinical benefit.

Methods for the screening of antibodies and/or activatable antibodies that possess the desired specificity include, but are not limited to, enzyme linked immunosorbent assay (ELISA) and other immunologically mediated techniques known within the art.

In another embodiment, an antibody and/or an activatable antibody directed against Jagged 1 and/or Jagged 2 are used in methods known within the art relating to the localization and/or quantitation of Jagged 1 and/or Jagged 2 (e.g., for use in measuring levels of Jagged 1 and/or Jagged 2 within appropriate physiological samples, for use in diagnostic methods, for use in imaging the protein, and the like). In a given embodiment, an antibody and/or an activatable antibody specific to Jagged 1 and/or Jagged 2, or a derivative, fragment, analog or homolog thereof, that contain the antibody derived antigen binding domain, are utilized as pharmacologically active compounds (referred to hereinafter as "Therapeutics").

In another embodiment, an antibody and/or an activatable antibody specific for Jagged 1 and/or Jagged 2 is used to isolate a Jagged 1 and/or Jagged 2 polypeptide by standard techniques, such as immunoaffinity, chromatography or immunoprecipitation. Antibodies directed against Jagged 1 and/or Jagged 2 and/or an activatable antibody (or a fragment thereof) are used diagnostically to monitor protein levels in tissue as part of a clinical testing procedure, e.g., to determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

In yet another embodiment, an antibody and/or an activatable antibody according to the invention can be used as an agent for detecting the presence of Jagged 1 and/or Jagged 2 (or a fragment thereof) in a sample. In some embodiments, the antibody contains a detectable label. Antibodies are polyclonal, or in some embodiments, monoclonal. An intact antibody, or a fragment thereof (e.g., $F_{ab}$, scFv, or $F_{(ab)2}$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of an antibody with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect a protein in a biological sample in vitro as well as in vivo. For example, in vitro techniques for detection of an analyte protein include enzyme linked immunosorbent assays (ELISAs), Western blots, immunoprecipitations, and immunofluorescence. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

The anti-Jagged antibodies and/or activatable anti-Jagged antibodies of the invention are also useful in a variety of diagnostic and prophylactic formulations. In one embodiment, an anti-Jagged antibody and/or activatable anti-Jagged antibody is administered to patients that are at risk of developing one or more of the aforementioned cancer or fibrotic disorders. A patient's or organ's predisposition to one or more of the aforementioned disorders can be determined using genotypic, serological or biochemical markers.

In another embodiment of the invention, an anti-Jagged antibody and/or activatable anti-Jagged antibody is administered to human individuals diagnosed with a clinical indication associated with one or more of the aforementioned disorders. Upon diagnosis, an anti-Jagged antibody and/or activatable anti-Jagged antibody is administered to mitigate or reverse the effects of the clinical indication.

Antibodies and/or activatable antibodies of the invention are also useful in the detection of Jagged 1 and/or Jagged 2 in patient samples and accordingly are useful as diagnostics. For example, the anti-Jagged antibodies and/or activatable anti-Jagged antibodies of the invention are used in in vitro assays, e.g., ELISA, to detect Jagged 1 and/or Jagged 2 levels in a patient sample.

In one embodiment, an anti-Jagged antibody and/or activatable anti-Jagged antibody of the invention is immobilized on a solid support (e.g., the well(s) of a microtiter plate). The immobilized antibody and/or activatable antibody serves as a capture antibody for any Jagged 1 and/or Jagged 2 that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of Jagged antigen in the test sample is determined by comparison with a standard curve developed from the standard samples.

It will be appreciated that based on the results obtained using the anti-Jagged antibodies of the invention in an in vitro diagnostic assay, it is possible to stage a disease in a subject based on expression levels of the Jagged antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

Anti-Jagged antibodies and/or activatable anti-Jagged antibodies can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, activatable anti-Jagged antibodies having an enzymatically cleavable CM can be used to detect the presence or absence of an enzyme that is capable of cleaving the CM. Such activatable anti-Jagged antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated anti-Jagged antibodies (i.e., antibodies resulting from cleavage of an activatable anti-Jagged antibody) in a given cell or tissue of a given host organism. Such accumulation of activated anti-Jagged antibodies indicates not only that the tissue expresses enzymatic activity (or an increased reduction potential depending on the nature of the CM) but also that the tissue expresses target to which the activated antibody binds.

For example, the CM can be selected to be a protease substrate for a protease found at the site of a tumor, at the site of a viral or bacterial infection at a biologically confined site (e.g., such as in an abscess, in an organ, and the like), and the like. The AB can be one that binds a target antigen. Using methods familiar to one skilled in the art, a detectable label (e.g., a fluorescent label or radioactive label or radiotracer) can be conjugated to an AB or other region of an anti-Jagged antibody and/or activatable anti-Jagged antibody. Suitable detectable labels are discussed in the context of the above screening methods and additional specific examples are provided below. Using an AB specific to a protein or peptide of the disease state, along with a protease whose activity is elevated in the disease tissue of interest, activatable anti-Jagged antibodies will exhibit an increased rate of binding to disease tissue relative to tissues where the CM specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM is not present at a detectable level (or is present at lower levels in non-disease tissues or is present in inactive conformation), accumulation of activated anti-Jagged antibodies in the disease tissue is enhanced relative to non-disease tissues.

In another example, activatable anti-Jagged antibodies can be used to detect the presence or absence of a cleaving agent in a sample. For example, where the activatable anti-Jagged antibodies contain a CM susceptible to cleavage by an enzyme, the activatable anti-Jagged antibodies can be used to detect (either qualitatively or quantitatively) the presence of an enzyme in the sample. In another example, where the activatable anti-Jagged antibodies contain a CM susceptible to cleavage by reducing agent, the activatable anti-Jagged antibodies can be used to detect (either qualitatively or quantitatively) the presence of reducing conditions in a sample. To facilitate analysis in these methods, the activatable antibodies can be detectably labeled, and can be bound to a support (e.g., a solid support, such as a slide or bead). The detectable label can be positioned on a portion of the activatable anti-Jagged antibody that is not released following cleavage, for example, the detectable label can be a quenched fluorescent label or other label that is not detectable until cleavage has occurred. The assay can be conducted by, for example, contacting the immobilized, detectably labeled activatable anti-Jagged antibodies with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the activatable anti-Jagged antibodies prior to contacting with the sample e.g., the presence of and/or an increase in detectable signal due to cleavage of the activatable antibody by the cleaving agent in the sample.

Such detection methods can be adapted to also provide for detection of the presence or absence of a target that is capable of binding the AB of the activatable anti-Jagged antibodies when cleaved. Thus, the assays can be adapted to assess the presence or absence of a cleaving agent and the presence or absence of a target of interest. The presence or absence of the cleaving agent can be detected by the presence of and/or an increase in detectable label of the activatable anti-Jagged antibodies as described above, and the presence or absence of the target can be detected by detection of a target-AB complex e.g., by use of a detectably labeled anti-target antibody.

Activatable anti-Jagged antibodies are also useful in in situ imaging for the validation of activatable antibody activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable anti-Jagged antibody is labeled with a detectable label. The detectable label may be a fluorescent dye, (e.g. a fluorophore, Fluorescein Isothiocyanate (FITC), Rhodamine Isothiocyanate (TRITC), an Alexa Fluor® label), a near infrared (NIR) dye (e.g., Qdot® nano crystals), a colloidal metal, a hapten, a radioactive marker, biotin and an amplification reagent such as streptavidin, or an enzyme (e.g. horseradish peroxidase or alkaline phosphatase).

Detection of the label in a sample that has been incubated with the labeled, activatable anti-Jagged antibody indicates that the sample contains the target, i.e., Jagged 1 and/or Jagged 2, and contains a protease that is specific for the CM of the activatable anti-Jagged antibody. In some embodiments, the presence of the protease can be confirmed using broad spectrum protease inhibitors such as those described herein, and/or by using an agent that is specific for the protease, for example, an antibody such as A11, which is specific for the protease matriptase (MT-SP1) and inhibits the proteolytic activity of MT-SP1; see e.g., International Publication Number WO 2010/129609, published 11 Nov. 2010. The same approach of using broad spectrum protease inhibitors such as those described herein, and/or by using a more selective inhibitory agent can be used to identify a protease or class of proteases specific for the CM of the activatable anti-Jagged antibody. In some embodiments, the presence of the target can be confirmed using an agent that is specific for the target, e.g., another anti-Jagged 1 and/or anti-Jagged 2 antibody, or the detectable label can be competed with unlabeled Jagged 1 and/or Jagged 2. In some embodiments, unlabeled activatable anti-Jagged antibody could be used, with detection by a labeled secondary antibody or more complex detection system.

Similar techniques are also useful for in vivo imaging where detection of the fluorescent signal in a subject, e.g., a mammal, including a human, indicates that the disease site contains the target, i.e., Jagged 1 and/or Jagged 2, and contains a protease that is specific for the CM of the activatable anti-Jagged antibody.

These techniques are also useful in kits and/or as reagents for the detection, identification or characterization of protease activity in a variety of cells, tissues, and organisms based on the protease-specific CM in the activatable anti-Jagged antibody.

The invention provides methods of using the anti-Jagged antibodies and/or activatable anti-Jagged antibodies in a variety of diagnostic and/or prophylactic indications. For example, the invention provides methods of detecting presence or absence of a cleaving agent and a target of interest in a subject or a sample by (i) contacting a subject or sample with an activatable anti-Jagged antibody, wherein the activatable anti-Jagged antibody comprises a masking moiety (MM), a cleavable moiety (CM) that is cleaved by the cleaving agent, and an antigen binding domain or fragment thereof (AB) that specifically binds the target of interest, wherein the activatable anti-Jagged antibody in an uncleaved, non-activated state comprises a structural arrangement from N-terminus to C-terminus as follows: MM-CM-AB or AB-CM-MM; (a) wherein the MM is a peptide that inhibits binding of the AB to the Jagged target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the Jagged target, and in a cleaved, activated state the MM does not interfere or compete with specific binding of the AB to the Jagged target; and (ii) measuring a level of activated activatable anti-Jagged antibody in the subject or sample, wherein a detectable level of activated activatable anti-Jagged antibody in the subject or sample indicates that the cleaving agent and a Jagged target are present in the subject or sample and wherein no detectable level of activated activatable anti-Jagged antibody in the subject or sample indicates that the cleaving agent, a Jagged target or both the cleaving agent and a Jagged target are absent and/or not sufficiently present in the subject or sample. In some embodiments, the activatable anti-Jagged antibody is an activatable anti-Jagged antibody to which a therapeutic agent is conjugated. In some embodiments, the activatable anti-Jagged antibody is not conjugated to an agent. In some embodiments, the activatable anti-Jagged antibody comprises a detectable label. In some embodiments, the detectable label is positioned on the AB. In some embodiments, measuring the level of activatable anti-Jagged antibody in the subject or sample is accomplished using a secondary reagent that specifically binds to the activated antibody, wherein the reagent comprises a detectable label. In some embodiments, the secondary reagent is an antibody comprising a detectable label.

The invention also provides methods of detecting presence or absence of a cleaving agent in a subject or a sample by (i) contacting a subject or sample with an activatable anti-Jagged antibody in the presence of a Jagged target of interest, e.g., Jagged 1 and/or Jagged 2, wherein the activatable anti-Jagged antibody comprises a masking moiety (MM), a cleavable moiety (CM) that is cleaved by the cleaving agent, and an antigen binding domain or fragment thereof (AB) that specifically binds the target of interest, wherein the activatable anti-Jagged antibody in an uncleaved, non-activated state comprises a structural arrangement from N-terminus to C-terminus as follows: MM-CM-AB or AB-CM-MM; (a) wherein the MM is a peptide that inhibits binding of the AB to the Jagged target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the Jagged target, and in a cleaved, activated state the MM does not interfere or compete with specific binding of the AB to the Jagged target; and (ii) measuring a level of activated activatable anti-Jagged antibody in the subject or sample, wherein a detectable level of activated activatable anti-Jagged antibody in the subject or sample indicates that the cleaving agent is present in the subject or sample and wherein no detectable level of activated activatable anti-Jagged antibody in the subject or sample indicates that the cleaving agent is absent and/or not sufficiently present in the subject or sample. In some embodiments, the activatable anti-Jagged antibody is an activatable anti-Jagged antibody to which a therapeutic agent is conjugated. In some embodiments, the activatable anti-Jagged antibody is not conjugated to an agent. In some embodiments, the activatable anti-Jagged antibody comprises a detectable label. In some embodiments, the detectable label is positioned on the AB. In some embodiments, measuring the level of activatable anti-Jagged antibody in the subject or sample is accomplished using a secondary reagent that specifically binds to the activated antibody, wherein the reagent comprises a detectable label. In some embodiments, the secondary reagent is an antibody comprising a detectable label.

The invention also provides kits for use in methods of detecting presence or absence of a cleaving agent and a Jagged target of interest (e.g., Jagged 1 and/or Jagged 2) in a subject or a sample, where the kits include at least an activatable anti-Jagged antibody comprises a masking moiety (MM), a cleavable moiety (CM) that is cleaved by the cleaving agent, and an antigen binding domain or fragment thereof (AB) that specifically binds the target of interest, wherein the activatable anti-Jagged antibody in an uncleaved, non-activated state comprises a structural arrangement from N-terminus to C-terminus as follows: MM-CM-AB or AB-CM-MM; (a) wherein the MM is a peptide that inhibits binding of the AB to the Jagged target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the Jagged target, and in a cleaved, activated state the MM does not interfere or compete with specific binding of the AB to the Jagged target; and (ii) measuring a level of activated activatable anti-Jagged antibody in the subject or sample, wherein a detectable level of activated activatable anti-Jagged antibody in the subject or sample indicates that the cleaving agent is present in the subject or sample and wherein no detectable level of activated activatable anti-Jagged antibody in the subject or sample indicates that the cleaving agent is absent and/or not sufficiently present in the subject or sample. In some embodiments, the activatable anti-Jagged antibody is an activatable anti-Jagged antibody to which a therapeutic agent is conjugated. In some embodiments, the activatable anti-Jagged antibody is not conjugated to an agent. In some embodiments, the activatable anti-Jagged antibody comprises a detectable label. In some embodiments, the detectable label is positioned on the AB. In some embodiments, measuring the level of activatable anti-Jagged antibody in the subject or sample is accomplished using a secondary reagent that specifically binds to the activated antibody, wherein the reagent comprises a detectable label. In some embodiments, the secondary reagent is an antibody comprising a detectable label.

The invention also provides methods of detecting presence or absence of a cleaving agent in a subject or a sample by (i) contacting a subject or sample with an activatable anti-Jagged antibody, wherein the activatable anti-Jagged antibody comprises a masking moiety (MM), a cleavable moiety (CM) that is cleaved by the cleaving agent, an antigen binding domain (AB) that specifically binds a Jagged target, e.g., Jagged 1 and/or Jagged 2, and a detectable label, wherein the activatable anti-Jagged antibody in an uncleaved, non-activated state comprises a structural arrangement from N-terminus to C-terminus as follows: MM-CM-AB or AB-CM-MM; wherein the MM is a peptide that inhibits binding of the AB to the Jagged target, and wherein the MM does not have an amino acid sequence of a naturally occurring binding partner of the AB and is not a modified form of a natural binding partner of the AB; wherein, in an uncleaved, non-activated state, the MM interferes with specific binding of the AB to the Jagged target, and in a cleaved, activated state the MM does not interfere or compete with specific binding of the AB to the Jagged target; and wherein the detectable label is positioned on a portion of the activatable anti-Jagged antibody that is released following cleavage of the CM; and (ii) measuring a level of detectable label in the subject or sample, wherein a detectable level of the detectable label in the subject or sample indicates that the cleaving agent is absent and/or not sufficiently present in the subject or sample and wherein no detectable level of the detectable label in the subject or sample indicates that the cleaving agent is present in the subject or sample. In some embodiments, the activatable anti-Jagged antibody is an activatable anti-Jagged antibody to which a therapeutic agent is conjugated. In some embodiments, the activatable anti-Jagged antibody is not conjugated to an agent. In some embodiments, the activatable anti-Jagged antibody comprises a detectable label. In some embodiments, the detectable label is positioned on the AB. In some embodiments, measuring the level of activatable anti-Jagged antibody in the subject or sample is accomplished using a secondary reagent that specifically binds to the activated antibody, wherein the reagent comprises a detectable label. In some embodiments, the secondary reagent is an antibody comprising a detectable label.

The invention also provides kits for use in methods of detecting presence or absence of a cleaving agent and a Jagged target of interest (e.g., Jagged 1 and/or Jagged 2) in a subject or a sample, where the kits include at least an activatable anti-Jagged antibody and/or conjugated activatable anti-Jagged antibody (e.g., an activatable antibody to which a therapeutic agent is conjugated) described herein for use in contacting a subject or biological sample and means for detecting the level of activated activatable anti-Jagged antibody and/or conjugated activatable anti-Jagged antibody in the subject or biological sample, wherein a detectable level of activated activatable anti-Jagged antibody in the subject or biological sample indicates that the cleaving agent and the Jagged target are present in the subject or biological sample and wherein no detectable level of activated activatable anti-Jagged antibody in the subject or biological sample indicates that the cleaving agent, the Jagged target or both the cleaving agent and the Jagged target are absent and/or not sufficiently present in the subject or biological sample, such that Jagged target binding and/or protease cleavage of the activatable anti-Jagged antibody cannot be detected in the subject or biological sample.

The invention also provides methods of detecting presence or absence of a cleaving agent in a subject or a sample by (i) contacting a subject or biological sample with an activatable anti-Jagged antibody in the presence of the Jagged target, and (ii) measuring a level of activated activatable anti-Jagged antibody in the subject or biological sample, wherein a detectable level of activated activatable anti-Jagged antibody in the subject or biological sample indicates that the cleaving agent is present in the subject or biological sample and wherein no detectable level of activated activatable anti-Jagged antibody in the subject or biological sample indicates that the cleaving agent is absent and/or not sufficiently present in the subject or biological sample at a detectable level, such that protease cleavage of the activatable anti-Jagged antibody cannot be detected in the subject or biological sample. Such an activatable anti-Jagged antibody includes a masking moiety (MM), a cleavable moiety (CM) that is cleaved by the cleaving agent, and an antigen binding domain or fragment thereof (AB) that specifically binds the Jagged target, wherein the activatable anti-Jagged antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the Jagged target, and wherein the MM does not have an amino acid sequence of a naturally occurring binding partner of the AB; and (b) wherein the MM of the activatable anti-Jagged antibody in an uncleaved state interferes with specific binding of the AB to the Jagged target, and wherein the MM of an activatable anti-Jagged antibody in a cleaved (i.e., activated) state does not interfere or compete with specific binding of the AB to the Jagged target. In some embodiments, the activatable anti-Jagged antibody is an activatable anti-Jagged antibody to which a therapeutic agent is conjugated. In some embodiments, the activatable anti-Jagged antibody is not conjugated to an agent. In some embodiments, the detectable label is attached to the masking moiety. In some embodiments, the detectable label is attached to the cleavable moiety N-terminal to the protease cleavage site. In some embodiments, a single antigen binding site of the AB is masked. In some embodiments wherein an antibody of the disclosure has at least two antigen binding sites, at least one antigen binding site is masked and at least one antigen binding site is not masked. In some embodiments all antigen binding sites are masked. In some embodiments, the measuring step includes use of a secondary reagent comprising a detectable label.

The invention also provides kits for use in methods of detecting presence or absence of a cleaving agent and a Jagged target of interest (e.g., Jagged 1 and/or Jagged 2) in a subject or a sample, where the kits include at least an activatable anti-Jagged antibody and/or conjugated activatable anti-Jagged antibody described herein for use in contacting a subject or biological sample with an activatable anti-Jagged antibody in the presence of the Jagged target, and measuring a level of activated activatable anti-Jagged antibody in the subject or biological sample, wherein a detectable level of activated activatable anti-Jagged antibody in the subject or biological sample indicates that the cleaving agent is present in the subject or biological sample and wherein no detectable level of activated activatable anti-Jagged antibody in the subject or biological sample indicates that the cleaving agent is absent and/or not sufficiently present in the subject or biological sample at a detectable level, such that protease cleavage of the activatable anti-Jagged antibody cannot be detected in the subject or biological sample. Such an activatable anti-Jagged antibody includes a masking moiety (MM), a cleavable moiety (CM) that is cleaved by the cleaving agent, and an antigen binding domain or fragment thereof (AB) that specifically binds the Jagged target, wherein the activatable anti-Jagged antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the Jagged target, and wherein the MM does not have an amino acid sequence of a naturally occurring binding partner of the AB; and (b) wherein the MM of the activatable anti-Jagged antibody in an uncleaved state interferes with specific binding of the AB to the Jagged target, and wherein the MM of an activatable anti-Jagged antibody in a cleaved (i.e., activated) state does not interfere or compete with specific binding of the AB to the Jagged target. In some embodiments, the activatable anti-Jagged antibody is an activatable anti-Jagged antibody to which a therapeutic agent is conjugated. In some embodiments, the activatable anti-Jagged antibody is not conjugated to an agent. In some embodiments, the detectable label is attached to the masking moiety. In some embodiments, the detectable label is attached to the cleavable moiety N-terminal to the protease cleavage site. In some embodiments, a single antigen binding site of the AB is masked. In some embodiments wherein an antibody of the disclosure has at least two antigen binding sites, at least one antigen binding site is masked and at least one antigen binding site is not masked. In some embodiments all antigen binding sites are masked. In some embodiments, the measuring step includes use of a secondary reagent comprising a detectable label.

The invention also provides kits for use in methods of detecting presence or absence of a cleaving agent in a subject or a sample, where the kits include at least an activatable anti-Jagged antibody and/or conjugated activatable anti-Jagged antibody described herein for use in contacting a subject or biological sample and means for detecting the level of activated activatable anti-Jagged antibody and/or conjugated activatable anti-Jagged antibody in the subject or biological sample, wherein the activatable anti-Jagged antibody includes a detectable label that is positioned on a portion of the activatable anti-Jagged antibody that is released following cleavage of the CM, wherein a detectable level of activated activatable anti-Jagged antibody in the subject or biological sample indicates that the cleaving agent is absent and/or not sufficiently present in the subject or biological sample such that Jagged target binding and/or protease cleavage of the activatable anti-Jagged antibody cannot be detected in the subject or biological sample, and wherein no detectable level of activated activatable anti-Jagged antibody in the subject or biological sample indicates that the cleaving agent is present in the subject or biological sample at a detectable level.

The invention provides methods of detecting presence or absence of a cleaving agent and the Jagged target in a subject or a sample by (i) contacting a subject or biological sample with an activatable anti-Jagged antibody, wherein the activatable anti-Jagged antibody includes a detectable label that is positioned on a portion of the activatable anti-Jagged antibody that is released following cleavage of the CM and (ii) measuring a level of activated activatable anti-Jagged antibody in the subject or biological sample, wherein a detectable level of activated activatable anti-Jagged antibody in the subject or biological sample indicates that the cleaving agent, the Jagged target or both the cleaving agent and the Jagged target are absent and/or not sufficiently present in the subject or biological sample, such that Jagged target binding and/or protease cleavage of the activatable anti-Jagged antibody cannot be detected in the subject or biological sample, and wherein a reduced detectable level of activated activatable anti-Jagged antibody in the subject or biological sample indicates that the cleaving agent and the Jagged target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. Such an activatable anti-Jagged antibody includes a masking moiety (MM), a cleavable moiety (CM) that is cleaved by the cleaving agent, and an antigen binding domain or fragment thereof (AB) that specifically binds the Jagged target, wherein the activatable anti-Jagged antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the Jagged target, and wherein the MM does not have an amino acid sequence of a naturally occurring binding partner of the AB; and (b) wherein the MM of the activatable anti-Jagged antibody in an uncleaved state interferes with specific binding of the AB to the Jagged target, and wherein the MM of an activatable anti-Jagged antibody in a cleaved (i.e., activated) state does not interfere or compete with specific binding of the AB to the Jagged target. In some embodiments, the activatable anti-Jagged antibody is an activatable anti-Jagged antibody to which a therapeutic agent is conjugated. In some embodiments, the activatable anti-Jagged antibody is not conjugated to an agent. In some embodiments, the activatable anti-Jagged antibody comprises a detectable label. In some embodiments, the detectable label is positioned on the AB. In some embodiments, measuring the level of activatable anti-Jagged antibody in the subject or sample is accomplished using a secondary reagent that specifically binds to the activated antibody, wherein the reagent comprises a detectable label. In some embodiments, the secondary reagent is an antibody comprising a detectable label.

The invention also provides kits for use in methods of detecting presence or absence of a cleaving agent and a Jagged target of interest in a subject or a sample, where the kits include at least an activatable anti-Jagged antibody and/or conjugated activatable anti-Jagged antibody described herein for use in contacting a subject or biological sample and means for detecting the level of activated activatable anti-Jagged antibody and/or conjugated activatable anti-Jagged antibody in the subject or biological sample, wherein a detectable level of activated activatable anti-Jagged antibody in the subject or biological sample indicates that the cleaving agent, the Jagged target or both the cleaving agent and the Jagged target are absent and/or not sufficiently present in the subject or biological sample, such that Jagged target binding and/or protease cleavage of the activatable anti-Jagged antibody cannot be detected in the subject or biological sample, and wherein a reduced detectable level of activated activatable anti-Jagged antibody in the subject or biological sample indicates that the cleaving agent and the Jagged target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

The invention also provides methods of detecting presence or absence of a cleaving agent in a subject or a sample by (i) contacting a subject or biological sample with an activatable anti-Jagged antibody, wherein the activatable anti-Jagged antibody includes a detectable label that is positioned on a portion of the activatable anti-Jagged antibody that is released following cleavage of the CM; and (ii) measuring a level of detectable label in the subject or biological sample, wherein a detectable level of the detectable label in the subject or biological sample indicates that the cleaving agent is absent and/or not sufficiently present in the subject or biological sample at a detectable level, such that protease cleavage of the activatable anti-Jagged antibody cannot be detected in the subject or biological sample, and wherein a reduced detectable level of the detectable label in the subject or biological sample indicates that the cleaving agent is present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. Such an activatable anti-Jagged antibody includes a masking moiety (MM), a cleavable moiety (CM) that is cleaved by the cleaving agent, and an antigen binding domain or fragment thereof (AB) that specifically binds the Jagged target, wherein the activatable anti-Jagged antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the Jagged target, and wherein the MM does not have an amino acid sequence of a naturally occurring binding partner of the AB; and (b) wherein the MM of the activatable anti-Jagged antibody in an uncleaved state interferes with specific binding of the AB to the Jagged target, and wherein the MM of an activatable anti-Jagged antibody in a cleaved (i.e., activated) state does not interfere or compete with specific binding of the AB to the Jagged target. In some embodiments, the activatable anti-Jagged antibody is an activatable anti-Jagged antibody to which a therapeutic agent is conjugated. In some embodiments, the activatable anti-Jagged antibody is not conjugated to an agent. In some embodiments, the activatable anti-Jagged antibody comprises a detectable label. In some embodiments, the detectable label is positioned on the AB. In some embodiments, measuring the level of activatable anti-Jagged antibody in the subject or sample is accomplished using a secondary reagent that specifically binds to the activated antibody, wherein the reagent comprises a detectable label. In some embodiments, the secondary reagent is an antibody comprising a detectable label.

The invention also provides kits for use in methods of detecting presence or absence of a cleaving agent of interest in a subject or a sample, where the kits include at least an activatable anti-Jagged antibody and/or conjugated activatable anti-Jagged antibody described herein for use in contacting a subject or biological sample and means for detecting the level of activated activatable anti-Jagged antibody and/or conjugated activatable anti-Jagged antibody in the subject or biological sample, wherein the activatable anti-Jagged antibody includes a detectable label that is positioned on a portion of the activatable anti-Jagged antibody that is released following cleavage of the CM, wherein a detectable level of the detectable label in the subject or biological sample indicates that the cleaving agent, the Jagged target, or both the cleaving agent and the Jagged target are absent and/or not sufficiently present in the subject or biological sample, such that Jagged target binding and/or protease cleavage of the activatable anti-Jagged antibody cannot be detected in the subject or biological sample, and wherein a reduced detectable level of the detectable label in the subject or biological sample indicates that the cleaving agent and the Jagged target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

In some embodiments of these methods and kits, the activatable anti-Jagged antibody includes a detectable label. In some embodiments of these methods and kits, the detectable label includes an imaging agent, a contrasting agent, an enzyme, a fluorescent label, a chromophore, a dye, one or more metal ions, or a ligand-based label. In some embodiments of these methods and kits, the imaging agent comprises a radioisotope. In some embodiments of these methods and kits, the radioisotope is indium or technetium. In some embodiments of these methods and kits, the contrasting agent comprises iodine, gadolinium or iron oxide. In some embodiments of these methods and kits, the enzyme comprises horseradish peroxidase, alkaline phosphatase, or β-galactosidase. In some embodiments of these methods and kits, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods and kits, the luminescent label comprises an N-methylacrydium derivative. In some embodiments of these methods, the label comprises an Alexa Fluor® label, such as Alex Fluor® 680 or Alexa Fluor® 750. In some embodiments of these methods and kits, the ligand-based label comprises biotin, avidin, streptavidin or one or more haptens.

In some embodiments of these methods and kits, the subject is a mammal. In some embodiments of these methods and kits, the subject is a human. In some embodiments, the subject is a non-human mammal, such as a non-human primate, companion animal (e.g., cat, dog, horse), farm animal, work animal, or zoo animal. In some embodiments, the subject is a rodent.

In some embodiments of these methods, the method is an in vivo method. In some embodiments of these methods, the method is an in situ method. In some embodiments of these methods, the method is an ex vivo method. In some embodiments of these methods, the method is an in vitro method.

In some embodiments, in situ imaging and/or in vivo imaging are useful in methods to identify which patients to treat. For example, in in situ imaging, the activatable anti-Jagged antibodies are used to screen patient samples to identify those patients having the appropriate protease(s) and target(s) at the appropriate location, e.g., at a tumor site.

In some embodiments in situ imaging is used to identify or otherwise refine a patient population suitable for treatment with an activatable anti-Jagged antibody of the disclosure. For example, patients that test positive for both the target (e.g., Jagged 1 and/or Jagged 2) and a protease that cleaves the substrate in the cleavable moiety (CM) of the activatable anti-Jagged antibody being tested (e.g., accumulate activated antibodies at the disease site) are identified as suitable candidates for treatment with such an activatable anti-Jagged antibody comprising such a CM. Likewise, patients that test negative for either or both of the target (e.g., Jagged 1 and/or Jagged 2) and the protease that cleaves the substrate in the CM in the activatable antibody being tested using these methods might be identified as suitable candidates for another form of therapy. In some embodiments, such patients that test negative with respect to a first activatable anti-Jagged antibody can be tested with other activatable anti-Jagged antibodies comprising different CMs until a suitable activatable anti-Jagged antibody for treatment is identified (e.g., an activatable anti-Jagged antibody comprising a CM that is cleaved by the patient at the site of disease).

In some embodiments in vivo imaging is used to identify or otherwise refine a patient population suitable for treatment with an activatable anti-Jagged antibody of the disclosure. For example, patients that test positive for both the target (e.g., Jagged 1 and/or Jagged 2) and a protease that cleaves the substrate in the cleavable moiety (CM) of the activatable anti-Jagged antibody being tested (e.g., accumulate activated antibodies at the disease site) are identified as suitable candidates for treatment with such an activatable anti-Jagged antibody comprising such a CM. Likewise, patients that test negative might be identified as suitable candidates for another form of therapy. In some embodiments, such patients that test negative with respect to a first activatable anti-Jagged antibody can be tested with other activatable anti-Jagged antibodies comprising different CMs until a suitable activatable anti-Jagged antibody for treatment is identified (e.g., an activatable anti-Jagged antibody comprising a CM that is cleaved by the patient at the site of disease).

In some embodiments of the methods and kits, the method or kit is used to identify or otherwise refine a patient population suitable for treatment with an activatable anti-Jagged antibody of the disclosure. For example, patients that test positive for both the target (e.g., Jagged 1 and/or Jagged 2) and a protease that cleaves the substrate in the cleavable moiety (CM) of the activatable anti-Jagged antibody being tested in these methods are identified as suitable candidates for treatment with such an activatable anti-Jagged antibody comprising such a CM. Likewise, patients that test negative for both of the targets (e.g., Jagged 1 and Jagged 2) and the protease that cleaves the substrate in the CM in the activatable antibody being tested using these methods might be identified as suitable candidates for another form of therapy. In some embodiments, such patients can be tested with other activatable anti-Jagged antibodies until a suitable activatable anti-Jagged antibody for treatment is identified (e.g., an activatable anti-Jagged antibody comprising a CM that is cleaved by the patient at the site of disease). In some embodiments, patients that test negative for either of the targets (e.g., Jagged 1 or Jagged 2) are identified as suitable candidates for treatment with such an activatable anti-Jagged antibody comprising such a CM. In some embodiments, patients that test negative for either of the targets (e.g., Jagged 1 or Jagged 2) are identified as not being suitable candidates for treatment with such an activatable anti-Jagged antibody comprising such a CM. In some embodiments, such patients can be tested with other activatable anti-Jagged antibodies until a suitable activatable anti-Jagged antibody for treatment is identified (e.g., an activatable anti-Jagged antibody comprising a CM that is cleaved by the patient at the site of disease). In some embodiments, the activatable anti-Jagged antibody is an activatable anti-Jagged antibody to which a therapeutic agent is conjugated. In some embodiments, the activatable anti-Jagged antibody is not conjugated to an agent. In some embodiments, the activatable anti-Jagged antibody comprises a detectable label. In some embodiments, the detectable label is positioned on the AB. In some embodiments, measuring the level of activatable anti-Jagged antibody in the subject or sample is accomplished using a secondary reagent that specifically binds to the activated antibody, wherein the reagent comprises a detectable label. In some embodiments, the secondary reagent is an antibody comprising a detectable label.

In some embodiments, a method or kit is used to identify or otherwise refine a patient population suitable for treatment with an anti-Jagged activatable antibody and/or conjugated activatable anti-Jagged antibody (e.g., activatable antibody to which a therapeutic agent is conjugated) of the disclosure, followed by treatment by administering that activatable anti-Jagged antibody and/or conjugated activatable anti-Jagged antibody to a subject in need thereof. For example, patients that test positive for both the targets (e.g., Jagged 1 and Jagged 2) and a protease that cleaves the substrate in the cleavable moiety (CM) of the activatable anti-Jagged antibody and/or conjugated activatable anti-Jagged antibody being tested in these methods are identified as suitable candidates for treatment with such antibody and/or such a conjugated activatable anti-Jagged antibody comprising such a CM, and the patient is then administered a therapeutically effective amount of the activatable anti-Jagged antibody and/or conjugated activatable anti-Jagged antibody that was tested. Likewise, patients that test negative for either or both of the target (e.g., Jagged 1 and/or Jagged 2) and the protease that cleaves the substrate in the CM in the activatable anti-Jagged antibody being tested using these methods might be identified as suitable candidates for another form of therapy. In some embodiments, such patients can be tested with other antibody and/or conjugated activatable anti-Jagged antibody until a suitable antibody and/or conjugated activatable anti-Jagged antibody for treatment is identified (e.g., an activatable anti-Jagged antibody and/or conjugated activatable anti-Jagged antibody comprising a CM that is cleaved by the patient at the site of disease). In some embodiments, the patient is then administered a therapeutically effective amount of the activatable anti-Jagged antibody and/or conjugated for which the patient tested positive.

In some embodiments of these methods and kits, the MM is a peptide having a length from about 4 to 40 amino acids. In some embodiments of these methods and kits, the activatable anti-Jagged antibody comprises a linker peptide, wherein the linker peptide is positioned between the MM and the CM. In some embodiments of these methods and kits, the activatable anti-Jagged antibody comprises a linker peptide, where the linker peptide is positioned between the AB and the CM. In some embodiments of these methods and kits, the activatable anti-Jagged antibody comprises a first linker peptide (L1) and a second linker peptide (L2), wherein the first linker peptide is positioned between the MM and the CM and the second linker peptide is positioned between the AB and the CM. In some embodiments of these methods and kits, each of L1 and L2 is a peptide of about 1 to 20 amino acids in length, and wherein each of L1 and L2 need not be the same linker. In some embodiments of these methods and kits, one or both of L1 and L2 comprises a glycine-serine polymer. In some embodiments of these methods and kits, at least one of L1 and L2 comprises an amino acid sequence selected from the group consisting of (GS)n, (GSGGS)n (SEQ ID NO: 123) and (GGGS)n (SEQ ID NO: 124), where n is an integer of at least one. In some embodiments of these methods and kits, at least one of L1 and L2 comprises an amino acid sequence having the formula (GGS)n, where n is an integer of at least one. In some embodiments of these methods and kits, at least one of L1 and L2 comprises an amino acid sequence selected from the group consisting of Gly-Gly-Ser-Gly (SEQ ID NO: 125), Gly-Gly-Ser-Gly-Gly (SEQ ID NO: 126), Gly-Ser-Gly-Ser-Gly (SEQ ID NO: 127), Gly-Ser-Gly-Gly-Gly (SEQ ID NO: 128), Gly-Gly-Gly-Ser-Gly (SEQ ID NO: 129), and Gly-Ser-Ser-Ser-Gly (SEQ ID NO: 130).

In some embodiments of these methods and kits, the AB comprises an antibody or antibody fragment sequence selected from the cross-reactive anti-Jagged antibody sequences presented herein. In some embodiments of these methods and kits, the AB comprises a Fab fragment, a scFv or a single chain antibody (scAb).

In some embodiments of these methods and kits, the cleaving agent is a protease that is co-localized in the subject or sample with the Jagged target and the CM is a polypeptide that functions as a substrate for the protease, wherein the protease cleaves the CM in the activatable anti-Jagged antibody when the activatable anti-Jagged antibody is exposed to the protease. In some embodiments of these methods and kits, the CM is a polypeptide of up to 15 amino acids in length. In some embodiments of these methods and kits, the CM is coupled to the N-terminus of the AB. In some embodiments of these methods and kits, the CM is coupled to the C-terminus of the AB. In some embodiments of these methods and kits, the CM is coupled to the N-terminus of a VL chain of the AB.

In some embodiments of these methods and kits, the cleaving agent is an enzyme and the CM is a substrate for the enzyme. In some embodiments of these methods and kits, the enzyme is a protease disclosed herein. In some embodiments of these methods and kits, the protease is one of the proteases disclosed herein. In some embodiments of these methods and kits, the protease is selected from the group consisting of uPA, legumain, MT-SP1, ADAM17, BMP-1, TMPRSS3, TMPRSS4, MMP-9, MMP-12, MMP-13, and MMP-14. In some embodiments, the protease is a cathepsin.

Therapeutic Administration and Formulations of Anti-Jagged Antibodies

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2): 210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

In some embodiments, the anti-Jagged antibodies, the activatable anti-Jagged antibodies and the anti-Jagged antibody compositions used to treat a cancer or fibrotic disorder are administered in conjunction with one or more additional agents, or a combination of additional agents. Suitable additional agents include current pharmaceutical and/or surgical therapies for an intended application. For example, the anti-Jagged antibodies and/or activatable anti-Jagged antibodies can be used in conjunction with an additional chemotherapeutic or anti-neoplastic agent. For example, the anti-Jagged antibody and/or activatable anti-Jagged antibody and additional agent are formulated into a single therapeutic composition, and the anti-Jagged antibody and/or activatable anti-Jagged antibody and additional agent are administered simultaneously. Alternatively, the anti-Jagged antibody and/or activatable anti-Jagged antibody and additional agent are separate from each other, e.g., each is formulated into a separate therapeutic composition, and the anti-Jagged antibody and/or activatable anti-Jagged antibody and the additional agent are administered simultaneously, or the anti-Jagged antibody and/or activatable anti-Jagged antibody and the additional agent are administered at different times during a treatment regimen. For example, the anti-Jagged antibody and/or activatable anti-Jagged antibody is administered prior to the administration of the additional agent, the anti-Jagged antibody and/or activatable anti-Jagged antibody is administered subsequent to the administration of the additional agent, or the anti-Jagged antibody and/or activatable anti-Jagged antibody and the additional agent are administered in an alternating fashion. As described herein, the anti-Jagged antibody and/or activatable anti-Jagged antibody and additional agent are administered in single doses or in multiple doses.

In some embodiments, the additional agent is coupled or otherwise attached to the anti-Jagged antibody and/or activatable anti-Jagged antibody.

Suitable additional agents are selected according to the purpose of the intended application (i.e., killing, prevention of cell proliferation, hormone therapy or gene therapy). Such agents may include but is not limited to, for example, pharmaceutical agents, toxins, fragments of toxins, alkylating agents, enzymes, antibiotics, antimetabolites, antiproliferative agents, hormones, neurotransmitters, DNA, RNA, siRNA, oligonucleotides, antisense RNA, aptamers, diagnostics, radioopaque dyes, radioactive isotopes, fluorogenic compounds, magnetic labels, nanoparticles, marker compounds, lectins, compounds that alter cell membrane permeability, photochemical compounds, small molecules, liposomes, micelles, gene therapy vectors, viral vectors, and the like. Finally, combinations of agents or combinations of different classes of agents may be used.

The antibodies and/or activatable antibodies of the invention (also referred to herein as "active compounds"), and derivatives, fragments, analogs and homologs thereof, can be incorporated into pharmaceutical compositions suitable for administration. Principles and considerations involved in preparing such compositions, as well as guidance in the choice of components are provided, for example, in Remington's Pharmaceutical Sciences: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Such compositions typically comprise the antibody and a pharmaceutically acceptable carrier. Where activatable antibody includes a fragment of the AB domain, the smallest fragment of the AB that specifically binds to the binding domain of the target protein can be used. For example, based upon the variable-region sequences of an antibody, peptide molecules can be designed that retain the ability of the AB to bind the target protein sequence. Such peptides can be synthesized chemically and/or produced by recombinant DNA technology. (See, e.g., Marasco et al., Proc. Natl. Acad. Sci. USA, 90: 7889-7893 (1993)).

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Suitable examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated.

The formulations to be used for in vivo administration must be sterile. This is readily accomplished by filtration through sterile filtration membranes.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be suitable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as sustained/controlled release formulations, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

For example, the active ingredients can be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods.

The materials can also be obtained commercially from Alza Corporation and Nova Pharmaceuticals, Inc. Liposomal suspensions (including liposomes targeted to infected cells with monoclonal antibodies to viral antigens) and can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The formulation can also contain more than one active compound as necessary for the particular indication being treated, for example, those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

In one embodiment, the active compounds are administered in combination therapy, i.e., combined with other agents, e.g., therapeutic agents, that are useful for treating pathological conditions or disorders, such as autoimmune disorders and inflammatory diseases. The term "in combination" in this context means that the agents are given substantially contemporaneously, either simultaneously or sequentially. If given sequentially, at the onset of administration of the second compound, the first of the two compounds is still detectable at effective concentrations at the site of treatment.

For example, the combination therapy can include one or more antibodies of the invention coformulated with, and/or coadministered with, one or more additional therapeutic agents, e.g., one or more cytokine and growth factor inhibitors, immunosuppressants, anti-inflammatory agents, metabolic inhibitors, enzyme inhibitors, and/or cytotoxic or cytostatic agents, as described in more detail below. Furthermore, one or more antibodies described herein may be used in combination with two or more of the therapeutic agents described herein. Such combination therapies may advantageously utilize lower dosages of the administered therapeutic agents, thus avoiding possible toxicities or complications associated with the various monotherapies.

In other embodiments, one or more antibodies of the invention can be coformulated with, and/or coadministered with, one or more anti-inflammatory drugs, immunosuppressants, or metabolic or enzymatic inhibitors. Nonlimiting examples of the drugs or inhibitors that can be used in combination with the antibodies described herein, include, but are not limited to, one or more of: nonsteroidal anti-inflammatory drug(s) (NSAIDs), e.g., ibuprofen, tenidap, naproxen, meloxicam, piroxicam, diclofenac, and indomethacin; sulfasalazine; corticosteroids such. as prednisolone; cytokine suppressive anti-inflammatory drug(s) (CSAIDs); inhibitors of nucleotide biosynthesis, e.g., inhibitors of purine biosynthesis, folate antagonists (e.g., methotrexate (N-[4-[[(2,4-diamino-6-pte-ridinyl)methyl]methylamino]benzoyl]-L-glutamic acid); and inhibitors of pyrimidine biosynthesis, e.g., dihydroorotate dehydrogenase (DHODH) inhibitors. Suitable therapeutic agents for use in combination with the antibodies of the invention include NSAIDs, CSAIDs, (DHODH) inhibitors (e.g., leflunomide), and folate antagonists (e.g., methotrexate).

Examples of additional inhibitors include one or more of: corticosteroids (oral, inhaled and local injection); immunosuppresants, e.g., cyclosporin, tacrolimus (FK-506); and mTOR inhibitors, e.g., sirolimus (rapamycin—RAPAMUNE™ or rapamycin derivatives, e.g., soluble rapamycin derivatives (e.g., ester rapamycin derivatives, e.g., CCI-779); agents that interfere with signaling by proinflammatory cytokines such as TNFα or IL-1 (e.g. IRAK, NIK, IKK, p38 or MAP kinase inhibitors); COX2 inhibitors, e.g., celecoxib, rofecoxib, and variants thereof; phosphodiesterase inhibitors, e.g., R973401 (phosphodiesterase Type IV inhibitor); phospholipase inhibitors, e.g., inhibitors of cytosolic phospholipase 2 (cPLA2) (e.g., trifluoromethyl ketone analogs); inhibitors of vascular endothelial cell growth factor or growth factor receptor, e.g., VEGF inhibitor and/or VEGF-R inhibitor; and inhibitors of angiogenesis. Suitable therapeutic agents for use in combination with the antibodies of the invention are immunosuppresants, e.g., cyclosporin, tacrolimus (FK-506); mTOR inhibitors, e.g., sirolimus (rapamycin) or rapamycin derivatives, e.g., soluble rapamycin derivatives (e.g., ester rapamycin derivatives, e.g., CCI-779); COX2 inhibitors, e.g., celecoxib and variants thereof; and phospholipase inhibitors, e.g., inhibitors of cytosolic phospholipase 2 (cPLA2), e.g., trifluoromethyl ketone analogs.

Additional examples of therapeutic agents that can be combined with an antibody of the invention include one or more of: 6-mercaptopurines (6-MP); azathioprine sulphasalazine; mesalazine; olsalazine; chloroquine/hydroxychloroquine (PLAQUENIL®); pencillamine; aurothiornalate (intramuscular and oral); azathioprine; coichicine; beta-2 adrenoreceptor agonists (salbutamol, terbutaline, salmeteral); xanthines (theophylline, aminophylline); cromoglycate; nedocromil; ketotifen; ipratropium and oxitropium; mycophenolate mofetil; adenosine agonists; antithrombotic agents; complement inhibitors; and adrenergic agents.

Design and Generation of Other Therapeutics

In accordance with the present invention and based on the activity of the antibodies that are produced and characterized herein with respect to Jagged 1 and/or Jagged 2, the design of other therapeutic modalities beyond antibody moieties is facilitated. Such modalities include, without limitation, advanced antibody therapeutics, such as bispecific antibodies, immunotoxins, and radiolabeled therapeutics, generation of peptide therapeutics, gene therapies, particularly intrabodies, antisense therapeutics, and small molecules.

For example, in connection with bispecific antibodies, bispecific antibodies can be generated that comprise (i) two antibodies one with a specificity to Jagged 1 and Jagged 2 and another to a second molecule that are conjugated together, (ii) a single antibody that has one chain specific to Jagged 1 and Jagged 2, and a second chain specific to a second molecule, or (iii) a single chain antibody that has specificity to Jagged 1 and Jagged 2 and a second molecule. Such bispecific antibodies are generated using techniques that are well known for example, in connection with (i) and (ii) See e.g., Fanger et al. Immunol Methods 4:72-81 (1994) and Wright et al. Crit, Reviews in Immunol. 12125-168 (1992), and in connection with (iii) See e.g., Traunecker et al. Int. J. Cancer (Suppl.) 7:51-52 (1992).

In connection with immunotoxins, antibodies can be modified to act as immunotoxins utilizing techniques that are well known in the art. See e.g., Vitetta Immunol Today 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in Cancer Chemotherapy and Biotherapy 655-686 (2d edition, Chafner and Longo, eds., Lippincott Raven (1996)). See also U.S. Pat. Nos. 4,681,581, 4,735,210, 5,101,827, 5,102,990 (RE 35,500), 5,648,471, and 5,697,902. Each of immunotoxins and radiolabeled molecules would be likely to kill cells expressing Jagged 1, Jagged 2 and/or both Jagged 1 and Jagged 2.

In connection with the generation of therapeutic peptides, through the utilization of structural information related to Jagged 1, Jagged 2 and/or both Jagged 1 and Jagged 2 and antibodies thereto, such as the antibodies of the invention or screening of peptide libraries, therapeutic peptides can be generated that are directed against Jagged 1, Jagged 2 and/or both Jagged 1 and Jagged 2. Design and screening of peptide therapeutics is discussed in connection with Houghten et al. Biotechniques 13:412-421 (1992), Houghten PNAS USA 82:5131-5135 (1985), Pinalla et al. Biotechniques 13:901-905 (1992), Blake and Litzi-Davis BioConjugate Chem. 3:510-513 (1992). Immunotoxins and radiolabeled molecules can also be prepared, and in a similar manner, in connection with peptidic moieties as discussed above in connection with antibodies. Assuming that the Jagged 1 molecule, the Jagged 2 molecule and/or both the Jagged 1 molecule and the Jagged 2 molecule (or a form, such as a splice variant or alternate form) is functionally active in a disease process, it will also be possible to design gene and antisense therapeutics thereto through conventional techniques. Such modalities can be utilized for modulating the function of Jagged 1, Jagged 2 and/or both Jagged 1 and Jagged 2. In connection therewith the antibodies of the present invention facilitate design and use of functional assays related thereto. A design and strategy for antisense therapeutics is discussed in detail in International Patent Application No. WO 94/29444. Design and strategies for gene therapy are well known. However, in particular, the use of gene therapeutic techniques involving intrabodies could prove to be particularly advantageous. See e.g., Chen et al. Human Gene Therapy 5:595-601 (1994) and Marasco Gene Therapy 4:11-15 (1997). General design of and considerations related to gene therapeutics is also discussed in International Patent Application No. WO 97/38137.

Knowledge gleaned from the structure of the Jagged 1 molecule, the Jagged 2 molecule and/or both the Jagged 1 molecule and the Jagged 2 molecule and its interactions with other molecules in accordance with the present invention, such as the antibodies of the invention, and others can be utilized to rationally design additional therapeutic modalities. In this regard, rational drug design techniques such as X-ray crystallography, computer-aided (or assisted) molecular modeling (CAMM), quantitative or qualitative structure-activity relationship (QSAR), and similar technologies can be utilized to focus drug discovery efforts. Rational design allows prediction of protein or synthetic structures that can interact with the molecule or specific forms thereof that can be used to modify or modulate the activity of Jagged 1, Jagged 2 and/or both Jagged 1 and Jagged 2. Such structures can be synthesized chemically or expressed in biological systems. This approach has been reviewed in Capsey et al. Genetically Engineered Human Therapeutic Drugs (Stockton Press, N.Y. (1988)). Further, combinatorial libraries can be designed and synthesized and used in screening programs, such as high throughput screening efforts.

Screening Methods

The invention provides methods (also referred to herein as "screening assays") for identifying modulators, i.e., candidate or test compounds or agents (e.g., peptides, peptidomimetics, small molecules or other drugs) that modulate, block, inhibit, reduce, antagonize, neutralize or otherwise interfere with binding of Jagged 1, Jagged 2 and/or both Jagged 1 and Jagged 2 to their innate receptor, or candidate or test compounds or agents that modulate, block, inhibit, reduce, antagonize, neutralize or otherwise interfere with the signaling function of Jagged 1, Jagged 2 and/or both Jagged 1 and Jagged 2. Also provided are methods of identifying compounds useful to treat disorders associated with Jagged 1, Jagged 2 and/or both Jagged 1 and Jagged 2 signaling. The invention also includes compounds identified in the screening assays described herein.

In one embodiment, the invention provides assays for screening candidate or test compounds that modulate the signaling function of Jagged 1, Jagged 2 and/or both Jagged 1 and Jagged 2. The test compounds of the invention are obtained using any of the numerous approaches in combinatorial library methods known in the art, including biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other approaches are applicable to peptide, non-peptide oligomer or small molecule libraries of compounds. (See, e.g., Lam, 1997. Anticancer Drug Design 12: 145).

A "small molecule" as used herein, is meant to refer to a composition that has a molecular weight of less than about 5 kD and in some embodiments less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37: 1233.

Libraries of compounds may be presented in solution (see e.g., Houghten, 1992. Biotechniques 13: 412-421), or on beads (see Lam, 1991. Nature 354: 82-84), on chips (see Fodor, 1993. Nature 364: 555-556), bacteria (see U.S. Pat. No. 5,223,409), spores (see U.S. Pat. No. 5,233,409), plasmids (see Cull, et al., 1992. Proc. Natl. Acad. Sci. USA 89: 1865-1869) or on phage (see Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; and U.S. Pat. No. 5,233, 409).

In one embodiment, a candidate compound is introduced to an antibody-antigen complex and determining whether the candidate compound disrupts the antibody-antigen complex, wherein a disruption of this complex indicates that the candidate compound modulates the signaling function of Jagged 1, Jagged 2 and/or both Jagged 1 and Jagged 2.

In another embodiment, both Jagged 1 and Jagged are provided and exposed to at least one monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat disorders associated with Jagged 1, Jagged 2 and/or both Jagged 1 and Jagged 2 signaling.

In another embodiment, a soluble protein of the invention is provided and exposed to at least one neutralizing monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat disorders associated with Jagged 1, Jagged 2 and/or both Jagged 1 and Jagged 2 signaling.

Determining the ability of the test compound to interfere with or disrupt the antibody-antigen complex can be accomplished, for example, by coupling the test compound with a radioisotope or enzymatic label such that binding of the test compound to the antigen or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product.

In one embodiment, the assay comprises contacting an antibody-antigen complex with a test compound, and determining the ability of the test compound to interact with the antigen or otherwise disrupt the existing antibody-antigen complex. In this embodiment, determining the ability of the test compound to interact with the antigen and/or disrupt the antibody-antigen complex comprises determining the ability of the test compound to preferentially bind to the antigen or a biologically-active portion thereof, as compared to the antibody.

In another embodiment, the assay comprises contacting an antibody-antigen complex with a test compound and determining the ability of the test compound to modulate the antibody-antigen complex. Determining the ability of the test compound to modulate the antibody-antigen complex can be accomplished, for example, by determining the ability of the antigen to bind to or interact with the antibody, in the presence of the test compound.

The screening methods disclosed herein may be performed as a cell-based assay or as a cell-free assay. The cell-free assays of the invention are amenable to use soluble Jagged 1, Jagged 2 and/or both Jagged 1 and Jagged 2, and fragments thereof.

In more than one embodiment, it may be desirable to immobilize either the antibody or the antigen to facilitate separation of complexed from uncomplexed forms of one or both following introduction of the candidate compound, as well as to accommodate automation of the assay. Observation of the antibody-antigen complex in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-antibody fusion proteins or GST-antigen fusion proteins can be adsorbed onto glutathione sepharose beads (Sigma Chemical, St. Louis, Mo.) or glutathione derivatized microtiter plates, that are then combined with the test compound, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of antibody-antigen complex formation can be determined using standard techniques.

Other techniques for immobilizing proteins on matrices can also be used in the screening assays of the invention. For example, either the antibody or the antigen (e.g. Jagged 1, Jagged 2 and/or both Jagged 1 and Jagged 2) can be immobilized utilizing conjugation of biotin and streptavidin. Biotinylated antibody or antigen molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, other antibodies reactive with the antibody or antigen of interest, but that do not interfere with the formation of the antibody-antigen complex of interest, can be derivatized to the wells of the plate, and unbound antibody or antigen trapped in the wells by antibody conjugation. Methods for detecting such complexes, in addition to those described above for the GST-immobilized complexes, include immunodetection of complexes using such other antibodies reactive with the antibody or antigen.

The invention further pertains to novel agents identified by any of the aforementioned screening assays and uses thereof for treatments as described herein.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1

Selection of Human ScFvs of the Embodiments that Bind Human Jagged 1

This Example demonstrates that ScFvs (single-chain variable fragments) of the embodiments that bind Jagged 1 can be selected from a phage display library of ScFvs with diverse CDR sequences, and that such binding can be inhibited by Notch 1.

ScFvs were selected from a fully human ScFv library displayed on M13 bacteriophage; ScFv phage selection was conducted under contract with Creative Biolabs, Shirley, N.Y.). A fusion protein comprised of the extracellular domain (ECD) of human Jagged 1 fused to the Fc portion of human IgG1 (R&D Systems, Minneapolis, Minn., Cat#1277-JG-050) was used as the antigen in three rounds of selection for ScFvs displayed on M13 bacteriophage that bind human Jagged 1. All selections were done in the presence of $CA_2^{++}$, required for the native conformation of Jagged 1, and human IgG1 to prevent human Fc binding. In the first round, bound phage were released by trypsin digestion, and in subsequent rounds, phage were eluted by human Notch 1-Fc fusion protein (R&D Systems; Cat #3637-TK-050) competition. Five (5) unique ScFvs that bind human Jagged1 were isolated. Table 1 lists the 5 ScFvs and SEQ ID NOs of their respective nucleic acid sequences and amino acid sequences.

TABLE 1

| SEQ ID NOs of selected ScFvs | | |
|---|---|---|
| ScFv | Nucleic acid sequence | Amino acid sequence |
| Jagged 2 | SEQ ID NO: 1 | SEQ ID NO: 2 |
| Jagged 7 | SEQ ID NO: 3 | SEQ ID NO: 4 |
| Jagged 13 | SEQ ID NO: 5 | SEQ ID NO: 6 |
| Jagged 42 | SEQ ID NO: 7 | SEQ ID NO: 8 |
| Jagged 32 | SEQ ID NO: 9 | SEQ ID NO: 10 |

The nucleic acid and amino acid sequences of each of the anti-Jagged ScFvs are shown below:

SEQ ID NO: 1

```
gaggtgcagctgttggagtctgggggaggcttggtacagcctggggggtccctgagactctcctgtgcagcctctggattcacctttagcag ctatgccatgagctgggtccgccaggctccagggagggctggagtgggtctcagcgattgcggagctgggtgcgcttacatagtacgcag actccgtgaagggccggttcaccatctccagagacaattccaagaacacgctgtatctgcaaatgaacagctagagccgaggacacggcc gtatattactgtgcgagagctcatactagttttgactactggggccagggaaccctggtcaccgtctcgagcggtggaggcggttcaggcgg aggtggcagcggcggggggtcgacggacatccagatgacccagtctccatcctccctgtctgcatctgtaggagacagagtcaccatca cttgccgggcaagtcagagcattagcagctatttaaattggtatcagcagaaccgggaaagcccctaagctcctgatctataaggcatccact ttgcaaagtggggtcccatcaaggttcagtggcagtggatctgggacagatttcactctcaccatcagcagtctgcaacctgaaatttgcaac ttactactgtcaacaggctatggatcagcctcctacgttcggccaagggaccaaggtggaaatcaaacgg-3'
```

SEQ ID NO: 2

EVQLLESGGGLVQPGGSLRLSCAASGFTFSSYAMSWVRQAPGKGLEWVSAIAELGALT
QYADSVKGRFTISRDNSKNTLYLQMNSLRAEDTAVYYCARAHTSFDYWGQGTLVTVSS
GGGGSGGGGSGGGGSTDIQMTQSPSSLSASVGDRVTITCRASQSISSYLNWYQQKPGKA
PKLLIYKASTLSGVPSRFSGSGSGTDFTLTISSLQPEDFATYYCQQAMDQPPTFGQGTKVE
IKR

SEQ ID NO: 3 gaggtgcagctgttggagtctggggggaggcttggtacagcctggggggtccctgagactctcctgtgcagcctctggattcacctttagcag
ctatgccatgagctgggtccgccaggctccagggagggctggagtgggtctcaacgattgctgcttagggtaagcatacagattacgcaga
ctccgtgaagggccggttcaccatctccagagacaattccaagaacacgctgtatctgcaaatgaacagctagagccgaggacacggccg
tatattactgtgcgaaatcgatgcgtggttttgacaactggggccagggaaccctggtcaccgtctcgagcggtggaggcggttcaggcgg
aggtggcagcggcggggggtcgacggacatccagatgacccagtctccatcctccctgtctgcatctgtaggagacagagtcaccatca
cttgccgggcaagtcagagcattagcagctatttaaattggtatcagcagaaccgggaaagcccctaagctcctgatctatcggcatcctct
ttgcaaagtggggtcccatcaaggttcagtggcagtggatctgggacagatttcactctcaccatcagcagtctgcaacctgaaatttgcaac
ttactactgtcaacaggatgcgactggtcctgcgacgttcggccaagggaccaaggtggaaatcaaacgg-3'

SEQ ID NO: 4

EVQLLESGGGLVQPGGSLRLSCAASGFTFSSYAMSWVRQAPGKGLEWVSTIAA*GKHT
DYADSVKGRFTISRDNSKNTLYLQMNSLRAEDTAVYYCAKSMRGFDNWGQGTLVTVS
SGGGGSGGGGSGGGGSTDIQMTQSPSSLSASVGDRVTITCRASQSISSYLNWYQQKPGK
APKLLIYASSLQSGVPSRFSGSGSGTDFTLTISSLQPEDFATYYCQQDATGPATFGQGTKV
EIKR

SEQ ID NO: 5 gaggtgcagctgttggagtctggggggaggcttggtacagcctggggggtccctgagactctcctgtgcagcctctggattcacctttagcag
ctatgccatgagctgggtccgccaggctccagggagggctggagtgggtctcatcgattgagacttagggtccgactacactgtacgcaga
ctccgtgaagggccaggttcaccatctccagagacaattccaagaacacgctgtatctgcaaatgaacagctagagccgaggacacggccg
tatattactgtgcgaaaacgtctagtgcgttttgactactggggccagggaaccctggtcaccgtctcgagcggtggaggcggttcaggcgg
aggtggcagcggcggggggtcgacggacatccagatgacccagtctccatcctccctgtctgcatctgtaggagacagagtcaccatca
cttgccgggcaagtcagagcattagcagctatttaaattggtatcagcagaaccgggaaagcccctaagctcctgatctatcatgcatcctcg
ttgcaaagtggggtcccatcaaggttcagtggcagtggatctgggacagatttcactctcaccatcggcagtctgcaacctgaaatttgcaac
ttactactgtcaacagaatgttgctactcctctgacgttcggccaagggaccaaggtggaaatcaaacgg-3'

SEQ ID NO: 6

EVQLLESGGGLVQPGGSLRLSCAASGFTFSSYAMSWVRQAPGKGLEWVSSIETQGPTTL
YADSVKGRFTISRDNSKNTLYLQMNSLRAEDTAVYYCAKTSSAFDYWGQGTLVTVSSG
GGGSGGGGSGGGGSTDIQMTQSPSSLSASVGDRVTITCRASQSISSYLNWYQQKPGKAP
KLLIYASSLQSGVPSRFSGSGSGTDFTLTIGSLQPEDFATYYCQQNVATPLTFGQGTKVEI
KR

SEQ ID NO: 7 gaggtgcagctgttggagtctggggggaggcttggtacagcctggggggtccctgagactctcctgtgcagcctctggattcacctttagcag
ctatgccatgagctgggtccgccaggctccagggagggctggagtgggtctcaacgattgagccgtagggttcggctacagagtacgca
gactccgtgaagggccggttcaccatctccagagacaattccaagaacacgctgtatctgcaaatgaacagctagagccgaggacacggc
cgtatattactgtgcgaaaacgcagacgggttttgactactggggccagggaaccctggtcaccgtctcgagcggtggaggcggttcagg
cggaggtggcagcggcggggggtcgacggacatccagatgacccagtctccatcctccctgtctgcatctgtaggagacagagtcacc
atcacttgccgggcaagtcagagcattagcagctatttaaattggtatcagcagaaccgggaaagcccctaagctcctgatctataaggcatc -continued
cactttgcaaagtggggtcccatcaaggttcagtggcagtggatctgggacagatttcactctcaccatcagcagtctgcaacctgaaatttg caacttactactgtcaacaggatgttgagcctcctgctacgttcggccaagggaccaaggtggaaatcaaacgg-3'

SEQ ID NO: 8

EVQLLESGGGLVQPGGSLRLSCAASGFTFSSYAMSWVRQAPGKGLEWVSTIEP*GSATE

YADSVKGRFTISRDNSKNTLYLQMNSLRAEDTAVYYCAKTQTGFDYWGQGTLVTVSS

GGGGSGGGGSGGGGSTDIQMTQSPSSLSASVGDRVTITCRASQSISSYLNWYQQKPGKA

PKLLIYASTLQSGVPSRFSGSGSGTDFTLTISSLQPEDFATYYCQQDVEPPATFGQGTKVE

IKR

SEQ ID NO: 9

Gaggtgcagctgttggagtctgggggaggcttggtacagcctggggggtccctgagactctcctgtgcagcctctggattcacctttagca gctatgccatgagctgggtccgccaggctccagggagggctggagtgggtctcaagtattgagcagatggttggtagacatattacgcag actccgtgaagggccggttcaccatctccagagacaattccaagaacacgctgtatctgcaaatgaacagctagagccgaggacacggcc gtatattactgtgcgaaatcggctgctgcttttgactactggggccagggaaccctggtcaccgtctcgagcggtggaggcggttcaggcg gaggtggcagcggcggggggtcgacggacatccagatgacccagtctccatcctccctgtctgcatctgtaggagacagagtcaccatc acttgccgggcaagtcagagcattagcagctatttaaattggtatcagcagaaccgggaaagcccctaagctcctgatctatgcggcatcca gtttgcaaagtggggtcccatcaaggttcagtggcagtggatctgggacagatttcactctcaccatcagcagtctgcaacctgaaatttgca acttactactgtcaacagacggttgtggcgcctttgacgttcggccaagggaccaaggtggaaatcaaacgg-3'

SEQ ID NO: 10

EVQLLESGGGLVQPGGSLRLSCAASGFTFSSYAMSWVRQAPGKGLEWVSSIEQMGWQT

YYADSVKGRFTISRDNSKNTLYLQMNSLRAEDTAVYYCAKSAAAFDYWGQGTLVTVS

SGGGGSGGGGSGGGGSTDIQMTQSPSSLSASVGDRVTITCRASQSISSYLNWYQQKPGK

APKLLIYAASLQSGVPSRFSGSGSGTDFTLTISSLQPEDFATYYCQQTVVAPLTFGQGTKV

EIKR

ELISA-based binding of Jagged 13 ScFv-phage and Jagged 32 ScFv-phage to human Jagged 1 was shown to be inhibited by human Notch 1. Briefly, human Jagged 1-Fc (R&D Systems; ibid.) was adsorbed to the wells of a 96-well ELISA plate. Phage were applied to the plate in the presence or absence of human notch 1-Fc and allowed to bind. Bound phage were visualized with an anti-M13-HRP conjugate (GE Healthcare, Piscataway, N.Y.) and developed with the chromogenic substrate tetramethyl benzidine (TMB) (Thermo Scientific, Rockford, Ill.).

Example 2

Production and Testing of Fully Human Jagged IgG Antibodies of the Embodiments

This Example demonstrates that Jagged ScFv-phage that bind human Jagged 1 can be converted into fully human IgG antibodies that bind both human Jagged 1 and human Jagged 2, as well as mouse Jagged 1. Human Notch 1 can inhibit such binding.

Production of fully human IgGs comprising the variable domains of Jagged 13 and Jagged 32 was accomplished using techniques similar to those described in PCT Publication No. WO 2010/081173, ibid. DNA encoding the Jagged 13 and 32 variable domains of Jagged 13 ScFv-phage and Jagged 32 ScFv-phage were cloned into expression vectors for the expression of fully human IgGs. Light chain (Lc) variable domains were amplified from the ScFv templates using primer CX1197 (cacttgtcacgaattcggacatccagatgacccagtc) (SEQ ID NO: 83) and primer CX1198 (gtgcagccaccgtacgtttgatttccaccttggtccc) (SEQ ID NO: 84). Vector (LcpOP (modified from pcDNA3, Invitrogen, Carlsbad, Calif.)) and amplified DNA were cut with BsiWI and EcoRI overnight, combined by ligation and transformed into E. coli MC1061 cells. Heavy chain (Hc) variable domains were amplified from ScFv templates using primer CX1199 (ttgcacttgtcacgaattcggaggtgcagctgttggagtc) (SEQ ID NO: 85) and primer CX1202 (ggcccttggtgctagcgctcgagacggtgaccagggttc) (SEQ ID NO: 86). DNA encoding the interleukin 2 (IL2) signal sequence was amplified from HcpPOP (modified from pcDNA3, Invitrogen) using primer CX1184 (gaaccgtcagatcactagaagc) (SEQ ID NO: 81) and primer CX1185 (cgaattcgtgacaagtgcaagacttagtg) (SEQ ID NO: 82), and annealed with the Hc variable domains. Vector (HcpOP (modified from pcDNA3, Invitrogen)) and the IL2-Hc-variable domains were cleaved with HindIII and NheI overnight, combined by ligation and transformed into E. coli MC1061 cells. Fully human IgGs (i.e., Jagged 13 IgG and Jagged 32 IgG, also referred to herein as anti-Jagged 13 (or anti-Jag 13) and anti-Jagged 32 (or anti-Jag 32), respectively) were expressed from transiently transfected HEK-293 cells and purified from the culture supernatant by Protein A chromatography.

As shown in FIG. 1, ELISA-binding experiments revealed that anti-Jagged 13 IgG and anti-Jagged 32 IgG bound human and mouse Jagged 1 and human Jagged 2, with affinities above 30 nM: Human Jagged 1-Fc (R&D Systems; ibid.), human Jagged 2-Fc (R&D Systems; Cat #1726-JG-050), or rat Jagged 1-Fc (R&D Systems; Cat #599-JG-100) was adsorbed to the wells of a 96-well ELISA plate. Purified anti-Jagged 13 and anti-Jagged 32 antibodies were applied to the plate and allowed to bind. Bound antibody was visualized with an anti-human IgG-HRP conjugate, Fab specific, (Sigma, St Louis, Mo.; Cat # A0293-1ML) and developed with the chromogenic substrate TMB.

Figure 2:
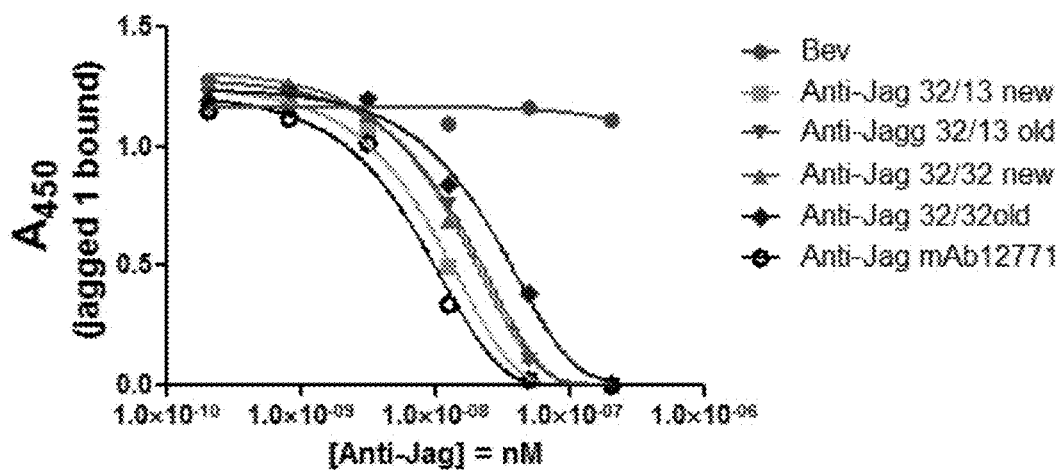
FIG. 2 is a graph depicting the ability of Anti-Jagged 13 and Anti-Jagged 32 to inhibit Jagged1 binding to human Notch 1.

As shown in FIG. 2, ELISA-binding experiments demonstrated that Jagged 1 binding by anti-Jagged 13 and anti-Jagged 32 binding was inhibited by human Notch 1: For the competition experiments, Notch 1-Fc (R&D Systems; ibid.) was adsorbed to the wells of a 96-well ELISA plate. Biotinylated human Jagged 1-Fc (R&D Systems; ibid.) was applied to the plate in increasing concentrations of anti-Jagged 13 and anti-Jagged 32 antibodies, and allowed to bind. Bound Jagged 1 was visualized with Streptavidin-HRP (Thermo Scientific) and developed with the chromogenic substrate TMB. Anti-Jagged MAB-12771 (R&D Systems; Cat# MAB12771) was used as a positive control for inhibition and bevacizumab as a negative control. The terms "old" and "new" refer to different lots of antibody production. Antibody 32/13 has an anti-Jagged 32 light chain and an anti-13 heavy chain. Antibody 32/32 has anti-Jagged 32 light and heavy chains.

Example 3

Affinity Maturation of Anti-Jagged Antibodies of the Embodiments

This Example demonstrates the isolation of antibodies of the embodiments with improved binding kinetics and Jagged binding specificities.

Anti-Jagged antibodies were isolated from libraries with CDRs modified from anti-Jagged 32. Such libraries were designed as shown in Table 2. Six libraries of antibodies, based on the sequence of anti-Jagged 32, were constructed using Dut/Ung mutagenesis (see, e.g., Kunkel T A, 1985, Proc Natl Acad Sci 82, 488-492). Residues were either varied by soft randomization at each indicated nucleotide, by retaining 70% of the original nucleotide and 10% of each of the other three possible nucleotides (superscript 1 in Table 2), or by total randomization (superscript 2 in Table 2). In addition, within libraries 3 and 6, additional residues were added to CD3 of the heavy chain. Libraries were transfected into *E. coli* strain TG1 and phage were prepared following superinfection with M13KO7 (Invitrogen).

Three rounds of selection were performed for each library with increasing stringency. For round three, human Jagged 1 (R&D Systems; ibid.) was adsorbed to immunotubes (Nunc, Denmark) at 5 micrograms per ml (µg/mL). Phage were blocked with 100 µg/mL pooled human IgG (huIgG, or hIgG) and 2% non-fat dried milk (NFDM) in Tris-buffered saline (TBS; 40 mM Tris, 129 mM NaCl, pH 7.4), and then added to the coated tubes for binding. Following binding, the tubes were washed extensively including four 37° C. washes for 30 minutes each. Following the washes the remaining bound phage were eluted with 100 mM triethanolamine (TEA) (Sigma, St. Louis, Mo.) and expanded through *E. coli* TG1. Libraries 1, 2 and 5 were combined to form library 125, and libraries 3, 4 and 6 were combined to form library 346; each library was subjected to an additional round of selection, also referred to herein as round four selection of library 125 and round four selection of library 346, respectively, as described for round three.

TABLE 2

CDR sequences for affinity maturation libraries

| Lib # | | CDR1 | CDR2 | CDR3 |
|---|---|---|---|---|
| 1 | Light chain | RASQSISSLYN (SEQ ID NO: 197) | AASLQS (SEQ ID NO: 198) | QQT$^1$V$^1$V$^1$A$^1$PL$^1$T$^1$ (SEQ ID NO: 199) |
| | Heavy chain | SAYMS (SEQ ID NO: 200) | SIEQMGGWQTYYADSSVKG (SEQ ID NO: 201) | SAAAFDY (SEQ ID NO: 202) |
| 2 | Light chain | RASQSISSLYN (SEQ ID NO: 197) | AASLQS (SEQ ID NO: 198) | QQTVVAPLT (SEQ ID NO: 203) |
| | Heavy chain | SAYMS (SEQ ID NO: 200) | S$^1$IE$^1$Q$^1$M$^1$GGW$^1$Q$^1$TYYADSSVKG (SEQ ID NO: 204) | SAAAFDY (SEQ ID NO: 202) |
| 3 | Light chain | RASQSISSLYN (SEQ ID NO: 197) | AASLQS (SEQ ID NO: 198) | QQTVVAPLT (SEQ ID NO: 203) |
| | Heavy chain | SAYMS (SEQ ID NO: 200) | SIEQMGGWQTYYADSSVKG (SEQ ID NO: 201) | SA$^2$A$^2$A$^2$FDYXXXX (SEQ ID NO: 205) |
| 4 | Light chain | RASQSISSLYN (SEQ ID NO: 197) | AASLQS (SEQ ID NO: 198) | QQTVVAPLT (SEQ ID NO: 203) |
| | Heavy chain | SAYMS (SEQ ID NO: 200) | S$^1$IE$^1$Q$^1$M$^1$GGW$^1$Q$^1$TYYADSSVKG (SEQ ID NO: 204) | SA$^2$A$^2$A$^2$FDY (SEQ ID NO: 206) |
| 5 | Light chain | RASQSISSLYN (SEQ ID NO: 197) | AASLQS (SEQ ID NO: 198) | QQT$^1$V$^1$V$^1$A$^1$PL$^1$T$^1$ SEQ ID NO: 199) |
| | Heavy chain | SAYMS (SEQ ID NO: 200) | SIEQMGGWQTYYADSSVKG (SEQ ID NO: 201) | SA$^2$A$^2$A$^2$FDY (SEQ ID NO: 206) |
| 6 | Light chain | RASQSISSLYN (SEQ ID NO: 197) | AASLQS (SEQ ID NO: 198) | QQTVVAPLT (SEQ ID NO: 203) |

TABLE 2-continued

CDR sequences for affinity maturation libraries

| Lib # | | CDR1 | CDR2 | CDR3 |
|---|---|---|---|---|
| | Heavy chain | SAYMS (SEQ ID NO: 200) | SIEQMGGWQTYYADSSVKG (SEQ ID NO: 201) | SA²A²A²FDYXXXXxxx (SEQ ID NO: 207) |

Superscript 1 denotes residues that were varied by soft randomization at each indicated nucleotide, by retaining 70% of the original nucleotide and 10% of each of the other three possible nucleotides, while superscript 2 denotes residues that were varied by total randomization.

Example 4

Binding Characteristics of Affinity Matured Anti-Jagged Antibodies

This Example demonstrates the binding characteristics of affinity-matured anti-Jagged antibodies of the embodiments isolated from affinity maturation processes.

Forty-eight (48) clones from each round four selection of library 125 and round four selection of library 346 were grown and infected with M13KO7 to generate phage. Each phage was analyzed for its ability to bind human Jagged 1-Fc (R&D Systems; ibid.), rat Jagged 1-Fc (R&D Systems; ibid.), and human Jagged 2-Fc (R&D Systems; ibid.) by phage ELISA. Jagged ligands were adsorbed to the wells of a 96-well ELISA plate, each ligand on a separate plate. Phage were applied to correlative wells on each plate and allowed to bind. Bound phage were visualized with an anti-M13-HRP conjugate and developed with the chromogenic substrate TMB. Individual isolates displayed divergent binding specificities; these specificities are shown in Table 3. Also shown are the SEQ ID NOs for the each of these isolates.

TABLE 3

Unique isolates have distinct binding specificities

| | hJag1 | hJag2 | rJag1 | SEQ ID NO of light chain amino acid sequence | SEQ ID NO of heavy chain amino acid sequence |
|---|---|---|---|---|---|
| 346.4 | ++ | | ++ | SEQ ID NO: 11 | SEQ ID NO: 12 |
| 346.5 | ++ | | ++ | SEQ ID NO: 13 | SEQ ID NO: 14 |
| 346.7 | +++ | +++ | +++ | SEQ ID NO: 15 | SEQ ID NO: 16 |
| 346.8 | + | | ++ | SEQ ID NO: 17 | SEQ ID NO: 18 |
| 346.13 | | ++ | | SEQ ID NO: 19 | SEQ ID NO: 20 |
| 346.16 | +++ | + | +++ | SEQ ID NO: 21 | SEQ ID NO: 22 |
| 346.19 | + | | ++ | SEQ ID NO: 23 | SEQ ID NO: 24 |
| 346.21 | + | | +/− | SEQ ID NO: 25 | SEQ ID NO: 26 |
| 346.24 | + | + | +/− | SEQ ID NO: 27 | SEQ ID NO: 28 |
| 346.26 | ++ | | + | SEQ ID NO: 29 | SEQ ID NO: 30 |
| 346.27 | ++ | | ++ | SEQ ID NO: 31 | SEQ ID NO: 32 |
| 346.28 | +++ | +++ | +++ | SEQ ID NO: 33 | SEQ ID NO: 34 |
| 346.30 | | ++ | | SEQ ID NO: 35 | SEQ ID NO: 36 |
| 346.31 | ++ | | + | SEQ ID NO: 37 | SEQ ID NO: 38 |
| 346.32 | | + | | SEQ ID NO: 39 | SEQ ID NO: 40 |
| 346.37 | + | | | SEQ ID NO: 41 | SEQ ID NO: 42 |
| 346.39 | + | +++ | | SEQ ID NO: 43 | SEQ ID NO: 44 |
| 346.40 | +++ | ++ | +++ | SEQ ID NO: 45 | SEQ ID NO: 46 |
| 346.47 | | +++ | | SEQ ID NO: 47 | SEQ ID NO: 48 |

The amino acid sequences of each of the clones in Table 3 are shown below:

Lc4
SEQ ID NO: 11
DIQMTQSPSSLSASVGDRVTITCRASQSISSYLNWYQQKPGKAPKLLIY
AASSLQSGVPSRFSGSGSGTDFTLTISSLQPEDFATYYCQQSVVAPLTF
GQGTKVEIKR

Hc4
SEQ ID NO: 12
EVQLLESGGGLVQPGGSLRLSCAASGFTFSSYAMSWVRQAPGKGLEWVS
SIEQMGWQTYYADSVKGRFTISRDNSKNTLYLQMNSLRAEDTAVYYCAK
DIGGRSAFDYWGQGTLVTVSS

Lc5
SEQ ID NO: 13
DIQMTQSPSSLSASVGDRVTITCRASQSISSYLNWYQQKPGKAPKLLIY
AASSLQSGVPSRFSGSGSGTDFTLTISSLQPEDFATYYCQQSVVAPLTF
GQGTKVEIKR

Hc5
SEQ ID NO: 14
EVQLLESGGGLVQPGGSLRLSCAASGFTFSSYAMSWVRQAPGKGLEWVS
SIEQMGWQTYYADSVKGRFTISRDNSKNTLYLQMNSLRAEDTAVYYCAK
SPPYHGQFDYWGQGTLVTVSS

Lc7
SEQ ID NO: 15
DIQMTQSPSSLSASVGDRVTITCRASQSISSYLNWYQQKPGKAPKLLIY
AASSLQSGVPSRFSGSGSGTDFTLTISSLQPEDFATYYCQQSVVAPLTF
GQGTKVEIKR

Hc7
SEQ ID NO: 16
EVQLLESGGGLVQPGGSLRLSCAASGFTFSSYAMSWVRQAPGKGLEWVS
SIEQMGWQTYYADSVKGRFTISRDNSKNTLYLQMNSLRAEDTAVYYCAK
SPPFFGQFDYWGQGTLVTVSS

Lc8
SEQ ID NO: 17
DIQMTQSPSSLSASVGDRVTITCRASQSISSYLNWYQQKPGKAPKLLIY
AASSLQSGVPSRFSGSGSGTDFTLTISSLQPEDFATYYCQQSVVAPLTF
GQGTKVEIKR

Hc8
SEQ ID NO: 18
EVQLLESGGGLVQPGGSLRLSCAASGFTFSSYAMSWVRQAPGKGLEWVS
SIEQMGWQTYYADSVKGRFTISRDNSKNTLYLQMNSLRAEDTAVYYCAK
HIGRTNPFDYWGQGTLVTVSS

Lc13
SEQ ID NO: 19
DIQMTQSPSSLSASVGDRVTITCRASQSISSYLNWYQQKPGKAPKLLIY
AASSLQSGVPSRFSGSGSGTDFTLTISSLQPEDFATYYCQQSVVAPLTF
GQGTKVEIKR

Hc13
SEQ ID NO: 20
EVQLLESGGGLVQPGGSLRLSCAASGFTFSSYAMSWVRQAPGKGLEWVS
SIEQMGWQTEYADSVKGRFTISRDNSKNTLYLQMNSLRAEDTAVYYCAK
SAAAFDYWGQGTLVTVSS

Lc16
SEQ ID NO: 21
DIQMTQSPSSLSASVGDRVTITCRASQSISSYLNWYQQKPGKAPKLLIY
AASSLQSGVPSRFSGSGSGTDFTLTISSLQPEDFATYYCQQSVVAPLTF
GQGTKVEIKR

Hc16
SEQ ID NO: 22
EVQLLESGGGLVQPGGSLRLSCAASGFTFSSYAMSWVRQAPGKGLEWVS
SIEQMGWQTYYADSVKGRFTISRDNSKNTLYLQMNSLRAEDTAVYYCAK
SPPYYGQFDYWGQGTLVTVSS

Lc19
SEQ ID NO: 23
DIQMTQSPSSLSASVGDRVTITCRASQSISSYLNWYQQKPGKAPKLLIY
AASSLQSGVPSRFSGSGSGTDFTLTISSLQPEDFATYYCQQSVVAPLTF
GQGTKVEIKR

Hc19
SEQ ID NO: 24
EVQLLESGGGLVQPGGSLRLSCAASGFTFSSYAMSWVRQAPGKGLEWVS
SIEQMGWQTYYADSVKGRFTISRDNSKNTLYLQMNSLRAEDTAVYYCAK
SPPFFGQFDYWGQGTLVTVSS

Lc21
SEQ ID NO: 25
DIQMTQSPSSLSASVGDRVTITCRASQSISSYLNWYQQKPGKAPKLLIY
AASSLQSGVPSRFSGSGSGTDFTLTISSLQPEDFATYYCQQSVVAPLTF
GQGTKVEIKR

Hc21
SEQ ID NO: 26
EVQLLESGGGLVQPGGSLRLSCAASGFTFSSYAMSWVRQAPGKGLEWVS
SIEQMGWQTYYADSVKGRFTISRDNSKNTLYLQMNSLRAEDTAVYYCAK
DIGGRSAFDYWGQGTLVTVSS

Lc24
SEQ ID NO: 27
DIQMTQSPSSLSASVGDRVTITCRASQSISSYLNWYQQKPGKAPKLLIY
AASSLQSGVPSRFSGSGSGTDFTLTISSLQPEDFATYYCQQSVVAPLTF
GQGTKVEIKR

Hc24
SEQ ID NO: 28
EVQLLESGGGLVQPGGSLRLSCAASGFTFSSYAMSWVRQAPGKGLEWVS
SIEEMGWQTLYADSVKGRFTISRDNSKNTLYLQMNSLRAEDTAVYYCAK
SAAAFDYWGQGTLVTVSS

Lc26
SEQ ID NO: 29
DIQMTQSPSSLSASVGDRVTITCRASQSISSYLNWYQQKPGKAPKLLIY
AASSLQSGVPSRFSGSGSGTDFTLTISSLQPEDFATYYCQQSVVAPLTF
GQGTKVEIKR

Hc26
SEQ ID NO: 30
EVQLLESGGGLVQPGGSLRLSCAASGFTFSSYAMSWVRQAPGKGLEWVS
SIEQMGWQTYYADSVKGRFTISRDNSKNTLYLQMNSLRAEDTAVYYCAK
DIGGRSAFDYWGQGTLVTVSS

Lc27
SEQ ID NO: 31
DIQMTQSPSSLSASVGDRVTITCRASQSISSYLNWYQQKPGKAPKLLIY
AASSLQSGVPSRFSGSGSGTDFTLTISSLQPEDFATYYCQQSVVAPLTF
GQGTKVEIKR

Hc27
SEQ ID NO: 32
EVQLLESGGGLVQPGGSLRLSCAASGFTFSSYAMSWVRQAPGKGLEWVS
SIEQMGWQTYYADSVKGRFTISRDNSKNTLYLQMNSLRAEDTAVYYCAK
SPPFYGQFDYWGQGTLVTVSS

Lc28
SEQ ID NO: 33
DIQMTQSPSSLSASVGDRVTITCRASQSISSYLNWYQQKPGKAPKLLIY
AASSLQSGVPSRFSGSGSGTDFTLTISSLQPEDFATYYCQQSVVAPLTF
GQGTKVEIKR

Hc28
SEQ ID NO: 34
EVQLLESGGGLVQPGGSLRLSCAASGFTFSSYAMSWVRQAPGKGLEWVS
SIEQMGWQTYYADSVKGRFTISRDNSKNTLYLQMNSLRAEDTAVYYCAK
SPPFFGQFDYWGQGTLVTVSS

Lc30
SEQ ID NO: 35
DIQMTQSPSSLSASVGDRVTITCRASQSISSYLNWYQQKPGKAPKLLIY
AASSLQSGVPSRFSGSGSGTDFTLTISSLQPEDFATYYCQQSVVAPLTF
GQGTKVEIKR

Hc30
SEQ ID NO: 36
EVQLLESGGGLVQPGGSLRLSCAASGFTFSSYAMSWVRQAPGKGLEWVS
SIEEMGWQTLYADSVKGRFTISRDNSKNTLYLQMNSLRAEDTAVYYAKS
AAAFDYWGQGTLVTVSS

Lc31
SEQ ID NO: 37
DIQMTQSPSSLSASVGDRVTITCRASQSISSYLNWYQQKPGKAPKLLIY
AASSLQSGVPSRFSGSGSGTDFTLTISSLQPEDFATYYCQQSVVAPLTF
GQGTKVEIKR

Hc31
SEQ ID NO: 38
EVQLLESGGGLVQPGGSLRLSCAASGFTFSSYAMSWVRQAPGKGLEWVS
SIEQMGWQTYYADSVKGRFTISRDNSKNTLYLQMNSLRAEDTAVYYCAK
DIGGRSAFDYWGQGTLVTVSS

Lc32
SEQ ID NO: 39
DIQMTQSPSSLSASVGDRVTITCRASQSISSYLNWYQQKPGKAPKLLIY
AASSLQSGVPSRFSGSGSGTDFTLTISSLQPEDFATYYCQQSVVAPLTF
GQGTKVEIKR

Hc32
SEQ ID NO: 40
EVQLLESGGGLVQPGGSLRLSCAASGFTFSSYAMSWVRQAPGKGLEWVS
SIDPEGWQTYYADSVKGRFTISRDNSKNTLYLQMNSLRAEDTAVYYCAK
SAAAFDYWGQGTLVTVSS

Lc37
SEQ ID NO: 41
DIQMTQSPSSLSASVGDRVTITCRASQSISSYLNWYQQKPGKAPKLLIY
AASSLQSGVPSRFSGSGSGTDFTLTISSLQPEDFATYYCQQSVVAPLTF
GQGTKVEIKR

Hc37
SEQ ID NO: 42
EVQLLESGGGLVQPGGSLRLSCAASGFTFSSYAMSWVRQAPGKGLEWVS
SIEQMGWQTYYADSVKGRFTISRDNSKNTLYLQMNSLRAEDTAVYYCAK
SPPHNGQFDYWGQGTLVTVSS

Lc39
SEQ ID NO: 43
DIQMTQSPSSLSASVGDRVTITCRASQSISSYLNWYQQKPGKAPKLLIY
AASSLQSGVPSRFSGSGSGTDFTLTISSLQPEDFATYYCQQSVVAPLTF
GQGTKVEIKR

Hc39
SEQ ID NO: 44
EVQLLESGGGLVQPGGSLRLSCAASGFTFSSYAMSWVRQAPGKGLEWVS
SIEQMGWQTEYADSVKGRFTISRDNSKNTLYLQMNSLRAEDTAVYYCAK
SAAAFDYWGQGTLVTVSS

Lc40
SEQ ID NO: 45
DIQMTQSPSSLSASVGDRVTITCRASQSISSYLNWYQQKPGKAPKLLIY
AASSLQSGVPSRFSGSGSGTDFTLTISSLQPEDFATYYCQQSVVAPLTF
GQGTKVEIKR

Hc40
SEQ ID NO: 46
EVQLLESGGGLVQPGGSLRLSCAASGFTFSSYAMSWVRQAPGKGLEWVS
SIEQMGWQTYYADSVKGRFTISRDNSKNTLYLQMNSLRAEDTAVYYCAK
SPPFFGQFDYWGQGTLVTVSS

Lc47
SEQ ID NO: 47
DIQMTQSPSSLSASVGDRVTITCRASQSISSYLNWYQQKPGKAPKLLIY
AASSLQSGVPSRFSGSGSGTDFTLTISSLQPEDFATYYCQQSVVAPLTF
GQGTKVEIKR

Hc47
SEQ ID NO: 48
EVQLLESGGGLVQPGGSLRLSCAASGFTFSSYAMSWVRQAPGKGLEWVS
SIDEMGWQTEYADSVKGRFTISRDNSKNTLYLQMNSLRAEDTAVYYCAK
SAAAFDYWGQGTLVTVSS

Example 5

Isolation and Testing of Affinity Matured Anti-Jagged 1 and Anti-Jagged 2 Antibodies of the Embodiments This Example describes the use of CDR shuffling to isolate antibodies of the embodiments that exhibit enhanced binding affinities for Jagged 1 and/or Jagged 2.

A seventh library was constructed by combining the light chains from the round four selection of library 125 and the heavy chains from the round four selection of library 346. This H/L library was selected through two additional rounds. In round one, the library was divided in two parts: one part was selected for binding to human Jagged 1-Fc (R&D Systems; ibid.) and the second part was selected for binding to human Jagged 2-Fc (R&D Systems, ibid.). In round two, the human Jagged 1-selected phage from round 1 were selected for binding to human Jagged 1-Fc (R&D Systems; ibid.) or human Jagged 2-Fc (R&D Systems, ibid.) in separate binding reactions, yielding two pools, designated Jagged 1/1 and Jagged 1/2, respectively. Similarly, the human Jagged 2-selected phage from round one were selected for binding to human Jagged 1-Fc (R&D Systems; ibid.) or human Jagged 2 (R&D Systems; ibid.) in separate binding reactions, yielding two pools, designated Jagged 2/1 and Jagged 2/2, respectively.

Ninety-five (95) individual isolates were chosen from each of the four pools. Phage were derived from each isolate and assayed for binding to human Jagged 1-Fc (R&D Systems; ibid.) or human Jagged 2-Fc (R&D Systems; ibid). The Jagged ligands were adsorbed to the wells of a 96-well ELISA plate, each ligand on a separate plate. Phage were applied to correlative wells on each plate and allowed to bind. Bound phage were visualized with an anti-M13-HRP conjugate and developed with the chromogenic substrate TMB. Based on the results of the ELISA and DNA sequence, 6 unique clones were chosen for further study. Table 4 lists the antibodies encoded by the 6 clones and SEQ ID NOs for the nucleic acid sequences and amino acid sequences of their respective light chains and heavy chains.

TABLE 4

SEQ ID NOs of the six clones encoding affinity matured antibodies

| | Light chain | | Heavy chain | |
| --- | --- | --- | --- | --- |
| Antibody | Nucleic acid sequence | Amino acid sequence | Nucleic acid sequence | Amino acid sequence |
| 4B2 | SEQ ID NO: 49 | SEQ ID NO: 50 | SEQ ID NO: 51 | SEQ ID NO: 52 |
| 4D11 | SEQ ID NO: 53 | SEQ ID NO: 54 | SEQ ID NO: 55 | SEQ ID NO: 56 |
| 4E7 | SEQ ID NO: 57 | SEQ ID NO: 58 | SEQ ID NO: 59 | SEQ ID NO: 60 |
| 4E11 | SEQ ID NO: 61 | SEQ ID NO: 62 | SEQ ID NO: 63 | SEQ ID NO: 64 |
| 6B7 | SEQ ID NO: 65 | SEQ ID NO: 66 | SEQ ID NO: 67 | SEQ ID NO: 68 |
| 6F8 | SEQ ID NO: 69 | SEQ ID NO: 70 | SEQ ID NO: 71 | SEQ ID NO: 72 |

The amino acid sequences of each of the final clones in Table 4 after chain shuffle are shown below:

4B2
Light Chain

SEQ ID NO: 49
GACATCCAGATGACCCAGTCTCCATCCTCCCTGTCTGCATCTGTAGGAG
ACAGAGTCACCATCACTTGCCGGGCAAGTCAGAGCATTAGCAGCTATTT
AAATTGGTATCAGCAGAAACCAGGGAAAGCCCCTAAGCTCCTGATCTAT
GCGGCATCCAGTTTGCAAAGTGGGGTCCCATCAAGGTTCAGTGGCAGTG
GATCTGGGACAGATTTCACTCTCACCATCAGCAGTCTGCAACCTGAAGA
TTTTGCAACTTACTACTGTCAACAGACGCTAGACGCTCCTCCGCAATTC
GGCCAAGGGACCAAGGTGGAAATCAAACGT

SEQ ID NO: 50
D I Q M T Q S P S S L S A S V G D R V T I T C R A
S Q S I S S Y L N W Y Q Q K P G K A P K L L I Y A
A S S L Q S G V P S R F S G S G S G T D F T L T I
S S L Q P E D F A T Y Y C Q Q T L D A P P Q F G Q
G T K V E I K R

Heavy Chain

SEQ ID NO: 51
GAGGTGCAGCTGTTGGAGTCTGGGGGAGGCTTGGTACAGCCTGGGGGGT
CCCTGAGACTCTCCTGTGCAGCCTCTGGATTCACCTTTAGCAGCTATGC
CATGAGCTGGGTCCGCCAGGCTCCAGGGAAGGGGCTGGAGTGGGTCTCA
AGTATTGAGCAGATGGGTTGGCAGACATATTACGCAGACTCCGTGAAGG
GCCGGTTCACCATCTCCAGAGACAATTCCAAGAACACGCTGTATCTGCA
AATGAACAGCCTGAGAGCCGAGGACACGGCCGTATATTACTGTGCGAAA
GACATCGGCGGCAGGTCGGCCTTTGACTACTGGGGCCAGGGAACCCTGG
TCACCGTCTCCTCA

SEQ ID NO: 52
E V Q L L E S G G G L V Q P G G S L R L S C A A S
G F T F S S Y A M S W V R Q A P G K G L E W V S S
I E Q M G W Q T Y Y A D S V K G R F T I S R D N S
K N T L Y L Q M N S L R A E D T A V Y Y C A K D I
G G R S A F D Y W G Q G T L V T V S S

4D11
Light Chain

SEQ ID NO: 53
GACATCCAGATGACCCAGTCTCCATCCTCCCTGTCTGCATCTGTAGGAG
ACAGAGTCACCATCACTTGCCGGGCAAGTCAGAGCATTAGCAGCTATTT
AAATTGGTATCAGCAGAAACCAGGGAAAGCCCCTAAGCTCCTGATCTAT
GCGGCATCCAGTTTGCAAAGTGGGGTCCCATCAAGGTTCAGTGGCAGTG
GATCTGGGACAGATTTCACTCTCACCATCAGCAGTCTGCAACCTGAAGA
TTTTGCAACTTACTACTGTCAACAGACGGTTGTGGCGCCTCCGTTATTC
GGCCAAGGGACCAAGGTGGAAATCAAACGT

SEQ ID NO: 54
D I Q M T Q S P S S L S A S V G D R V T I T C R A
S Q S I S S Y L N W Y Q Q K P G K A P K L L I Y A
A S S L Q S G V P S R F S G S G S G T D F T L T I
S S L Q P E D F A T Y Y C Q Q T V V A P P L F G Q
G T K V E I K R

Heavy Chain

SEQ ID NO: 55
GAGGTGCAGCTGTTGGAGTCTGGGGGAGGCTTGGTACAGCCTGGGGGGT
CCCTGAGACTCTCCTGTGCAGCCTCTGGATTCACCTTTAGCAGCTATGC
CATGAGCTGGGTCCGCCAGGCTCCAGGGAAGGGGCTGGAGTGGGTGTCA
AGTATTGACCCGGAAGGTCGGCAGACATATTACGCAGACTCCGTGAAGG
GCCGGTTCACCATCTCCAGAGACAATTCCAAGAACACGCTGTATCTGCA
AATGAACAGCCTGAGAGCCGAGGACACGGCCGTATATTACTGTGCGAAA
GACATCGGCGGCAGGTCGGCCTTTGACTACTGGGGCCAGGGAACCCTGG
TCACCGTCTCCTCA

SEQ ID NO: 56
E V Q L L E S G G G L V Q P G G S L R L S C A A S
G F T F S S Y A M S W V R Q A P G K G L E W V S S
I D P E G R Q T Y Y A D S V K G R F T I S R D N S
K N T L Y L Q M N S L R A E D T A V Y Y C A K D I
G G R S A F D Y W G Q G T L V T V S S

4E7
Light Chain

SEQ ID NO: 57
GACATCCAGATGACCCAGTCTCCATCCTCCCTGTCTGCATCTGTAGGAG
ACAGAGTCACCATCACTTGCCGGGCAAGTCAGAGCATTAGCAGCTATTT
AAATTGGTATCAGCAGAAACCAGGGAAAGCCCCTAAGCTCCTGATCTAT
GCGGCATCCAGTTTGCAAAGTGGGGTCCCATCAAGGTTCAGTGGCAGTG
GATCTGGGACAGATTTCACTCTCACCATCAGCAGTCTGCAACCTGAAGA
TTTTGCAACTTACTACTGTCAACAGTCGCTGGTGGCGCCTCTTACCTTC
GGCCAAGGGACCAAGGTGGAAATCAAACGT

SEQ ID NO: 58
D I Q M T Q S P S S L S A S V G D R V T I T C R A
S Q S I S S Y L N W Y Q Q K P G K A P K L L I Y A
A S S L Q S G V P S R F S G S G S G T D F T L T I

```
S S L Q P E D F A T Y Y C Q Q S L V A P L T F G Q
G T K V E I K R
```

Heavy Chain

SEQ ID NO: 59
```
GAGGTGCAGCTGTTGGAGTCTGGGGGAGGCTTGGTACAGCCTGGGGGGT
CCCTGAGACTCTCCTGTGCAGCCTCTGGATTCACCTTTAGCAGCTATGC
CATGAGCTGGGTCCGCCAGGCTCCAGGGAAGGGGCTGGAGTGGGTGTCA
AGTATTGAAGAGATGGGTTGGCAGACAAAGTACGCAGACTCCGTGAAGG
GCCGGTTCACCATCTCCAGAGACAATTCCAAGAACACGCTGTATCTGCA
AATGAACAGCCTGAGAGCCGAGGACACGGCCGTATATTACTGTGCGAAA
TCGGCTGCTGCTTTTGACTACTGGGGCCAGGGAACCCTGGTCACCGTCT
CCTCA
```

SEQ ID NO: 60
```
E V Q L L E S G G G L V Q P G G S L R L S C A A S
G F T F S S Y A M S W V R Q A P G K G L E W V S S
I E E M G W Q T K Y A D S V K G R F T I S R D N S
K N T L Y L Q M N S L R A E D T A V Y Y C A K S A
A A F D Y W G Q G T L V T V S S
```

4E11
Light Chain

SEQ ID NO: 61
```
GACATCCAGATGACCCAGTCTCCATCCTCCCTGTCTGCATCTGTAGGAG
ACAGAGTCACCATCACTTGCCGGGCAAGTCAGAGCATTAGCAGCTATTT
AAATTGGTATCAGCAGAAACCAGGGAAAGCCCCTAAGCTCCTGATCTAT
GCGGCATCCAGTTTGCAAAGTGGGGTCCCATCAAGGTTCAGTGGCAGTG
GATCTGGGACAGATTTCACTCTCACCATCAGCAGTCTGCAACCTGAAGA
TTTTGCAACTTACTACTGTCAACAGGCGTTAGATGCCCCTCTGATGTTC
GGCCAAGGGACCAAGGTGGAAATCAAACGT
```

SEQ ID NO: 62
```
D I Q M T Q S P S S L S A S V G D R V T I T C R A
S Q S I S S Y L N W Y Q Q K P G K A P K L L I Y A
A S S L Q S G V P S R F S G S G S G T D F T L T I
S S L Q P E D F A T Y Y C Q Q A L D A P L M F G Q
G T K V E I K R
```

Heavy Chain

SEQ ID NO: 63
```
GAGGTGCAGCTGTTGGAGTCTGGGGGAGGCTTGGTACAGCCTGGGGGGT
CCCTGAGACTCTCCTGTGCAGCCTCTGGATTCACCTTTAGCAGCTATGC
CATGAGCTGGGTCCGCCAGGCTCCAGGGAAGGGGCTGGAGTGGGTGTCA
AGTATTGAGCCTATGGGTTGACTAACAGAATACGCAGACTCCGTGAAGG
GCCGGTTCACCATCTCCAGAGACAATTCCAAGAACACGCTGTATCTGCA
AATGAACAGCCTGAGAGCCGAGGACACGGCCGTATATTACTGTGCGAAA
GACATCGGCGGCAGGTCGGCCTTTGACTACTGGGGCCAGGGAACCCTGG
TCACCGTCTCCTCA
```

SEQ ID NO: 64
```
E V Q L L E S G G G L V Q P G G S L R L S C A A S
G F T F S S Y A M S W V R Q A P G K G L E W V S S
I E P M G Q L T E Y A D S V K G R F T I S R D N S
K N T L Y L Q M N S L R A E D T A V Y Y C A K D I
G G R S A F D Y W G Q G T L V T V SS
```

6B7
Light Chain

SEQ ID NO: 65
```
GACATCCAGATGACCCAGTCTCCATCCTCCCTGTCTGCATCTGTAGGAG
ACAGAGTCACCATCACTTGCCGGGCAAGTCAGAGCATTAGCAGCTATTT
AAATTGGTATCAGCAGAAACCAGGGAAAGCCCCTAAGCTCCTGATCTAT
GCGGCATCCAGTTTGCAAAGTGGGGTCCCATCAAGGTTCAGTGGCAGTG
GATCTGGGACAGATTTCACTCTCACCATCAGCAGTCTGCAACCTGAAGA
TTTTGCAACTTACTACTGTCAACAGGCGCTTGTCGCCCCTCTGACGTTC
GGCCAAGGGACCAAGGTGGAAATCAAACGT
```

SEQ ID NO: 66
```
D I Q M T Q S P S S L S A S V G D R V T I T C R A
S Q S I S S Y L N W Y Q Q K P G K A P K L L I Y A
A S S L Q S G V P S R F S G S G S G T D F T L T I
S S L Q P E D F A T Y Y C Q Q A L V A P L T F G Q
G T K V E I K R
```

Heavy Chain

SEQ ID NO: 67
```
GAGGTGCAGCTGTTGGAGTCTGGGGGAGGCTTGGTACAGCCTGGGGGGT
CCCTGAGACTCTCCTGTGCAGCCTCTGGATTCACCTTTAGCAGCTATGC
CATGAGCTGGGTCCGCCAGGCTCCAGGGAAGGGGCTGGAGTGGGTGTCA
AGTATTGATGAGATGGGTTGGCAGACATATTACGCAGACTCCGTGAAGG
GCCGGTTCACCATCTCCAGAGACAATTCCAAGAACACGCTGTATCTGCA
AATGAACAGCCTGAGAGCCGAGGACACGGCCGTATATTACTGTGCGAAA
TCGGCTGCTGCTTTTGACTACTGGGGCCAGGGAACCCTGGTCACCGTCT
CCTCA
```

SEQ ID NO: 68
```
E V Q L L E S G G G L V Q P G G S L R L S C A A S
G F T F S S Y A M S W V R Q A P G K G L E W V S S
I D E M G W Q T Y Y A D S V K G R F T I S R D N S
K N T L Y L Q M N S L R A E D T A V Y Y C A K S A
A A F D Y W G Q G T L V T V S S
```

6F8
Light Chain

SEQ ID NO: 69
```
GACATCCAGATGACCCAGTCTCCATCCTCCCTGTCTGCATCTGTAGGAG
ACAGAGTCACCATCACTTGCCGGGCAAGTCAGAGCATTAGCAGCTATTT
AAATTGGTATCAGCAGAAACCAGGGAAAGCCCCTAAGCTCCTGATCTAT
GCGGCATCCAGTTTGCAAAGTGGGGTCCCATCAAGGTTCAGTGGCAGTG
GATCTGGGACAGATTTCACTCTCACCATCAGCAGTCTGCAACCTGAAGA
TTTTGCAACTTACTACTGTCAACAGGCGCTTGTCGCCCCTCTGACGTTC
GGCCAAGGGACCAAGGTGGAAATCAAACGTAC
```

SEQ ID NO: 70
```
D I Q M T Q S P S S L S A S V G D R V T I T C R A
S Q S I S S Y L N W Y Q Q K P G K A P K L L I Y A
A S S L Q S G V P S R F S G S G S G T D F T L T I
S S L Q P E D F A T Y Y C Q Q A L V A P L T F G Q
G T K V E I K R
```

Heavy Chain

SEQ ID NO: 71
```
GAGGTGCAGCTGTTGGAGTCTGGGGGAGGCTTGGTACAGCCTGGGGGGT
CCCTGAGACTCTCCTGTGCAGCCTCTGGATTCACCTTTAGCAGCTATGC
CATGAGCTGGGTCCGCCAGGCTCCAGGGAAGGGGCTGGAGTGGGTGTCA
AGTATTGATGAGATGGGTTGGCAGACATATTACGCAGACTCCGTGAAGG
GCCGGTTCACCATCTCCAGAGACAATTCCAAGAACACGCTGTATCTGCA
AATGAACAGCCTGAGAGCCGAGGACACGGCCGTATATTACTGTGCGAAA
TCGGCTGCTGCTTTTGACTACTGGGGCCAGGGAACCCTGGTCACCGTCT
CCTCA
```

SEQ ID NO: 72
```
E V Q L L E S G G G L V Q P G G S L R L S C A A S
G F T F S S Y A M S W V R Q A P G K G L E W V S S
I D E M G W Q T Y Y A D S V K G R F T I S R D N S
K N T L Y L Q M N S L R A E D T A V Y Y C A K S A
A A F D Y W G Q G T L V T V S S
```

The libraries were configured with a His tag carboxy to the Fab, and an amber stop codon carboxy to the His tag, such that, when the phagemids encoding the six affinity matured antibodies were in a non-amber suppressor strain, the phagemids directed the expression of a C-terminal His tagged Fab that could be purified from the periplasmic space of *E. coli*. To measure the affinities of the six matured isolates, as well as the affinities of anti-Jagged 13 and anti-Jagged 32 Fabs, Fabs were expressed and purified from *E. coli* DH12b.

Off rates for individual Fabs were measured using an Octet (ForteBio, Menlo Park, Calif.). Anti-human Fc Octet tips (ForteBio, Cat #18-5060) were blocked with biocytin and 100 µg/mL BSA and then loaded with 25 micromolar (25 µM) Jagged ligand, namely human Jagged 1-Fc (R&D Systems; ibid.), human Jagged2-Fc (R&D Systems; ibid.) or murine Jagged 2-Fc (R&D Systems, ibid.). Following a wash, the loaded tips were exposed to 25 µM Fab until binding had reached equilibrium. The tips were then removed to a fresh solution with no Fab, and the rate of Fab dissociation was measured. The dissociation constants listed in Table 5 show that the off-rates of the affinity matured antibodies have been decreased 10 to 100 fold compared to ScFv antibodies Jagged 13 and Jagged 32.

TABLE 5

Dissociation constants for anti-Jagged Fabs

| Antibody | h Jagged 1 | h Jagged 2 | m Jagged 2 |
|---|---|---|---|
| 4B2 | $5 \times 10^{-4}$ | $6.5 \times 10^{-3}$ | $1.1 \times 10^{-3}$ |
| 4D11 | $1.2 \times 10^{-4}$ | $4.5 \times 10^{-4}$ | $4.2 \times 10^{-4}$ |
| 4E7 | $6.9 \times 10^{-4}$ | $1.9 \times 10^{-3}$ | $5.8 \times 10^{-3}$ |
| 4E11 | $1.4 \times 10^{-3}$ | $5.7 \times 10^{-4}$ | $2.5 \times 10^{-5}$ |
| 6B7 | $3.5 \times 10^{-4}$ | $2 \times 10^{-3}$ | $2.4 \times 10^{-3}$ |
| 6F8 | $1.2 \times 10^{-3}$ | $4.9 \times 10^{-3}$ | $1.6 \times 10^{-3}$ |
| Jag13 | $2.2 \times 10^{-2}$ | $1 \times 10^{-3}$ | $2.8 \times 10^{-3}$ |
| Jag32 | $2.7 \times 10^{-2}$ | $2.3 \times 10^{-3}$ | $2.5 \times 10^{-3}$ |

$k_{diss}$ (s$^{-1}$)

Example 6

Production of Anti-Jagged Antibodies of the Embodiments

This Example demonstrates the expression and purification of anti-Jagged antibodies of the embodiments.

Vectors were made in the following manner: The IL2 signal sequence coding region was moved from pINFUSE-hIgG1-Fc2 (InvivoGen, San Diego, Calif.) as a KasI/NcoI fragment to pFUSE2-CLIg-hk (InvivoGen) digested with KasI/NcoI, resulting in plasmid pFIL2-CL-hk. The IL2 signal sequence coding region was also moved from pINFUSE-hIgG1-Fc2 as a KasI/EcoRI fragment to pFUSE-CHIg-hG1 (InvivoGen) digested with KasI/EcoRI (large and medium fragments) in a three-way ligation, resulting in plasmid pFIL-CHIg-hG1.

The light chain coding region from the pFIL2-CL-hk vector was amplified using primers CX1170 and CX1168 and cloned into the pOP Neo vector using the NheI and NotI sites using the infusion cloning system (HD EcoDry, Clontech, Mountain View, Calif.), mutating the NotI site in the process. The 4D11 variable light chain coding region was PCR amplified from the isolated 4D11 coding sequence using primers CX1197 and CX1198 and cloned into the EcoRI and BsiWI restriction sites. The primers are provided Table 6. The 4D11 light chain nucleic acid sequence is represented by SEQ ID NO:73, and the amino acid sequence is represented by SEQ ID NO:74.

4D11 Light Chain sequence:

SEQ ID NO: 73
```
gacatccagatgacccagtctccatcctccctgtctgcatctgtaggag
acagagtcaccatcacttgccgggcaagtcagagcattagcagctattt
aaattggtatcagcagaaaccagggaaagcccctaagctcctgatctat
gcggcatccagtttgcaaagtggggtcccatcaaggttcagtggcagtg
gatctgggacagatttcactctcaccatcagcagtctgcaacctgaaga
ttttgcaacttactactgtcaacagactggttgtggcgcctccgttattc
ggccaagggaccaaggtggaaatcaaacgtacggtggctgcaccatctg
tcttcatcttcccgccatctgatgagcagttgaaactggaactgcctc
tgttgtgtgcctgctgaataacttctatcccagagaggccaaagtacag
tggaaggtggataacgccctccaatcgggtaactcccaggagagtgtca
cagagcaggacagcaaggacagcacctacagcctcagcagcaccctgac
gctgagcaaagcagactacgagaaacacaaagtctacgcctgcgaagtc
acccatcagggcctgagctcgcccgtcacaaagagcttcaacaggggag
agtgt
```

SEQ ID NO: 74
```
DIQMTQSPSSLSASVGDRVTITCRASQSISSYLNWYQQKPGKAPKLLIY
AASSLQSGVPSRFSGSGSGTDFTLTISSLQPEDFATYYCQQTVVAPPLF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC
```

The heavy chain coding region from the pFIL-CHIg-hG1 vector was cloned into the pOP Hygr vector (modification of pcDNA3, Invitrogen) as follows: Two overlapping fragments were amplified, the first was the 5' non-coding region from the pOP Hygr vector using primers CX1184 and CX1185 and the second was the coding region from pFIL-CHIg-hG1 using primers CX1172 and CX1169. These two PCR products were then combined for a final amplification using primers CX1184 and CX1169 and cloned into the pOP Hygr vector using the HindIII and NotI restriction sites. The 4D11 variable heavy chain coding region was cloned in a similar way, using the same first DNA fragment and the second fragment being amplified from the isolated 4D11 coding sequence using primers CX1199 and CX1202. The two fragments were amplified using primers CX1184 and CX1202 and cloned into the HindIII and NheI restriction sites. The primers are provided in Table 6. The 4D11 light chain nucleic acid sequence is represented by SEQ ID NO:75, and the amino acid sequence is represented by SEQ ID NO:76.

4D11 Heavy Chain sequence:

SEQ ID NO: 75
```
gaggtgcagctgttggagtctgggggaggcttggtacagcctggggagt
ccctgagactctcctgtgcagcctctggattcacctttagcagctatgc
catgagctgggtccgccaggctccagggaaggggctggagtgggtgtca
agtattgacccggaaggtcggcagacatattacgcagactccgtgaagg
gccggttcaccatctccagagacaattccaagaacacgctgtatctgca
aatgaacagcctgagagccgaggacacggccgtatattactgtgcgaaa
gacatcggcggcaggtcggccttttgactactggggccagggaaccctgg
tcaccgtctcctcagctagcaccaagggcccatcggtcttccccctggc
accctcctccaagagcacctctgggggcacagcggccctgggctgcctg
gtcaaggactacttccccgaaccggtgacggtgtcgtggaactcaggcg
ccctgaccagcggcgtgcacaccttcccggctgtcctacagtcctcagg
actctactccctcagcagcgtggtgaccgtgccctccagcagcttgggc
acccagacctacatctgcaacgtgaatcacaagcccagcaacaccaagg
tggacaagaaagttgagcccaaatcttgtgacaaaactcacacatgccc
accgtgcccagcacctgaactcctggggggaccgtcagtcttcctcttc
ccccaaaacccaaggacaccctcatgatctcccggacccctgaggtca
catgcgtggtggtggacgtgagccacgaagaccctgaggtcaagttcaa
ctggtacgtggacggcgtggaggtgcataatgccaagacaaagccgcg
gaggagcagtacaacagcacgtaccgtgtggtcagcgtcctcaccgtcc
tgcaccaggactggctgaatggcaaggagtacaagtgcaaggtctccaa
caaagcccctcccagcccccatcgagaaaaccatctccaaagccaaaggg
cagccccgagaaccacaggtgtacaccctgcccccatcccgggaggaga
tgaccaagaaccaggtcagcctgacctgcctggtcaaaggcttctatcc
cagcgacatcgccgtggagtgggagagcaatgggcagccggagaacaac
tacaagaccacgcctcccgtgctggactccgacggctccttcttcctct
acagcaagctcaccgtggacaagagcaggtggcagcaggggaacgtctt
ctcatgctccgtgatgcatgaggctctgcacaaccactacacgcagaag
agcctctccctgtctccgggtaaa
```

SEQ ID NO: 76
```
EVQLLESGGGLVQPGGSLRLSCAASGFTFSSYAMSWVRQAPGKGLEWVS
SIDPEGRQTYYADSVKGRFTISRDNSKNTLYLQMNSLRAEDTAVYYCAK
DIGGRSAFDYWGQGTLVTVSSASTKGPSVFPLAPSSKSTSGGTAALGCL
VKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKG
QPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQK
SLSLSPGK
```

TABLE 6

Primer sequences

| Primer | Nucleic acid sequence | SEQ ID NO |
|---|---|---|
| CX1168 | tagactcgagcggccgcctaacac tctcccctgttgaagc | SEQ ID NO: 77 |
| CX1169 | tagactcgagcggccgctcatttaccc ggagacagggag | SEQ ID NO: 78 |
| CX1170 | ctcactataggctagcgccaccatgt acaggatgcaactc | SEQ ID NO: 79 |

TABLE 6-continued

Primer sequences

| Primer | Nucleic acid sequence | SEQ ID NO |
|---|---|---|
| CX1172 | ctcactataggctagagccaccatgtac aggatgcaactc | SEQ ID NO: 80 |
| CX1184 | gaaccgtcagatcactagaagc | SEQ ID NO: 81 |
| CX1185 | cgaattcgtgacaagtgcaagacttagtg | SEQ ID NO: 82 |
| CX1197 | cacttgtcacgaattcggacatccagatg acccagtc | SEQ ID NO: 83 |
| CX1198 | gtgcagccaccgtacgtttgatttccacc ttggtccc | SEQ ID NO: 84 |
| CX1199 | ttgcacttgtcacgaattcggaggtgcagc tgttggagtc | SEQ ID NO: 85 |
| CX1202 | ggcccttggtgctagcgctcgagacggtgac cagggttc | SEQ ID NO: 86 |

Fully human IgGs were expressed from transiently transfected HEK-293 cells and purified from the culture supernatant by Protein A chromatography.

Example 7

An Anti-Jagged Antibody of the Embodiments Reduces BxPC-3 Tumors in Mice

In this Example, anti-Jagged 4D11 was analyzed for the ability to reduce the growth of BxPC-3 xenograft tumors.

The human pancreatic cancer cell line BxPC-3 was obtained from *Cell Bank of Shanghai Institute for Biological Sciences, Chinese Academy of Sciences*. The BxPC-3 xenografts were developed by injecting BxPC-3 cells subcutaneously into the right flank of Balb/c nude mice. Upon reaching 500-700 mm3, the tumor was harvested for in vitro cell culture and serial passage. The in vivo adapted BxPC-3 cells (xenograft derived cells) were grown in RPMI-1640 supplemented with 10% fetal bovine serum at 37° C. in an atmosphere of 5% $CO_2$ in air. The tumor cells were routinely subcultured twice weekly. Cells were harvested during the logarithmic growth period, resuspended in physical PBS with proper cell concentration, and kept on ice for tumor induction.

Each mouse was inoculated subcutaneously at the right flank with $5 \times 10^6$ of BxPC-3 cells in 0.1 ml of PBS for tumor development. The treatments were started when the mean tumor size reached approximately 150 mm³. Tumor sizes were measured twice weekly in two dimensions using a caliper, and the volume was expressed in mm³ using the formula: $V=0.5 \ a \times b^2$ where a and b are the long and short diameters of the tumor, respectively.

The mice were grouped and dosed as set forth in Table 7.

TABLE 7

Groups and doses for BxPC-3 xenograft study

| Group | n | Treatment | Dose (mg/kg) | Dosing Route | Schedule |
|---|---|---|---|---|---|
| 1 | 8 | IVIg (CTX000) | 20 mg/kg | i.p | q3dx 4 |
| 2 | 6 | CTX-014 (4D11) | 20 mg/kg | i.p. | q3dx 4 |

Figure 3:
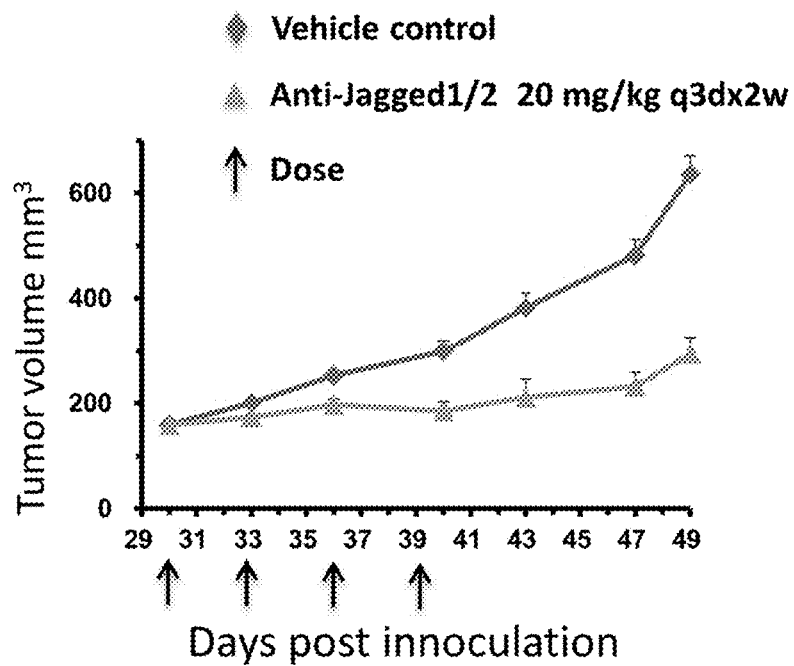
FIG. 3 is a graph depicting the ability of an anti-Jagged antibody referred to herein as 4D11 (also referred to herein as anti-Jagged 4D11, anti-Jagged 4D11 antibody, 4D11 antibody, or antibody 4D11) to inhibit the growth of BxPC3 xenograft tumors.
Figure 4:
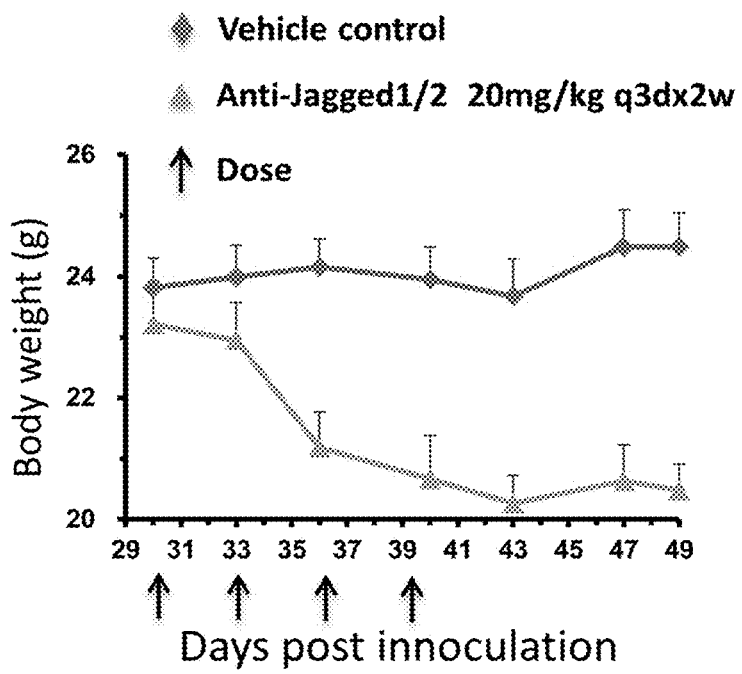
FIG. 4 is a graph depicting weight loss by mice administered anti-Jagged 4D11.
Figure 5:
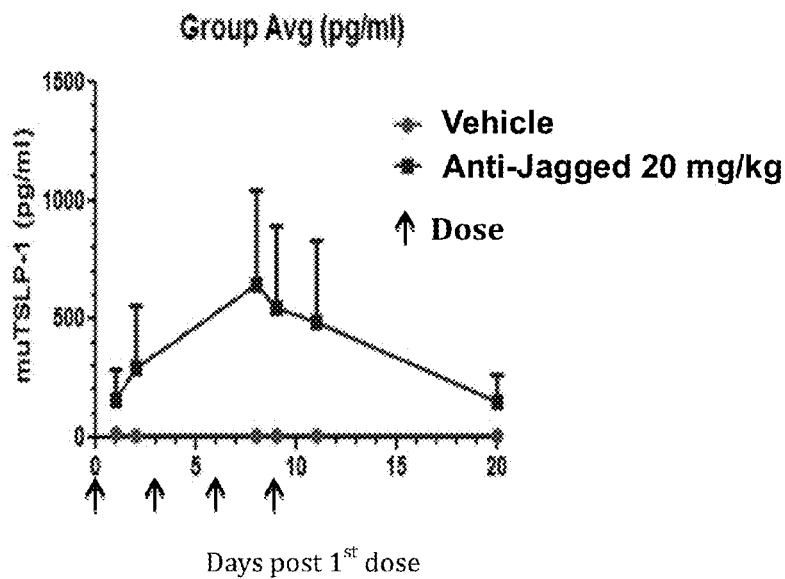
FIG. 5 is a graph depicting serum concentration of TSLP in mice administered anti-Jagged 4D11.

FIG. 3, which plots tumor volume versus number of days post initial dose, demonstrates that anti-Jagged AD11 antibody inhibits the growth of BxPC-3 xenograft tumors. FIG. 4 indicates weight loss by animals in Groups 1 and 2. The serum concentration of mouse thymic stromal lymphopoietin (TSLP) was measured using the Quantikine mouse TSLP immunoassay (R&D Systems) following the manufacturer's protocol. The serum levels of mouse TSLP was quantified for individual mice from each group and averaged to generate FIG. 5.

Anti-Jagged 4D11 was also tested for the ability to reduce the growth of BxPC-3 xenograft tumors in a dose dependent matter, using a method similar to that described above, using the groups and doses set forth in Table 8.

TABLE 8

Groups and doses for dose dependent BxPC-3 xenograft study

| Group | n | Treatment | Dose (mg/kg) | Dosing Route | Schedule |
|---|---|---|---|---|---|
| 1 | 8 | PBS | 20 mg/kg | i.p | q3dx 4 |
| 2 | 8 | 4D11 | 20 mg/kg | i.p. | q7dx 4 |
| 3 | 8 | 4D11 | 6.7 mg/kg | i.p. | q7dx 4 |
| 4 | 8 | 4D11 | 2 mg/kg | i.p. | q7dx 4 |
| 5 | 8 | Gemcitabine | 100 mg/kg | i.p. | qdx 4 |

Figure 6:
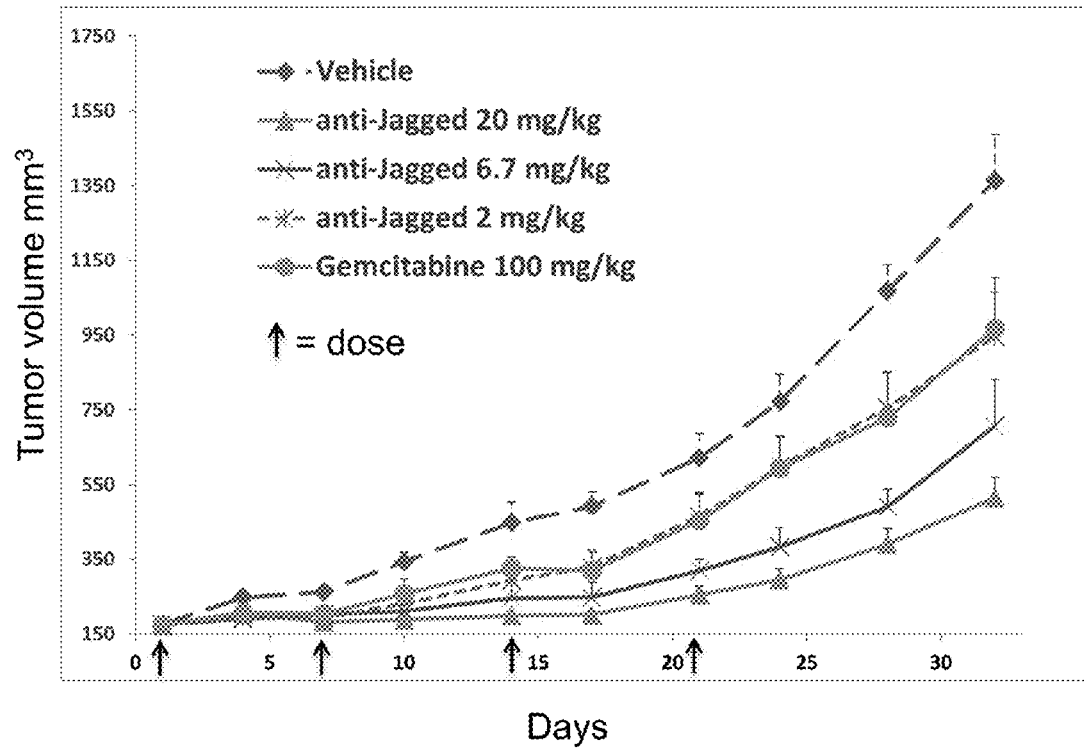
FIG. 6 is a graph depicting the ability of the anti-Jagged 4D11 antibody to inhibit the growth of BxPC3 xenograft tumors for more than 30 days post-inoculation.
Figure 7:
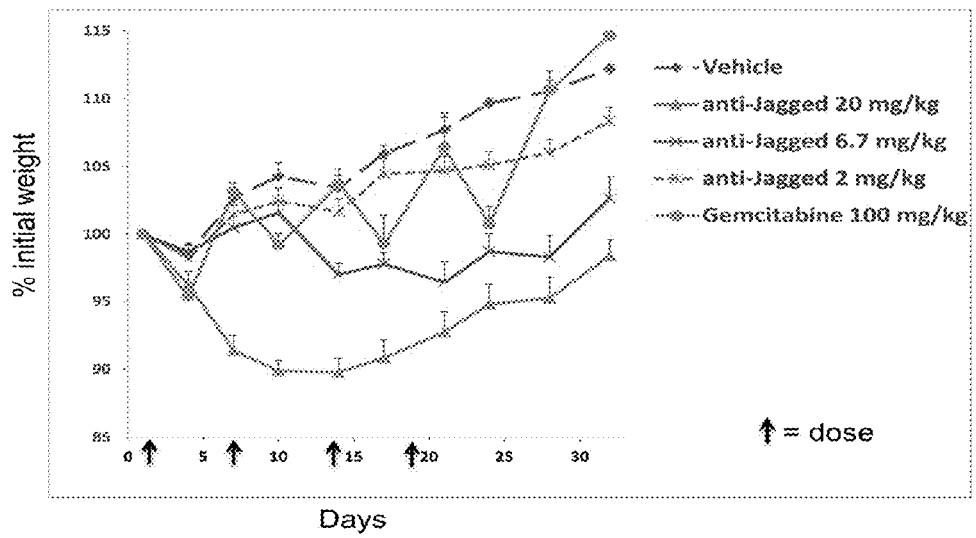
FIG. 7 is a graph depicting weight loss by mice administered anti-Jagged 4D11.

FIG. 6, which plots tumor volume versus number of days post initial dose, demonstrates that anti-Jagged AD11 antibody inhibits the growth of BxPC-3 xenograft tumors. FIG. 7 indicates weight loss by the animals.

Figure 23:
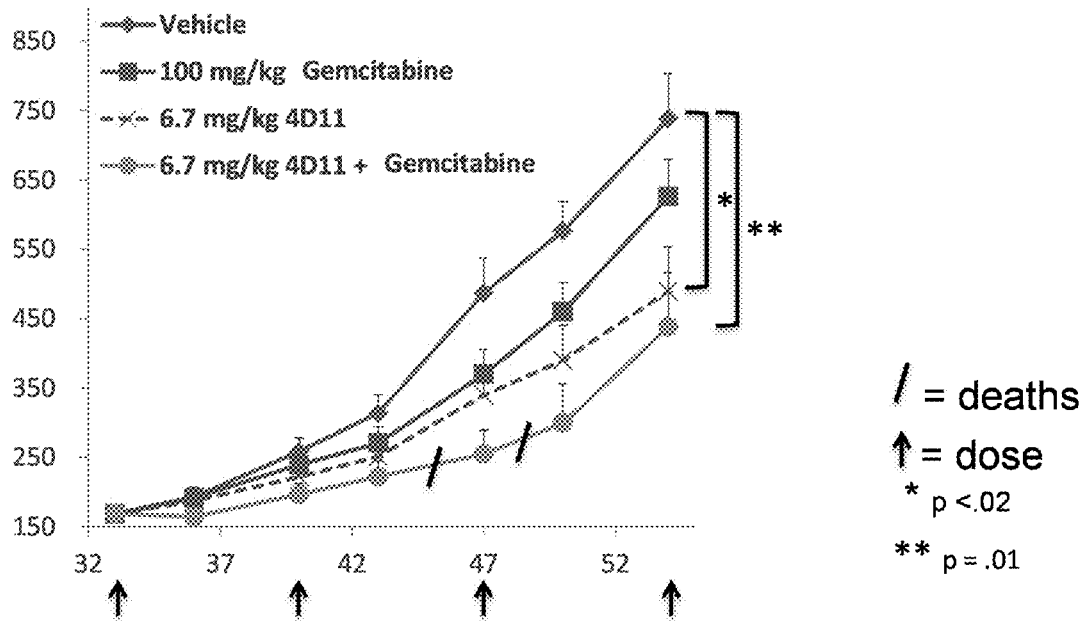
FIG. 23 is a graph depicting the effect of the anti-Jagged 4D11 antibody to inhibit the growth of tumors in the BxPC3 xenograft mouse model when administered alone or in combination with an additional anti-cancer agent, gemcitabine.

In a second study, anti-Jagged 4D11 was also tested for the ability to reduce the growth of BxPC-3 xenograft tumors in combination with a second anti-cancer agent. In this study, anti-Jagged 4D11 was administered alone or in combination with gemcitabine, the current standard-of-care chemotherapy in pancreatic cancer, using a method similar to that described above, and using the doses set forth in FIG. 23. In these studies, antibody toxicity was apparent from weight loss and mortality. These studies demonstrate that the combination of anti-Jagged 4D11 and gemcitabine inhibits the growth of BxPC-3 xenograft tumors. As seen in FIG. 23, the combination of anti-Jagged antibody and gemcitabine produced an additive effect in the BXPC3 pancreatic xenograft model.

Example 8

An Anti-Jagged Antibody of the Embodiments Inhibits the Growth of RPMI 8226 in Human Bone Marrow Co-Cultures This Example demonstrates that anti-Jagged 4D11 inhibits the growth of RPMI 8226 in human bone marrow co-cultures In multiple myeloma, interaction between the myeloma cells and the stromal cells of the bone marrow is important for the survival and proliferation of myeloma cells and the development of the accompanying osteolytic disease. Notch receptors and ligands are upregulated in multiple myeloma. The ability of anti-Jagged 4D11 to inhibit proliferation of the multiple myeloma cell line RPMI 8226 was measured in vitro in co-cultures of RPMI 8226 and human bone marrow aspirates. Human bone marrow was purchased from AllCells, LLC (Emeryville, Calif.). RPMI 8226 cells were labeled with CFSE as per manufacturer's instructions (Invitrogen, Carlsbad, Calif.). Briefly, bone marrow was diluted 2-fold in RPMI-1640, 10% FBS, and 2 mL were plated into the wells of a 6-well tissue culture dish. 50,000 CFSE-labeled RPMI 8226 cells, in 1 ml RPMI1640, 10% FBS, were plated into wells containing bone marrow. Test articles, i.e., anti-Jagged 4D11, anti-EGFR (antibody c225, cetuximab UCSF Pharmacy, manufactured and sold by Bristol-Myers Squibb, NY, N.Y.) or gamma secretase inhibitor BMS299897 (Sigma, St. Louis, Mo.), were added, and the cultures were incubated at 37° C. and 5% $CO_2$ for five days. Following incubation, red blood cells were lysed, and live cells were collected by centrifugation. The fluorescent intensity of the cells was measured by FACS.

Figure 8:
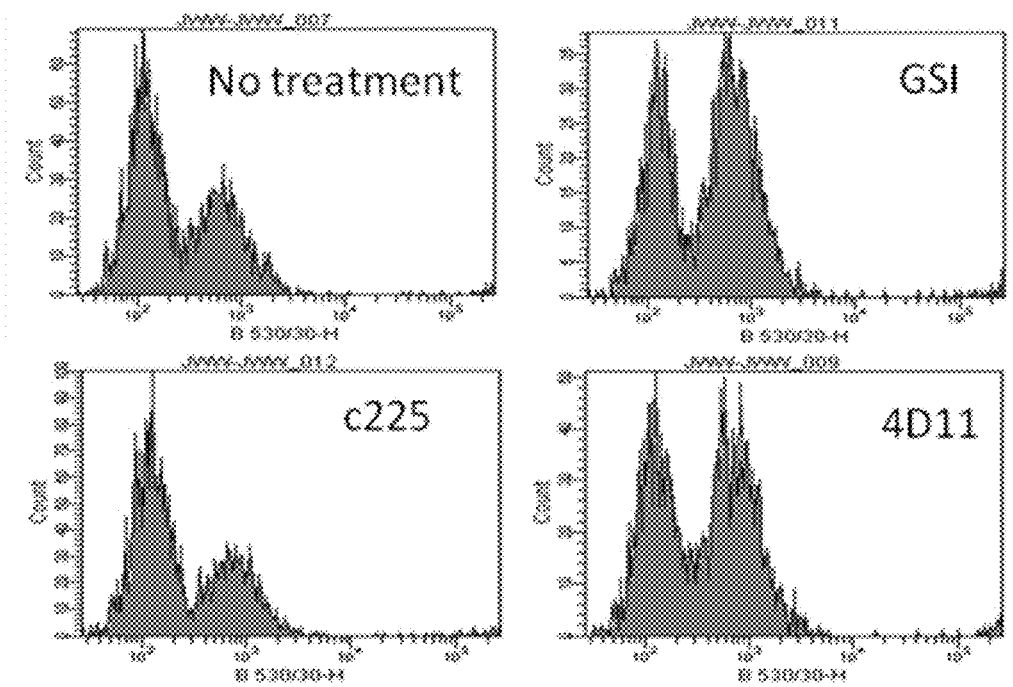
FIG. 8 is a graph depicting the ability of the anti-Jagged 4D11 antibody to inhibit the proliferation of the multiple myeloma cell line RPMI 8226 in co-cultures with human bone marrow.

Results are shown in FIG. 8. Reduced fluorescence, indicating proliferation, was measured in the absence of any treatment or in the presence of anti-EGFR. In contrast, both BMS299897 (GSI) and anti-Jagged 4D11 inhibited the proliferation of CFSE-labeled RPMI 8226.

Example 9

An Anti-Jagged Antibody of the Embodiments Inhibits Development of Fibrosis In Vitro This Example demonstrates that anti-Jagged 4D11 inhibits the development of fibrosis in vitro.

The rat fibroblast cell line NRK-49F (ATCC, Manassas, Va.) responds to human transforming growth factor beta 1 (TGFβ1) by loss of cell-cell contact, elevated production and deposition of collagen, and foci development. NRK-F49 cells were plated at 50,000 cells/well, in a 6-well tissue culture dish and cultured overnight in RPMI-1640, 10% fetal bovine serum (FBS) to allow for attachment and monolayer formation. Medium was removed, and cells were washed twice with RPMI-1640, 1% heat inactivated FBS and cultured overnight in RPMI-1640, 1% heat inactivated FBS. Following overnight incubation, anti-Jagged 4D11, TGFβ1, or the combination of TGFβ1 and anti-Jagged 4D11 was added to cells in culture. Cells were cultured for 5 days and observed for a response to TGFβ1.

Figure 9:
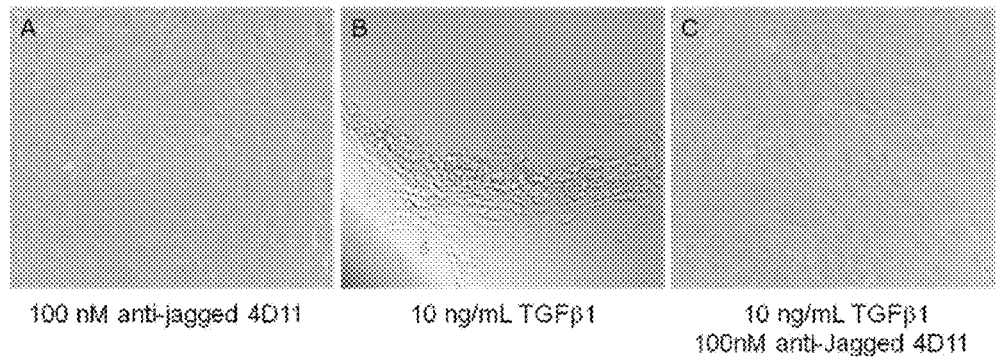
FIGS. 9A, 9B and 9C are a series of photographs depicting the effect of anti-Jagged antibodies on rat fibroblast cell line NRK-49F in the presence or absence of TGFβ1.
Figure 10:
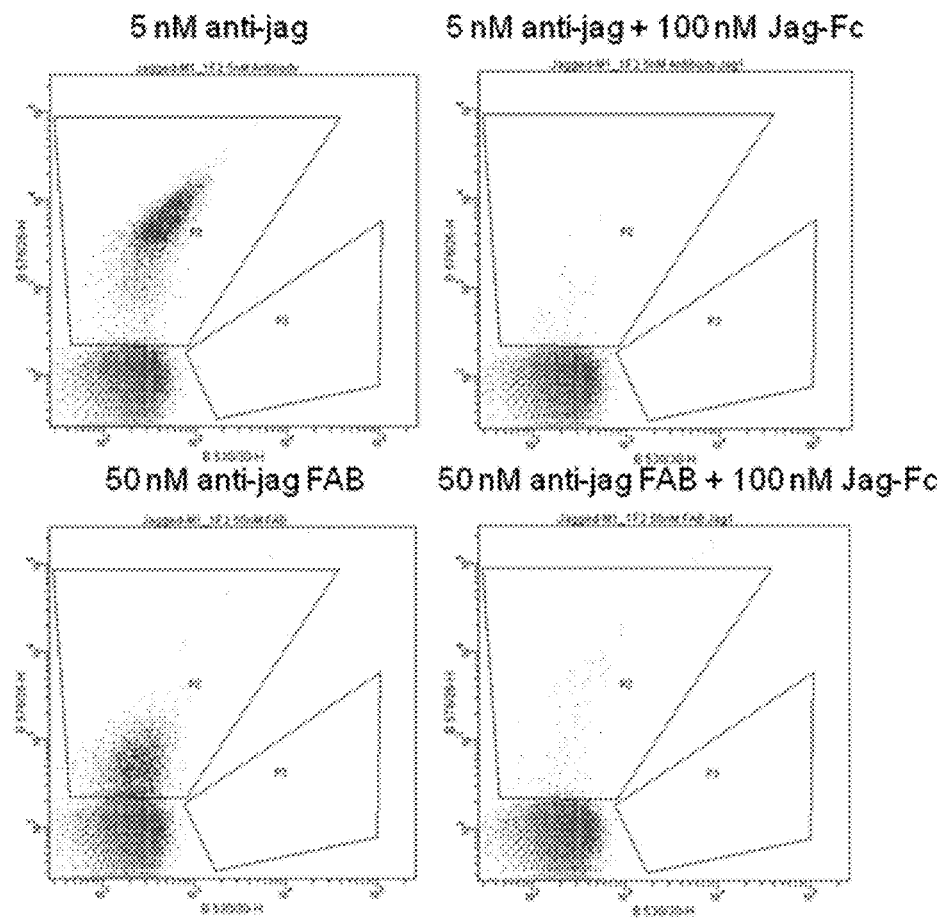
FIG. 10 is a series of illustrations depicting the results of screening a random peptide library in the presence of the anti-Jagged 4D11 antibody and Fab fragment. The screening consisted of one round of MACS and two rounds of FACS sorting. The positive population from the second FACS round was verified to be inhibited by recombinant Jagged protein from binding to the anti-Jagged 4D11 antibody and Fab.

Results are illustrated in FIG. 9. Panel A shows that cultures of NRK-F49 retain a characteristic monolayer when cultured in the presence of 100 nM anti-Jagged 4D11. Panel B shows characteristic foci formation for NRK-F49 cultured in the presence of 10 ng/mL TGFβ1. Panel C shows that TGFb1-stimulated, fibrotic foci formation is completely inhibited by 100 nM anti-Jagged 4D11 in cultures treated with 10 ng/mL TGFβ1.

Example 10

Activatable Anti-Jagged Antibody Masking Moieties

This Example describes identification of masking moieties (MM) to reduce binding of activatable anti-Jagged antibodies to their target.

Anti-Jagged 4D11 antibody and Fab were used to screen a random $X_{15}$ peptide library with a total diversity of $2\times10^{10}$, where X is any amino acid, using a method similar to that described in PCT International Publication Number WO 2010/081173, published 15 Jul. 2010. The screening consisted of one round of MACS and two rounds of FACS sorting. The initial MACS was done with protein-A Dynabeads (Invitrogen) and the anti-Jagged 4D11 antibody at a concentration of 250 nM. For MACS, approximately $1\times10^{11}$ cells were screened for binding and $6\times10^{6}$ cells were collected. StreptAvidin-PE was used as a fluorescent probe for the initial FACS and anti-biotin-PE (Miltenyi) for the second FACS. The biotinylated anti-Jagged 4D11 antibody was used at a concentration of 100 nM and 10 nM in the first and second round of FACS, respectively. The positive population from the second FACS round was verified to be inhibited by recombinant Jagged protein from binding to the anti-Jagged 4D11 antibody and Fab. Individual peptide clones were identified by sequence analysis and subsequently verified for their ability to bind the anti-Jagged 4D11 antibody and Fab, as shown in FIG. 10.

The sequences of the anti-Jagged masking moieties are listed in Table 9.

TABLE 9

| Anti-Jagged masking moieties (MM) | | |
|---|---|---|
| MM | Amino Acid Sequence | SEQ ID NO |
| JS4874 | PWCMQRQDFLRCPQP | SEQ ID NO: 87 |
| JS4879 | QLGLPAYMCTFECLR | SEQ ID NO: 88 |
| JS4896 | CNLWVSGGDCGGLQG | SEQ ID NO: 89 |
| JS4897 | SCSLWTSGSCLPHSP | SEQ ID NO: 90 |
| JS4899 | YCLQLPHYMQAMCGR | SEQ ID NO: 91 |
| JS4906 | CFLYSCTDVSYWNNT | SEQ ID NO: 92 |

Example 11

Affinity Maturation of Anti-Jagged Masking Moieties

This Example describes affinity maturation of anti-Jagged masking moieties.

The anti-Jagged binding peptides JS4874, JS4896, JS4899, and JS4906 were affinity matured by using a soft randomization approach. An eCPX cell display library, such as that described in PCT International Publication Number WO 2009/014726, was constructed with the nucleotide ratios shown in Table 10. Four libraries were constructed: 4874SR, 4896SR, 4899SR, and 4906SR. The final diversity for each library was approximately $5\times10^{9}$.

TABLE 10

| Nucleotide ratios | |
|---|---|
| Original Base | Ratio of Bases |
| G | G = 70%; T = 8%; A = 11%; C = 11% |
| T | T = 70%; G = 8%; A = 11%; C = 11% |
| A | A = 80%; G = 5%; T = 6%; C = 9% |
| C | C = 80%; G = 5%; T = 6%; A = 9% |

Each affinity maturation library was screened separately. An initial MACS round was performed with a number of cells that provided greater than 100× oversampling of the library. All labeling was performed at 4° C. under constant gentle agitation. Cells were labeled with 25 nM anti-Jagged Fab (library 4896SR) or 50 nM anti-Jagged antibody (libraries 4874SR, 4899SR, and 4906SR) and then bound to approximately 500 μg streptavidin or protein-A labeled magnetic beads (Dynabeads Invitrogen). Beads were subsequently washed extensively with PBS containing 0.5% BSA. Approximately $2\times10^{6}$ to $2\times10^{7}$ cells from each library were recovered from the initial MACS round.

Bacterial cells for all FACS rounds were labeled with biotinylated anti-Jagged Fab. The secondary fluorescent label used was either anti-biotin-PE (Miltenyi) or streptavidin-PE (Invitrogen) depending on the observed background binding of secondary label alone. For all FACS rounds, the brightest 2% of positive cells were sorted. For library 4896SR, cells for FACS round 1 (F1) and FACS round 2 (F2) were labeled with 2 nM and 1 nM Fab, respectively. For libraries 4874SR, 4899SR, and 4906SR, cells for F1 were labeled with 100 nM Fab. For the 4874SR library, cells for F2 were labeled with 1 nM Fab while cells for libraries 4899SR and 4906SR were labeled with 10 nM Fab. Sequences from the FACS round 2 from each library are shown in Tables 11 through 14.

TABLE 11

Masking moiety sequences from FACS round 2 of library 4874SR
4874SR M1F2 peptide sequences

| JF5336 | PWCMQRQDYLRCPQP | SEQ ID NO: 93 |
|---|---|---|

TABLE 12

Masking moiety sequences from FACS round 2 of library 4896SR
4896SR M1F2 peptide sequences

| JF5411 | CNLWISGGDCRGLAG | SEQ ID NO: 94 |
|---|---|---|
| JF5416 | CNLWVSGGDCRGVQG | SEQ ID NO: 95 |
| JF5421 | CNLWVSGGDCRGLRG | SEQ ID NO: 96 |
| JF5432 | CNLWISGGDCRGLPG | SEQ ID NO: 97 |
| JF5436 | CNLWVSGGDCRDAPW | SEQ ID NO: 98 |
| JF5439 | CNLWVSGGDCRDLLG | SEQ ID NO: 99 |
| JF5424 | CNLWVSGGDCRGLQG | SEQ ID NO: 100 |
| JS5340 | CNLWLHGGDCRGWQG | SEQ ID NO: 101 |
| JS5342 | CNIWLVGGDCRGWQG | SEQ ID NO: 102 |
| JS5345 | CTTWFCGGDCGVMRG | SEQ ID NO: 103 |
| JS5347 | CNIWGPSVDCGALLG | SEQ ID NO: 104 |
| JS5358 | CNIWVNGGDCRSFEG | SEQ ID NO: 105 |

TABLE 13

Masking moiety sequences from FACS round 2 of library 4899SR
4899SR M1F2 peptide sequences

| JF5366 | YCLNLPRYMQDMCWA | SEQ ID NO: 106 |
|---|---|---|
| JF5372 | YCLALPHYMQADCAR | SEQ ID NO: 107 |

TABLE 14

Masking moiety sequences from FACS round 2 of library 4906SR
4906SR M1F2 peptide sequences

| JF5386 | CFLYSCGDVSYWGSA | SEQ ID NO: 108 |
|---|---|---|
| JF5387 | CYLYSCTDSAFWNNR | SEQ ID NO: 109 |
| JF5388 | CYLYSCNDVSYWSNT | SEQ ID NO: 110 |
| JF5389 | CFLYSCTDVSYW | SEQ ID NO: 111 |
| JF5390 | CFLYSCTDVAYWNSA | SEQ ID NO: 112 |
| JF5391 | CFLYSCTDVSYWGDT | SEQ ID NO: 113 |
| JF5394 | CFLYSCTDVSYWGNS | SEQ ID NO: 114 |

TABLE 14-continued

Masking moiety sequences from FACS round 2 of library 4906SR
4906SR M1F2 peptide sequences

| JF5395 | CFLYSCTDVAYWNNT | SEQ ID NO: 115 |
|---|---|---|
| JF5399 | CFLYSCGDVSYWGNPGLS | SEQ ID NO: 116 |
| JF5402 | CFLYSCTDVAYWSGL | SEQ ID NO: 117 |
| JF5404 | CYLYSCTDGSYWNST | SEQ ID NO: 118 |
| JF5405 | CFLYSCSDVSYWGNI | SEQ ID NO: 119 |
| JF5407 | CFLYSCTDVAYW | SEQ ID NO: 120 |
| JF5409 | CFLYSCTDVSYWGST | SEQ ID NO: 121 |
| JF5410 | CFLYSCTDVAYWGDT | SEQ ID NO: 122 |

Figure 11:
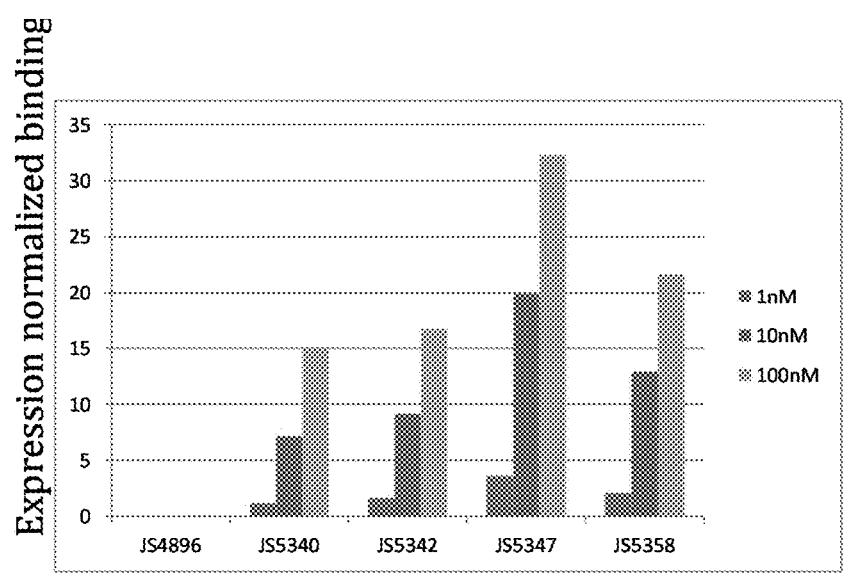
FIG. 11 is a graph that compares binding of anti-Jagged masking moiety JS4896 to binding of affinity matured anti-Jagged masking moieties JS5340, JS5342, JS5347, and JS5358.

The binding of the parental masking moiety peptide JS4896 was compared to the binding of masking moiety peptides selected from the 4896SR library (clones JS5340, JS5342, JS5347, and JS5358). Cells containing the indicated clones were analyzed on FACS at 3 different concentrations of biotinylated anti-Jagged Fab, i.e., 1 nM, 10 nM, 100 nM. Streptavidin-PE was used as a secondary fluorescent label. Peptide expression was quantified by labeling with yPet-MONA using techniques similar to those described in PCT WO 2007/027935. Results are shown in FIG. 11.

Example 12

Activatable Anti-Jagged Antibodies

This Example describes examples of activatable anti-Jagged antibodies of the disclosure.

Activatable anti-Jagged antibodies comprising an anti-Jagged masking moiety, a cleavable moiety, and an anti-Jagged antibody of the disclosure were produced according to methods similar to those described in PCT Publication Nos. WO 2009/025846 and WO 2010/081173. Quality control of the resultant activatable antibodies indicated that most comprised at least 95% monomer. The amino acid and nucleic acid sequences of several activatable anti-Jagged antibodies of the disclosure are provided below.

The nucleic acid and amino acid sequences of the light chains (Lc) of several activatable anti-Jagged antibodies comprising masking moiety JS5342 (also referred to herein as MM 5342 or 5342), a CM that can be cleaved by at least one protease, and the light chain of AB 4D11 are shown below.

5342-1203-4D11 Lc
Amino acid
(SEQ ID NO: 132)
QGQSGQCNIWLVGGDCRGWQGGSSGGSGGSGGTGRGPSWVGGGSDIQMT
QSPSSLSASVGDRVTITCRASQSISSYLNWYQQKPGKAPKLLIYAASSL
QSGVPSRFSGSGSGTDFTLTISSLQPEDFATYYCQQTVVAPPLFGQGTK
VEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGL
SSPVTKSFNRGEC Nucleotide sequence
(SEQ ID NO: 131)
CAAGGCCAGTCTGGCCAATGCAATATTTGGCTCGTAGGTGGTGATTGCA
GGGGCTGGCAGGGGGGCTCGAGCGGTGGCAGCGGTGGCTCTGGTGGTAC
TGGCCGTGGTCCAAGCTGGGTTGGCGGCGGTTCTGACATCCAGATGACC
CAGTCTCCATCCTCCCTGTCTGCATCTGTAGGAGACAGAGTCACCATCA
CTTGCCGGGCAAGTCAGAGCATTAGCAGCTATTTAAATTGGTATCAGCA

```
GAAACCAGGGAAAGCCCCTAAGCTCCTGATCTATGCGGCATCCAGTTTG
CAAAGTGGGGTCCCATCAAGGTTCAGTGGCAGTGGATCTGGGACAGATT
TCACTCTCACCATCAGCAGTCTGCAACCTGAAGATTTTGCAACTTACTA
CTGTCAACAGACGGTTGTGGCGCCTCCGTTATTCGGCCAAGGGACCAAG
GTGGAAATCAAACGTACGGTGGCTGCCACCATCTGTCTTCATCTTCCCGC
CATCTGATGAGCAGTTGAAATCTGGAACTGCCTCTGTTGTGTGCCTGCT
GAATAACTTCTATCCCAGAGAGGCCAAAGTACAGTGGAAGGTGGATAAC
GCCCTCCAATCGGGTAACTCCCAGGAGAGTGTCACAGAGCAGGACAGCA
AGGACAGCACCTACAGCCTCAGCAGCACCCTGACGCTGAGCAAAGCAGA
CTACGAGAAACACAAAGTCTACGCCTGCGAAGTCACCCATCAGGGCCTG
AGCTCGCCCGTCACAAAGAGCTTCAACAGGGGAGAGTGT
```

5342-1204-4D11 Lc
Amino acid sequence
(SEQ ID NO: 134)
QGQSGQCNIWLVGGDCRGWQGGSSGGSGGSGGLSGRSDNHGGGSDIQMT
QSPSSLSASVGDRVTITCRASQSISSYLNWYQQKPGKAPKLLIYAASSL
QSGVPSRFSGSGSGTDFTLTISSLQPEXFATYYCQQTVVAPPLFGQGTK
VEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGL
SSPVTKSFNRGEC Nucleotide sequence
(SEQ ID NO: 133)
```
CAAGGCCAGTCTGGCCAGTGCAATATTTGGCTCGTAGGTGGTGATTGCA
GGGGCTGGCAGGGGGCTCGAGCGGTGGCAGCGGTGGCTCTGGTGGTCT
GAGCGGCCGTTCCGATAATCATGGCGGCGGTTCTGACATCCAGATGACC
CAGTCTCCATCCTCCCTGTCTGCATCTGTAGGAGACAGAGTCACCATCA
CTTGCCGGGCAAGTCAGAGCATTAGCAGCTATTTAAATTGGTATCAGCA
GAAACCAGGGAAAGCCCCTAAGCTCCTGATCTATGCGGCATCCAGTTTG
CAAAGTGGGGTCCCATCAAGGTTCAGTGGCAGTGGATCTGGGACAGATT
TCACTCTCACCATCAGCAGTCTGCAACCTGAAGATTTTGCAACTTACTA
CTGTCAACAGACGGTTGTGGCGCCTCCGTTATTCGGCCAAGGGACCAAG
GTGGAAATCAAACGTACGGTGGCTGCCACCATCTGTCTTCATCTTCCCGC
CATCTGATGAGCAGTTGAAATCTGGAACTGCCTCTGTTGTGTGCCTGCT
GAATAACTTCTATCCCAGAGAGGCCAAAGTACAGTGGAAGGTGGATAAC
GCCCTCCAATCGGGTAACTCCCAGGAGAGTGTCACAGAGCAGGACAGCA
AGGACAGCACCTACAGCCTCAGCAGCACCCTGACGCTGAGCAAAGCAGA
CTACGAGAAACACAAAGTCTACGCCTGCGAAGTCACCCATCAGGGCCTG
AGCTCGCCCGTCACAAAGAGCTTCAACAGGGGAGAGTGT
```

5342-1214-4D11 Lc
Amino acid sequence
(SEQ ID NO: 136)
QGQSGQCNIWLVGGDCRGWQGGSSGGSGGSGGSPLTGRSGGGGSDIQMT
QSPSSLSASVGDRVTITCRASQSISSYLNWYQQKPGKAPKLXIYAASSL
QSGVPSRFSGSGSGTDFTLTISRLQPEDFATYYCQQTVVAPPLFGQGTK
VEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGL
SSPVTKSFNRGEC Nucleotide sequence
(SEQ ID NO: 135)
```
CAAGGCCAGTCTGGCCAGTGCAATATTTGGCTCGTAGGTGGTGATTGCA
GGGGCTGGCAGGGGGCTCGAGCGGTGGCAGCGGTGGCTCTGGTGGCTC
ACCACTGACTGGTCGTTCCGGTGGCGGCGGTTCTGACATCCAGATGACC
CAGTCTCCATCCTCCCTGTCTGCATCTGTAGGAGACAGAGTCACCATCA
CTTGCCGGGCAAGTCAGAGCATTAGCAGCTATTTAAATTGGTATCAGCA
GAAACCAGGGAAAGCCCCTAAGCTCCTGATCTATGCGGCATCCAGTTTG
CAAAGTGGGGTCCCATCAAGGTTCAGTGGCAGTGGATCTGGGACAGATT
TCACTCTCACCATCAGCAGTCTGCAACCTGAAGATTTTGCAACTTACTA
CTGTCAACAGACGGTTGTGGCGCCTCCGTTATTCGGCCAAGGGACCAAG
GTGGAAATCAAACGTACGGTGGCTGCCACCATCTGTCTTCATCTTCCCGC
CATCTGATGAGCAGTTGAAATCTGGAACTGCCTCTGTTGTGTGCCTGCT
GAATAACTTCTATCCCAGAGAGGCCAAAGTACAGTGGAAGGTGGATAAC
GCCCTCCAATCGGGTAACTCCCAGGAGAGTGTCACAGAGCAGGACAGCA
AGGACAGCACCTACAGCCTCAGCAGCACCCTGACGCTGAGCAAAGCAGA
CTACGAGAAACACAAAGTCTACGCCTGCGAAGTCACCCATCAGGGCCTG
AGCTCGCCCGTCACAAAGAGCTTCAACAGGGGAGAGTGT
```

5342-PLGL-4D11 Lc
Amino acid sequence
(SEQ ID NO: 138)
QGQSGQCNIWLVGGDCRGWQGGSSGGSGGSGGSGGGSPLGLGGGSDIQMT
QSPSSLSASVGDRVTITCRASQSISSYLNWYQQKPGKAPKLLIYAASSL
QSGVPSRFSGSGSGTDFTLTISSLQPEDFATYYCQQTVVAPPLFGQGTK
VEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGL
SSPVTKSFNRGEC Nucleotide sequence
(SEQ ID NO: 137)
```
CAAGGCCAGTCTGGCCAGTGCAATATTTGGCTCGTAGGTGGTGATTGCA
GGGGCTGGCAGGGGGCTCGAGCGGTGGCAGCGGTGGCTCTGGTGGCTC
AGGTGGAGGCTCGCCACTGGGCCTGGGCGGTTCTGACATCCAGATGACC
CAGTCTCCATCCTCCCTGTCTGCATCTGTAGGAGACAGAGTCACCATCA
CTTGCCGGGCAAGTCAGAGCATTAGCAGCTATTTAAATTGGTATCAGCA
GAAACCAGGGAAAGCCCCTAAGCTCCTGATCTATGCGGCATCCAGTTTG
CAAAGTGGGGTCCCATCAAGGTTCAGTGGCAGTGGATCTGGGACAGATT
TCACTCTCACCATCAGCAGTCTGCAACCTGAAGATTTTGCAACTTACTA
CTGTCAACAGACGGTTGTGGCGCCTCCGTTATTCGGCCAAGGGACCAAG
GTGGAAATCAAACGTACGGTGGCTGCACCATCTGTCTTCATCTTCCCGC
CATCTGATGAGCAGTTGAAATCTGGAACTGCCTCTGTTGTGTGCCTGCT
GAATAACTTCTATCCCAGAGAGGCCAAAGTACAGTGGAAGGTGGATAAC
GCCCTCCAATCGGGTAACTCCCAGGAGAGTGTCACAGAGCAGGACAGCA
AGGACAGCACCTACAGCCTCAGCAGCACCCTGACGCTGAGCAAAGCAGA
CTACGAGAAACACAAAGTCTACGCCTGCGAAGTCACCCATCAGGGCCTG
AGCTCGCCCGTCACAAAGAGCTTCAACAGGGGAGAGTGT
```

The nucleic acid and amino acid sequences of the light chain of a masked antibody comprising masking moiety 5342, a noncleavable linker, and the light chain of AB 4D11 are shown below:

5342-NSub-4D11 Lc
Amino acid sequence
(SEQ ID NO: 140)
QGQSGQCNIWLVGGDCRGWQGGSSGGSSGSGGSGGGSGGGSGGSDIQMT
QSPSSLSASVGDRVTITCRASQSISSYLNWYQQKPGKAPKLLIYAASSL
QSGVPSRFSGSGSGTDFTLTISSLQPEDFATYYCQQTVVAPPLFGQGTK
VEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGL
SSPVTKSFNRGEC Nucleotide sequence
(SEQ ID NO: 139)
```
CAAGGCCAGTCTGGCCAGTGCAATATTTGGCTCGTAGGTGGTGATTGCA
GGGGCTGGCAGGGGGCTCGAGCGGTGGCAGCAGTGGCTCTGGTGGCTC
AGGTGGAGGCTCGGGCGGTGGGAGCGGCCGGTTCTGACATCCAGATGACC
CAGTCTCCATCCTCCCTGTCTGCATCTGTAGGAGACAGAGTCACCATCA
CTTGCCGGGCAAGTCAGAGCATTAGCAGCTATTTAAATTGGTATCAGCA
GAAACCAGGGAAAGCCCCTAAGCTCCTGATCTATGCGGCATCCAGTTTG
CAAAGTGGGGTCCCATCAAGGTTCAGTGGCAGTGGATCTGGGACAGATT
TCACTCTCACCATCAGCAGTCTGCAACCTGAAGATTTTGCAACTTACTA
CTGTCAACAGACGGTTGTGGCGCCTCCGTTATTCGGCCAAGGGACCAAG
GTGGAAATCAAACGTACGGTGGCTGCACCATCTGTCTTCATCTTCCCGC
CATCTGATGAGCAGTTGAAATCTGGAACTGCCTCTGTTGTGTGCCTGCT
GAATAACTTCTATCCCAGAGAGGCCAAAGTACAGTGGAAGGTGGATAAC
GCCCTCCAATCGGGTAACTCCCAGGAGAGTGTCACAGAGCAGGACAGCA
AGGACAGCACCTACAGCCTCAGCAGCACCCTGACGCTGAGCAAAGCAGA
CTACGAGAAACACAAAGTCTACGCCTGCGAAGTCACCCATCAGGGCCTG
AGCTCGCCCGTCACAAAGAGCTTCAACAGGGGAGAGTGT
```

The nucleic acid and amino acid sequences of several polypeptides including MM 5342 and a CM that can be joined to an anti-Jagged antibody of the disclosure using methods such as those described herein to produce an activatable anti-Jagged antibody of the disclosure are provided below:

5342-Cath.E
Amino acid sequence
(SEQ ID NO: 142)
QGQSGQCNIWLVGGDCRGWQGGSSGGSGGSGGSAGFSLPAGGGS Nucleotide sequence
(SEQ ID NO: 141)
```
CAAGGCCAGTCTGGCCAGTGCAATATTTGGCTCGTAGGTGGTGATTGCA
GGGGCTGGCAGGGGGCTCGAGCGGTGGCAGCGGTGGCTCTGGTGGCTC
AGCTGGCTTCTCCCTCCCCGCAGGTGGCGGTTCT
```

5342-MMP-14
(SEQ ID NO: 144)
QGQSGQCNIWLVGGDCRGWQGGSSGGSGGSGGSLAPLGLQRRGGS

Nucleotide sequence
(SEQ ID NO: 143)
CAAGGCCAGTCTGGCCAGTGCAATATTTGGCTCGTAGGTGGTGATTGCA
GGGGCTGGCAGGGGGGCTCGAGCGGTGGCAGCGGTGGCTCTGGTAGCCT
GGCACCTCTGGGTCTGCAACGCCGTGGCGGTTCT 5342-panMMP
Amino acid sequence
(SEQ ID NO: 146)
QGQSGQCNIWLVGGDCRGWQGGSSGGSGGSGGSGGPLGVRGGGS Nucleotide sequence
(SEQ ID NO: 145)
CAAGGCCAGTCTGGCCAGTGCAATATTTGGCTCGTAGGTGGTGATTGCA
GGGGCTGGCAGGGGGGCTCGAGCGGTGGCAGCGGTGGCTCTGGTGGCTC
AGGTGGACCTTTGGGAGTCAGAGGTGGCGGTTCT The Cathepsin E (Cath E), MMP-14, and panMMP substrates (CMs) used to produce these polypeptides have been reported in the literature: Cruz-Monserrate Z et al., 2011, Gut, doi:10.1136/gutjnl-2011-300544; Abeer J et al., 2011, Chem. Biol. 18, 392-401; Zhu L et al., 2011, Theranostics 1, 18-27.

Examples of antibodies to which such MM and CM containing polypeptides can be joined include anti-Jagged antibody 4D11 or a variant thereof. The amino acid and nucleic acid sequences of the heavy chain of the 4D11 variant, referred to as 4D11 Hc QΔH, are provided below:

4D11 Hc QAH
Amino acid
(SEQ ID NO: 148)
EVHLLESGGGLVQPGGSLRLSCAASGFTFSSYAMSWVRQAPGKGLEWVS
SIDPEGRQTYYADSVKGRFTISRDNSKNTLYLQMNSLRAEDTAVYYCAK
DIGGRSAFDYWGQGTLVTVSSASTKGPSVFPLAPSSKSTSGGTAALGCL
VKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKG
QPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQK
SLSLSPGK Nucleotide
(SEQ ID NO: 147)
GAGGTGCACCTGTTGGAGTCTGGGGGAGGCTTGGTACAGCCTGGGGGGT
CCCTGAGACTCTCCTGTGCAGCCTCTGGATTCACCTTTAGCAGCTATGC
CATGAGCTGGGTCCGCCAGGCTCCAGGGAAGGGGCTGGAGTGGGTGTCA
AGTATTGACCCGGAAGGTCGGCAGACATATTACGCAGACTCCGTGAAGG
GCCGGTTCACCATCTCCAGAGACAATTCCAAGAACACGCTGTATCTGCA
AATGAACAGCCTGAGAGCCGAGGACACGGCCGTATATTACTGTGCGAAA
GACATCGGCGGCAGGTCGGCCTTTGACTACTGGGGCCAGGGAACCCTGG
TCACCGTCTCCTCAGCTAGCACCAAGGGCCCATCGGTCTTCCCCCTGGC
ACCCTCCTCCAAGAGCACCTCTGGGGGCACAGCGGCCCTGGGCTGCCTG
GTCAAGGACTACTTCCCCGAACCGGTGACGGTGTCGTGGAACTCAGGCG
CCCTGACCAGCGGCGTGCACACCTTCCCGGCTGTCCTACAGTCCTCAGG
ACTCTACTCCCTCAGCAGCGTGGTGACCGTGCCCTCCAGCAGCTTGGGC
ACCCAGACCTACATCTGCAACGTGAATCACAAGCCCAGCAACACCAAGG
TGGACAAGAAAGTTGAGCCCAAATCTTGTGACAAAACTCACACATGCCC
ACCGTGCCCAGCACCTGAACTCCTGGGGGGACCGTCAGTCGTTCCTCTTC
CCCCCAAAACCCAAGGACACCCTCATGATCTCCCGGACCCCTGAGGTCA
CATGCGTGGTGGTGGACGTGAGCCACGAAGACCCTGAGGTCAAGTTCAA
CTGGTACGTGGACGGCGTGGAGGTGCATAATGCCAAGACAAAGCCGCGG
GAGGAGCAGTACAACAGCACGTACCGTGTGGTCAGCGTCCTCACCGTCC
TGCACCAGGACTGGCTGAATGGCAAGGAGTACAAGTGCAAGGTCTCCAA
CAAAGCCCTCCCAGCCCCCATCGAGAAAACCATCTCCAAAGCCAAAGGG
CAGCCCCGAGAACCACAGGTGTACACCCTGCCCCCATCCCGGGAGGAGA
TGACCAAGAACCAGGTCAGCCTGACCTGCCTGGTCAAAGGCTTCTATCC
CAGCGACATCGCCGTGGAGTGGGAGAGCAATGGGCAGCCGGAGAACAAC
TACAAGACCACGCCTCCCGTGCTGGACTCCGACGGCTCCTTCTTCCTCT
ACAGCAAGCTCACCGTGGACAAGAGCAGGTGGCAGCAGGGGAACGTCTT
CTCATGCTCCGTGATGCATGAGGCTCTGCACAACCACTACACGCAGAAG
AGCCTCTCCCTGTCTCCGGGTAAA

Example 13

In Vitro Characterization of Activatable Anti-Jagged Antibodies

This Example describes the ability of a masking moiety of the disclosure to reduce the ability of activatable anti-Jagged antibodies comprising such a masking moiety to bind to a Jagged target. This Example also describes proteolytic activation of such activatable antibodies.

Figure 12:
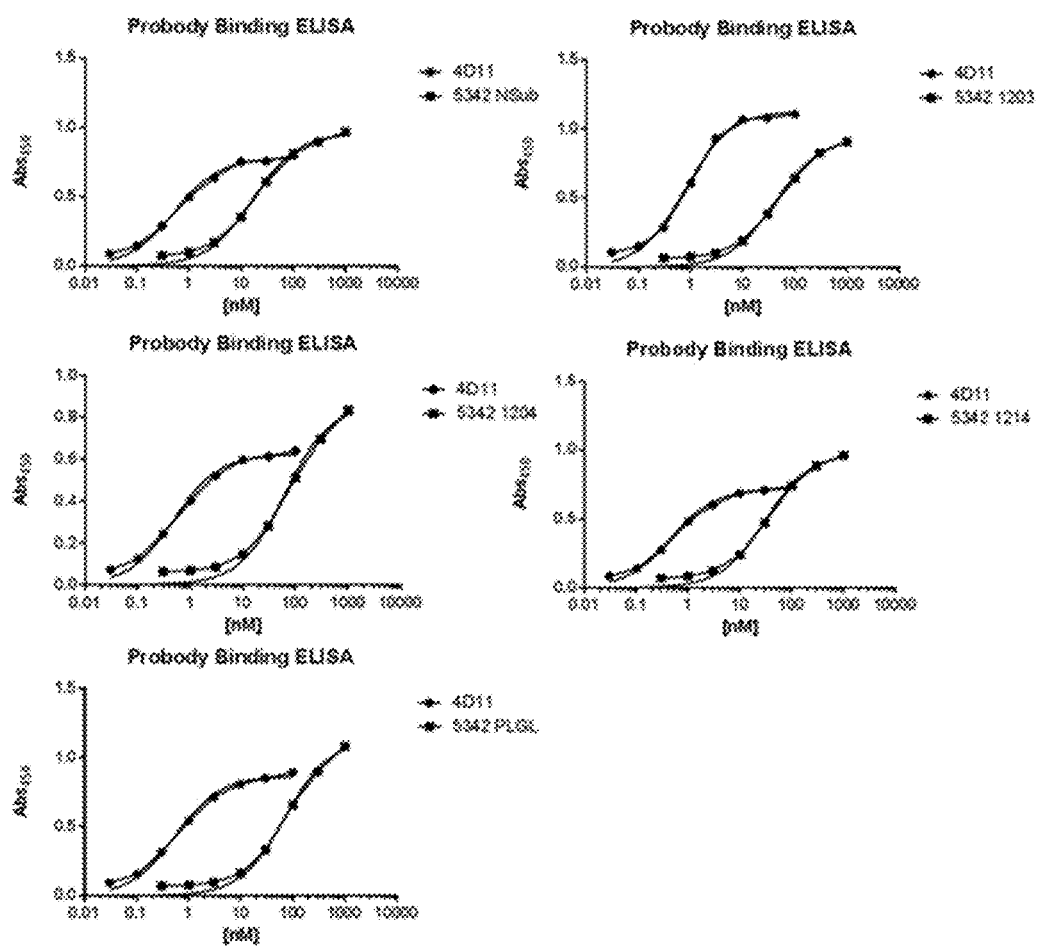
FIG. 12 is a series of graphs depicting the ability of MM 5342 to inhibit binding of activatable anti-Jagged antibodies and an anti-Jagged masked antibody to a Jagged target in an in vitro binding ELISA.

The abilities of activatable antibodies 5342-1203-4D11, 5342-1204-4D11, 5342-1214-4D11, and 5342-PLGL-4D11, as well as masked antibody 5342-NSub-4D11, to bind to a human Jagged 1 target were compared to the ability of anti-Jagged antibody 4D11 to bind to the same target in an in vitro binding assay as described herein. The ability of MM 5342 to inhibit such target binding is demonstrated in FIG. 12 and Table 15.

TABLE 15

Comparison of Jagged target binding by anti-Jagged antibody 4D11 and by a masked antibody and activatable antibodies thereof. Fold masking calculated as ($K_D$ apparent for activatable antibody/$K_D$ apparent for antibody 4D11).

| | Fold masking |
|---|---|
| Activatable antibody | |
| 5342-1203-4D11 | 52.7 |
| 5342-1204-4D11 | 127.0 |
| 5342-1214-4D11 | 64.7 |
| 5342-PLGL-4D11 | 131.7 |
| Masked antibody | |
| 5342-NSub-4D11 | 31.2 |

Figure 13:
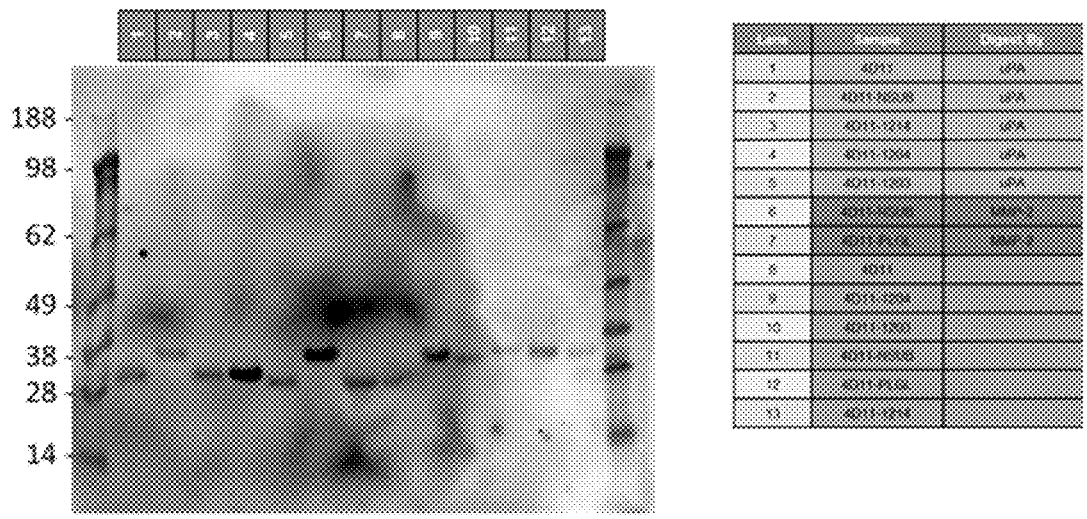
FIG. 13 is a photograph and a table depicting proteolytic activation of activatable anti-Jagged antibodies.

Activatable anti-Jagged antibodies 5342-1203-4D11, 5342-1204-4D11, 5342-1214-4D11, and 5342-PLGL-4D11, as well as masked antibody 5342-NSub-4D11, were assessed for their abilities to be cleaved by proteases. Briefly, 250 ng of activatable antibody was digested by 1 uM uPA or 387 nM MMP-2 for 24 hours at 37° C. in the appropriate buffer (for uPA: 0.1M Tris pH 8.0 in HBSS; for MMP-2: TCNB (50 mM Tris, 150 mM NaCl, 0.05% Brij, 10 mM CaCl2, pH 9.5)). The digested material was subsequently analyzed by SDS-PAGE and western blotting, using goat anti-human IgG Fab'2 HRP as a detection agent. FIG. 13 demonstrates that proteolytic digestion yielded a protein with a mobility similar to that of the parental (i.e., antibody 4D11) light chain, indicating that the respective activatable antibodies were cleaved with uPA or MMP-2 proteases, respectively.

Example 14

In Vivo Characterization of Activatable Anti-Jagged Antibodies

This Example describes the in vivo efficacy and safety of activatable anti-Jagged antibodies of the disclosure in a mouse BxPC3 tumor model.

Figure 14:
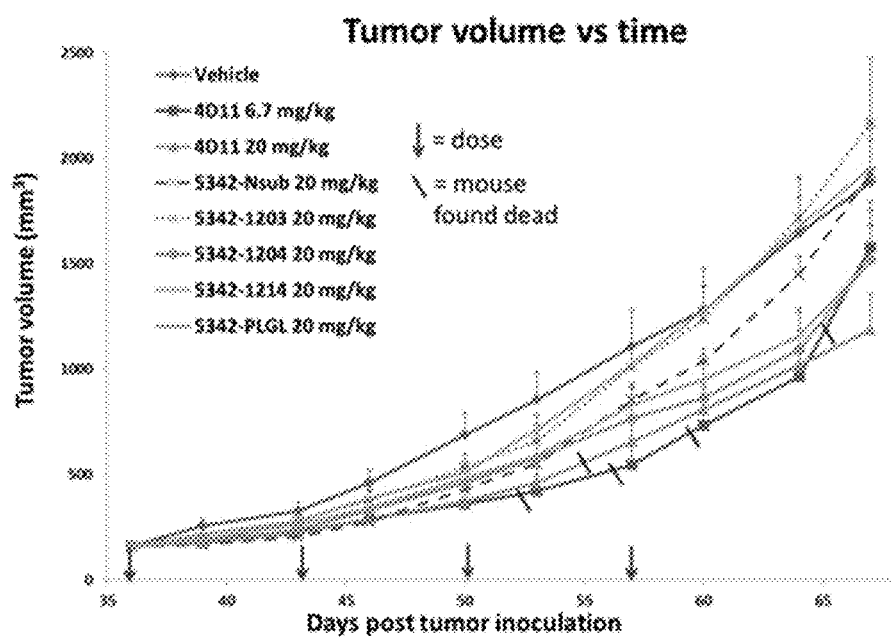
FIG. 14 is a graph depicting that activatable anti-Jagged antibodies inhibited the growth of BxPC-3 xenograft tumors in mice, as did anti-Jagged antibody 4D11 (parental antibody). The graph is plotted as tumor volume versus number of days post initial dose.
Figure 15:
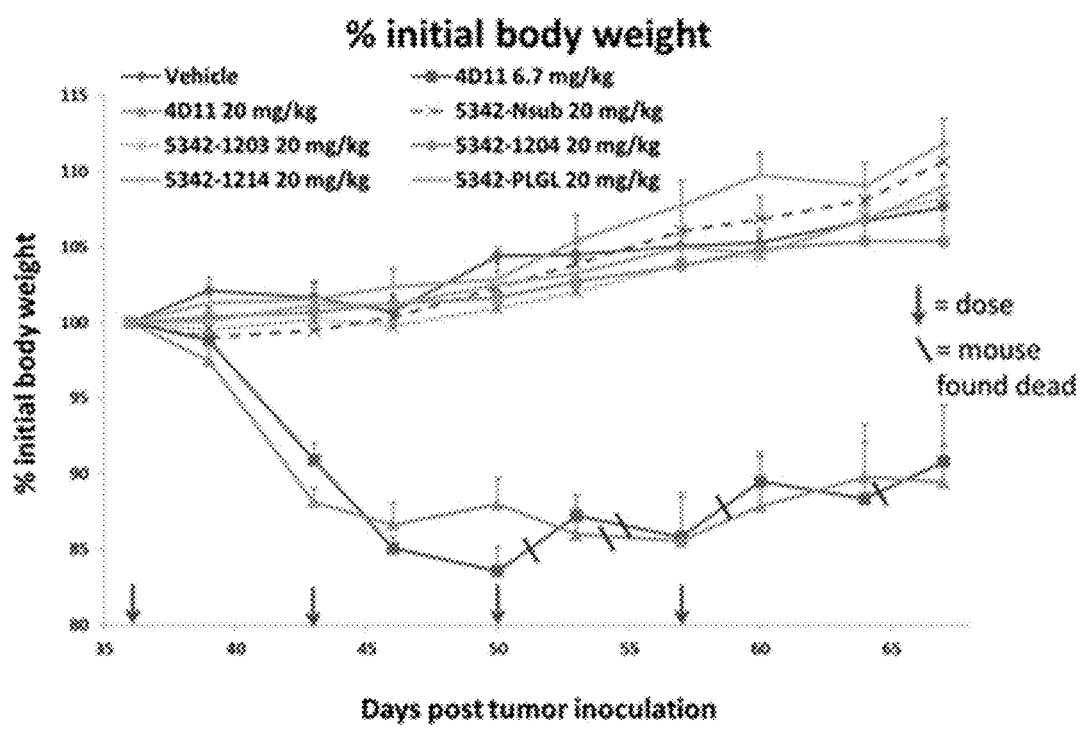
FIG. 15 is a graph depicting a comparison of weight loss of mice that were administered activatable anti-Jagged antibodies, masked antibody, or parental antibody.
Figure 16A:
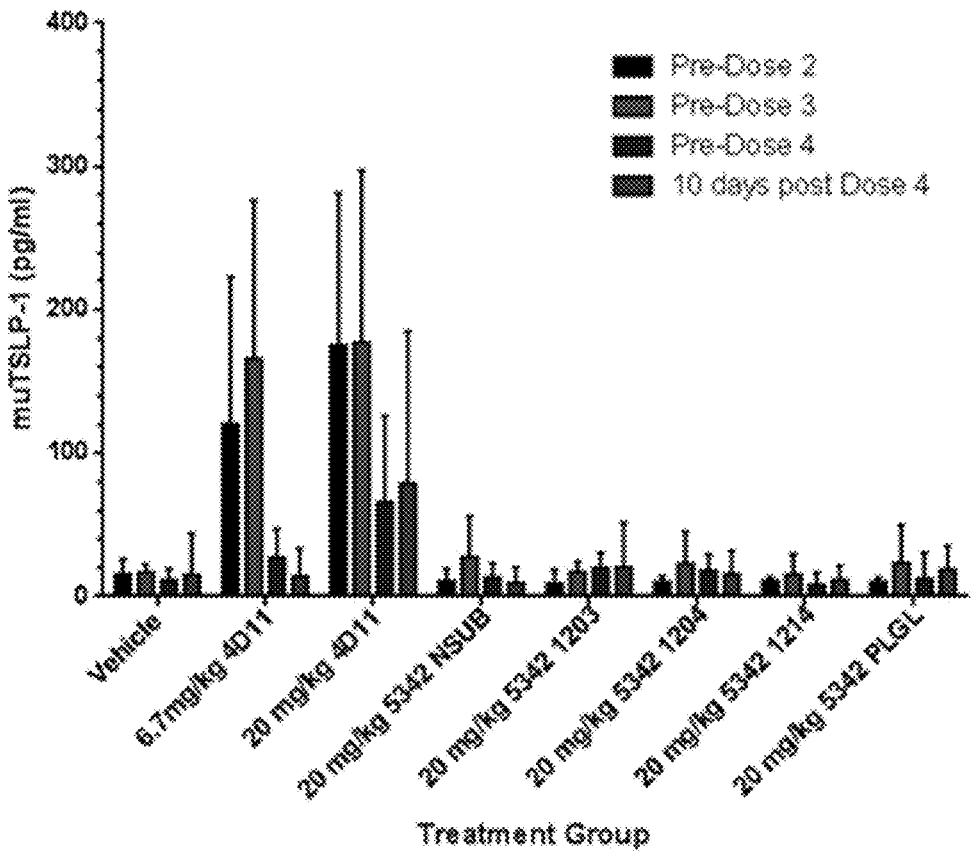
FIG. 16A is a graph depicting the serum levels of mouse TSLP, where the serum level of mouse TSLP was quantified for individual mice before each dose and 10 days after the final dose from each group and was then averaged.

Activatable anti-Jagged antibodies 5342-1203-4D11, 5342-1204-4D11, 5342-1214-4D11, and 5342-PLGL-4D11, as well as masked antibody 5342-NSub-4D11, were tested for their abilities to reduce the growth of BxPC3 xenograft tumors implanted into mice, using a method similar to that described herein. Also tested was the ability of these activatable and masked antibodies to reduce weight loss in such a tumor model compared to weight loss caused by anti-Jagged antibody 4D11. The groups, doses, dosing route, and dosing schedule are set forth in Table 16. Efficacy results (reduction in tumor size) are shown in FIG. 14. Safety results (reduction in weight loss) are shown in FIG. 15. Serum concentrations of mouse thymic stromal lymphopoietin (TSLP) are shown in FIG. 16A.

TABLE 16

Groups and doses for the activatable anti-Jagged antibody BxPC3 efficacy study

| Group | N | Treatment | Dose (mg/kg) | Dosing Route | Schedule |
|---|---|---|---|---|---|
| 1 | 8 | PBS | NA | i.p. | q7dx 4 |
| 2 | 8 | 4D11 | 6.7 mg/kg | i.p. | q7dx 4 |
| 3 | 8 | 4D11 | 20 mg/kg | i.p. | q7dx 4 |
| 4 | 8 | 5342-NSub-4D11 | 20 mg/kg | i.p. | q7dx 4 |
| 5 | 8 | 5342-1203-4D11 | 20 mg/kg | i.p. | q7dx 4 |
| 6 | 8 | 5342-1204-4D11 | 20 mg/kg | i.p. | q7dx 4 |
| 7 | 8 | 5342-1214-4D11 | 20 mg/kg | i.p. | q7dx 4 |
| 8 | 8 | 5342-PLGL-4D11 | 20 mg/kg | i.p. | q7dx 4 |

FIG. 14, which plots tumor volume versus number of days post initial dose, demonstrates that activatable anti-Jagged antibodies inhibited the growth of BxPC-3 xenograft tumors in mice, as did anti-Jagged antibody 4D11 (parental antibody).

FIG. 15 compares weight loss of mice administered activatable anti-Jagged antibodies, masked antibody, or parental antibody. While the animals dosed with parental antibody 4D11 showed significant weight loss, animals dosed with an activatable anti-Jagged antibody showed no significant weight loss.

Figure 16B:
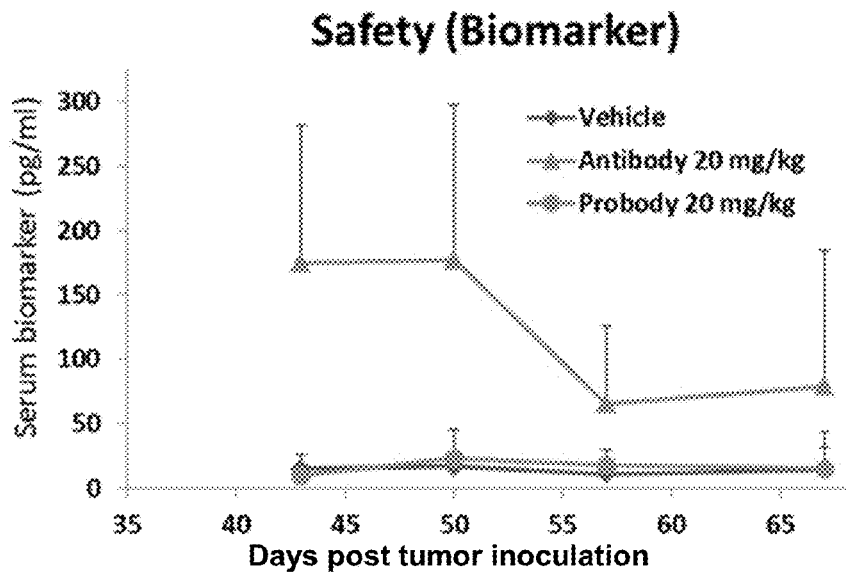
FIG. 16B depicts a time course of TSLP serum concentrations for anti-Jagged antibody 4D11 and activatable anti-Jagged antibody 5342-1204-4D11.

Serum concentrations of mouse thymic stromal lymphopoietin (TSLP) were measured as described herein. The serum levels of mouse TSLP was quantified for individual mice before each dose and 10 days after the final dose from each group and averaged to generate FIG. 16A. FIG. 16B depicts a time course of TSLP serum concentrations for anti-Jagged antibody 4D11 and activatable anti-Jagged antibody 5342-1204-4D11. Serum mouse TSLP is elevated in the parenteral anti-Jagged antibody 4D11 groups compared to serum mouse TSLP levels in the groups administered activatable anti-Jagged antibodies.

Example 15

Pharmacokinetic Data of Activatable Anti-Jagged Antibodies

This Example compares the pharmacokinetics of anti-Jagged parental and activatable antibodies in the sera of mice administered such antibodies.

Single dose pharmacokinetics in non-tumor-bearing female Balb/c nude mice administered anti-Jagged antibody 4D11 or activatable anti-Jagged antibody 5342-1204-4D11 were evaluated. The mice were dosed as outlined in Table 17. Cohorts of five mice were bled in rotation at 0.5, 3, 8, 24, 72, 168, and 240 hrs. Plasma samples were analyzed for hIgG content using an anti-hFc capture with subsequent detection with an anti-hIgG Fab'2 HRP conjugate.

TABLE 17

Groups and doses for the study comparing pharmacokinetics of parental and activatable anti-Jagged antibodies.

| Group | Count | Treatment | Dose (mg/kg) | Route |
|---|---|---|---|---|
| 1 | 20 | 4D11 | 6.7 mg/kg | IP |
| 2 | 20 | 5342-1204-4D11 | 6.7 mg/kg | IP |

Figure 17:
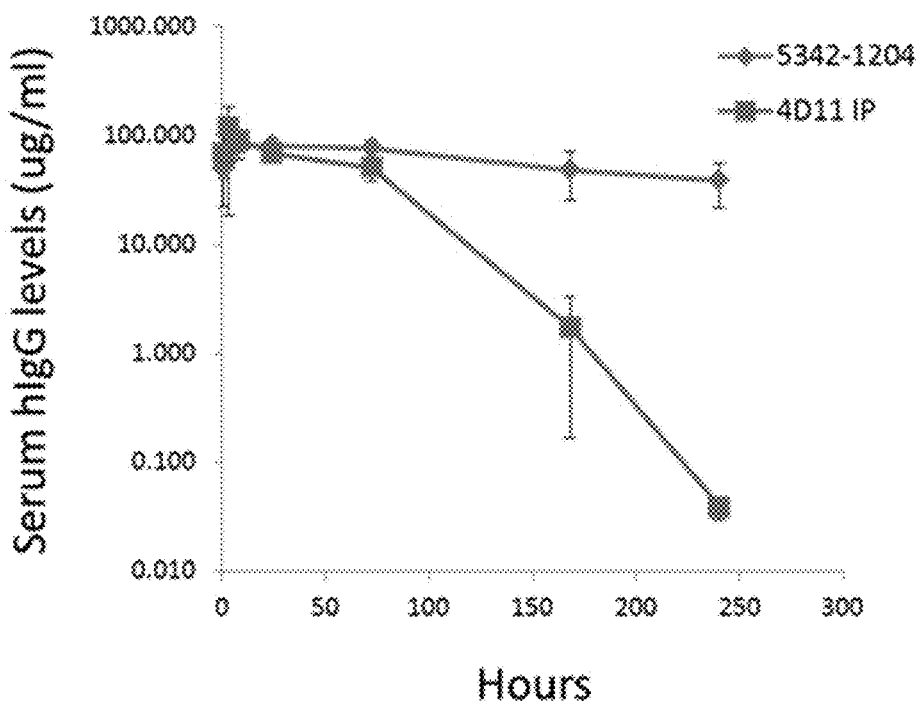
FIG. 17 compares the average human IgG levels over time in the sera of mice administered activatable anti-Jagged antibody 5342-1204-4D11 or anti-Jagged antibody 4D11.

FIG. 17 compares the average human IgG levels over time in the sera of mice following intraperitoneal administration of activatable anti-Jagged antibody 5342-1204-4D11 (also referred to herein as 5342-1204) or anti-Jagged antibody 4D11. Mice administered anti-Jagged antibody 4D11 intravenously showed similar human IgG levels over time as mice administered the same antibody intraperitoneally.

Table 18 provides a preliminary noncompartmental analysis through day 7. The data were analyzed using Phoenix WinNonlin version 6.3, sparse sampling mode.

TABLE 18

Anti-Jagged pharmacokinetics (PK) study preliminary noncompartmental analysis through day 7.

| Group | Half life hr | Tmax hr | Cmax ug/mL | AUClast hr * ug/mL | SE_AUClast hr * ug/mL |
|---|---|---|---|---|---|
| 4D11 | 28 | 3 | 118 | 7,431 | 432 |
| 5342-1204 | 187 | 8 | 81 | 11,613 | 690 |

Example 16

Additional Maturation of Anti-Jagged Masking Moieties

This Example describes the production of additional anti-Jagged masking moieties of the disclosure.

To further affinity mature masking moiety peptide family JS4896 (also referred to herein as MM 4896 or 4896), the sequences from the SR library screens described above were used to design four directed affinity maturation libraries. An eCPX cell display library, such as that described in PCT International Publication Number WO 2009/014726, was constructed with the nucleotide sequence shown in Table 19. The final diversity for each library was approximately $5 \times 10^9$ cells.

TABLE 19

Peptide family 4896-directed library designs

| Name | Library design (nucleotides) |
|---|---|
| 1517/1519 | TGCAATMTKTGGVBCNNKGGTGGTGATTGCCGCGG GTGGNNKNNKNNKNNKNNK (SEQ ID NO: 149) |
| 1518/1521 | NNKNNKNNKNNKTGCAATMTKTGGVBCNNKGGTGGT GATTGCCGCGGGTGGNNK (SEQ ID NO: 150) |
| 1559 | TGCAATMTKTGGVBCNNKGGTGGTGATTGCCGCNNKN NKNNKNNKNNK (SEQ ID NO: 151) |
| 1561 | NNKNNKNNKNNKTGCAATMTKTGGVBCNNKGGTG GTGATTGCCGCNNK (SEQ ID NO: 152) |

Libraries 1517/1519 and 1518/1521

Each affinity maturation library was screened separately but in the same manner. An initial MACS round was performed with a number of cells that provided greater than 100× oversampling of the library. All labeling was performed at 4° C. under constant gentle agitation. Cells were labeled with 25 nM Fab 4D11 labeled with biotin. Cells that bound to the Fab were captured using streptavidin-labeled magnetic beads (Dynabeads, Invitrogen). Beads were subsequently washed extensively with PBS containing 0.5% BSA. Approximately 1×10$^6$ cells from each library were recovered from the initial MACS round.

Bacterial cells for all FACS rounds were labeled with DyLight-488 labeled anti-Jagged Fab 4D11 (i.e., the Fab of anti-Jagged IgG antibody 4D11). For all FACS rounds, the brightest 0.1% to 0.2% of positive cells were sorted. Cells for FACS round 1 (F1) and FACS round 2 (F2) were labeled with 1 nM and 100 pM Fab 4D11, respectively. For FACS rounds 3 and 4, cells were labeled with 1 nM DyLight-labeled anti-Jagged Fab 4D11, resuspended in 500 µl PBS and incubated at 37° C. for between 5 and 10 minutes before sorting. The clones that were sorted in FACS round 4 were sequenced and the results are shown in Tables 20 and 21.

TABLE 20

Anti-Jagged masking moieties (MM)
4896 directed library 1517/1519 peptide sequences

| JS5872 | GCNIWLNGGDCRGWVDPLQG (SEQ ID NO: 153) |
| JS5877 | GCNIWLVGGDCRGWIGDTNG (SEQ ID NO: 154) |
| JS5885 | GCNIWLVGGDCRGWIEDSNG (SEQ ID NO: 155) |
| JS5887 | GCNIWANGGDCRGWIDNIDG (SEQ ID NO: 156) |
| JS5937 | GCNIWLVGGDCRGWLGEAVG (SEQ ID NO: 157) |
| JS5954 | GCNIWLVGGDCRGWLEEAVG (SEQ ID NO: 158) |

TABLE 21

Anti-Jagged masking moieties (MM)
4896 directed library 1518/1521 peptide sequences

| JS5892 | GGPALCNIWLNGGDCRGWSG (SEQ ID NO: 159) |
| JS5893 | GAPVFCNIWLNGGDCRGWMG (SEQ ID NO: 160) |
| JS5894 | GQQQWCNIWINGGDCRGWNG (SEQ ID NO: 161) |
| JS5899 | GKSEFCNIWLNGGDCRGWIG (SEQ ID NO: 162) |
| JS5902 | GTPGGCNIWANGGDCRGWEG (SEQ ID NO: 163) |
| JS5908 | GASQYCNLWINGGDCRGWRG (SEQ ID NO: 164) |

Figure 18:
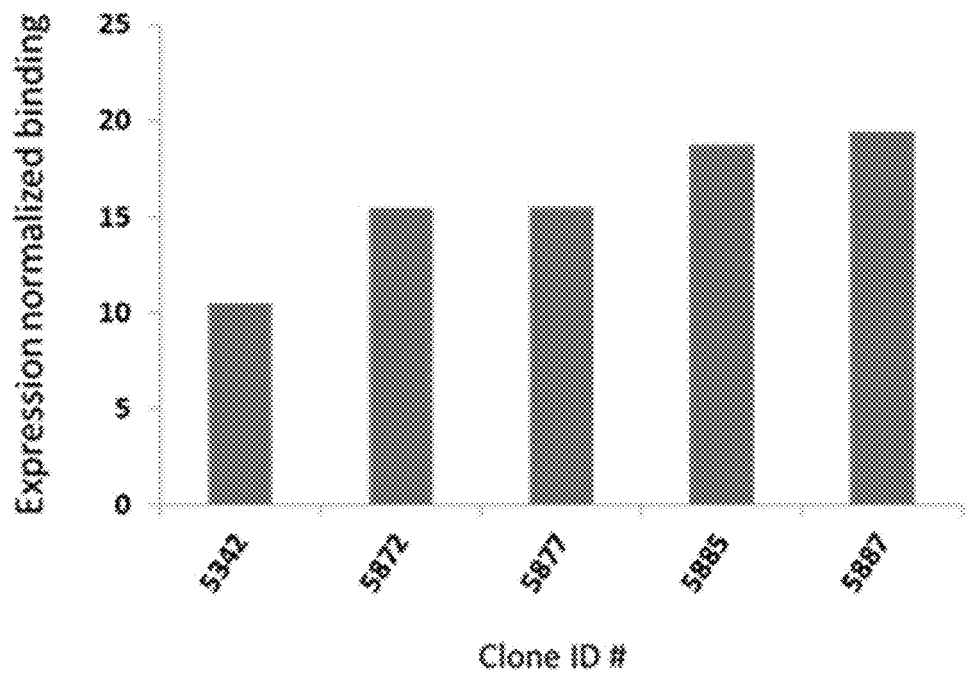
FIG. 18 is a graph depicting on cell expression normalized binding to the anti-Jagged Fab 4D11.

Individual clones were evaluated by FACS for Fab binding. An example is shown in FIG. 18. The clones expressing masking moieties from the directed libraries (MM 5872, 5877, 5885, and 5887) bound the Fab 4D11 better than a single clone expressing MM 5342 from the SR library sorts. Libraries 1559 and 1561

Affinity maturation libraries 1559 and 1561 were screened separately but in the same manner. An initial MACS round was performed as above but with 50 nM Fab 4D11 labeled with biotin. Approximately 1×10$^6$ cells from each library were recovered from the initial MACS round.

Bacterial cells for all FACS rounds were labeled with DyLight-488 labeled anti-Jagged Fab 4D11. For all FACS rounds, the brightest 0.2% of positive cells were sorted. Cells for FACS round 1 (F1) and FACS round 2 (F2) were labeled with 1 nM Fab 4D11. For FACS rounds 3 and 4, cells were labeled with 1 nM DyLight-labeled anti-Jagged Fab 4D11, resuspended in 500 µl PBS and incubated at 37° C. for between 5 and 10 minutes before sorting. The clones that were sorted in FACS round 4 were sequenced, and the results are shown in Tables 22 and 23.

TABLE 22

Anti-Jagged masking moieties (MM)
4896-directed library 1559 peptide sequences

| JS6094 | GCNIWLVGGDCRPWVEGG (SEQ ID NO: 165) |
| JS6095 | GCNIWAVGGDCRPFVDGG (SEQ ID NO: 166) |
| JS6097 | GCNIWLNGGDCRAWVDTG (SEQ ID NO: 167) |
| JS6098 | GCNIWIVGGDCRPFINDG (SEQ ID NO: 168) |
| JS6099 | GCNIWLNGGDCRPVVFGG (SEQ ID NO: 169) |
| JS6101 | GCNIWLSGGDCRMFMNEG (SEQ ID NO: 170) |
| JS6104 | GCNIWVNGGDCRSFVYSG (SEQ ID NO: 171) |
| JS6108 | GCNIWLNGGDCRGWEASG (SEQ ID NO: 172) |
| JS6110 | GCNIWAHGGDCRGFIEPG (SEQ ID NO: 173) |
| JS6112 | GCNIWLNGGDCRTFVASG (SEQ ID NO: 174) |
| JS6116 | GCNIWAHGGDCRGFIEPG (SEQ ID NO: 175) |

TABLE 23

Anti-Jagged masking moieties (MM)
4896 directed library 1561 peptide sequences

| JS6118 | GFLENCNIWLNGGDCRTG (SEQ ID NO: 176) |
| JS6119 | GIYENCNIWLNGGDCRMG (SEQ ID NO: 177) |
| JS6126 | GIPDNCNIWINGGDCRYG (SEQ ID NO: 178) |

Example 17

Additional Activatable Anti-Jagged Antibodies

This Example describes additional examples of activatable anti-Jagged antibodies of the disclosure.

The nucleic acid and amino acid sequences of several polypeptides including masking moiety JS5894 (also referred to herein as MM 5894 or 5894) and a CM that can be joined to an anti-Jagged antibody of the disclosure using methods such as those described herein to produce an activatable anti-Jagged antibody of the disclosure are provided below:

Mask 5894 that also includes a 6-amino acid
N-terminal spacer

Amino acid sequence
(SEQ ID NO: 180)
QGQSGQGQQQWCNIWINGGDCRGWNG

Nucleic acid sequence
(SEQ ID NO: 179)
CAAGGCCAGTCTGGCCAGGGTCAGCAGCAGTGGTGCAATATTTGGATCAA
TGGTGGTGATTGCCGCGGGTGGAATGGT 5894-1203
Amino acid sequence
(SEQ ID NO: 182)
QGQSGQGQQQWCNIWINGGDCRGWNGGSSGGSGGSGGTGRGPSWVGGGS

Mask 5894 that also includes a 6-amino acid N-terminal spacer

Nucleotide sequence
(SEQ ID NO: 181)
CAAGGCCAGTCTGGCCAGGGTCAGCAGCAGTGGTGCAATATTTGGATCAA
TGGTGGTGATTGCCGCGGGTGGAATGGTGGCTCGAGCGGTGGCAGCGGTG
GCTCTGGTGGTACTGGCCGTGGTCCAAGCTGGGTTGGCGGCGGTTCT 5894-1203-4D11 Lc
Amino acid sequence
(SEQ ID NO: 263)
QGQSGQGQQQWCNIWINGGDCRGWNGGSSGGSGGSGGTGRGPSWVGGGSD
IQMTQSPSSLSASVGDRVTITCRASQSISSYLNWYQQKPGKAPKLLIYAA
SSLQSGVPSRFSGSGSGTDFTLTISSLQPEDFATYYCQQTVVAPPLFGQG
TKVEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGL
SSPVTKSFNRGEC Nucleotide sequence
(SEQ ID NO: 264)
CAAGGCCAGTCTGGCCAGGGTCAGCAGCAGTGGTGCAATATTTGGATCAA
TGGTGGTGATTGCCGCGGGTGGAATGGTGGCTCGAGCGGTGGCAGCGGTG
GCTCTGGTGGTACTGGCCGTGGTCCAAGCTGGGTTGGCGGCGGTTCTGAC
ATCCAGATGACCCAGTCTCCATCCTCCCTGTCTGCATCTGTAGGAGACAG
AGTCACCATCACTTGCCGGGCAAGTCAGAGCATTAGCAGCTATTTAAATT
GGTATCAGCAGAAACCAGGGAAAGCCCCTAAGCTCCTGATCTATGCGGCA
TCCAGTTTGCAAAGTGGGGTCCCATCAAGGTTCAGTGGCAGTGGATCTGG
GACAGATTTCACTCTCACCATCAGCAGTCTGCAACCTGAAGATTTTGCAA
CTTACTACTGTCAACAGACGGTTGTGGCGCCTCCGTTATTCGGCCAAGGG
ACCAAGGTGGAAATCAAACGTACGGTGGCTGCACCATCTGTCTTCATCTT
CCCGCCATCTGATGAGCAGTTGAAATCTGGAACTGCCTCTGTTGTGTGCC
TGCTGAATAACTTCTATCCCAGAGAGGCCAAAGTACAGTGGAAGGTGGAT
AACGCCCTCCAATCGGGTAACTCCCAGGAGAGTGTCACAGAGCAGGACAG
CAAGGACAGCACCTACAGCCTCAGCAGCACCCTGACGCTGAGCAAAGCAG
ACTACGAGAAACACAAAGTCTACGCCTGCGAAGTCACCCATCAGGGCCTG
AGCTCGCCCGTCACAAAGAGCTTCAACAGGGGAGAGTGT 5894-1204
Amino acid sequence
(SEQ ID NO: 184)
QGQSGQGQQQWCNIWINGGDCRGWNGGSSGGSGGSGGLSGRSDNHGGGS Nucleotide sequence
(SEQ ID NO: 183)
CAAGGCCAGTCTGGCCAGGGTCAGCAGCAGTGGTGCAATATTTGGATCAA
TGGTGGTGATTGCCGCGGGTGGAATGGTGGCTCGAGCGGTGGCAGCGGTG
GCTCTGGTGGTCTGAGCGGCCGTTCCGATAATCATGGCGGCGGTTCT 5894-1204-4D11 Lc
Amino acid sequence
(SEQ ID NO: 265)
QGQSGQGQQQWCNIWINGGDCRGWNGGSSGGSGGSGGLSGRSDNHGGGSD
IQMTQSPSSLSASVGDRVTITCRASQSISSYLNWYQQKPGKAPKLLIYAA
SSLQSGVPSRFSGSGSGTDFTLTISSLQPEDFATYYCQQTVVAPPLFGQG
TKVEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGL
SSPVTKSFNRGEC Nucleotide sequence
(SEQ ID NO: 266)
CAAGGCCAGTCTGGCCAGGGTCAGCAGCAGTGGTGCAATATTTGGATCAA
TGGTGGTGATTGCCGCGGGTGGAATGGTGGCTCGAGCGGTGGCAGCGGTG
GCTCTGGTGGTCTGAGCGGCCGTTCCGATAATCATGGCGGCGGTTCTGAC
ATCCAGATGACCCAGTCTCCATCCTCCCTGTCTGCATCTGTAGGAGACAG
AGTCACCATCACTTGCCGGGCAAGTCAGAGCATTAGCAGCTATTTAAATT
GGTATCAGCAGAAACCAGGGAAAGCCCCTAAGCTCCTGATCTATGCGGCA
TCCAGTTTGCAAAGTGGGGTCCCATCAAGGTTCAGTGGCAGTGGATCTGG
GACAGATTTCACTCTCACCATCAGCAGTCTGCAACCTGAAGATTTTGCAA
CTTACTACTGTCAACAGACGGTTGTGGCGCCTCCGTTATTCGGCCAAGGG
ACCAAGGTGGAAATCAAACGTACGGTGGCTGCACCATCTGTCTTCATCTT
CCCGCCATCTGATGAGCAGTTGAAATCTGGAACTGCCTCTGTTGTGTGCC
TGCTGAATAACTTCTATCCCAGAGAGGCCAAAGTACAGTGGAAGGTGGAT
AACGCCCTCCAATCGGGTAACTCCCAGGAGAGTGTCACAGAGCAGGACAG
CAAGGACAGCACCTACAGCCTCAGCAGCACCCTGACGCTGAGCAAAGCAG
ACTACGAGAAACACAAAGTCTACGCCTGCGAAGTCACCCATCAGGGCCTG
AGCTCGCCCGTCACAAAGAGCTTCAACAGGGGAGAGTGT 5894-1214
Amino acid sequence
(SEQ ID NO: 186)
QGQSGQGQQQWCNIWINGGDCRGWNGGSSGGSGGSGGSGGSPLTGRSGGGGS Nucleotide sequence
(SEQ ID NO: 185)
CAAGGCCAGTCTGGCCAGGGTCAGCAGCAGTGGTGCAATATTTGGATCAA
TGGTGGTGATTGCCGCGGGTGGAATGGTGGCTCGAGCGGTGGCAGCGGTG
GCTCTGGTGGCTCACCACTGACTGGTCGTTCCGGTGGCGGCGGTTCT 5894-1214-4D11 Lc
Amino acid sequence
(SEQ ID NO: 267)
QGQSGQGQQQWCNIWINGGDCRGWNGGSSGGSGGSGGSGGSPLTGRSGGGGSD
IQMTQSPSSLSASVGDRVTITCRASQSISSYLNWYQQKPGKAPKLLIYAA
SSLQSGVPSRFSGSGSGTDFTLTISSLQPEDFATYYCQQTVVAPPLFGQG
TKVEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGL
SSPVTKSFNRGEC Nucleotide sequence
(SEQ ID NO: 268)
CAAGGCCAGTCTGGCCAGGGTCAGCAGCAGTGGTGCAATATTTGGATCAA
TGGTGGTGATTGCCGCGGGTGGAATGGTGGCTCGAGCGGTGGCAGCGGTG
GCTCTGGTGGCTCACCACTGACTGGTCGTTCCGGTGGCGGCGGTTCTGAC
ATCCAGATGACCCAGTCTCCATCCTCCCTGTCTGCATCTGTAGGAGACAG
AGTCACCATCACTTGCCGGGCAAGTCAGAGCATTAGCAGCTATTTAAATT
GGTATCAGCAGAAACCAGGGAAAGCCCCTAAGCTCCTGATCTATGCGGCA
TCCAGTTTGCAAAGTGGGGTCCCATCAAGGTTCAGTGGCAGTGGATCTGG
GACAGATTTCACTCTCACCATCAGCAGTCTGCAACCTGAAGATTTTGCAA
CTTACTACTGTCAACAGACGGTTGTGGCGCCTCCGTTATTCGGCCAAGGG
ACCAAGGTGGAAATCAAACGTACGGTGGCTGCACCATCTGTCTTCATCTT
CCCGCCATCTGATGAGCAGTTGAAATCTGGAACTGCCTCTGTTGTGTGCC
TGCTGAATAACTTCTATCCCAGAGAGGCCAAAGTACAGTGGAAGGTGGAT
AACGCCCTCCAATCGGGTAACTCCCAGGAGAGTGTCACAGAGCAGGACAG
CAAGGACAGCACCTACAGCCTCAGCAGCACCCTGACGCTGAGCAAAGCAG
ACTACGAGAAACACAAAGTCTACGCCTGCGAAGTCACCCATCAGGGCCTG
AGCTCGCCCGTCACAAAGAGCTTCAACAGGGGAGAGTGT 5894-PLGL
Amino acid sequence
(SEQ ID NO: 188)
QGQSGQGQQQWCNIWINGGDCRGWNGGSSGGSGGSGGSGGGSPLGLGGS Nucleotide sequence
(SEQ ID NO: 187)
CAAGGCCAGTCTGGCCAGGGTCAGCAGCAGTGGTGCAATATTTGGATCAA
TGGTGGTGATTGCCGCGGGTGGAATGGTGGCTCGAGCGGTGGCAGCGGTG
GCTCTGGTGGCTCAGGTGGAGGCTCGCCACTGGGCCTGGGCGGTTCT 5894-PLGL-4D11 Lc
Amino acid sequence
(SEQ ID NO: 269)
QGQSGQGQQQWCNIWINGGDCRGWNGGSSGGSGGSGGSGGGSPLGLGGSD
IQMTQSPSSLSASVGDRVTITCRASQSISSYLNWYQQKPGKAPKLLIYAA
SSLQSGVPSRFSGSGSGTDFTLTISSLQPEDFATYYCQQTVVAPPLFGQG
TKVEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGL
SSPVTKSFNRGEC Nucleotide sequence
(SEQ ID NO: 270)
CAAGGCCAGTCTGGCCAGGGTCAGCAGCAGTGGTGCAATATTTGGATCAA
TGGTGGTGATTGCCGCGGGTGGAATGGTGGCTCGAGCGGTGGCAGCGGTG
GCTCTGGTGGCTCAGGTGGAGGCTCGCCACTGGGCCTGGGCGGTTCTGAC
ATCCAGATGACCCAGTCTCCATCCTCCCTGTCTGCATCTGTAGGAGACAG
AGTCACCATCACTTGCCGGGCAAGTCAGAGCATTAGCAGCTATTTAAATT
GGTATCAGCAGAAACCAGGGAAAGCCCCTAAGCTCCTGATCTATGCGGCA
TCCAGTTTGCAAAGTGGGGTCCCATCAAGGTTCAGTGGCAGTGGATCTGG
GACAGATTTCACTCTCACCATCAGCAGTCTGCAACCTGAAGATTTTGCAA
CTTACTACTGTCAACAGACGGTTGTGGCGCCTCCGTTATTCGGCCAAGGG
ACCAAGGTGGAAATCAAACGTACGGTGGCTGCACCATCTGTCTTCATCTT
CCCGCCATCTGATGAGCAGTTGAAATCTGGAACTGCCTCTGTTGTGTGCC
TGCTGAATAACTTCTATCCCAGAGAGGCCAAAGTACAGTGGAAGGTGGAT

Mask 5894 that also includes a 6-amino acid N-terminal spacer

AACGCCCTCCAATCGGGTAACTCCCAGGAGAGTGTCACAGAGCAGGACAG
CAAGGACAGCACCTACAGCCTCAGCAGCACCCTGACGCTGAGCAAAGCAG
ACTACGAGAAACACAAAGTCTACGCCTGCGAAGTCACCCATCAGGGCCTG
AGCTCGCCCGTCACAAAGAGCTTCAACAGGGGAGAGTGT

5894-Cath.E
Amino acid sequence
(SEQ ID NO: 190)
QGQSGQGQQQWCNIWINGGDCRGWNGGSSGGSGGSGGSAGFSLPAGGGS Nucleotide sequence
(SEQ ID NO: 189)
CAAGGCCAGTCTGGCCAGGGTCAGCAGCAGTGGTGCAATATTTGGATCAA
TGGTGGTGATTGCCGCGGGTGGAATGGTGGCTCGAGCGGTGGCAGCGGTG
GCTCTGGTGGCTCAGCTGGCTTCTCCCTCCCCGCAGGTGGCGGTTCT 5894-Cath.E-4D11 Lc
Amino acid sequence
(SEQ ID NO: 271)
QGQSGQGQQQWCNIWINGGDCRGWNGGSSGGSGGSGGSAGFSLPAGGGSD
IQMTQSPSSLSASVGDRVTITCRASQSISSYLNWYQQKPGKAPKLLIYAA
SSLQSGVPSRFSGSGSGTDFTLTISSLQPEDFATYYCQQTVVAPPLFGQG
TKVEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGL
SSPVTKSFNRGEC Nucleotide sequence
(SEQ ID NO: 272)
CAAGGCCAGTCTGGCCAGGGTCAGCAGCAGTGGTGCAATATTTGGATCAA
TGGTGGTGATTGCCGCGGGTGGAATGGTGGCTCGAGCGGTGGCAGCGGTG
GCTCTGGTGGCTCAGCTGGCTTCTCCCTCCCCGCAGGTGGCGGTTCTGAC
ATCCAGATGACCCAGTCTCCATCCTCCCTGTCTGCATCTGTAGGAGACAG
AGTCACCATCACTTGCCGGCAAGTCAGAGCATTAGCAGCTATTTAAATT
GGTATCAGCAGAAACCAGGGAAAGCCCCTAAGCTCCTGATCTATGCGGCA
TCCAGTTTGCAAAGTGGGGTCCCATCAAGGTTCAGTGGCAGTGGATCTGG
GACAGATTTCACTCTCACCATCAGCAGTCTGCAACCTGAAGATTTTGCAA
CTTACTACTGTCAACAGACGGTTGTGGCGCCTCCGTTATTCGGCCAAGGG
ACCAAGGTGGAAATCAAACGTACGGTGGCTGCACCATCTGTCTTCATCTT
CCCGCCATCTGATGAGCAGTTGAAATCTGGAACTGCCTCTGTTGTGTGCC
TGCTGAATAACTTCTATCCCAGAGAGGCCAAAGTACAGTGGAAGGTGGAT
AACGCCCTCCAATCGGGTAACTCCCAGGAGAGTGTCACAGAGCAGGACAG
CAAGGACAGCACCTACAGCCTCAGCAGCACCCTGACGCTGAGCAAAGCAG
ACTACGAGAAACACAAAGTCTACGCCTGCGAAGTCACCCATCAGGGCCTG
AGCTCGCCCGTCACAAAGAGCTTCAACAGGGGAGAGTGT 5894-MMP-14
Amino acid sequence
(SEQ ID NO: 192)
QGQSGQGQQQWCNIWINGGDCRGWNGGSSGGSGGSGGSLAPLGLQRRGGS Nucleotide sequence
(SEQ ID NO: 191)
CAAGGCCAGTCTGGCCAGGGTCAGCAGCAGTGGTGCAATATTTGGATCAA
TGGTGGTGATTGCCGCGGGTGGAATGGTGGCTCGAGCGGTGGCAGCGGTG
GCTCTGGTAGCCTGGCACCTCTGGGTCTGCAACGCCGTGGCGGTTCT 5894-MMP-14-4D11 Lc
Amino acid sequence
(SEQ ID NO: 273)
QGQSGQGQQQWCNIWINGGDCRGWNGGSSGGSGGSGGSLAPLGLQRRGGSD
IQMTQSPSSLSASVGDRVTITCRASQSISSYLNWYQQKPGKAPKLLIYAA
SSLQSGVPSRFSGSGSGTDFTLTISSLQPEDFATYYCQQTVVAPPLFGQG
TKVEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGL
SSPVTKSFNRGEC Nucleotide sequence
(SEQ ID NO: 274)
CAAGGCCAGTCTGGCCAGGGTCAGCAGCAGTGGTGCAATATTTGGATCAA
TGGTGGTGATTGCCGCGGGTGGAATGGTGGCTCGAGCGGTGGCAGCGGTG
GCTCTGGTAGCCTGGCACCTCTGGGTCTGCAACGCCGTGGCGGTTCTGAC
ATCCAGATGACCCAGTCTCCATCCTCCCTGTCTGCATCTGTAGGAGACAG
AGTCACCATCACTTGCCGGCAAGTCAGAGCATTAGCAGCTATTTAAATT
GGTATCAGCAGAAACCAGGGAAAGCCCCTAAGCTCCTGATCTATGCGGCA
TCCAGTTTGCAAAGTGGGGTCCCATCAAGGTTCAGTGGCAGTGGATCTGG
GACAGATTTCACTCTCACCATCAGCAGTCTGCAACCTGAAGATTTTGCAA
CTTACTACTGTCAACAGACGGTTGTGGCGCCTCCGTTATTCGGCCAAGGG
ACCAAGGTGGAAATCAAACGTACGGTGGCTGCACCATCTGTCTTCATCTT
CCCGCCATCTGATGAGCAGTTGAAATCTGGAACTGCCTCTGTTGTGTGCC
TGCTGAATAACTTCTATCCCAGAGAGGCCAAAGTACAGTGGAAGGTGGAT
AACGCCCTCCAATCGGGTAACTCCCAGGAGAGTGTCACAGAGCAGGACAG
CAAGGACAGCACCTACAGCCTCAGCAGCACCCTGACGCTGAGCAAAGCAG
ACTACGAGAAACACAAAGTCTACGCCTGCGAAGTCACCCATCAGGGCCTG
AGCTCGCCCGTCACAAAGAGCTTCAACAGGGGAGAGTGT 5894-panMMP
Amino acid sequence
(SEQ ID NO: 194)
QGQSGQGQQQWCNIWINGGDCRGWNGGSSGGSGGSGGSGGPLGVRGGGS Nucleotide sequence
(SEQ ID NO: 193)
CAAGGCCAGTCTGGCCAGGGTCAGCAGCAGTGGTGCAATATTTGGATCAA
TGGTGGTGATTGCCGCGGGTGGAATGGTGGCTCGAGCGGTGGCAGCGGTG
GCTCTGGTGGCTCAGGTGGACCTTTGGGAGTCAGAGGTGGCGGTTCT 5894-panMMP-4D11 Lc
Amino acid sequence
(SEQ ID NO: 275)
QGQSGQGQQQWCNIWINGGDCRGWNGGSSGGSGGSGGSGGPLGVRGGGSD
IQMTQSPSSLSASVGDRVTITCRASQSISSYLNWYQQKPGKAPKLLIYAA
SSLQSGVPSRFSGSGSGTDFTLTISSLQPEDFATYYCQQTVVAPPLFGQG
TKVEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGL
SSPVTKSFNRGEC Nucleotide sequence
(SEQ ID NO: 276)
CAAGGCCAGTCTGGCCAGGGTCAGCAGCAGTGGTGCAATATTTGGATCAA
TGGTGGTGATTGCCGCGGGTGGAATGGTGGCTCGAGCGGTGGCAGCGGTG
GCTCTGGTGGCTCAGGTGGACCTTTGGGAGTCAGAGGTGGCGGTTCTGAC
ATCCAGATGACCCAGTCTCCATCCTCCCTGTCTGCATCTGTAGGAGACAG
AGTCACCATCACTTGCCGGCAAGTCAGAGCATTAGCAGCTATTTAAATT
GGTATCAGCAGAAACCAGGGAAAGCCCCTAAGCTCCTGATCTATGCGGCA
TCCAGTTTGCAAAGTGGGGTCCCATCAAGGTTCAGTGGCAGTGGATCTGG
GACAGATTTCACTCTCACCATCAGCAGTCTGCAACCTGAAGATTTTGCAA
CTTACTACTGTCAACAGACGGTTGTGGCGCCTCCGTTATTCGGCCAAGGG
ACCAAGGTGGAAATCAAACGTACGGTGGCTGCACCATCTGTCTTCATCTT
CCCGCCATCTGATGAGCAGTTGAAATCTGGAACTGCCTCTGTTGTGTGCC
TGCTGAATAACTTCTATCCCAGAGAGGCCAAAGTACAGTGGAAGGTGGAT
AACGCCCTCCAATCGGGTAACTCCCAGGAGAGTGTCACAGAGCAGGACAG
CAAGGACAGCACCTACAGCCTCAGCAGCACCCTGACGCTGAGCAAAGCAG
ACTACGAGAAACACAAAGTCTACGCCTGCGAAGTCACCCATCAGGGCCTG
AGCTCGCCCGTCACAAAGAGCTTCAACAGGGGAGAGTGT The nucleic acid and amino acid sequences of a polypeptide including masking moiety JS 5894 and a noncleavable linker that can be joined to an anti-Jagged antibody using methods such as those described herein to form a masked antibody are provided below:

5894-NSUB
Amino acid sequence
(SEQ ID NO: 196)
QGQSGQGQQQWCNIWINGGDCRGWNGGSSGGSGGSGGSGGGSGGGSGGS Nucleotide sequence
(SEQ ID NO: 195)
CAAGGCCAGTCTGGCCAGGGTCAGCAGCAGTGGTGCAATATTTGGATCAA
TGGTGGTGATTGCCGCGGGTGGAATGGTGGCTCGAGCGGTGGCAGCGGTG
GCTCTGGTGGCTCAGGTGGAGGCTCGGGCGGTGGGAGCGGCGGTTCT 5894-NSUB-4D11 Lc
Amino acid sequence
(SEQ ID NO: 278)
QGQSGQGQQQWCNIWINGGDCRGWNGGSSGGSGGSGGSGGGSGGGSGGSD
IQMTQSPSSLSASVGDRVTITCRASQSISSYLNWYQQKPGKAPKLLIYAA
SSLQSGVPSRFSGSGSGTDFTLTISSLQPEDFATYYCQQTVVAPPLFGQG
TKVEIKRTVAAPSVFIFPPSDEQLKSGTASVVCLLNNFYPREAKVQWKVD -continued
```
NALQSGNSQESVTEQDSKDSTYSLSSTLTLSKADYEKHKVYACEVTHQGL
SSPVTKSFNRGEC Nucleotide sequence
                                            (SEQ ID NO: 279)
CAAGGCCAGTCTGGCCAGGGTCAGCAGCAGTGGTGCAATATTTGGATCAA
TGGTGGTGATTGCCGCGGGTGGAATGGTGGCTCGAGCGGTGGCAGCGGTG
GCTCTGGTGGCTCAGGTGGAGGCTCGGGCGGTGGGAGCGGCGGTTCTGAC
ATCCAGATGACCCAGTCTCCATCCTCCCTGTCTGCATCTGTAGGAGACGA
AGTCACCATCACTTGCCGGGCAAGTCAGAGCATTAGCAGCTATTTAAATT
GGTATCAGCAGAAACCAGGGAAAGCCCCTAAGCTCCTGATCTATGCGGCA
TCCAGTTTGCAAAGTGGGGTCCCATCAAGGTTCAGTGGCAGTGGATCTGG
GACAGATTTCACTCTCACCATCAGCAGTCTGCAACCTGAAGATTTTGCAA
CTTACTACTGTCAACAGACGGTTGTGGCGCCTCCGTTATTCGGCCAAGGG
ACCAAGGTGGAAATCAAACGTACGGTGGCTGCACCATCTGTCTTCATCTT
CCCGCCATCTGATGAGCAGTTGAAATCTGGAACTGCCTCTGTTGTGTGCC
TGCTGAATAACTTCTATCCCAGAGAGGCCAAAGTACAGTGGAAGGTGGAT
AACGCCCTCCAATCGGGTAACTCCCAGGAGAGTGTCACAGAGCAGGACAG
CAAGGACAGCACCTACAGCCTCAGCAGCACCCTGACGCTGAGCAAAGCAG
ACTACGAGAAACACAAAGTCTACGCCTGCGAAGTCACCCATCAGGGCCTG
AGCTCGCCCGTCACAAAGAGCTTCAACAGGGGAGAGTGT
```

Examples of antibodies to which such MM and CM containing polypeptides can be joined include anti-Jagged antibody 4D11 or variants thereof, such as the 4D11 QΔH variant described above.

Example 18

In Situ Imaging of Activatable Anti-Jagged Antibodies

The present Example describes the use of in situ imaging of the activation and binding of an activatable anti-Jagged antibody of the disclosure. The results indicate that activatable anti-Jagged antibodies of the disclosure can be activated by proteases expressed by a tissue and bind Jagged targets on that tissue.

Figure 19:
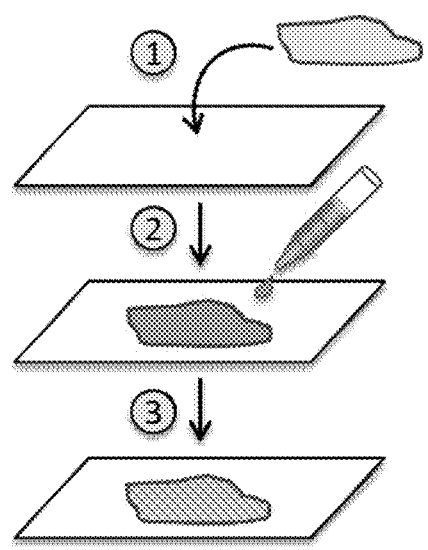
FIG. 19 is a schematic overview of in situ imaging of an activatable antibody: 1. A tissue section is laid over the slide. 2. The slide is covered with solution containing labeled activatable antibody and incubated. 3. After extensive washing, binding of activated antibody is visualized.

In situ imaging of activatable antibodies represents a unique approach to characterize protease activity in cells and tissue. This technology enables validation of activatable antibody activation and binding to a target in histological sections of cells and tissues expressing proteases capable of cleaving the activatable antibody. A schematic of such an in situ approach is presented in FIG. 19.

In situ imaging of the activation and binding of an activatable anti-Jagged antibody (also referred to herein as in situ imaging) by a cell or tissue capable of cleaving the activatable antibody at a site co-localized with the target recognized by the activated antibody was conducted as follows: Frozen tissue sections were laid over glass slides. A solution containing labeled activatable anti-Jagged antibodies (labeled, e.g., with a fluorescent tag) was applied on the tissue and incubated, e.g., for 1 hour at room temperature (about 22-24° C.) in an incubation buffer of 50 mM Tris-HCl buffer pH 7.4, containing 150 mM NaCl, 100 μM $ZnCl_2$, 5 mM $CaCl_2$ and 0.05% Tween 20; activatable antibody at a concentration of about 1 μg/ml. The tissue was then extensively washed to remove non-bound material and detectable label was measured. For example, when a fluorescent tag was used, the tissue was submitted to fluorescent microscopy. Detection of activated antibody on the tissue indicated that the tissue expressed proteases that cleaved the activatable antibody and also expressed Jagged targets to which the activated antibody bound.

The abilities of activatable anti-Jagged antibodies 5342-1204-4D11 and 5342-PLGL-4D11 to be activated and to bind BxPC3 xenograft tumor tissue were evaluated using in situ imaging. The activatable antibodies were labeled with Alexa Fluor® 680 (Invitrogen) to produce labeled activatable antibodies 5342-1204-4D11-AF680 and 5342-PLGL-4D11-AF680, also referred to herein as 1204-4D11-AF680 and PLGL-4D11-AF680, respectively. Also tested was labeled anti-Jagged parental antibody 4D11-AF680. Each of 4D11-AF680, 1204-4D11-AF680 and PLGL-4D11-AF680 was incubated with a frozen BxPC3 xenograft tumor tissue sample as described above. The results are shown on FIG. 20, panels A, B, and C, respectively. The red fluorescent tissue images demonstrate binding of 4D11 antibody and of 4D 11 antibodies activated by tissue-derived proteolytic cleavage of the respectively activatable antibodies to Jagged. Panels D, E, and F represent the fluorescent images obtained after incubation of 4D11-AF680, 1204-4D11-AF680 and PLGL-4D11-AF680 with frozen BxPC3 xenograft tumor tissue pre-treated with a 1:100 dilution of broad spectrum protease inhibitor cocktail set III (Catalog No. 539134, EMD Millipore) and 50 mM EDTA. Reduced red fluorescence in panels E and F indicates that the binding of activatable antibodies 1204-4D11-AF680 and PLGL-4D11-AF680 seen in panels B and C was effected by cleavage of the activatable antibodies by tissue-derived proteases; the protease inhibitor cocktail inhibited such proteolysis. Blue staining represents DAPI nuclear staining. Binding of anti-Jagged parental antibody 4D11 or of activatable anti-Jagged antibodies 5342-1204-4D11 and 5342-PLGL-4D11 to frozen BxPC3 xenograft tumor tissue was inhibited by pre-treating such tissue with unlabeled anti-Jagged parental antibody 4D11 or by pre-treating such tissue with Jagged 1, Jagged 2, or a combination thereof.

Figure 21:
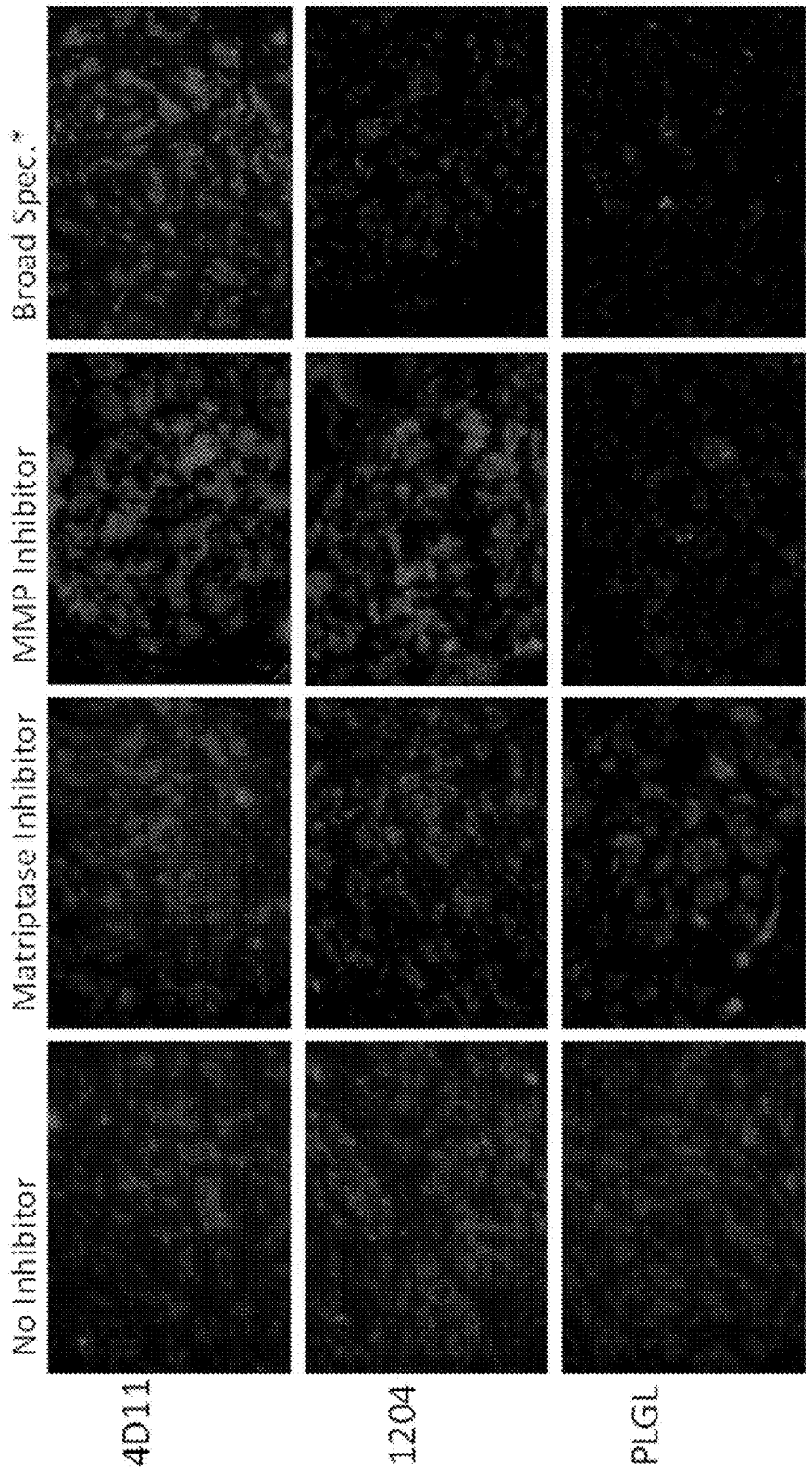
FIG. 21 is a series of images depicting activation of activatable anti-Jagged antibodies 5342-1204-4D11 and 5342-PLGL-4D11 as demonstrated by in situ imaging of human pancreatic cancer tissue. Each of 4D11-AF680 (4D11) (column 1, row 1), 1204-4D11-AF680 (1204) (col. 1, row 2) and PLGL-4D11-AF680 (PLGL) (col. 1, row 3) was incubated with a frozen tissue sample isolated from a human patient with pancreatic cancer. The panels in Columns 2, 3, and 4, respectively, represent the fluorescent images obtained after incubation of 4D11-AF680, 1204-4D11-AF680 and PLGL-4D11-AF680 with frozen pancreatic cancer patient tissue pre-treated antibody A11, an antibody that specifically binds to the active site of the MT-SP1 protease, also known as matriptase; (col. 2); with an MMP inhibitor (FIG. 21, col. 3); or with a broad spectrum protease inhibitor cocktail (col. 4).

Activation of activatable anti-Jagged antibodies 5342-1204-4D11 and 5342-PLGL-4D11 were also evaluated by in situ imaging of human pancreatic cancer tissue. Each of 4D11-AF680 4D11), 1204-4D11-AF680 (1204) and PLGL-4D11-AF680 (PLGL) was incubated with a frozen tissue sample isolated from a human patient with pancreatic cancer. The results are shown on FIG. 21, panels in column 1, rows 1, 2, and 3, respectively. The panels in Columns 2, 3, and 4, respectively, represent the fluorescent images obtained after incubation of 4D11-AF680, 1204-4D11-AF680 and PLGL-4D11-AF680 with frozen pancreatic cancer patient tissue pre-treated with 10 μg/ml of antibody A11 (A11 is an antibody that specifically binds to the active site of the MT-SP1 protease, also known as matriptase) (FIG. 21, column 2) with 50 μM of broad spectrum MMP inhibitor Galardin (Calbiochem, Millipore) (FIG. 21, column 3) or with a 1:100 dilution of broad spectrum protease inhibitor cocktail set III (Cat. No. 539134, EMD Millipore) and 50 μM broad spectrum MMP inhibitor Galardin (Calbiochem, Millipore) (FIG. 21, column 4). Blue staining represents DAPI nuclear staining. The results suggest that the pancreatic tissue sample produces active matriptase and metalloprotease, the presence of which effects cleavage of respective activatable antibody cleavable moieties, thereby releasing the masking moiety and enabling stable binding of the activated antibody to Jagged targets on the tissue.

Example 19

In Vivo Imaging of an Anti-Jagged Antibody

The present Example describes the in vivo imaging of an anti-Jagged antibody of the disclosure.

Anti-Jagged antibody 4D11 was labeled with Alexa Fluor® 750 and purified from unconjugated dye using 40 kDa Thermo Scientific Zeba Spin Desalting Columns. A group of three mice bearing BxPC3-luc human pancreatic cancer tumors with tumor volumes of approximately 400-600 mm³ were administered intraperitoneally (i.p.) a single 10-mg/kg dose of Alexa Fluor® 750-labeled 4D11 antibodies (n=3). Mice were anesthetized with isoflurane and imaged for 750 nm near-infrared (NIR) fluorescence prior to injection and at 24 h, 48 h, and 72 h post injection using the Caliper IVIS SpectrumCT imaging system (Caliper, Perkin Elmer, Hopkinton Mass.). Mice were euthanized after the last imaging time-point. FIG. 22A provides a representation of the labeled 4D11 antibody fluorescence signal 48 hours post-injection in the BxPC3 tumor xenograft mouse model.

In vivo imaging data were normalized and analyzed using Living Image® 4.1 software. For quantitative comparison, the regions of interest (ROI) were drawn over tumor (T) and normal tissue (N). The fluorescence signal, quantified as Average Radiant Efficiency (photons×cm-2×s-1), for each area was measured. The ratio of the signal in the tumor ROI compared to the normal tissue ROI (T/N) was calculated to provide a measure of the rate of anti-Jagged antibody 4D11 accumulation in the tumor versus normal tissue. FIG. 22B provides a graph showing the mean T/N ratio of average radiant efficacy for the antibody 4D11 dose group±SD.

Example 20

In Situ Imaging of Activatable Anti-Jagged Antibodies

The present Example describes the use of in situ imaging to screen pancreatic cancer xenograft tumor tissue and human pancreatic cancer tissue for the activation and binding of an activatable anti-Jagged antibody. The results indicate that activatable anti-Jagged antibodies of the disclosure can be activated by proteases expressed by such tissues and bind Jagged targets on such tissues.

BxPC3 tumor samples and human pancreatic cancer tissue samples were profiled for Jagged and MT-SP1 expression by 1 hour treatment of frozen tissue with labeled anti-Jagged antibody 4D11 and anti-matriptase A11 antibody at 1 µg/ml and 5 µg/ml concentrations, respectively. The results are shown in Table 24, columns 2 and 3, respectively.

Figure 20:
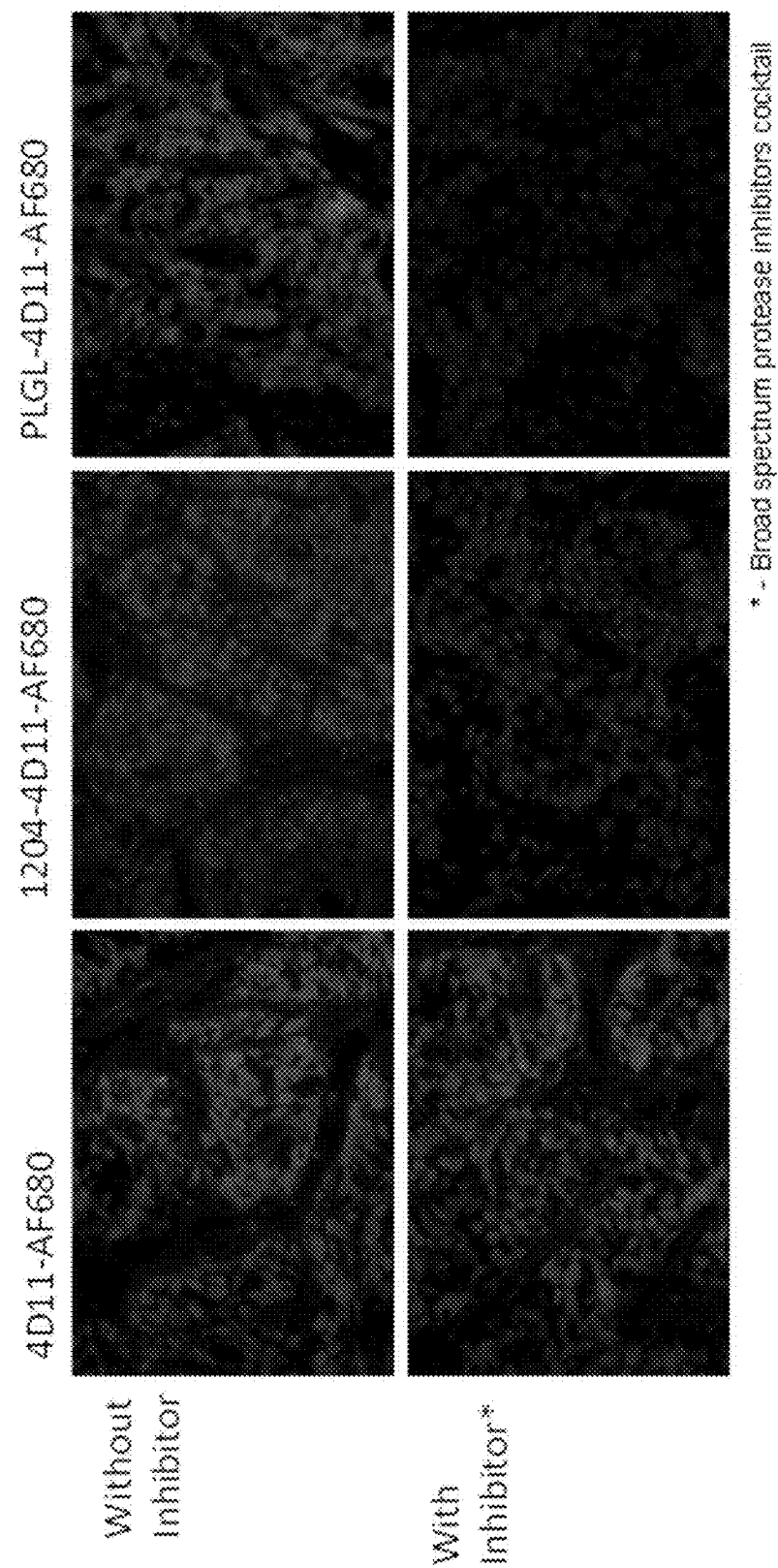
FIG. 20 is a series of images depicting the abilities of activatable anti-Jagged antibodies 5342-1204-4D11 and 5342-PLGL-4D11 to be activated and to bind BxPC3 xenograft tumor tissue as demonstrated using in situ imaging. The activatable antibodies were labeled with Alexa Fluor® 680 to produce labeled activatable antibodies 5342-1204-4D11-AF680 and 5342-PLGL-4D11-AF680, also referred to herein as 1204-4D11-AF680 and PLGL-4D11-AF680, respectively. Also tested was labeled anti-Jagged parental antibody 4D11-AF680. Each of 4D11-AF680 (column 1, row 1), 1204-4D11-AF680 (col. 2, row 1) and PLGL-4D11-AF680 (col. 3, row 1) was incubated with a frozen BxPC3 xenograft tumor tissue sample. The panels in row 2 represent the fluorescent images obtained after incubation of 4D11-AF680 (col. 1), 1204-4D11-AF680 (col. 2) and PLGL-4D11-AF680 (col. 3) with frozen BxPC3 xenograft tumor tissue pre-treated with a broad spectrum protease inhibitor cocktail.

In addition, the abilities of activatable anti-Jagged antibodies 5342-1204-4D11 and 5342-PLGL-4D11 to be activated and to bind BxPC3 xenograft and human pancreatic cancer tissues were evaluated using in situ imaging. The activatable antibodies were labeled with Alexa Fluor® 680 (Invitrogen) as described above (Example 18). These labeled activatable antibodies, i.e., 5342-1204-4D11-AF680 (also referred to herein as 1204-4D11-AF680) and 5342-PLGL-4D11-AF680 (also referred to herein as PLGL-4D11-AF680), were incubated with frozen BxPC3 xenograft tissue or with human pancreatic cancer tissue samples isolated from four patients according to the protocol of in situ imaging described above (Example 18). Table 24 summarizes the results demonstrating the ability of BxPC3 tumor and pancreatic cancer patients' tissue samples to activate and bind activated activatable anti-Jagged antibodies. In Table 24, the IHC staining that measured the amount of anti-Jagged antibody 4D11 or anti-matriptase antibody A11 binding to the tissue samples (columns 2 and 3) was scored from 0 to 3+: 0, no staining; 1+, weak staining; 2+, moderate staining; and 3+, strong staining. The in situ imaging staining (columns 4 and 5) scoring is based on comparison with 4D11 antibody staining and defined as follows: 0, no staining; 1+, weak staining as compared to parental antibody; 2+, moderate staining as compared to parental antibody; and 3+, analogous staining to parental antibody. The BxPC3 results are also shown in FIG. 20.

TABLE 24

Screening for Jagged and MT-SP1 expression and in situ imaging of activatable anti-Jagged antibodies in BxPC3 xenograft and human pancreatic cancer tissues.

| Specimen # | IHC | | in situ imaging | |
|---|---|---|---|---|
| | 4D11 | A11 | 4D11-1204-AF680 | 4D11-PLGL-AF680 |
| BxPC3 | ++ | ++ | +++ | +++ |
| 5587 | ++ | + | ++ | +++ |
| 5617 | +++ | ++ | +++ | ++ |
| 5623 | +++ | ++ | ++ | + |
| 5631 | ++ | − | ++ | + |

Example 21

In Vitro Characterization of an Activatable Antibody Conjugated to an Agent

This Example describes the ability of an activatable antibody-agent conjugate of the disclosure to inhibit proliferation of BxPC3 cells in culture.

Activatable anti-Jagged antibody 5342-1204-4D11, anti-Jagged antibody 4D11, and Rituxan were each conjugated to monomethylauristatin E (MMAE), a synthetic anti-mitotic tubulin polymerization inhibitor, to generate activatable antibody-agent conjugate 5342-1204-4D11-MMAE and antibody-agent conjugates 4D11-MMAE and Rituxan-MMAE.

The abilities of the following compounds to inhibit BxPC3 cell proliferation in cell culture were determined: Activatable anti-Jagged antibody-agent conjugate 5342-1204-4D11-MMAE; activatable anti-Jagged antibody-agent conjugate 5342-1204-4D11-MMAE activated by uPA; activatable anti-Jagged antibody 5342-1204-4D11; activatable anti-Jagged antibody 5342-1204-4D11 activated by uPA; anti-Jagged antibody 4D11; anti-Jagged antibody-agent conjugate 4D11-MMAE; Rituxan; and Rituxan-MMAE. Activation of activatable antibody and activatable antibody-agent conjugate was effected by digestion overnight at 37° C. with active site-titrated uPA (500 nM) in Tris pH 8.5; activation was measured by CE analysis (LabChip GXII). uPA-activated activatable antibody and uPA-activated activatable antibody-agent conjugate were purified using protein A and then stored at 4° C. prior to the study.

Figure 24:
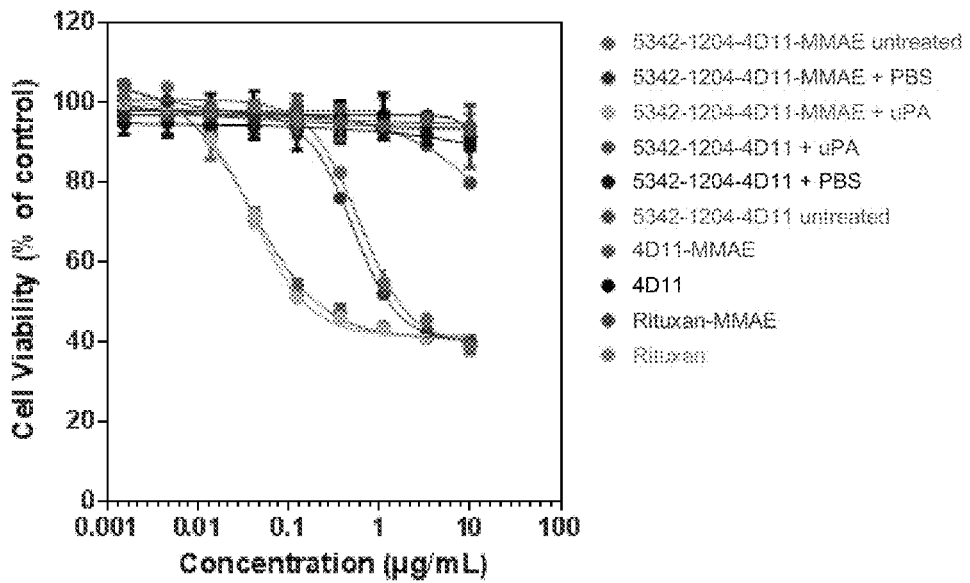
FIG. 24 is a graph depicting BxPC3 growth inhibition curves showing the activities of: the activated (+uPA) and non-activated (untreated or +PBS) activatable anti-Jagged antibody-agent conjugate; activated and non-activated activatable anti-Jagged antibody; and anti-Jagged and Rituxan antibodies and antibody-agent conjugates.

The human pancreatic cancer cell line BxPC-3 was obtained from ATCC. BxPC-3 cells were grown in complete media (RPMI-1640 supplemented with 10% fetal bovine serum) at 37° C. in an atmosphere of 5% CO2 in air. BxPC-3 cells were harvested during the logarithmic growth period, resuspended in complete medium, and plated at a density of 5000 cells per well in a 96-well white wall chimney plate. Following overnight incubation, a 10-point 1:3 serial dilution, starting at 10 ug/ml and ending in 0 of each compound was added to cells in culture in replicates. Cells were cultured for 3 days and cell viability was measured using CellTiterGlo (Promega) following manufacturer's protocol and a luminometer (Tecan). Data were analyzed using Prism GraphPad. The results are shown in FIG. 24.

Example 22

In Vivo Efficacy and Safety of an Activatable Antibody-Agent Conjugate

This Example describes the ability of an activatable antibody-agent conjugate of the disclosure to reduce the growth of BxPC3 xenograft tumors in vivo.

Activatable anti-Jagged antibodies and activatable anti-Jagged antibody-agent conjugates were tested for their ability to reduce the growth of BxPC3 xenograft tumors, using a method similar to that described above, using the compounds, groups, and doses set forth in Table 25.

TABLE 25

Groups and Dosing Regimens

| Group | N | Treatment | Dose (mg/kg) | Dosing Route | Schedule |
|---|---|---|---|---|---|
| 1 | 8 | PBS | NA | i.v. | q7dx 4 |
| 2 | 8 | 4D11 | 6.7 mg/kg | i.v. | q7dx 4 |
| 3 | 8 | 4D11-MMAE | 6.7 mg/kg | i.v. | q7dx 4 |
| 4 | 8 | 5342-1204-4D11 | 6.7 mg/kg | i.v. | q7dx 4 |
| 5 | 8 | 5342-1204-4D11-MMAE | 6.7 mg/kg | i.v. | q7dx 4 |

Figure 25:
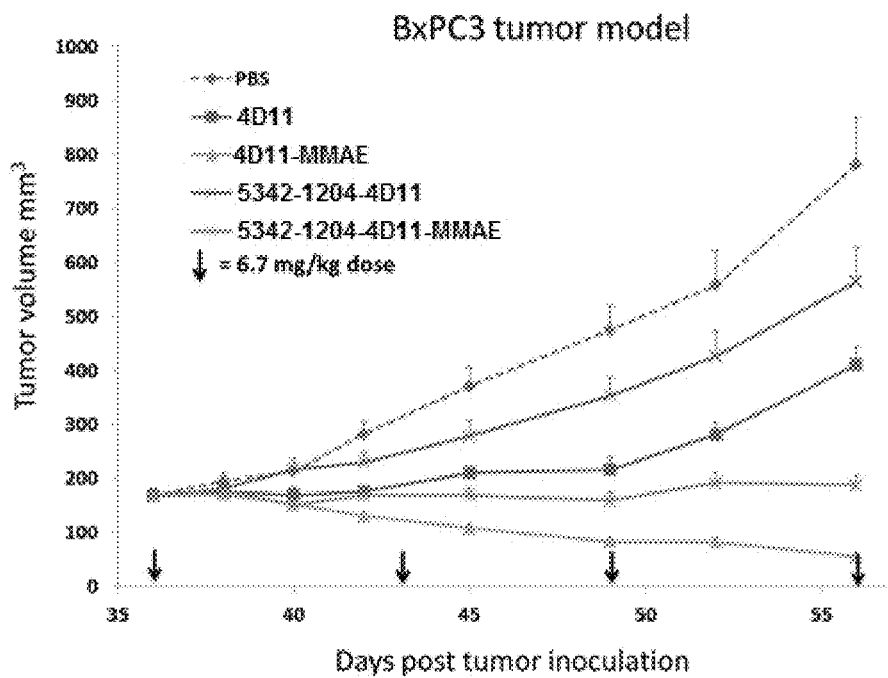
FIG. 25 is a graph depicting that both anti-Jagged antibody 4D11-MMAE and activatable anti-Jagged antibody 5342-1204-4D11-MMAE inhibited BxPC-3 xenograft tumor growth more effectively than their unconjugated counterparts.

FIG. 25, which plots tumor volume versus number of days post initial dose, demonstrates that both anti-Jagged antibody 4D11-MMAE and activatable anti-Jagged antibody 5342-1204-4D11-MMAE inhibited BxPC-3 xenograft tumor growth more effectively than their unconjugated counterparts.

Figure 26:
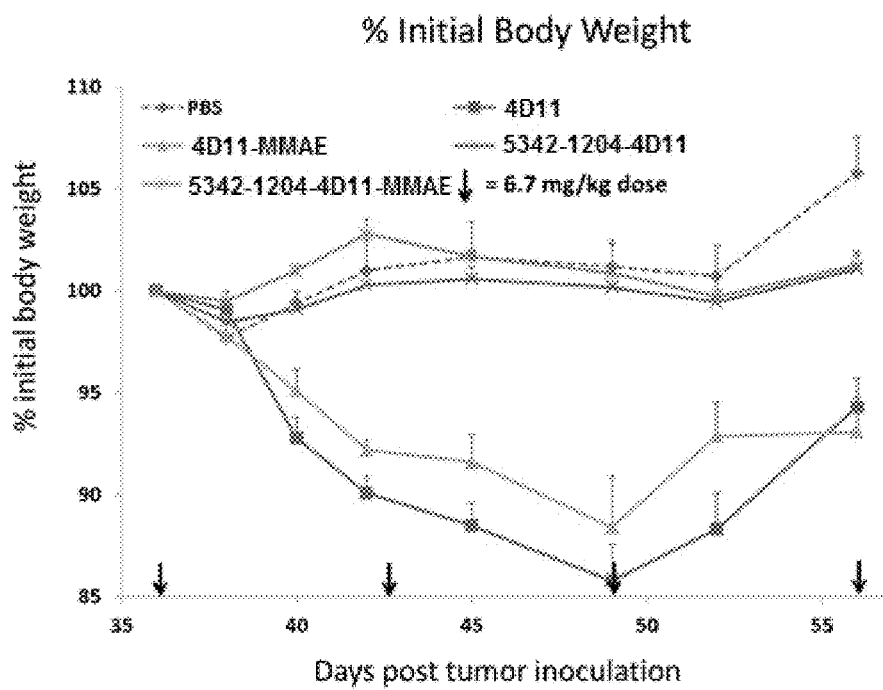
FIG. 26 is a graph depicting the weight loss observed in animals dosed with anti-Jagged antibody 4D11, anti-Jagged antibody-MMAE, activatable anti-Jagged antibody 5342-1204-4D11 or activatable anti-Jagged antibody-agent conjugate 5342-1204-4D11-MMAE.
Figure 27C:
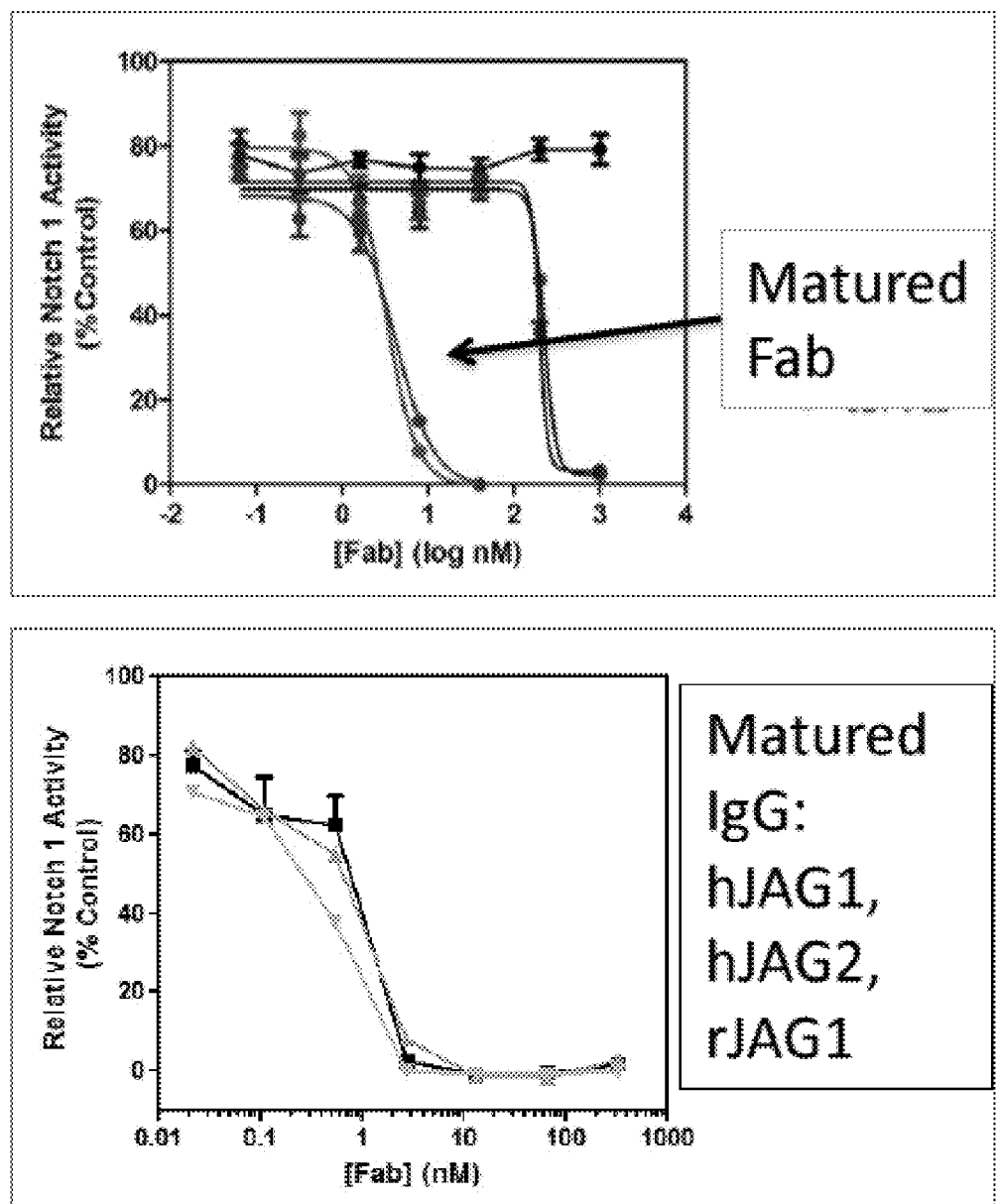
Figure 28:
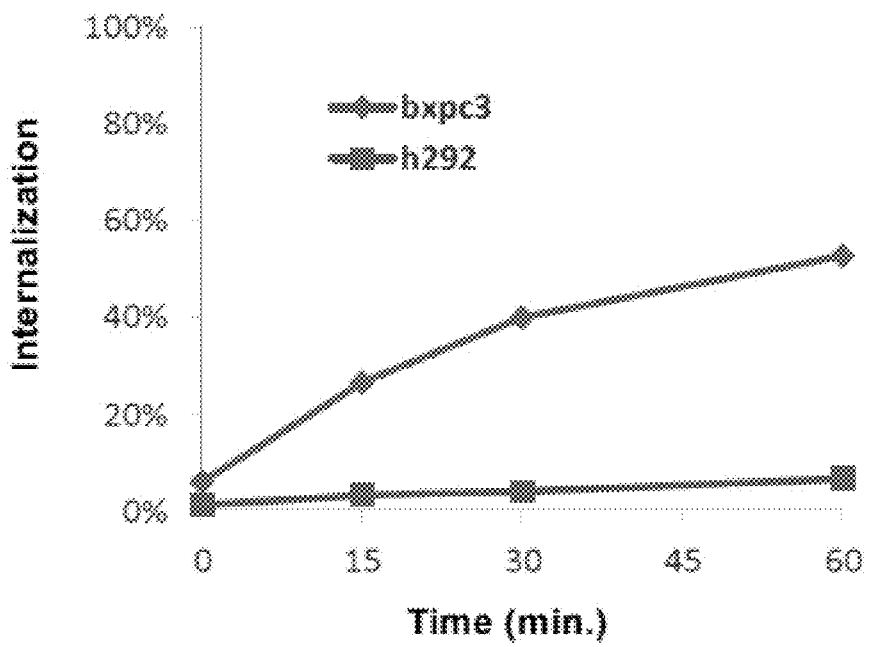
FIG. 28 is a graph depicting efficient internalization of an anti-Jagged antibody of the disclosure by the BxPC3 pancreatic cell line, plotted as percent internalization over time, particularly as compared to internalization by the H292 cell line, a human lung carcinoma cell line. Internalization was demonstrated using a method similar to that described in Gostring L et al, 2010, Int J Oncol 36, 757-763.

FIG. 26 shows the weight loss of the various groups. While the animals dosed with anti-Jagged antibody 4D11 or anti-Jagged antibody-MMAE showed significant weight loss, animals dosed with activatable anti-Jagged antibody 5342-1204-4D11 or activatable anti-Jagged antibody-agent conjugate 5342-1204-4D11-MMAE did not show significant weight loss.

Example 23

In Vivo Efficacy and Safety of Anti-Jagged Antibodies and Activatable Antibodies in Combination with Gemcitabine in the BxPC3 Tumor Model Anti-Jagged activatable antibodies were tested for their ability to reduce the growth of BxPC3 xenograft tumors, using a method similar to that described above, using the antibodies, activatable antibodies, groups, and doses set forth in Table 26.

TABLE 26

Groups and doses for the anti-Jagged activatable antibody BxPC3 efficacy study

| Group | N | Treatment | Dose (mg/kg) | Dosing Route | Schedule |
|---|---|---|---|---|---|
| 1 | 8 | PBS | NA | i.p | q7dx 4 |
| 2 | 8 | Gemcitabine | 100 mg/kg | i.p. | q7dx 4 |
| 3 | 8 | 2 mg/kg 4D11 + Gemcitabine | 2 mg/kg + 100 mg/kg | i.p. | q7dx 4 |
| 4 | 8 | 6.7 mg/kg 4D11 + Gemcitabine | 6.7 mg/kg + 100 | i.p. | q7dx 4 |
| 5 | 8 | 20.0 mg/kg 4D11 + Gemcitabine | 20 mg/kg + 100 mg/kg | i.p. | q7dx 4 |
| 6 | 8 | 2 mg/kg 5342-1204-4D11 + Gemcitabine | 2 mg/kg + 100 mg/kg | i.p. | q7dx 4 |
| 7 | 8 | 6.7 mg/kg 5342-1204-4D11 + Gemcitabine | 6.7 mg/kg + 100 mg/kg | i.p. | q7dx 4 |
| 8 | 8 | 20.0 mg/kg 5342-1204-4D11 + Gemcitabine | 20 mg/kg + 100 mg/kg | i.p. | q7dx 4 |

Figure 29:
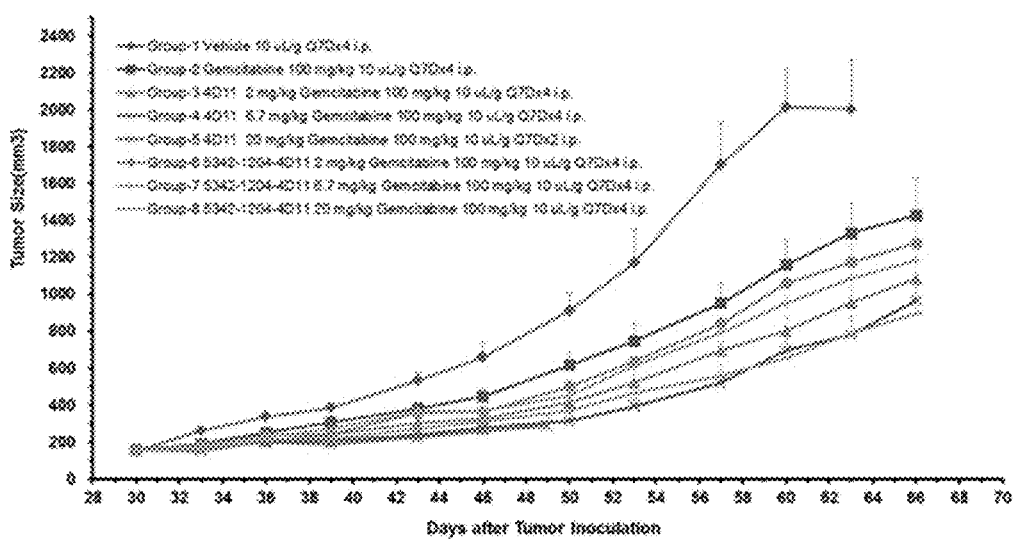
FIG. 29 is a graph depicting the ability of the anti-Jagged activatable antibody 5342-1204-4D11 in combination with Gemcitabine to inhibit the growth of BxPC-3 xenograft tumors.
Figure 30:
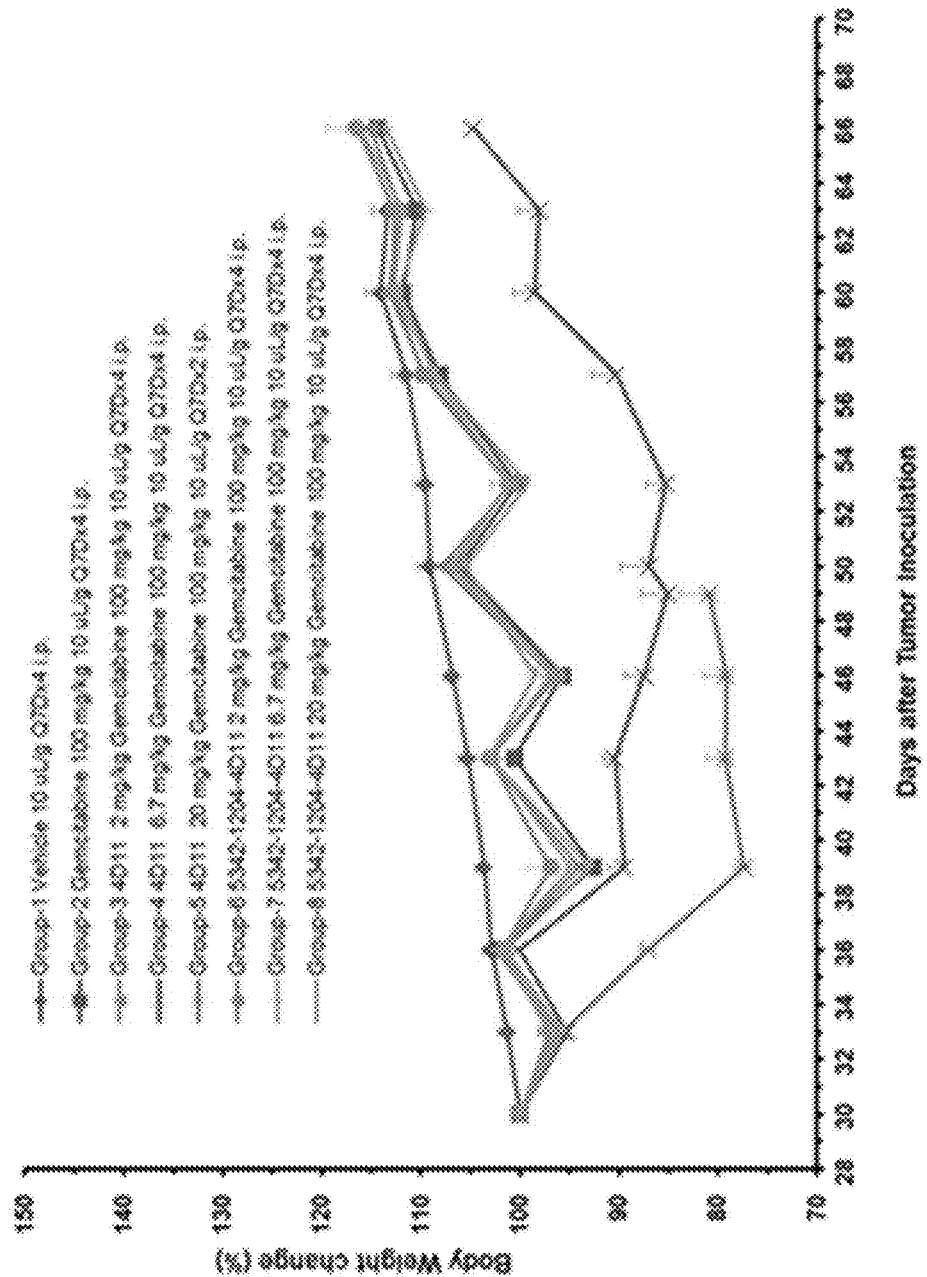
FIG. 30 is a graph depicting that the animals dosed with higher doses of antibody and Gemcitabine showed significant weight loss, but animals dosed with an activatable anti-Jagged antibody and Gemcitabine showed no weight loss over that of Gemcitabine alone.
Figure 31:
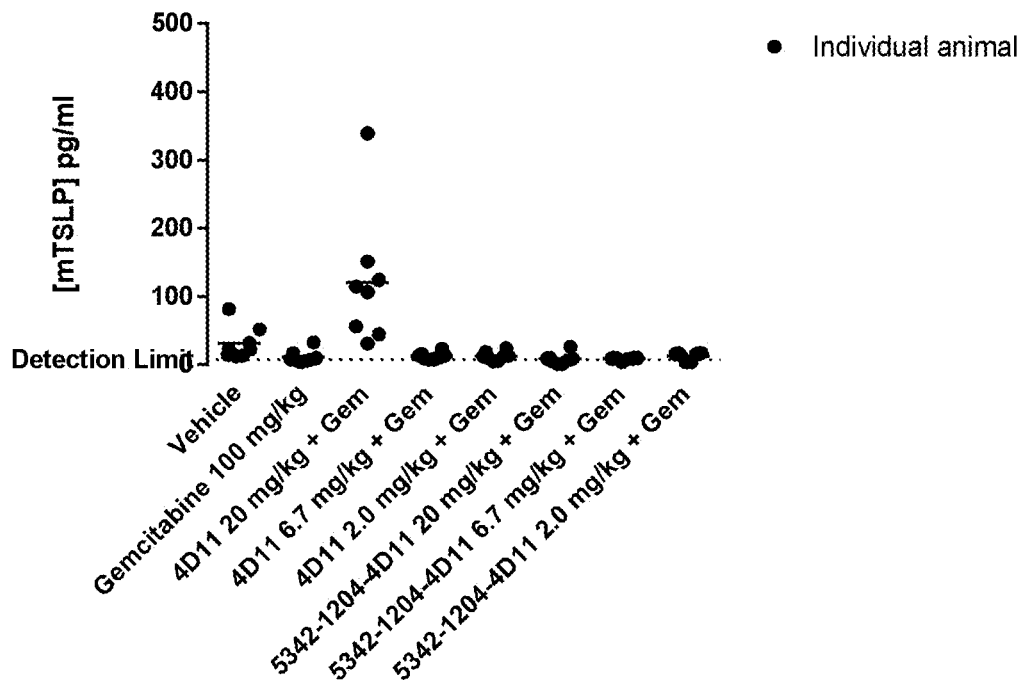
FIG. 31 is a graph depicting that only the administration of the 20 mg/kg anti-Jagged antibody in combination with Gemcitabine showed elevated serum mTSLP.

FIG. 29, which plots tumor volume versus number of days post tumor inoculation, demonstrates that the anti-Jagged activatable antibody 5342-1204-4D11 in combination with Gemcitabine inhibits the growth of BxPC-3 xenograft tumors. The first dose was given on day 30. FIG. 30 indicates the weight loss for the Gemcitabine alone group and for the group administered antibody in combination with Gemcitabine. While the animals dosed with higher doses of antibody and Gemcitabine showed significant weight loss, animals dosed with activatable antibody and Gemcitabine showed no weight loss over that of Gemcitabine alone. The antibody at 20 mg/kg was not tolerated when given in combination with Gemcitabine, resulting in the sacrifice of that group at day 49 due to body weight loss. However, the activatable antibody at 20 mg/kg in combination with Gemcitabine was tolerated and showed equivalent efficacy to that of the antibody at 6.7 and 20 mg/kg in combination with Gemcitabine. The serum concentration of mouse thymic stromal lymphopoietin (TSLP) was measured as described above. The serum levels of mouse TSLP (mTSLP) were quantified for individual mice before the second dose. Only the 20 mg/kg antibody in combination with Gemcitabine group showed elevated serum mTSLP, as indicated in FIG. 31.

Example 24

In Vivo Efficacy of an Anti-Jagged Antibody in Prostate and Mammary Tumor Models The efficacy of the anti-Jagged 4D11 antibody was evaluated in autocthonous tumor models for prostate and mammary cancer. These models mimic the human condition as the produced tumors undergo the distinct phases of tumor development and, importantly, allow the use of immunocompetent mice.

Prostate Cancer Model.

Figure 32:
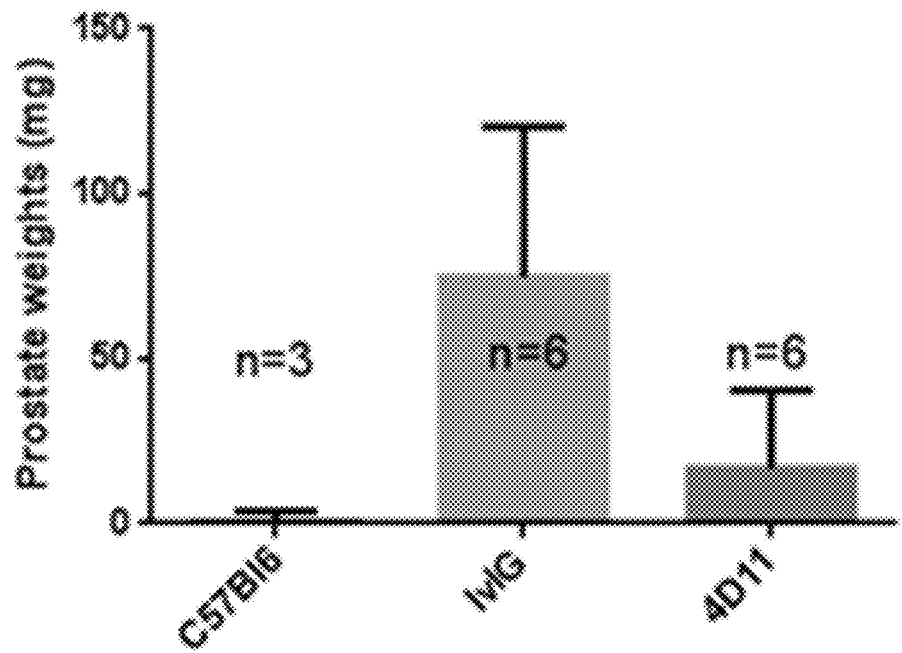
FIG. 32 is a graph depicting that the anti-Jagged antibody 4D11 was effective in limiting the growth of prostate tumors in TRAMP mice.

The TRAMPS mouse line is a widely used model of prostate cancer (Greenberg N M et al, 1995, Proc Natl Acad Sci USA. 92, 3439-3443). The initial lesions are prostatic intraepithelial hyperplasia (PIN) which progresses at about 12 weeks of age to a well differentiated adenocarcinoma. Poorly differentiated adenocarcinomas arise in 24-week-old TRAMP animals. At 18-24 weeks of age the TRAMP mice were separated into two groups, control and therapy, of 6 mice each. Anti-Jagged antibody 4D11 and IVIg control aliquots each were dosed IP to the respective group, q7DX5 at 20 mg/Kg. Seven days post final dose the animals were sacrificed, and tumor burden was measured as weight of genitourinary tract and compared to control wild type C57/B16 mice. FIG. 32 indicates that anti-Jagged antibody 4D11 was effective in limiting the growth of Prostate tumors in TRAMP mice.

Breast Cancer Model.

Figure 33:
FIG. 33 is a graph depicting that the anti-Jagged antibody 4D11 potently inhibited the growth of spontaneous tumors in Her2/neu transgenic mice.

A HER2/neu transgenic line develops mammary tumors in multiparous females at 20 weeks of age and 100% present lung metastasis at 25 weeks of age (Siegel P M et al., 1999, The EMBO Journal 18, 2149-2164). For experiments testing therapy for breast cancer, HER2/neu male mice were bred with FVB wild-type females and their progeny genotyped to select for HER2/neu females. At 20 weeks of age the HER2/neu females were separated into two groups, control and therapy. Anti-Jagged antibody 4D11 and IVIg control aliquots each were dosed IP, q7DX5 at 20 mg/Kg. FIG. 33 indicates that anti-Jagged antibody 4D11 potently inhibited the growth of spontaneous tumors in Her2/neu transgenic mice.

Example 25

In Situ Imaging of Labeled or Non-Labeled Anti-Jagged Activatable Antibodies with Detection by Secondary Antibodies The present Example describes the use of in situ imaging of labeled or non-labeled anti-Jagged activatable antibodies, wherein the cleavage and binding were detected using a secondary antibody that specifically binds to the AB portion of the activatable antibody. The results indicate the ability to evaluate the activation and binding of non-labeled activatable antibodies.

Figure 34:
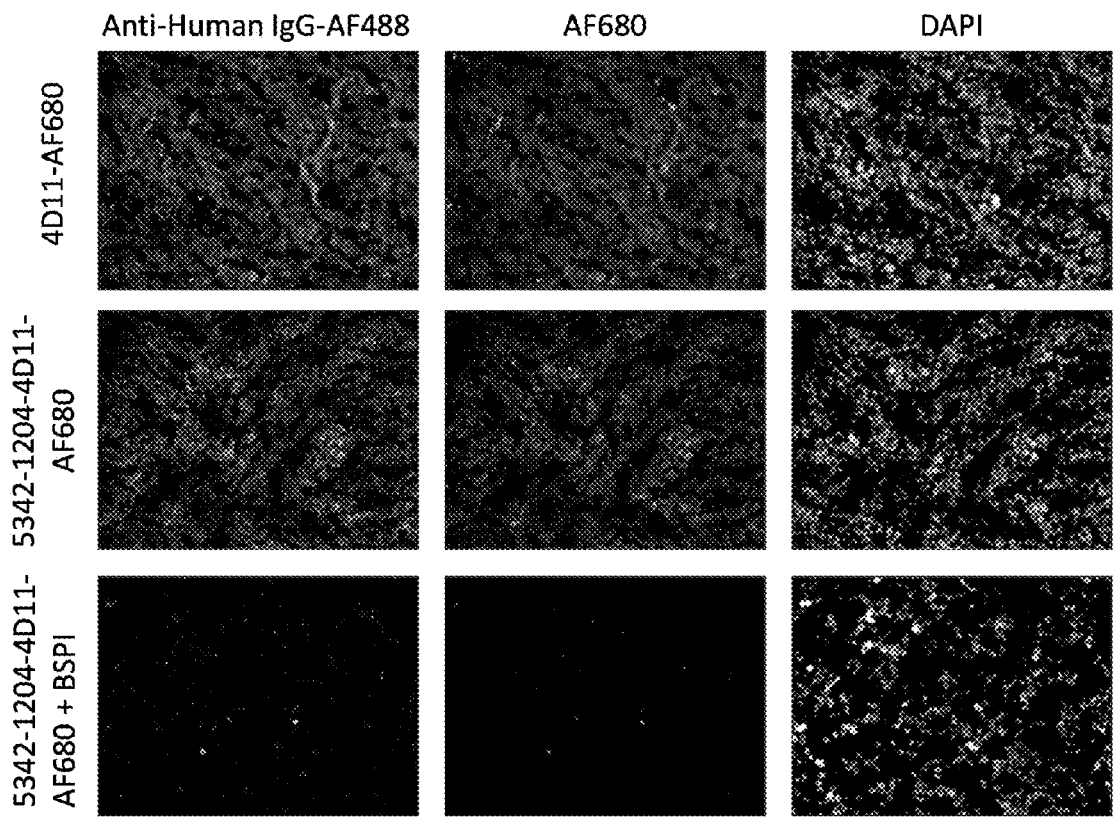
FIG. 34 is a series of images depicting the feasibility of conducting in situ imaging using non-labeled (i.e., unlabeled) activatable antibodies and a secondary reagent that comprises a detectable label and that specifically binds the AB of the activatable antibody.

In situ imaging of the activation and binding of an Alexa680-labeled anti-Jagged activatable antibody 5342-1204-4D11 on TRAMP prostate cancer tumor tissue was conducted as follows: Frozen tissue sections were laid over glass slides. A solution containing Alexa680-labeled anti-Jagged activatable antibodies was applied on the tissue and incubated, e.g., for 1 hour at room temperature (about 22-24° C.) in an incubation buffer of 50 mM Tris-HCl buffer pH 7.4, containing 150 mM NaCl, 100 µM $ZnCl_2$, 5 mM $CaCl_2$ and 0.05% Tween 20; activatable antibody at a concentration of about 4 µg/ml. The conditions of such an incubation can be adjusted to be conducive to the cleavage agent in the tissue section by, for example, varying the pH of the solution (e.g., within a range of about pH 7 to about pH 8.5), the temperature of the incubation (e.g., within a range of about 20° C. to about 40° C., e.g., room temperature or 37° C.), the incubation time (e.g., within a range of about 15 minutes to about 150 minutes, and/or the activatable antibody concentrations (e.g., within a range of about 0.05 µg/ml to about 10 µg/ml). The tissue was then extensively washed to remove non-bound material. The presence of activated antibody on the tissue was detected using imaging at 680 nm and a secondary anti-human IgG antibody labeled with AlexaFluor 488. The conditions of that detection can be adjusted to the detecting reagent and detection modality (e.g., fluorescently labeled). For example, when a fluorescent tag was used, the tissue was submitted to fluorescent microscopy. As shown in FIG. 34, anti-Jagged activatable antibody 5342-1204-4D11 demonstrated identical staining at both Alexa 680 (label of anti-Jagged activatable antibody) and FITC channels (label of anti-human IgG antibody), indicating that it is possible to conduct in situ imaging with non-labeled activatable antibodies and a secondary reagent that specifically binds to the activatable antibody, such as a labeled antibody. The fluorescent signal shown in both channels was inhibited by pre-treatment of the tissue with a 1:100 dilution of broad spectrum inhibitor cocktail set III (BSPI) (539134, EMD Millipore, Billerica, Mass.) and 50 µM of broad spectrum MMP inhibitor Galardin (Calbiochem, Millipore), as shown in FIG. 34, lower row.

Example 26

In Situ Imaging of Non-Labeled Anti-Jagged Activatable Antibodies

The present Example describes the use of in situ imaging of non-labeled anti-Jagged activatable antibodies. The cleavage and binding were detected using a secondary antibody that specifically binds to the AB portion of the activatable antibody.

Figure 35:
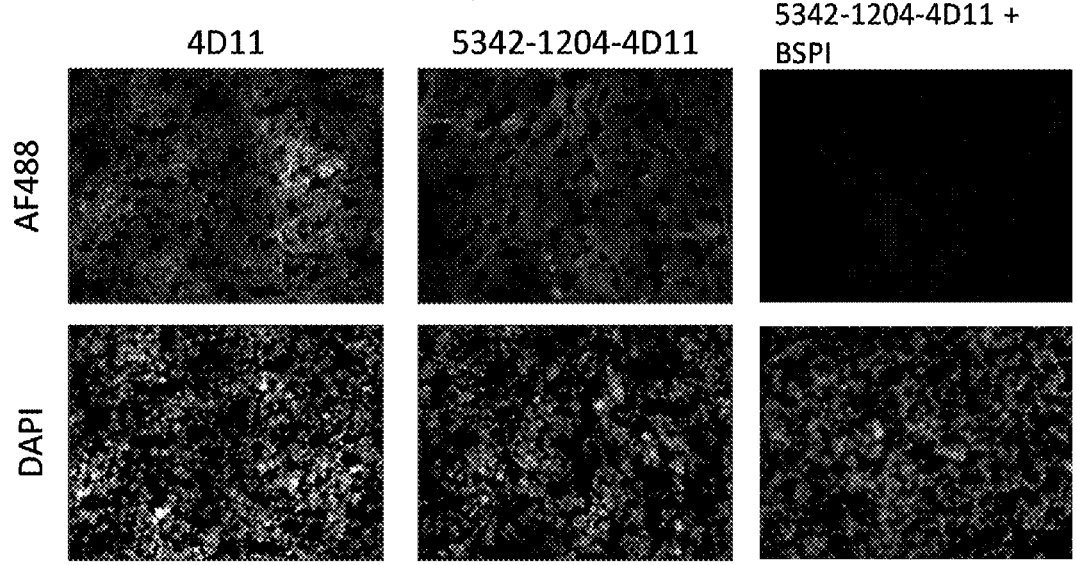
FIG. 35 is a series of images depicting the activation of non-labeled anti-Jagged activatable antibody 5342-1204-4D11 by tumor tissues of a transgenic prostate cancer model (TRAMP).

In situ imaging of the activation and binding of a non-labeled anti-Jagged activatable antibody 5342-1204-4D11 on TRAMP prostate cancer tumor tissue was conducted as follows: Frozen tissue sections were laid over glass slides. A solution containing non-labeled anti-Jagged activatable antibodies was applied on the tissue and incubated, e.g., for 1 hour at room temperature (about 22-24° C.) in an incubation buffer of 50 mM Tris-HCl buffer pH 7.4, containing 150 mM NaCl, 100 µM $ZnCl_2$, 5 mM $CaCl_2$ and 0.05% Tween 20; activatable antibody at a concentration of about 4 µg/ml. The conditions of such an incubation can be adjusted to be conducive to the cleavage agent in the tissue section by, for example, varying the pH of the solution (e.g., within a range of about pH 7 to about pH 8.5), the temperature of the incubation (e.g., within a range of about 20° C. to about 40° C., e.g., room temperature or 37° C.), the incubation time (e.g., within a range of about 15 minutes to about 150 minutes, and/or the activatable antibody concentrations (e.g., within a range of about 0.05 µg/ml to about 10 µg/ml). The tissue was then extensively washed to remove non-bound material. The presence of activated antibody on the tissue was detected using a secondary anti-human IgG antibody labeled with AlexaFluor 488. The conditions of that detection can be adjusted to the detecting reagent and detection modality (e.g., fluorescently labeled). For example, when a fluorescent tag was used, the tissue was submitted to fluorescent microscopy. As shown in FIG. 35, anti-Jagged activatable antibody 5342-1204-4D11 demonstrated staining with comparable intensity and pattern as parental anti-Jagged antibody (columns 2 and 1, respectively). The fluorescent signal of anti-Jagged activatable antibody 5342-1204-4D11 was inhibited by pre-treatment of the tissue with a 1:100 dilution of broad spectrum inhibitor cocktail set III (BSPI) (539134, EMD Millipore, Billerica, Mass.) and 50 µM of broad spectrum MMP inhibitor Galardin (Calbiochem, Millipore), as shown in FIG. 35, column 3. The data demonstrate the feasibility of conducting in situ imaging using non-labeled (i.e., unlabeled) activatable antibodies and a secondary reagent that comprises a detectable label and that specifically binds the AB of the activatable antibody.

Human triple-negative breast cancer (TNBC) and pancreatic cancer tissue samples were profiled for the ability of anti-Jagged activatable antibody 5342-1204-4D11 to be activated and to bind human tumor using in situ imaging. The activatable antibody was labeled with Alexa Fluor® 680 (Invitrogen) as described above. The resultant activatable antibody 5342-1204-4D11-AF680 was incubated with frozen patient tissue samples according to the protocol of in situ imaging described herein. The results on the ability of TNBC and pancreatic cancer patients' tissue samples to activate and bind anti-Jagged activatable antibodies are summarized in Table 27 and Table 28. The IHC staining that measures the amount of anti-Jagged (4D11) antibody binding to the tissue sample was scored from – to 3+: –, no staining; 1+ (i.e., "+"), weak staining; 2+ (i.e., "++"), moderate staining; and 3+ (i.e., "+++"), strong staining. The in situ imaging of anti-Jagged activatable antibodies staining was quantified based on comparison with anti-Jagged antibody staining Table 27 illustrates the expression level of Jagged 1 and/or Jagged 2 detected by 4D11 binding and ability of triple-negative breast cancer (TNBC) tissues to activate and bind anti-EGFR acti vatable antibodies. Table 28 illustrates the expression level of Jagged 1 and/or Jagged 2 detected by 4D11 binding and the ability of pancreatic cancer tissues to activate and bind anti-EGFR activatable antibodies.

TABLE 27

Screening for Jagged 1 and/or Jagged 2 expression using anti-Jagged antibody 4D11 and in situ imaging of anti-Jagged activatable antibody 5342-1204-4D11 in TNBC cancer patients' tumor tissues.

| Patient # | Stage | Her-2 neu | ER | PR | 4D11 | 5342-1204-4D11 (%) |
|---|---|---|---|---|---|---|
| 1 | IIIA | 0 | negative | negative | +++ | 100 |
| 2 | IIIB | 0 | negative | negative | + | 5 |
| 3 | IIA | 0 | negative | negative | +++ | 50 |
| 4 | IIA | 0 | negative | negative | +++ | 15 |
| 5 | IIA | 0 | negative | negative | +++ | 85 |
| 6 | IIIA | 0 | negative | negative | ++ | 95 |
| 7 | IIA | 1+ | negative | negative | +++ | 90 |
| 8 | IIA | 0 | negative | negative | +++ | 80 |
| 9 | IIA | 1+ | negative | negative | ++ | 25 |
| 10 | IIA | 0 | negative | negative | ++ | 95 |

TABLE 28

Screening for Jagged 1 and/or Jagged 2 expression using anti-Jagged antibody 4D11 and in situ imaging of anti-Jagged activatable antibody 5342-1204-4D11 in pancreatic cancer patients' tumor tissues.

| Patient # | Diagnosis | Stage | Grade | TNM status | 4D11 | 5342-1204-4D11 (%) |
|---|---|---|---|---|---|---|
| HF-0301-17 | adenocarcinoma | N/A | G1 Well Differentiated | pT3, pN1b, pMX | + | 35 |
| HF-0301-19 | adenocarcinoma | N/A | G2 Moderately Differentiated | pT4. pN1, pMX | +++ | 45 |
| HF-0301-20 | adenocarcinoma | N/A | G2 Moderately Differentiated | pT3, pN1b, pMX | + | 55 |
| HF-0301-21 | adenocarcinoma | N/A | G3 Poorly Differentiated | pT3, pN1, pMX | ++ | 100 |
| HF-0301-22 | adenocarcinoma | N/A | G2 Moderately Differentiated | pT3, pN1, pMX | ++ | 80 |
| HF-0301-23 | adenocarcinoma | N/A | Moderately to poorly differentiated | pT3, pN1, pMX | +++ | 55 |
| HF-0301-24 | adenocarcinoma | N/A | G2 to G3 Moderately to Poorly Differentiated | pT3, pN1, pM0 | +++ | 100 |
| HF-0301-10 | adenocarcinoma | IIB | G1 Well Differentiated | PT3, pN1, pM n/a | ++ | 100 |
| HF-0301-12 | adenocarcinoma | IIB | G2 Moderately Differentiated | pT3, pN1, pM n/a | ++ | 80 |
| HF-0301-13 | adenocarcinoma | I | G3 Poorly Differentiated | pT2, pN0, pM n/a | +++ | 30 |
| HF-0301-06 | Ductal Adenocarcinoma | II | G2 Moderately Differentiated | pT3, pN1 | ++ | 100 |
| HF-0301-16 | adenocarcinoma | IIB | G2 Moderately Differentiated | pT3, pN1 | ++ | 97 |
| HF-0301-15 | adenocarcinoma | IIB | G2 Moderately Differentiated | pT3, pN1, pM n/a | ++ | 50 |
| HF-0301-08 | Ductal Adenocarcinoma | IIB | G2 Moderately Differentiated | pT3, pN1 | ++ | 100 |
| HF-0301-14 | adenocarcinoma | IB | G3 Poorly Differentiated | pT2, pN0, pM n/a | − | — |
| TBD | adenocarcinoma | TBD | TBD | TBD | ++ | 80 |
| TBD | adenocarcinoma | TBD | TBD | TBD | + | 100 |
| HF-0301-01 | Ductal Adenocarcinoma | IIB | G2 Moderately Differentiated | pT2, pN1, pM n/a | ++ | +++ |
| HF-0301-02 | adenocarcinoma | II | Moderately differentiated | pT3, pN1, pMn/a | +++ | ++ |
| HF-0301-03 | adenocarcinoma | II | G2 Moderately Differentiated | pT3, pN0 | ++ | + |
| HF-0304-02 | adenocarcinoma | IIA | G3 Poorly Differentiated | pT3, pN0, pMn/a | ++ | + |

Example 27

Protease Activation and Binding of an Anti-Jagged Activatable Antibody

This Example demonstrates the ability of anti-Jagged antibody 5342-1204-4D11 to be activated in vitro.

Anti-Jagged activatable antibody 5342-1204-4D11 was activated by combining the activatable antibody and active site titrated MT-SP1 in PBS at final concentrations of 58.5 uM and 570 nM respectively. The mixture was incubated at 37° C. for 20 h. Prior to Protein A purification, an aliquot was removed and analyzed by SDS-PAGE to confirm that proteolytic digestion of 5342-1204-4D11 had gone to completion.

To remove the MT-SP1 and cleaved masking moiety, the activated 5342-1204-4D11 was purified using standard Protein A chromatography. Briefly, a 1 mL Hi-Trap Protein A column (GE Healthcare life sciences) was equilibrated with PBS. The digested protein was bound to the column and washed extensively with PBS. The bound protein was eluted using 1 M Glycine, pH 3.0 and neutralized with 0.1 M Tris, pH 8.0, and subsequently dialyzed overnight into PBS.

Figure 36:
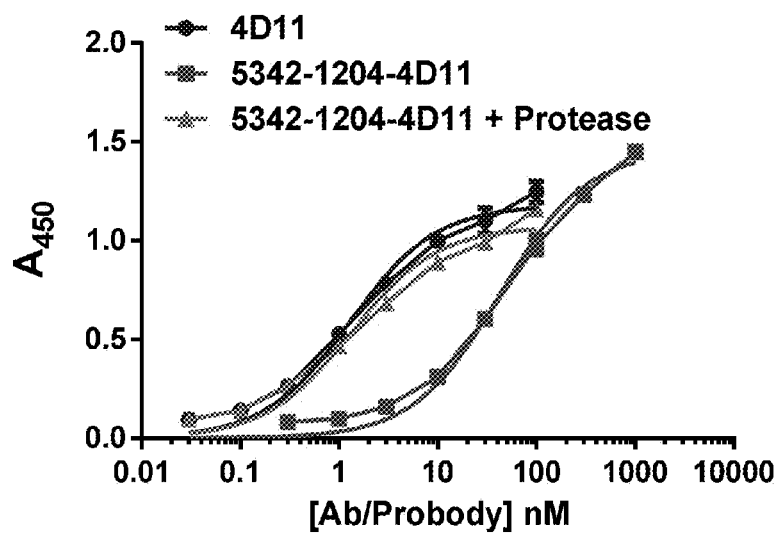
FIG. 36 is a graph depicting the abilities of antibody 4D11, activatable antibody 5342-1204-4D11), and MT-SP1-activated antibody 5342-1204-4D11 to bind to human Jagged 1.

The binding of anti-Jagged antibody 4D11, anti-Jagged activatable antibody 5342-1204-4D11, and anti-Jagged activated antibody 5342-1204-4D11 to recombinant human Jagged 1-Fc was measured with an enzyme-linked immunosorbent assay (ELISA). Briefly, recombinant hJag1-Fc (R&D Systems) was absorbed to wells of a 96-well ELISA plate at a concentration of 1 µg/ml in HANKS buffer overnight at 4° C. All subsequent steps were done at room temperature. The plates were blocked with HANKS, 0.05% Tween, 4.0% non-fat dry milk for 1 hour. The 4D11 antibody and activated antibody 5342-1204-4D11 were added to the plate at 100, 30, 10, 3, 1, 0.3, 0.1, and 0.03 nM and the activatable antibody 5342-1204-4D11 was added to the plate at 1000, 300, 100, 30, 10, 3, 1, 0.3 nM and incubated for 1 hour. All measurements were done in triplicate. After the plates were washed 5× with HANKS, 0.05% Tween an anti-human FAB-goat-HRP secondary (Sigma) was added to the plate at a concentration of 1:5000 in HANKS, 0.05% Tween, 4.0% non-fat dry milk and incubated for 1 hour, washed 5× as before, and then developed using 1-STEP-TMB1 ELISA solution (Thermo Scientific). The absorbance at 450 nm was measured using a TECAN plate reader. FIG. 36 shows that the ability of activated antibody 5342-1204-4D11 to bind Jagged 1 is indistinguishable from 4D11 antibody binding to Jagged 1.

Example 28

In Vivo Efficacy and Safety of an Anti-Jagged Activatable Antibody in the H292 Tumor Model Anti-Jagged activatable antibody 5342-1204-4D11 was tested for the ability to reduce the growth of H292 xenograft tumors using the following method. Female nu/nu mice, age 6-8 weeks, were implanted subcutaneously with 5×10⁶ H292 cells in serum-free medium with matrigel (1:1). Tumors were measured every other day until 48-60 mice with tumors in the target range (~100-250 mm3) could be randomized into groups of equal average tumor volume when the mean tumor size reached 150-200 mm3. (n=8-10/group). Animals were treated using the doses set forth in Table 29.

TABLE 29

Groups and doses for the H292 efficacy study.

| Group | N | Treatment | Dose (mg/kg) | Dosing Route | Schedule |
|---|---|---|---|---|---|
| 1 | 8 | IVIg | 20 mg/kg | i.p | q7dx 4 |
| 2 | 8 | 4D11 (CTX-014) | 2 mg/kg | i.p. | q7dx 4 |
| 3 | 8 | 4D11 (CTX-014) | 6.7 mg/kg | i.p. | q7dx 4 |
| 4 | 8 | 4D11 (CTX-014) | 20 mg/kg | i.p. | q7dx 4 |
| 5 | 8 | 5342-1204-4D11 (CTX-033) | 6.7 mg/kg | i.p. | q7dx 4 |
| 6 | 8 | 5342-1204-4D11 (CTX-033) | 20 mg/kg | i.p. | q7dx 4 |

Figure 37:
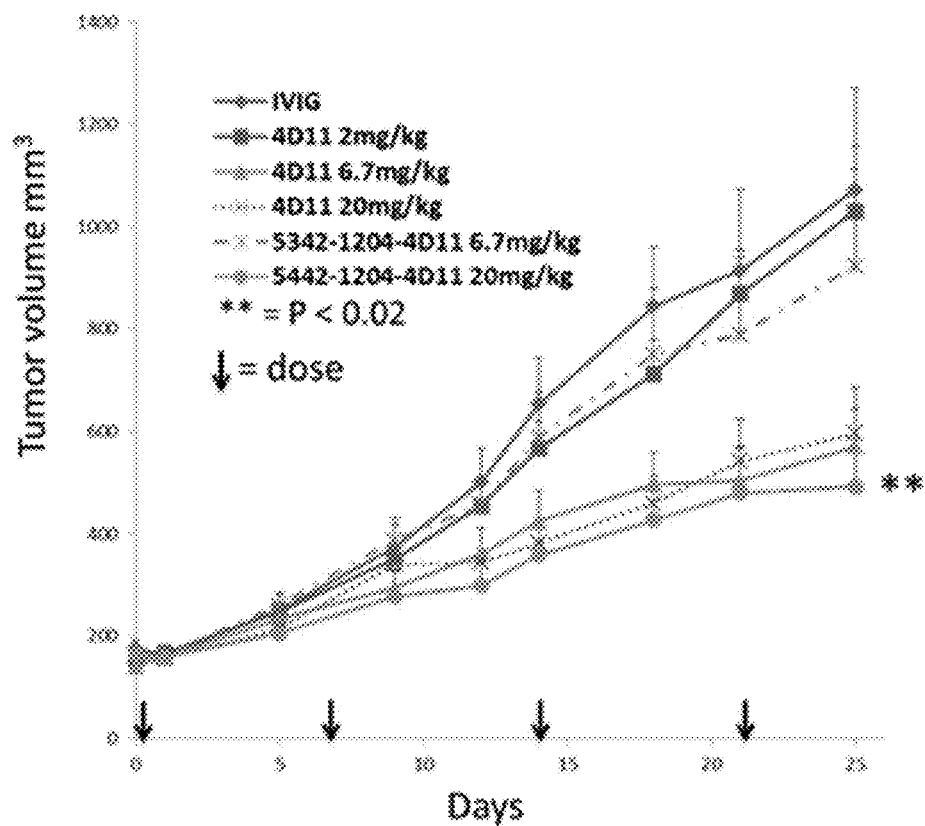
FIG. 37 is a graph depicting that the anti-Jagged activatable antibody 5342-1204-4D11 inhibited the growth of the H292 xenograft tumors.
Figure 38:
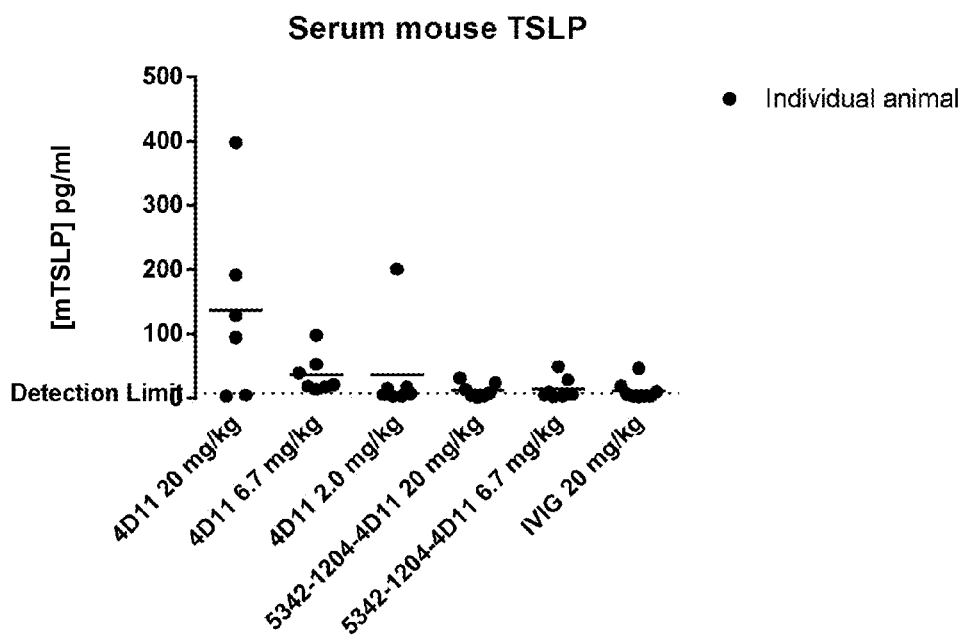
FIG. 38 is a graph depicting that the activatable anti-Jagged antibody 5342-1204-4D11 showed no elevation in TSLP, while animals that were administered the antibody at 6.7 and 20 mg/kg showed increased TSLP as compared to the IVIg treated group.

FIG. 37, which shows tumor volume, demonstrates that the anti-Jagged activatable antibody 5342-1204-4D11 inhibited the growth of the H292 xenograft tumors. The serum concentration of mouse thymic stromal lymphopoietin (TSLP) was measured as described above. The serum levels of mouse TSLP (mTSLP) were quantified for individual mice upon sacrifice; results are shown in FIG. 38. Activatable antibody 5342-1204-4D11 showed no elevation in TSLP while animals in the antibody at 6.7 and 20 mg/kg showed increased TSLP as compared to the IVIg treated group.

Figure 39:
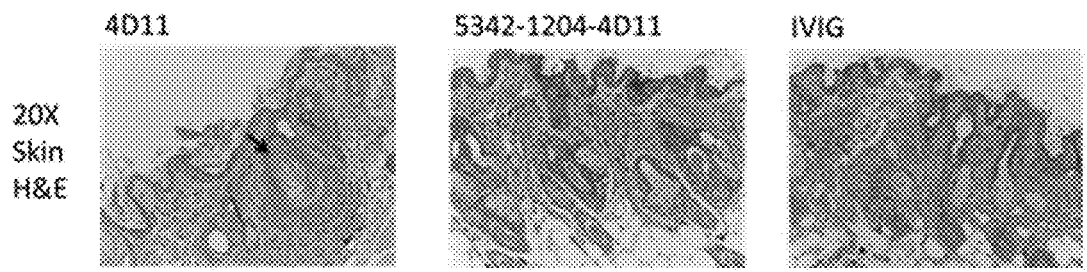
FIG. 39 is a series of images depicting that hyperkeratosis was observed in the antibody-treated group, while the activatable antibody-treated group showed limited or no hyperkeratosis.

Upon sacrifice, skin was taken from the abdomen of animals treated with 20 mg/kg of IVIg, antibody 4D11, or activatable antibody 5342-1204-4D11. The skin was formalin-fixed, paraffin-embedded and H&E stained. As FIG. 39 depicts, hyperkeratosis was observed in the antibody-treated group, while the activatable antibody-treated group showed limited or no hyperkeratosis. The arrow points to a hair follicle showing significant hyperkeratosis.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of alleviating a symptom of a clinical indication associated with a cancer associated with aberrant expression or activity of Jagged 1, Jagged 2, or both Jagged 1 and Jagged 2 in a subject, the method comprising administering an isolated fully human monoclonal antibody that binds Jagged 1 and Jagged 2 and inhibits at least one biological activity of Jagged 1, Jagged 2, or both Jagged 1 and Jagged 2 and/or inhibits Jagged 1-mediated signaling, Jagged 2-mediated signaling, or both Jagged 1-mediated signaling and Jagged 2-mediated signaling to a subject in need thereof in an amount sufficient to alleviate the symptom of the clinical indication associated with cancer, wherein the isolated fully human monoclonal antibody comprises a VH CDR1 sequence comprising the amino acid sequence SYAMS (SEQ ID NO: 200); a VH CDR2 sequence comprising the amino acid sequence SIDPEGRQTYYADSVKG (SEQ ID NO: 208); a VH CDR3 sequence comprising the amino acid sequence DIGGRSAFDY (SEQ ID NO: 209); a VL CDR1 sequence comprising the amino acid sequence RASQSISSY (SEQ ID NO: 210); a VL CDR2 sequence comprising the amino acid sequence AASSLQS (SEQ ID NO: 211); and a VL CDR3 sequence comprising the amino acid sequence QQTVAPPL (SEQ ID NO: 212).

2. A method of alleviating a symptom of a clinical indication associated with a cancer associated with aberrant expression or activity of Jagged 1, Jagged 2, or both Jagged 1 and Jagged 2 in a subject, the method comprising administering an activatable antibody that in an activated state binds Jagged 1 and Jagged 2 and inhibits at least one biological activity of Jagged 1, Jagged 2, or both Jagged 1 and Jagged 2 and/or inhibits Jagged 1-mediated signaling, Jagged 2-mediated signaling, or both Jagged 1-mediated signaling and Jagged 2-mediated signaling to a subject in need thereof in an amount sufficient to alleviate the symptom of the clinical indication associated with cancer, wherein the activatable antibody comprises:
- an antibody or an antigen binding fragment thereof (AB) that specifically binds to Jagged 1 and Jagged 2, wherein the AB comprises a VH CDR1 sequence comprising the amino acid sequence SYAMS (SEQ ID NO: 200); a VH CDR2 sequence comprising the amino acid sequence SIDPEGRQTYYADSVKG (SEQ ID NO: 208); a VH CDR3 sequence comprising the amino acid sequence DIGGRSAFDY (SEQ ID NO: 209); a VL CDR1 sequence comprising the amino acid sequence RASQSISSY (SEQ ID NO: 210); a VL CDR2 sequence comprising the amino acid sequence AASSLQS (SEQ ID NO: 211); and a VL CDR3 sequence comprising the amino acid sequence QQTVVAPPL (SEQ ID NO: 212);
- a masking moiety (MM) that inhibits the binding of the AB to Jagged 1 and Jagged 2 when the activatable antibody is in an uncleaved state, wherein (i) the MM is a polypeptide of no more than 40 amino acids, (ii) the dissociation constant (Kd) of the MM towards the AB is greater than the dissociation constant (Kd) of the AB towards Jagged 1, Jagged 2, or both Jagged 1 and Jagged 2, (iii) the MM polypeptide sequence is different from that of Jagged 1, Jagged 2, or both Jagged 1 and Jagged 2, and (iv) the MM of the activatable antibody in a cleaved state does not interfere or compete with the AB for binding to Jagged 1, Jagged 2, or both Jagged 1 and Jagged 2; and
- a cleavable moiety (CM) coupled to the AB, wherein the CM is a polypeptide that functions as a substrate for a protease,
- wherein the activatable antibody in the uncleaved state has the structural arrangement from N-terminus to C-terminus as follows: MM-CM-AB or AB-CM-MM.

3. The method of claim 1, wherein said subject is a human.

4. The method of claim 2, wherein said subject is a human.

5. The method of claim 1, wherein the antibody comprises a variable heavy chain comprising the amino acid sequence of SEQ ID NO: 56 and a variable light chain comprising the amino acid sequence of SEQ ID NO: 54.

6. The method of claim 1, wherein the antibody comprises a heavy chain comprising the amino acid sequence of SEQ ID NO: 76 and a light chain comprising the amino acid sequence of SEQ ID NO: 74.

7. The method of claim 1, wherein the antibody binds Jagged 1 and Jagged 2 and prevents one or more of Jagged 1 or Jagged 2 from binding a Notch receptor.

8. The method of claim 1, wherein said antibody is an IgG isotype.

9. The method of claim 8, wherein said antibody is an IgG1 isotype.

10. The method of claim 1, wherein the antibody comprises an agent conjugated to the antibody.

11. The method of claim 10, wherein the agent is a therapeutic agent, an antineoplastic agent, a toxin or fragment thereof, a detectable moiety or a diagnostic agent.

12. The method of claim 10, wherein the agent is conjugated to the antibody via a linker.

13. The method of claim 12, wherein the linker is a cleavable linker.

14. The method of claim 2, wherein the protease is co-localized with Jagged 1 and/or Jagged 2 in a tissue, and wherein the protease cleaves the CM in the activatable antibody when the activatable antibody is exposed to the protease.

15. The method of claim 2, wherein the activatable antibody comprises a linking peptide between the MM and the CM.

16. The method of claim 2, wherein the activatable antibody comprises a linking peptide between the CM and the AB.

17. The method of claim 2, wherein the activatable antibody comprises a first linking peptide (LP1) and a second linking peptide (LP2), and wherein the activatable antibody follows in the uncleaved state has the structural arrangement from N-terminus to C-terminus as: MM-LP1-CM-LP2-AB or AB-LP2-CM-LP1-MM.

18. The method of claim 17, wherein the two linking peptides need not be identical to each other.

19. The method of claim 17, wherein each of LP1 and LP2 is a peptide of about 1 to 20 amino acids in length.

20. The method of claim 2, wherein the MM polypeptide sequence is no more than 50% identical to any natural binding partner of the AB.

21. The method of claim 2, wherein the CM is a polypeptide of up to 15 amino acids in length.

22. The method of claim 2, wherein the antigen binding fragment thereof is selected from the group consisting of a Fab fragment, a F(ab')$_2$ fragment, a scFv, a scab, a dAb, a single domain heavy chain antibody, and a single domain light chain antibody.

23. The method of claim 2, wherein the CM is a substrate for an enzyme selected from the group consisting of uPA, legumain, MT-SP1, ADAM17, BMP-1, TMPRSS3, TMPRSS4, MMP-9, MMP-12, MMP-13, and MMP-14.

24. The method of claim 2, wherein the activatable antibody comprises an agent conjugated to the AB.

25. The method of claim 24, wherein the agent is a therapeutic agent, an antineoplastic agent, a toxin or fragment thereof, a detectable moiety or a diagnostic agent.

26. The method of claim 24, wherein the agent is conjugated to the AB via a linker.

27. The method of claim 26, wherein the linker is a cleavable linker.

28. The method of claim 2, wherein the MM comprises a sequence selected from the group consisting of the sequences shown in Table 9, Table 11, Table 12, Table 13, Table 14, Table 19, Table 20, Table 21, Table 22, or Table 23.

29. The method of claim 2, wherein the AB comprises the variable heavy chain amino acid sequence of SEQ ID NO: 56 and the variable light chain amino acid sequence of SEQ ID NO: 54.

30. The method of claim 2, wherein the activatable antibody comprises a light chain amino acid sequence selected from the group consisting of SEQ ID NOs: 74, 132, 134, 136, 138, 140, 263, 265, 267, 269, 271, 273, 275, and 278, and a heavy chain amino acid sequence selected from the group consisting of SEQ ID NOs: 76 and 148.

31. The method of claim 2, wherein the activatable antibody comprises the heavy chain amino acid sequence of SEQ ID NO: 76 and the light chain sequence of SEQ ID NO: 134, wherein the X at residue 126 of SEQ ID NO: 134 is D.

32. The method of claim 2, wherein the AB comprises the variable heavy chain amino acid sequence of SEQ ID NO: 56 and the variable light chain amino acid sequence of SEQ ID NO: 54, wherein the MM comprises the amino acid sequence CNIWLVGGDCRGWQG (SEQ ID NO: 102), and wherein the CM comprises the amino acid sequence LSGRSDNH (SEQ ID NO: 213).

33. The method of claim 2, wherein the AB comprises a modified light chain amino acid sequence and a heavy chain amino acid sequence selected from the group consisting of SEQ ID NOs: 76 and 148, wherein the modified light chain amino acid sequence comprises the amino acid sequence of SEQ ID NO: 74 coupled to an amino acid sequence selected from the group consisting of SEQ ID NOs: 142, 144, 146, 180, 182, 184, 186, 188, 190, 192, 194, and 196.

* * * * *

SEQUENCE LISTING

<160> NUMBER OF SEQ ID NOS: 279

<210> SEQ ID NO 1
<211> LENGTH: 710
<212> TYPE: DNA
<213> ORGANISM: Artificial Sequence
<220> FEATURE:
<223> OTHER INFORMATION: chemically synthesized

<400> SEQUENCE: 1

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaggg ctggagtggg tctcagcgat tgcggagctg ggtgcgctta catagtacgc     180
agactccgtg aagggccggt tcaccatctc cagagacaat tccaagaaca cgctgtatct     240
gcaaatgaac agctagagcc gaggacacgg ccgtatatta ctgtgcgaga gctcatacta     300
gttttgacta ctggggccag ggaaccctgg tcaccgtctc gagcggtgga ggcggttcag     360
gcggaggtgg cagcggcggg ggggtcgacg gacatccaga tgacccagtc tccatcctcc     420
ctgtctgcat ctgtaggaga cagagtcacc atcacttgcc gggcaagtca gagcattagc     480
```

```
agctatttaa attggtatca gcagaaccgg gaaagcccct aagctcctga tctataaggc    540
atccactttg caaagtgggg tcccatcaag gttcagtggc agtggatctg ggacagattt    600
cactctcacc atcagcagtc tgcaacctga aatttgcaac ttactactgt caacaggcta    660
tggatcagcc tcctacgttc ggccaaggga ccaaggtgga aatcaaacgg                710
```

<210> SEQ ID NO 2
<211> LENGTH: 239
<212> TYPE: PRT
<213> ORGANISM: Artificial Sequence
<220> FEATURE:
<223> OTHER INFORMATION: chemically synthesized

<400> SEQUENCE: 2

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ala Glu Leu Gly Ala Leu Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala His Thr Ser Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Lys Ala Ser Thr Leu Ser Gly Val Pro Ser Arg
            180                 185                 190

Phe Ser Gly Ser Gly Ser Gly Thr Asp Phe Thr Leu Thr Ile Ser Ser
        195                 200                 205

Leu Gln Pro Glu Asp Phe Ala Thr Tyr Tyr Cys Gln Gln Ala Met Asp
    210                 215                 220

Gln Pro Pro Thr Phe Gly Gln Gly Thr Lys Val Glu Ile Lys Arg
225                 230                 235
```

<210> SEQ ID NO 3
<211> LENGTH: 710
<212> TYPE: DNA
<213> ORGANISM: Artificial Sequence
<220> FEATURE:
<223> OTHER INFORMATION: chemically synthesized

<400> SEQUENCE: 3

```
gaggtgcagc tgttggagtc tgggggaggc ttggtacagc ctggggggtc cctgagactc     60
tcctgtgcag cctctggatt cacctttagc agctatgcca tgagctgggt ccgccaggct    120
ccagggaggg ctggagtggg tctcaacgat tgctgcttag ggtaagcata cagattacgc    180
```

```
agactccgtg aagggccggt tcaccatctc cagagacaat tccaagaaca cgctgtatct    240
gcaaatgaac agctagagcc gaggacacgg ccgtatatta ctgtgcgaaa tcgatgcgtg    300
gttttgacaa ctggggccag ggaaccctgg tcaccgtctc gagcggtgga ggcggttcag    360
gcggaggtgg cagcggcggg ggggtcgacg gacatccaga tgacccagtc tccatcctcc    420
ctgtctgcat ctgtaggaga cagagtcacc atcacttgcc gggcaagtca gagcattagc    480
agctatttaa attggtatca gcagaaccgg gaaagcccct aagctcctga tctatcgggc    540
atcctctttg caaagtgggg tcccatcaag gttcagtggc agtggatctg ggacagattt    600
cactctcacc atcagcagtc tgcaacctga aatttgcaac ttactactgt caacaggatg    660
cgactggtcc tgcgacgttc ggccaaggga ccaaggtgga atcaaacgg               710
```

<210> SEQ ID NO 4
<211> LENGTH: 238
<212> TYPE: PRT
<213> ORGANISM: Artificial Sequence
<220> FEATURE:
<223> OTHER INFORMATION: chemically synthesized

<400> SEQUENCE: 4

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ala Ala Gly Lys His Thr Asp Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Ser Met Arg Gly Phe Asp Asn Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Thr Asp Ile Gln Met Thr Gln Ser Pro Ser Ser Leu Ser Ala
    130                 135                 140

Ser Val Gly Asp Arg Val Thr Ile Thr Cys Arg Ala Ser Gln Ser Ile
145                 150                 155                 160

Ser Ser Tyr Leu Asn Trp Tyr Gln Gln Lys Pro Gly Lys Ala Pro Lys
                165                 170                 175

Leu Leu Ile Tyr Ala Ser Ser Leu Gln Ser Gly Val Pro Ser Arg Phe
            180                 185                 190

Ser Gly Ser Gly Ser Gly Thr Asp Phe Thr Leu Thr Ile Ser Ser Leu
        195                 200                 205

Gln Pro Glu Asp Phe Ala Thr Tyr Tyr Cys Gln Gln Asp Ala Thr Gly
    210                 215                 220

Pro Ala Thr Phe Gly Gln Gly Thr Lys Val Glu Ile Lys Arg
225                 230                 235
```

<210> SEQ ID NO 5
<211> LENGTH: 710
<212> TYPE: DNA
<213> ORGANISM: Artificial Sequence
<220> FEATURE:
<223> OTHER INFORMATION: chemically synthesized

<400> SEQUENCE: 5

```
gaggtgcagc tgttggagtc tgggggaggc ttggtacagc ctgggggtc cctgagactc      60
tcctgtgcag cctctggatt cacctttagc agctatgcca tgagctgggt ccgccaggct    120
ccagggaggg ctggagtggg tctcatcgat tgagacttag ggtccgacta cactgtacgc    180
agactccgtg aagggcaggt tcaccatctc cagagacaat tccaagaaca cgctgtatct    240
gcaaatgaac agctagagcc gaggacacgg ccgtatatta ctgtgcgaaa acgtctagtg    300
cgtttgacta ctggggccag ggaaccctgg tcaccgtctc gagcggtgga ggcggttcag    360
gcggaggtgg cagcggcggg ggggtcgacg acatccaga tgacccagtc tccatcctcc    420
ctgtctgcat ctgtaggaga cagagtcacc atcacttgcc gggcaagtca gagcattagc    480
agctatttaa attggtatca gcagaaccgg gaaagcccct aagctcctga tctatcatgc    540
atcctcgttg caaagtgggg tcccatcaag gttcagtggc agtggatctg ggacagattt    600
cactctcacc atcggcagtc tgcaacctga aatttgcaac ttactactgt caacagaatg    660
ttgctactcc tctgacgttc ggccaaggga ccaaggtgga atcaaacgg              710
```

<210> SEQ ID NO 6
<211> LENGTH: 239
<212> TYPE: PRT
<213> ORGANISM: Artificial Sequence
<220> FEATURE:
<223> OTHER INFORMATION: chemically synthesized

<400> SEQUENCE: 6

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Thr Gln Gly Pro Thr Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Ser Ser Ala Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ala Ser Ser Leu Gln Ser Gly Val Pro Ser Arg
            180                 185                 190

Phe Ser Gly Ser Gly Ser Gly Thr Asp Phe Thr Leu Thr Ile Gly Ser
        195                 200                 205

Leu Gln Pro Glu Asp Phe Ala Thr Tyr Tyr Cys Gln Gln Asn Val Ala
```

```
                210                 215                 220
Thr Pro Leu Thr Phe Gly Gln Gly Thr Lys Val Glu Ile Lys Arg
225                 230                 235
```

<210> SEQ ID NO 7
<211> LENGTH: 710
<212> TYPE: DNA
<213> ORGANISM: Artificial Sequence
<220> FEATURE:
<223> OTHER INFORMATION: chemically synthesized

<400> SEQUENCE: 7

```
gaggtgcagc tgttggagtc tgggggaggc ttggtacagc ctgggggtc cctgagactc      60
tcctgtgcag cctctggatt caccttagc agctatgcca tgagctgggt ccgccaggct    120
ccagggaggc tggagtgggt ctcaacgat tgagccgtag ggttcggcta cagagtacgc    180
agactccgtg aagggccggt tcaccatctc cagagacaat tccaagaaca cgctgtatct    240
gcaaatgaac agctagagcc gaggacacgg ccgtatatta ctgtgcgaaa acgcagacgg    300
gttttgacta ctggggccag ggaaccctgg tcaccgtctc gagcggtgga ggcggttcag    360
gcggaggtgg cagcggcggg ggggtcgacg gacatccaga tgacccagtc tccatcctcc    420
ctgtctgcat ctgtaggaga cagagtcacc atcacttgcc gggcaagtca gagcattagc    480
agctatttaa attggtatca gcagaaccgg gaaagcccct aagctcctga tctataaggc    540
atccactttg caaagtgggg tcccatcaag gttcagtggc agtggatctg ggacagattt    600
cactctcacc atcagcagtc tgcaacctga aatttgcaac ttactactgt caacaggatg    660
ttgagcctcc tgctacgttc ggccaaggga ccaaggtgga aatcaaacgg              710
```

<210> SEQ ID NO 8
<211> LENGTH: 238
<212> TYPE: PRT
<213> ORGANISM: Artificial Sequence
<220> FEATURE:
<223> OTHER INFORMATION: chemically synthesized

<400> SEQUENCE: 8

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Glu Pro Gly Ser Ala Thr Glu Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Lys Thr Gln Thr Gly Phe Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Thr Asp Ile Gln Met Thr Gln Ser Pro Ser Ser Leu Ser Ala
    130                 135                 140

Ser Val Gly Asp Arg Val Thr Ile Thr Cys Arg Ala Ser Gln Ser Ile
145                 150                 155                 160
```

Ser Ser Tyr Leu Asn Trp Tyr Gln Gln Lys Pro Gly Lys Ala Pro Lys
            165                 170                 175

Leu Leu Ile Tyr Ala Ser Thr Leu Gln Ser Gly Val Pro Ser Arg Phe
            180                 185                 190

Ser Gly Ser Gly Ser Gly Thr Asp Phe Thr Leu Thr Ile Ser Ser Leu
        195                 200                 205

Gln Pro Glu Asp Phe Ala Thr Tyr Tyr Cys Gln Gln Asp Val Glu Pro
        210                 215                 220

Pro Ala Thr Phe Gly Gln Gly Thr Lys Val Glu Ile Lys Arg
225                 230                 235

<210> SEQ ID NO 9
<211> LENGTH: 710
<212> TYPE: DNA
<213> ORGANISM: Artificial Sequence
<220> FEATURE:
<223> OTHER INFORMATION: chemically synthesized

<400> SEQUENCE: 9

| | | | | | |
|---|---|---|---|---|---|
| gaggtgcagc | tgttggagtc | tgggggaggc | ttggtacagc | ctgggggtc | cctgagactc | 60 |
| tcctgtgcag | cctctggatt | cacctttagc | agctatgcca | tgagctgggt | ccgccaggct | 120 |
| ccagggaggg | ctggagtggg | tctcaagtat | tgagcagatg | ggttggtaga | catattacgc | 180 |
| agactccgtg | aagggccggt | tcaccatctc | cagagacaat | tccaagaaca | cgctgtatct | 240 |
| gcaaatgaac | agctagagcc | gaggacacgg | ccgtatatta | ctgtgcgaaa | tcggctgctg | 300 |
| cttttgacta | ctggggccag | ggaacccctgg | tcaccgtctc | gagcggtgga | ggcggttcag | 360 |
| gcggaggtgg | cagcggcggg | ggggtcgacg | gacatccaga | tgacccagtc | tccatcctcc | 420 |
| ctgtctgcat | ctgtaggaga | cagagtcacc | atcacttgcc | gggcaagtca | gagcattagc | 480 |
| agctatttaa | attggtatca | gcagaaccgg | gaaagcccct | aagctcctga | tctatgcggc | 540 |
| atccagtttg | caaagtgggg | tcccatcaag | gttcagtggc | agtggatctg | ggacagattt | 600 |
| cactctcacc | atcagcagtc | tgcaacctga | aatttgcaac | ttactactgt | caacagacgg | 660 |
| ttgtggcgcc | tttgacgttc | ggccaaggga | ccaaggtgga | aatcaaacgg | | 710 |

<210> SEQ ID NO 10
<211> LENGTH: 239
<212> TYPE: PRT
<213> ORGANISM: Artificial Sequence
<220> FEATURE:
<223> OTHER INFORMATION: chemically synthesized

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
            100                 105                 110

```
Thr Val Ser Ser Gly Gly Gly Ser Gly Gly Gly Ser Gly Gly
        115                 120                 125
Gly Gly Ser Thr Asp Ile Gln Met Thr Gln Ser Pro Ser Ser Leu Ser
        130                 135                 140
Ala Ser Val Gly Asp Arg Val Thr Ile Thr Cys Arg Ala Ser Gln Ser
145                 150                 155                 160
Ile Ser Ser Tyr Leu Asn Trp Tyr Gln Gln Lys Pro Gly Lys Ala Pro
                165                 170                 175
Lys Leu Leu Ile Tyr Ala Ala Ser Leu Gln Ser Gly Val Pro Ser Arg
                180                 185                 190
Phe Ser Gly Ser Gly Ser Gly Thr Asp Phe Thr Leu Thr Ile Ser Ser
            195                 200                 205
Leu Gln Pro Glu Asp Phe Ala Thr Tyr Tyr Cys Gln Gln Thr Val Val
        210                 215                 220
Ala Pro Leu Thr Phe Gly Gln Gly Thr Lys Val Glu Ile Lys Arg
225                 230                 235

<210> SEQ ID NO 11
<211> LENGTH: 108
<212> TYPE: PRT
<213> ORGANISM: Artificial Sequence
<220> FEATURE:
<223> OTHER INFORMATION: chemically synthesized

<400> SEQUENCE: 11

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Val Val Ala Pro Leu
                85                  90                  95
Thr Phe Gly Gln Gly Thr Lys Val Glu Ile Lys Arg
            100                 105

<210> SEQ ID NO 12
<211> LENGTH: 119
<212> TYPE: PRT
<213> ORGANISM: Artificial Sequence
<220> FEATURE:
<223> OTHER INFORMATION: chemically synthesized

<400> SEQUENCE: 12

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ser Ile Glu Gln Met Gly Trp Gln Thr Tyr Tyr Ala Asp Ser Val
    50                  55                  60
Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                    85                  90                  95

Ala Lys Asp Ile Gly Gly Arg Ser Ala Phe Asp Tyr Trp Gly Gln Gly
                100                 105                 110

Thr Leu Val Thr Val Ser Ser
        115

<210> SEQ ID NO 13
<211> LENGTH: 108
<212> TYPE: PRT
<213> ORGANISM: Artificial Sequence
<220> FEATURE:
<223> OTHER INFORMATION: chemically synthesized

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
                100                 105

<210> SEQ ID NO 14
<211> LENGTH: 119
<212> TYPE: PRT
<213> ORGANISM: Artificial Sequence
<220> FEATURE:
<223> OTHER INFORMATION: chemically synthesized

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Tyr His Gly Gln Phe Asp Tyr Trp Gly Gln Gly
                100                 105                 110

Thr Leu Val Thr Val Ser Ser
        115

<210> SEQ ID NO 15
<211> LENGTH: 108
```

<212> TYPE: PRT
<213> ORGANISM: Artificial Sequence
<220> FEATURE:
<223> OTHER INFORMATION: chemically synthesized

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 16
<211> LENGTH: 119
<212> TYPE: PRT
<213> ORGANISM: Artificial Sequence
<220> FEATURE:
<223> OTHER INFORMATION: chemically synthesized

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Phe Phe Gly Gln Phe Asp Tyr Trp Gly Gln Gly
            100                 105                 110

Thr Leu Val Thr Val Ser Ser
        115

<210> SEQ ID NO 17
<211> LENGTH: 108
<212> TYPE: PRT
<213> ORGANISM: Artificial Sequence
<220> FEATURE:
<223> OTHER INFORMATION: chemically synthesized

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile 35                  40                  45
Tyr Ala Ala Ser Ser Leu Gln Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Val Val Ala Pro Leu
                85                  90                  95
Thr Phe Gly Gln Gly Thr Lys Val Glu Ile Lys Arg
            100                 105

<210> SEQ ID NO 18
<211> LENGTH: 119
<212> TYPE: PRT
<213> ORGANISM: Artificial Sequence
<220> FEATURE:
<223> OTHER INFORMATION: chemically synthesized

<400> SEQUENCE: 18

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ser Ile Glu Gln Met Gly Trp Gln Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys His Ile Gly Arg Thr Asn Pro Phe Asp Tyr Trp Gly Gln Gly
            100                 105                 110
Thr Leu Val Thr Val Ser Ser
        115

<210> SEQ ID NO 19
<211> LENGTH: 108
<212> TYPE: PRT
<213> ORGANISM: Artificial Sequence
<220> FEATURE:
<223> OTHER INFORMATION: chemically synthesized

<400> SEQUENCE: 19

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Val Val Ala Pro Leu
                85                  90                  95
Thr Phe Gly Gln Gly Thr Lys Val Glu Ile Lys Arg
            100                 105

<210> SEQ ID NO 20
<211> LENGTH: 116
<212> TYPE: PRT
<213> ORGANISM: Artificial Sequence
<220> FEATURE:
<223> OTHER INFORMATION: chemically synthesized

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Glu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
            100                 105                 110

Thr Val Ser Ser
        115

<210> SEQ ID NO 21
<211> LENGTH: 108
<212> TYPE: PRT
<213> ORGANISM: Artificial Sequence
<220> FEATURE:
<223> OTHER INFORMATION: chemically synthesized

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 22
<211> LENGTH: 119
<212> TYPE: PRT
<213> ORGANISM: Artificial Sequence
<220> FEATURE:
<223> OTHER INFORMATION: chemically synthesized

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr

```
                    20                  25                  30
Ala Met Ser Trp Val Arg Gln Ala Pro Gly Lys Gly Leu Glu Trp Val
                35                  40                  45

Ser Ser Ile Glu Gln Met Gly Trp Gln Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Tyr Tyr Gly Gln Phe Asp Tyr Trp Gly Gln Gly
                100                 105                 110

Thr Leu Val Thr Val Ser Ser
            115

<210> SEQ ID NO 23
<211> LENGTH: 108
<212> TYPE: PRT
<213> ORGANISM: Artificial Sequence
<220> FEATURE:
<223> OTHER INFORMATION: chemically synthesized

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
                35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
                100                 105

<210> SEQ ID NO 24
<211> LENGTH: 119
<212> TYPE: PRT
<213> ORGANISM: Artificial Sequence
<220> FEATURE:
<223> OTHER INFORMATION: chemically synthesized

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
                35                  40                  45

Ser Ser Ile Glu Gln Met Gly Trp Gln Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Lys Ser Pro Pro Phe Phe Gly Gln Phe Asp Tyr Trp Gly Gln Gly
            100                 105                 110

Thr Leu Val Thr Val Ser Ser
        115

<210> SEQ ID NO 25
<211> LENGTH: 108
<212> TYPE: PRT
<213> ORGANISM: Artificial Sequence
<220> FEATURE:
<223> OTHER INFORMATION: chemically synthesized

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 26
<211> LENGTH: 119
<212> TYPE: PRT
<213> ORGANISM: Artificial Sequence
<220> FEATURE:
<223> OTHER INFORMATION: chemically synthesized

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
        115

<210> SEQ ID NO 27
<211> LENGTH: 108
<212> TYPE: PRT
<213> ORGANISM: Artificial Sequence
<220> FEATURE:
<223> OTHER INFORMATION: chemically synthesized

<400> SEQUENCE: 27

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Val Val Ala Pro Leu
                85                  90                  95
Thr Phe Gly Gln Gly Thr Lys Val Glu Ile Lys Arg
            100                 105

<210> SEQ ID NO 28
<211> LENGTH: 116
<212> TYPE: PRT
<213> ORGANISM: Artificial Sequence
<220> FEATURE:
<223> OTHER INFORMATION: chemically synthesized

<400> SEQUENCE: 28

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ser Ile Glu Glu Met Gly Trp Gln Thr Leu Tyr Ala Asp Ser Val
50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Ser Ala Ala Ala Phe Asp Tyr Trp Gly Gln Gly Thr Leu Val
            100                 105                 110
Thr Val Ser Ser
        115

<210> SEQ ID NO 29
<211> LENGTH: 108
<212> TYPE: PRT
<213> ORGANISM: Artificial Sequence
<220> FEATURE:
<223> OTHER INFORMATION: chemically synthesized

<400> SEQUENCE: 29

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Val Val Ala Pro Leu
                 85                  90                  95

Thr Phe Gly Gln Gly Thr Lys Val Glu Ile Lys Arg
            100                 105
```

<210> SEQ ID NO 30
<211> LENGTH: 119
<212> TYPE: PRT
<213> ORGANISM: Artificial Sequence
<220> FEATURE:
<223> OTHER INFORMATION: chemically synthesized

<400> SEQUENCE: 30

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ser Ile Glu Gln Met Gly Trp Gln Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ile Gly Gly Arg Ser Ala Phe Asp Tyr Trp Gly Gln Gly
            100                 105                 110

Thr Leu Val Thr Val Ser Ser
            115
```

<210> SEQ ID NO 31
<211> LENGTH: 108
<212> TYPE: PRT
<213> ORGANISM: Artificial Sequence
<220> FEATURE:
<223> OTHER INFORMATION: chemically synthesized

<400> SEQUENCE: 31

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Val Val Ala Pro Leu
                 85                  90                  95

Thr Phe Gly Gln Gly Thr Lys Val Glu Ile Lys Arg
            100                 105
```

<210> SEQ ID NO 32
<211> LENGTH: 119
<212> TYPE: PRT
<213> ORGANISM: Artificial Sequence

```
<220> FEATURE:
<223> OTHER INFORMATION: chemically synthesized

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Phe Tyr Gly Gln Phe Asp Tyr Trp Gly Gln Gly
            100                 105                 110

Thr Leu Val Thr Val Ser Ser
            115

<210> SEQ ID NO 33
<211> LENGTH: 108
<212> TYPE: PRT
<213> ORGANISM: Artificial Sequence
<220> FEATURE:
<223> OTHER INFORMATION: chemically synthesized

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 34
<211> LENGTH: 119
<212> TYPE: PRT
<213> ORGANISM: Artificial Sequence
<220> FEATURE:
<223> OTHER INFORMATION: chemically synthesized

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Pro Pro Phe Phe Gly Gln Phe Asp Tyr Trp Gly Gln Gly
                100                 105                 110

Thr Leu Val Thr Val Ser Ser
            115

<210> SEQ ID NO 35
<211> LENGTH: 108
<212> TYPE: PRT
<213> ORGANISM: Artificial Sequence
<220> FEATURE:
<223> OTHER INFORMATION: chemically synthesized

<400> SEQUENCE: 35

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Val Val Ala Pro Leu
                 85                  90                  95

Thr Phe Gly Gln Gly Thr Lys Val Glu Ile Lys Arg
                100                 105

<210> SEQ ID NO 36
<211> LENGTH: 115
<212> TYPE: PRT
<213> ORGANISM: Artificial Sequence
<220> FEATURE:
<223> OTHER INFORMATION: chemically synthesized

<400> SEQUENCE: 36

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ser Ile Glu Glu Met Gly Trp Gln Thr Leu Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Ala
                 85                  90                  95

Lys Ser Ala Ala Ala Phe Asp Tyr Trp Gly Gln Gly Thr Leu Val Thr
                100                 105                 110

Val Ser Ser
        115
```

<210> SEQ ID NO 37
<211> LENGTH: 108
<212> TYPE: PRT
<213> ORGANISM: Artificial Sequence
<220> FEATURE:
<223> OTHER INFORMATION: chemically synthesized

<400> SEQUENCE: 37

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105
```

<210> SEQ ID NO 38
<211> LENGTH: 119
<212> TYPE: PRT
<213> ORGANISM: Artificial Sequence
<220> FEATURE:
<223> OTHER INFORMATION: chemically synthesized

<400> SEQUENCE: 38

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
        115
```

<210> SEQ ID NO 39
<211> LENGTH: 108
<212> TYPE: PRT
<213> ORGANISM: Artificial Sequence
<220> FEATURE:
<223> OTHER INFORMATION: chemically synthesized

<400> SEQUENCE: 39

```
Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105
```

<210> SEQ ID NO 40
<211> LENGTH: 116
<212> TYPE: PRT
<213> ORGANISM: Artificial Sequence
<220> FEATURE:
<223> OTHER INFORMATION: chemically synthesized

<400> SEQUENCE: 40

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Pro Glu Gly Trp Gln Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
            100                 105                 110

Thr Val Ser Ser
        115
```

<210> SEQ ID NO 41
<211> LENGTH: 108
<212> TYPE: PRT
<213> ORGANISM: Artificial Sequence
<220> FEATURE:
<223> OTHER INFORMATION: chemically synthesized

<400> SEQUENCE: 41

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95
```

```
Thr Phe Gly Gln Gly Thr Lys Val Glu Ile Lys Arg
            100                 105
```

<210> SEQ ID NO 42
<211> LENGTH: 119
<212> TYPE: PRT
<213> ORGANISM: Artificial Sequence
<220> FEATURE:
<223> OTHER INFORMATION: chemically synthesized

<400> SEQUENCE: 42

```
Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ser Ile Glu Gln Met Gly Trp Gln Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Ser Pro Pro His Asn Gly Gln Phe Asp Tyr Trp Gly Gln Gly
            100                 105                 110

Thr Leu Val Thr Val Ser Ser
            115
```

<210> SEQ ID NO 43
<211> LENGTH: 108
<212> TYPE: PRT
<213> ORGANISM: Artificial Sequence
<220> FEATURE:
<223> OTHER INFORMATION: chemically synthesized

<400> SEQUENCE: 43

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
            85                  90                  95

Thr Phe Gly Gln Gly Thr Lys Val Glu Ile Lys Arg
            100                 105
```

<210> SEQ ID NO 44
<211> LENGTH: 116
<212> TYPE: PRT
<213> ORGANISM: Artificial Sequence
<220> FEATURE:
<223> OTHER INFORMATION: chemically synthesized

<400> SEQUENCE: 44

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
            100                 105                 110

Thr Val Ser Ser
            115
```

<210> SEQ ID NO 45
<211> LENGTH: 108
<212> TYPE: PRT
<213> ORGANISM: Artificial Sequence
<220> FEATURE:
<223> OTHER INFORMATION: chemically synthesized

<400> SEQUENCE: 45

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105
```

<210> SEQ ID NO 46
<211> LENGTH: 119
<212> TYPE: PRT
<213> ORGANISM: Artificial Sequence
<220> FEATURE:
<223> OTHER INFORMATION: chemically synthesized

<400> SEQUENCE: 46

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Ser Pro Pro Phe Phe Gly Gln Phe Asp Tyr Trp Gly Gln Gly
            100                 105                 110

Thr Leu Val Thr Val Ser Ser
        115

<210> SEQ ID NO 47
<211> LENGTH: 108
<212> TYPE: PRT
<213> ORGANISM: Artificial Sequence
<220> FEATURE:
<223> OTHER INFORMATION: chemically synthesized

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 48
<211> LENGTH: 116
<212> TYPE: PRT
<213> ORGANISM: Artificial Sequence
<220> FEATURE:
<223> OTHER INFORMATION: chemically synthesized

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Glu Met Gly Trp Gln Thr Glu Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
            100                 105                 110

Thr Val Ser Ser
        115

<210> SEQ ID NO 49
<211> LENGTH: 324
<212> TYPE: DNA
```

<213> ORGANISM: Artificial Sequence
<220> FEATURE:
<223> OTHER INFORMATION: chemically synthesized

<400> SEQUENCE: 49

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgcg catccagtt tgcaaagtgg ggtcccatca   180
aggttcagtg gcagtggatc tgggacagat tcactctca ccatcagcag tctgcaacct   240
gaagattttg caacttacta ctgtcaacag acgctagacg ctcctccgca attcggccaa   300
gggaccaagg tggaaatcaa acgt                                          324
```

<210> SEQ ID NO 50
<211> LENGTH: 108
<212> TYPE: PRT
<213> ORGANISM: Artificial Sequence
<220> FEATURE:
<223> OTHER INFORMATION: chemically synthesized

<400> SEQUENCE: 50

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Thr Leu Asp Ala Pro Pro
                85                  90                  95
Gln Phe Gly Gln Gly Thr Lys Val Glu Ile Lys Arg
            100                 105
```

<210> SEQ ID NO 51
<211> LENGTH: 357
<212> TYPE: DNA
<213> ORGANISM: Artificial Sequence
<220> FEATURE:
<223> OTHER INFORMATION: chemically synthesized

<400> SEQUENCE: 51

```
gaggtgcagc tgttggagtc tgggggaggc ttggtacagc ctggggggtc cctgagactc    60
tcctgtgcag cctctggatt caccttagc agctatgcca tgagctgggt ccgccaggct   120
ccagggaagg ggctggagtg ggtctcaagt attgagcaga tggttggca gacatattac   180
gcagactccg tgaagggccg gttcaccatc tccagagaca attccaagaa cacgctgtat   240
ctgcaaatga acagcctgag agccgaggac acggccgtat attactgtgc gaaagacatc   300
ggcggcaggt cggcctttga ctactggggc cagggaaccc tggtcaccgt ctcctca     357
```

<210> SEQ ID NO 52
<211> LENGTH: 119
<212> TYPE: PRT
<213> ORGANISM: Artificial Sequence
<220> FEATURE:
<223> OTHER INFORMATION: chemically synthesized

<400> SEQUENCE: 52

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ser Ile Glu Gln Met Gly Trp Gln Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Asp Ile Gly Gly Arg Ser Ala Phe Asp Tyr Trp Gly Gln Gly
            100                 105                 110
Thr Leu Val Thr Val Ser Ser
        115

<210> SEQ ID NO 53
<211> LENGTH: 324
<212> TYPE: DNA
<213> ORGANISM: Artificial Sequence
<220> FEATURE:
<223> OTHER INFORMATION: chemically synthesized

<400> SEQUENCE: 53
gacatccaga tgacccagtc tccatcctcc ctgtctgcat ctgtaggaga cagagtcacc     60
atcacttgcc gggcaagtca gagcattagc agctatttaa attggtatca gcagaaacca   120
gggaaagccc ctaagctcct gatctatgcg gcatccagtt tgcaaagtgg ggtcccatca   180
aggttcagtg gcagtggatc tgggacagat ttcactctca ccatcagcag tctgcaacct   240
gaagattttg caacttacta ctgtcaacag acggttgtgg cgcctccgtt attcggccaa   300
gggaccaagg tggaaatcaa acgt                                         324

<210> SEQ ID NO 54
<211> LENGTH: 108
<212> TYPE: PRT
<213> ORGANISM: Artificial Sequence
<220> FEATURE:
<223> OTHER INFORMATION: chemically synthesized

<400> SEQUENCE: 54

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Thr Val Val Ala Pro Pro
                85                  90                  95
Leu Phe Gly Gln Gly Thr Lys Val Glu Ile Lys Arg
            100                 105

<210> SEQ ID NO 55
<211> LENGTH: 357
<212> TYPE: DNA
<213> ORGANISM: Artificial Sequence
<220> FEATURE:
<223> OTHER INFORMATION: chemically synthesized

<400> SEQUENCE: 55

```
gaggtgcagc tgttggagtc tgggggaggc ttggtacagc ctgggggtc cctgagactc      60
tcctgtgcag cctctggatt cacctttagc agctatgcca tgagctgggt ccgccaggct    120
ccagggaagg ggctggagtg ggtgtcaagt attgacccgg aaggtcggca gacatattac    180
gcagactccg tgaagggccg gttcaccatc tccagagaca attccaagaa cacgctgtat    240
ctgcaaatga acagcctgag agccgaggac acggccgtat attactgtgc gaaagacatc    300
ggcggcaggt cggcctttga ctactggggc cagggaaccc tggtcaccgt ctcctca       357
```

<210> SEQ ID NO 56
<211> LENGTH: 119
<212> TYPE: PRT
<213> ORGANISM: Artificial Sequence
<220> FEATURE:
<223> OTHER INFORMATION: chemically synthesized

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Pro Glu Gly Arg Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
        115

<210> SEQ ID NO 57
<211> LENGTH: 324
<212> TYPE: DNA
<213> ORGANISM: Artificial Sequence
<220> FEATURE:
<223> OTHER INFORMATION: chemically synthesized

<400> SEQUENCE: 57

```
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatctatgcg catccagtt tgcaaagtgg ggtcccatca    180
aggttcagtg gcagtggatc tgggacagat ttcactctca ccatcagcag tctgcaacct    240
gaagattttg caacttacta ctgtcaacag tcgctggtgg cgcctcttac cttcggccaa    300
gggaccaagg tggaaatcaa acgt                                             324
```

-continued

<210> SEQ ID NO 58
<211> LENGTH: 108
<212> TYPE: PRT
<213> ORGANISM: Artificial Sequence
<220> FEATURE:
<223> OTHER INFORMATION: chemically synthesized

<400> SEQUENCE: 58

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Val Ala Pro Leu
                85                  90                  95

Thr Phe Gly Gln Gly Thr Lys Val Glu Ile Lys Arg
            100                 105
```

<210> SEQ ID NO 59
<211> LENGTH: 348
<212> TYPE: DNA
<213> ORGANISM: Artificial Sequence
<220> FEATURE:
<223> OTHER INFORMATION: chemically synthesized

<400> SEQUENCE: 59

```
gaggtgcagc tgttggagtc tgggggaggc ttggtacagc ctgggggggtc cctgagactc    60 tcctgtgcag cctctggatt cacctttagc agctatgcca tgagctgggt ccgccaggct   120
ccagggaagg ggctggagtg ggtgtcaagt attgaagaga tgggttggca gacaaagtac   180
gcagactccg tgaagggccg gttcaccatc tccagagaca attccaagaa cacgctgtat   240
ctgcaaatga acagcctgag agccgaggac acggccgtat attactgtgc gaaatcggct   300
gctgcttttg actactgggg ccagggaacc ctggtcaccg tctcctca              348
```

<210> SEQ ID NO 60
<211> LENGTH: 116
<212> TYPE: PRT
<213> ORGANISM: Artificial Sequence
<220> FEATURE:
<223> OTHER INFORMATION: chemically synthesized

<400> SEQUENCE: 60

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Glu Met Gly Trp Gln Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Lys Ser Ala Ala Ala Phe Asp Tyr Trp Gly Gln Gly Thr Leu Val
            100                 105                 110

Thr Val Ser Ser
        115

<210> SEQ ID NO 61
<211> LENGTH: 324
<212> TYPE: DNA
<213> ORGANISM: Artificial Sequence
<220> FEATURE:
<223> OTHER INFORMATION: chemically synthesized

<400> SEQUENCE: 61
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgcg gcatccagtt tgcaaagtgg ggtcccatca     180
aggttcagtg gcagtggatc tgggacagat ttcactctca ccatcagcag tctgcaacct     240
gaagattttg caacttacta ctgtcaacag gcgttagatg cccctctgat gttcggccaa     300
gggaccaagg tggaaatcaa acgt                                            324

<210> SEQ ID NO 62
<211> LENGTH: 108
<212> TYPE: PRT
<213> ORGANISM: Artificial Sequence
<220> FEATURE:
<223> OTHER INFORMATION: chemically synthesized

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Leu Asp Ala Pro Leu
                85                  90                  95

Met Phe Gly Gln Gly Thr Lys Val Glu Ile Lys Arg
            100                 105

<210> SEQ ID NO 63
<211> LENGTH: 357
<212> TYPE: DNA
<213> ORGANISM: Artificial Sequence
<220> FEATURE:
<223> OTHER INFORMATION: chemically synthesized

<400> SEQUENCE: 63
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtgtcaagt attgagccta tgggttgact aacagaatac     180
gcagactccg tgaagggccg gttcaccatc tccagagaca attccaagaa cacgctgtat     240
ctgcaaatga acagcctgag agccgaggac acggccgtat attactgtgc gaaagacatc     300

```
ggcggcaggt cggcctttga ctactggggc cagggaaccc tggtcaccgt ctcctca      357
```

<210> SEQ ID NO 64
<211> LENGTH: 119
<212> TYPE: PRT
<213> ORGANISM: Artificial Sequence
<220> FEATURE:
<223> OTHER INFORMATION: chemically synthesized

<400> SEQUENCE: 64

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Pro Met Gly Gln Leu Thr Glu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
        115
```

<210> SEQ ID NO 65
<211> LENGTH: 324
<212> TYPE: DNA
<213> ORGANISM: Artificial Sequence
<220> FEATURE:
<223> OTHER INFORMATION: chemically synthesized

<400> SEQUENCE: 65

```
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgcg gcatccagtt tgcaaagtgg ggtcccatca     180
aggttcagtg gcagtggatc tgggacagat ttcactctca ccatcagcag tctgcaacct     240
gaagattttg caacttacta ctgtcaacag gcgcttgtcg cccctctgac gttcggccaa     300
gggaccaagg tggaaatcaa acgt                                            324
```

<210> SEQ ID NO 66
<211> LENGTH: 108
<212> TYPE: PRT
<213> ORGANISM: Artificial Sequence
<220> FEATURE:
<223> OTHER INFORMATION: chemically synthesized

<400> SEQUENCE: 66

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
```

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Leu Val Ala Pro Leu
                 85                  90                  95

Thr Phe Gly Gln Gly Thr Lys Val Glu Ile Lys Arg
            100                 105
```

<210> SEQ ID NO 67
<211> LENGTH: 348
<212> TYPE: DNA
<213> ORGANISM: Artificial Sequence
<220> FEATURE:
<223> OTHER INFORMATION: chemically synthesized

<400> SEQUENCE: 67

```
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtgtcaagt attgatgaga tgggttggca gacatattac   180
gcagactccg tgaagggccg gttcaccatc tccagagaca attccaagaa cacgctgtat   240
ctgcaaatga acagcctgag agccgaggac acggccgtat attactgtgc gaaatcggct   300
gctgcttttg actactgggg ccagggaacc ctggtcaccg tctcctca                348
```

<210> SEQ ID NO 68
<211> LENGTH: 116
<212> TYPE: PRT
<213> ORGANISM: Artificial Sequence
<220> FEATURE:
<223> OTHER INFORMATION: chemically synthesized

<400> SEQUENCE: 68

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ser Ile Asp Glu Met Gly Trp Gln Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Ala Ala Ala Phe Asp Tyr Trp Gly Gln Gly Thr Leu Val
            100                 105                 110

Thr Val Ser Ser
        115
```

<210> SEQ ID NO 69
<211> LENGTH: 326
<212> TYPE: DNA
<213> ORGANISM: Artificial Sequence
<220> FEATURE:
<223> OTHER INFORMATION: chemically synthesized

<400> SEQUENCE: 69

```
gacatccaga tgacccagtc tccatcctcc ctgtctgcat ctgtaggaga cagagtcacc    60
```

```
atcacttgcc gggcaagtca gagcattagc agctatttaa attggtatca gcagaaacca    120
gggaaagccc ctaagctcct gatctatgcg catccagtt tgcaaagtgg ggtcccatca    180
aggttcagtg gcagtggatc tgggacagat tcactctca ccatcagcag tctgcaacct    240
gaagattttg caacttacta ctgtcaacag gcgcttgtcg ccctctgac gttcggccaa    300 gggaccaagg tggaaatcaa acgtac                                       326
```

<210> SEQ ID NO 70
<211> LENGTH: 108
<212> TYPE: PRT
<213> ORGANISM: Artificial Sequence
<220> FEATURE:
<223> OTHER INFORMATION: chemically synthesized

<400> SEQUENCE: 70

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Leu Val Ala Pro Leu
                85                  90                  95

Thr Phe Gly Gln Gly Thr Lys Val Glu Ile Lys Arg
            100                 105
```

<210> SEQ ID NO 71
<211> LENGTH: 348
<212> TYPE: DNA
<213> ORGANISM: Artificial Sequence
<220> FEATURE:
<223> OTHER INFORMATION: chemically synthesized

<400> SEQUENCE: 71

```
gaggtgcagc tgttggagtc tgggggaggc ttggtacagc ctggggggtc cctgagactc    60
tcctgtgcag cctctggatt caccttagc agctatgcca tgagctgggt ccgccaggct    120
ccagggaagg gctggagtg gtgtcaagt attgatgaga tgggttggca gacatattac    180
gcagactccg tgaagggccg gttcaccatc tccagagaca attccaagaa cacgctgtat    240
ctgcaaatga acagcctgag agccgaggac acggccgtat attactgtgc gaaatcggct    300 gctgctttg actactgggg ccagggaacc ctggtcaccg tctcctca                348
```

<210> SEQ ID NO 72
<211> LENGTH: 116
<212> TYPE: PRT
<213> ORGANISM: Artificial Sequence
<220> FEATURE:
<223> OTHER INFORMATION: chemically synthesized

<400> SEQUENCE: 72

```
Glu Val Gln Leu Leu Glu Ser Gly Gly Gly Leu Val Gln Pro Gly Gly
1               5                   10                  15

Ser Leu Arg Leu Ser Cys Ala Ser Gly Phe Thr Phe Ser Ser Tyr
            20                  25                  30
```

Ala Met Ser Trp Val Arg Gln Ala Pro Gly Lys Gly Leu Glu Trp Val
            35                  40                  45

Ser Ser Ile Asp Glu Met Gly Trp Gln Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Ala Ala Ala Phe Asp Tyr Trp Gly Gln Gly Thr Leu Val
                100                 105                 110

Thr Val Ser Ser
            115

<210> SEQ ID NO 73
<211> LENGTH: 642
<212> TYPE: DNA
<213> ORGANISM: Artificial Sequence
<220> FEATURE:
<223> OTHER INFORMATION: chemically synthesized

<400> SEQUENCE: 73
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgcg gcatccagtt tgcaaagtgg ggtcccatca    180
aggttcagtg gcagtggatc tgggacagat ttcactctca ccatcagcag tctgcaacct    240
gaagattttg caacttacta ctgtcaacag acggttgtgg cgcctccgtt attcggccaa    300
gggaccaagg tggaaatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                      642

<210> SEQ ID NO 74
<211> LENGTH: 214
<212> TYPE: PRT
<213> ORGANISM: Artificial Sequence
<220> FEATURE:
<223> OTHER INFORMATION: chemically synthesized

<400> SEQUENCE: 74

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Val Val Ala Pro Pro
                 85                  90                  95

Leu Phe Gly Gln Gly Thr Lys Val Glu Ile Lys Arg Thr Val Ala Ala

|   | 100 | | | | 105 | | | | | 110 | | | |
|---|---|---|---|---|---|---|---|---|---|---|---|---|---|

Pro Ser Val Phe Ile Phe Pro Pro Ser Asp Glu Gln Leu Lys Ser Gly
    115                    120                    125

Thr Ala Ser Val Val Cys Leu Leu Asn Asn Phe Tyr Pro Arg Glu Ala
    130                    135                140

Lys Val Gln Trp Lys Val Asp Asn Ala Leu Gln Ser Gly Asn Ser Gln
145                  150                    155                160

Glu Ser Val Thr Glu Gln Asp Ser Lys Asp Ser Thr Tyr Ser Leu Ser
            165                  170                175

Ser Thr Leu Thr Leu Ser Lys Ala Asp Tyr Glu Lys His Lys Val Tyr
            180                  185                190

Ala Cys Glu Val Thr His Gln Gly Leu Ser Ser Pro Val Thr Lys Ser
    195                    200                205

Phe Asn Arg Gly Glu Cys
    210

<210> SEQ ID NO 75
<211> LENGTH: 1347
<212> TYPE: DNA
<213> ORGANISM: Artificial Sequence
<220> FEATURE:
<223> OTHER INFORMATION: chemically synthesized

<400> SEQUENCE: 75

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtgtcaagt attgacccgg aaggtcggca gacatattac     180
gcagactccg tgaagggccg gttcaccatc tccagagaca attccaagaa cacgctgtat     240
ctgcaaatga acagcctgag agccgaggac acggccgtat attactgtgc gaaagacatc     300
ggcggcaggt cggcctttga ctactggggc cagggaaccc tggtcaccgt ctcctcagct     360
agcaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactcacac atgcccaccg tgcccagcac ctgaactcct ggggggaccg     720
tcagtcttcc tcttcccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
gccaaagggc agccccgaga accacaggtg tacaccctgc ccccatcccg ggaggagatg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaa                                        1347
```

```
<210> SEQ ID NO 76
<211> LENGTH: 449
<212> TYPE: PRT
<213> ORGANISM: Artificial Sequence
<220> FEATURE:
<223> OTHER INFORMATION: chemically synthesized

<400> SEQUENCE: 76

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Pro Glu Gly Arg Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365
```

```
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 77
<211> LENGTH: 40
<212> TYPE: DNA
<213> ORGANISM: Artificial Sequence
<220> FEATURE:
<223> OTHER INFORMATION: chemically synthesized

<400> SEQUENCE: 77
tagactcgag cggccgccta acactctccc ctgttgaagc                              40

<210> SEQ ID NO 78
<211> LENGTH: 39
<212> TYPE: DNA
<213> ORGANISM: Artificial Sequence
<220> FEATURE:
<223> OTHER INFORMATION: chemically synthesized

<400> SEQUENCE: 78
tagactcgag cggccgctca tttacccgga gacagggag                               39

<210> SEQ ID NO 79
<211> LENGTH: 40
<212> TYPE: DNA
<213> ORGANISM: Artificial Sequence
<220> FEATURE:
<223> OTHER INFORMATION: chemically synthesized

<400> SEQUENCE: 79
ctcactatag gctagcgcca ccatgtacag gatgcaactc                              40

<210> SEQ ID NO 80
<211> LENGTH: 40
<212> TYPE: DNA
<213> ORGANISM: Artificial Sequence
<220> FEATURE:
<223> OTHER INFORMATION: chemically synthesized

<400> SEQUENCE: 80
ctcactatag gctagagcca ccatgtacag gatgcaactc                              40

<210> SEQ ID NO 81
<211> LENGTH: 22
<212> TYPE: DNA
<213> ORGANISM: Artificial Sequence
<220> FEATURE:
<223> OTHER INFORMATION: chemically synthesized

<400> SEQUENCE: 81
gaaccgtcag atcactagaa gc                                                 22

<210> SEQ ID NO 82
```

```
<211> LENGTH: 29
<212> TYPE: DNA
<213> ORGANISM: Artificial Sequence
<220> FEATURE:
<223> OTHER INFORMATION: chemically synthesized

<400> SEQUENCE: 82
cgaattcgtg acaagtgcaa gacttagtg                                    29

<210> SEQ ID NO 83
<211> LENGTH: 37
<212> TYPE: DNA
<213> ORGANISM: Artificial Sequence
<220> FEATURE:
<223> OTHER INFORMATION: chemically synthesized

<400> SEQUENCE: 83
cacttgtcac gaattcggac atccagatga cccagtc                           37

<210> SEQ ID NO 84
<211> LENGTH: 37
<212> TYPE: DNA
<213> ORGANISM: Artificial Sequence
<220> FEATURE:
<223> OTHER INFORMATION: chemically synthesized

<400> SEQUENCE: 84
gtgcagccac cgtacgtttg atttccacct tggtccc                           37

<210> SEQ ID NO 85
<211> LENGTH: 40
<212> TYPE: DNA
<213> ORGANISM: Artificial Sequence
<220> FEATURE:
<223> OTHER INFORMATION: chemically synthesized

<400> SEQUENCE: 85
ttgcacttgt cacgaattcg gaggtgcagc tgttggagtc                        40

<210> SEQ ID NO 86
<211> LENGTH: 39
<212> TYPE: DNA
<213> ORGANISM: Artificial Sequence
<220> FEATURE:
<223> OTHER INFORMATION: chemically synthesized

<400> SEQUENCE: 86
ggcccttggt gctagcgctc gagacggtga ccagggttc                         39

<210> SEQ ID NO 87
<211> LENGTH: 15
<212> TYPE: PRT
<213> ORGANISM: Artificial Sequence
<220> FEATURE:
<223> OTHER INFORMATION: chemically synthesized

<400> SEQUENCE: 87

Pro Trp Cys Met Gln Arg Gln Asp Phe Leu Arg Cys Pro Gln Pro
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: chemically synthesized
```

<400> SEQUENCE: 88

```
Gln Leu Gly Leu Pro Ala Tyr Met Cys Thr Phe Glu Cys Leu Arg
1               5                   10                  15
```

<210> SEQ ID NO 89
<211> LENGTH: 15
<212> TYPE: PRT
<213> ORGANISM: Artificial Sequence
<220> FEATURE:
<223> OTHER INFORMATION: chemically synthesized

<400> SEQUENCE: 89

```
Cys Asn Leu Trp Val Ser Gly Gly Asp Cys Gly Gly Leu Gln Gly
1               5                   10                  15
```

<210> SEQ ID NO 90
<211> LENGTH: 15
<212> TYPE: PRT
<213> ORGANISM: Artificial Sequence
<220> FEATURE:
<223> OTHER INFORMATION: chemically synthesized

<400> SEQUENCE: 90

```
Ser Cys Ser Leu Trp Thr Ser Gly Ser Cys Leu Pro His Ser Pro
1               5                   10                  15
```

<210> SEQ ID NO 91
<211> LENGTH: 15
<212> TYPE: PRT
<213> ORGANISM: Artificial Sequence
<220> FEATURE:
<223> OTHER INFORMATION: chemically synthesized

<400> SEQUENCE: 91

```
Tyr Cys Leu Gln Leu Pro His Tyr Met Gln Ala Met Cys Gly Arg
1               5                   10                  15
```

<210> SEQ ID NO 92
<211> LENGTH: 15
<212> TYPE: PRT
<213> ORGANISM: Artificial Sequence
<220> FEATURE:
<223> OTHER INFORMATION: chemically synthesized

<400> SEQUENCE: 92

```
Cys Phe Leu Tyr Ser Cys Thr Asp Val Ser Tyr Trp Asn Asn Thr
1               5                   10                  15
```

<210> SEQ ID NO 93
<211> LENGTH: 15
<212> TYPE: PRT
<213> ORGANISM: Artificial Sequence
<220> FEATURE:
<223> OTHER INFORMATION: chemically synthesized

<400> SEQUENCE: 93

```
Pro Trp Cys Met Gln Arg Gln Asp Tyr Leu Arg Cys Pro Gln Pro
1               5                   10                  15
```

<210> SEQ ID NO 94
<211> LENGTH: 15
<212> TYPE: PRT
<213> ORGANISM: Artificial Sequence
<220> FEATURE:
<223> OTHER INFORMATION: chemically synthesized

<400> SEQUENCE: 94

```
Cys Asn Leu Trp Ile Ser Gly Gly Asp Cys Arg Gly Leu Ala Gly
1               5                   10                  15
```

<210> SEQ ID NO 95
<211> LENGTH: 15
<212> TYPE: PRT
<213> ORGANISM: Artificial Sequence
<220> FEATURE:
<223> OTHER INFORMATION: chemically synthesized

<400> SEQUENCE: 95

```
Cys Asn Leu Trp Val Ser Gly Gly Asp Cys Arg Gly Val Gln Gly
1               5                   10                  15
```

<210> SEQ ID NO 96
<211> LENGTH: 15
<212> TYPE: PRT
<213> ORGANISM: Artificial Sequence
<220> FEATURE:
<223> OTHER INFORMATION: chemically synthesized

<400> SEQUENCE: 96

```
Cys Asn Leu Trp Val Ser Gly Gly Asp Cys Arg Gly Leu Arg Gly
1               5                   10                  15
```

<210> SEQ ID NO 97
<211> LENGTH: 15
<212> TYPE: PRT
<213> ORGANISM: Artificial Sequence
<220> FEATURE:
<223> OTHER INFORMATION: chemically synthesized

<400> SEQUENCE: 97

```
Cys Asn Leu Trp Ile Ser Gly Gly Asp Cys Arg Gly Leu Pro Gly
1               5                   10                  15
```

<210> SEQ ID NO 98
<211> LENGTH: 15
<212> TYPE: PRT
<213> ORGANISM: Artificial Sequence
<220> FEATURE:
<223> OTHER INFORMATION: chemically synthesized

<400> SEQUENCE: 98

```
Cys Asn Leu Trp Val Ser Gly Gly Asp Cys Arg Asp Ala Pro Trp
1               5                   10                  15
```

<210> SEQ ID NO 99
<211> LENGTH: 15
<212> TYPE: PRT
<213> ORGANISM: Artificial Sequence
<220> FEATURE:
<223> OTHER INFORMATION: chemically synthesized

<400> SEQUENCE: 99

```
Cys Asn Leu Trp Val Ser Gly Gly Asp Cys Arg Asp Leu Leu Gly
1               5                   10                  15
```

<210> SEQ ID NO 100
<211> LENGTH: 15
<212> TYPE: PRT
<213> ORGANISM: Artificial Sequence
<220> FEATURE:
<223> OTHER INFORMATION: chemically synthesized

<400> SEQUENCE: 100

Cys Asn Leu Trp Val Ser Gly Gly Asp Cys Arg Gly Leu Gln Gly
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: chemically synthesized

<400> SEQUENCE: 101

Cys Asn Leu Trp Leu His Gly Gly Asp Cys Arg Gly Trp Gln Gly
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: chemically synthesized

<400> SEQUENCE: 102

Cys Asn Ile Trp Leu Val Gly Gly Asp Cys Arg Gly Trp Gln Gly
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: chemically synthesized

<400> SEQUENCE: 103

Cys Thr Thr Trp Phe Cys Gly Gly Asp Cys Gly Val Met Arg Gly
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: chemically synthesized

<400> SEQUENCE: 104

Cys Asn Ile Trp Gly Pro Ser Val Asp Cys Gly Ala Leu Leu Gly
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: chemically synthesized

<400> SEQUENCE: 105

Cys Asn Ile Trp Val Asn Gly Gly Asp Cys Arg Ser Phe Glu Gly
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: chemically synthesized

<400> SEQUENCE: 106

Tyr Cys Leu Asn Leu Pro Arg Tyr Met Gln Asp Met Cys Trp Ala

```
1               5                   10                  15
```

<210> SEQ ID NO 107
<211> LENGTH: 15
<212> TYPE: PRT
<213> ORGANISM: Artificial Sequence
<220> FEATURE:
<223> OTHER INFORMATION: chemically synthesized

<400> SEQUENCE: 107

```
Tyr Cys Leu Ala Leu Pro His Tyr Met Gln Ala Asp Cys Ala Arg
1               5                   10                  15
```

<210> SEQ ID NO 108
<211> LENGTH: 15
<212> TYPE: PRT
<213> ORGANISM: Artificial Sequence
<220> FEATURE:
<223> OTHER INFORMATION: chemically synthesized

<400> SEQUENCE: 108

```
Cys Phe Leu Tyr Ser Cys Gly Asp Val Ser Tyr Trp Gly Ser Ala
1               5                   10                  15
```

<210> SEQ ID NO 109
<211> LENGTH: 15
<212> TYPE: PRT
<213> ORGANISM: Artificial Sequence
<220> FEATURE:
<223> OTHER INFORMATION: chemically synthesized

<400> SEQUENCE: 109

```
Cys Tyr Leu Tyr Ser Cys Thr Asp Ser Ala Phe Trp Asn Asn Arg
1               5                   10                  15
```

<210> SEQ ID NO 110
<211> LENGTH: 15
<212> TYPE: PRT
<213> ORGANISM: Artificial Sequence
<220> FEATURE:
<223> OTHER INFORMATION: chemically synthesized

<400> SEQUENCE: 110

```
Cys Tyr Leu Tyr Ser Cys Asn Asp Val Ser Tyr Trp Ser Asn Thr
1               5                   10                  15
```

<210> SEQ ID NO 111
<211> LENGTH: 12
<212> TYPE: PRT
<213> ORGANISM: Artificial Sequence
<220> FEATURE:
<223> OTHER INFORMATION: chemically synthesized

<400> SEQUENCE: 111

```
Cys Phe Leu Tyr Ser Cys Thr Asp Val Ser Tyr Trp
1               5                   10
```

<210> SEQ ID NO 112
<211> LENGTH: 15
<212> TYPE: PRT
<213> ORGANISM: Artificial Sequence
<220> FEATURE:
<223> OTHER INFORMATION: chemically synthesized

<400> SEQUENCE: 112

```
Cys Phe Leu Tyr Ser Cys Thr Asp Val Ala Tyr Trp Asn Ser Ala
1               5                   10                  15
```

```
<210> SEQ ID NO 113
<211> LENGTH: 15
<212> TYPE: PRT
<213> ORGANISM: Artificial Sequence
<220> FEATURE:
<223> OTHER INFORMATION: chemically synthesized

<400> SEQUENCE: 113

Cys Phe Leu Tyr Ser Cys Thr Asp Val Ser Tyr Trp Gly Asp Thr
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: chemically synthesized

<400> SEQUENCE: 114

Cys Phe Leu Tyr Ser Cys Thr Asp Val Ser Tyr Trp Gly Asn Ser
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: chemically synthesized

<400> SEQUENCE: 115

Cys Phe Leu Tyr Ser Cys Thr Asp Val Ala Tyr Trp Asn Asn Thr
1               5                   10                  15

<210> SEQ ID NO 116
<211> LENGTH: 18
<212> TYPE: PRT
<213> ORGANISM: Artificial Sequence
<220> FEATURE:
<223> OTHER INFORMATION: chemically synthesized

<400> SEQUENCE: 116

Cys Phe Leu Tyr Ser Cys Gly Asp Val Ser Tyr Trp Gly Asn Pro Gly
1               5                   10                  15

Leu Ser

<210> SEQ ID NO 117
<211> LENGTH: 15
<212> TYPE: PRT
<213> ORGANISM: Artificial Sequence
<220> FEATURE:
<223> OTHER INFORMATION: chemically synthesized

<400> SEQUENCE: 117

Cys Phe Leu Tyr Ser Cys Thr Asp Val Ala Tyr Trp Ser Gly Leu
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: chemically synthesized

<400> SEQUENCE: 118

Cys Tyr Leu Tyr Ser Cys Thr Asp Gly Ser Tyr Trp Asn Ser Thr
```

```
<210> SEQ ID NO 119
<211> LENGTH: 15
<212> TYPE: PRT
<213> ORGANISM: Artificial Sequence
<220> FEATURE:
<223> OTHER INFORMATION: chemically synthesized

<400> SEQUENCE: 119

Cys Phe Leu Tyr Ser Cys Ser Asp Val Ser Tyr Trp Gly Asn Ile
1               5                   10                  15

<210> SEQ ID NO 120
<211> LENGTH: 12
<212> TYPE: PRT
<213> ORGANISM: Artificial Sequence
<220> FEATURE:
<223> OTHER INFORMATION: chemically synthesized

<400> SEQUENCE: 120

Cys Phe Leu Tyr Ser Cys Thr Asp Val Ala Tyr Trp
1               5                   10

<210> SEQ ID NO 121
<211> LENGTH: 15
<212> TYPE: PRT
<213> ORGANISM: Artificial Sequence
<220> FEATURE:
<223> OTHER INFORMATION: chemically synthesized

<400> SEQUENCE: 121

Cys Phe Leu Tyr Ser Cys Thr Asp Val Ser Tyr Trp Gly Ser Thr
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: chemically synthesized

<400> SEQUENCE: 122

Cys Phe Leu Tyr Ser Cys Thr Asp Val Ala Tyr Trp Gly Asp Thr
1               5                   10                  15

<210> SEQ ID NO 123
<211> LENGTH: 5
<212> TYPE: PRT
<213> ORGANISM: Artificial Sequence
<220> FEATURE:
<223> OTHER INFORMATION: chemically synthesized

<400> SEQUENCE: 123

Gly Ser Gly Gly Ser
1               5

<210> SEQ ID NO 124
<211> LENGTH: 4
<212> TYPE: PRT
<213> ORGANISM: Artificial Sequence
<220> FEATURE:
<223> OTHER INFORMATION: chemically synthesized

<400> SEQUENCE: 124

Gly Gly Gly Ser
1
```

<210> SEQ ID NO 125
<211> LENGTH: 4
<212> TYPE: PRT
<213> ORGANISM: Artificial Sequence
<220> FEATURE:
<223> OTHER INFORMATION: chemically synthesized

<400> SEQUENCE: 125

Gly Gly Ser Gly
1

<210> SEQ ID NO 126
<211> LENGTH: 5
<212> TYPE: PRT
<213> ORGANISM: Artificial Sequence
<220> FEATURE:
<223> OTHER INFORMATION: chemically synthesized

<400> SEQUENCE: 126

Gly Gly Ser Gly Gly
1               5

<210> SEQ ID NO 127
<211> LENGTH: 5
<212> TYPE: PRT
<213> ORGANISM: Artificial Sequence
<220> FEATURE:
<223> OTHER INFORMATION: chemically synthesized

<400> SEQUENCE: 127

Gly Ser Gly Ser Gly
1               5

<210> SEQ ID NO 128
<211> LENGTH: 5
<212> TYPE: PRT
<213> ORGANISM: Artificial Sequence
<220> FEATURE:
<223> OTHER INFORMATION: chemically synthesized

<400> SEQUENCE: 128

Gly Ser Gly Gly Gly
1               5

<210> SEQ ID NO 129
<211> LENGTH: 5
<212> TYPE: PRT
<213> ORGANISM: Artificial Sequence
<220> FEATURE:
<223> OTHER INFORMATION: chemically synthesized

<400> SEQUENCE: 129

Gly Gly Gly Ser Gly
1               5

<210> SEQ ID NO 130
<211> LENGTH: 5
<212> TYPE: PRT
<213> ORGANISM: Artificial Sequence
<220> FEATURE:
<223> OTHER INFORMATION: chemically synthesized

<400> SEQUENCE: 130

Gly Ser Ser Ser Gly
1               5

<210> SEQ ID NO 131
<211> LENGTH: 774
<212> TYPE: DNA
<213> ORGANISM: Artificial Sequence
<220> FEATURE:
<223> OTHER INFORMATION: chemically synthesized

<400> SEQUENCE: 131

```
caaggccagt ctggccaatg caatatttgg ctcgtaggtg gtgattgcag gggctggcag      60
ggggctcga gcggtggcag cggtggctct ggtggtactg gccgtggtcc aagctgggtt     120
ggcggcggtt ctgacatcca gatgacccag tctccatcct ccctgtctgc atctgtagga    180
gacagagtca ccatcacttg ccgggcaagt cagagcatta gcagctattt aaattggtat    240
cagcagaaac cagggaaagc ccctaagctc ctgatctatg cggcatccag tttgcaaagt    300
ggggtcccat caaggttcag tggcagtgga tctgggacag atttcactct caccatcagc    360
agtctgcaac tgaagatttt gcaacttac tactgtcaac agacggttgt ggcgcctccg     420
ttattcggcc aagggaccaa ggtggaaatc aaacgtacgg tggctgcacc atctgtcttc    480
atcttcccgc catctgatga gcagttgaaa tctggaactg cctctgttgt gtgcctgctg    540
aataacttct atcccagaga ggccaaagta cagtggaagg tggataacgc cctccaatcg    600
ggtaactccc aggagagtgt cacagagcag gacagcaagg acagcaccta cagcctcagc    660
agcaccctga cgctgagcaa agcagactac gagaaacaca agtctacgc ctgcgaagtc     720
acccatcagg gcctgagctc gcccgtcaca aagagcttca caggggaga gtgt            774
```

<210> SEQ ID NO 132
<211> LENGTH: 258
<212> TYPE: PRT
<213> ORGANISM: Artificial Sequence
<220> FEATURE:
<223> OTHER INFORMATION: chemically synthesized

<400> SEQUENCE: 132

```
Gln Gly Gln Ser Gly Gln Cys Asn Ile Trp Leu Val Gly Gly Asp Cys
1               5                   10                  15

Arg Gly Trp Gln Gly Gly Ser Ser Gly Gly Ser Gly Ser Gly Gly
            20                  25                  30

Thr Gly Arg Gly Pro Ser Trp Val Gly Gly Ser Asp Ile Gln Met
        35                  40                  45

Thr Gln Ser Pro Ser Ser Leu Ser Ala Ser Val Gly Asp Arg Val Thr
    50                  55                  60

Ile Thr Cys Arg Ala Ser Gln Ser Ile Ser Ser Tyr Leu Asn Trp Tyr
65                  70                  75                  80

Gln Gln Lys Pro Gly Lys Ala Pro Lys Leu Leu Ile Tyr Ala Ala Ser
                85                  90                  95

Ser Leu Gln Ser Gly Val Pro Ser Arg Phe Ser Gly Ser Gly Ser Gly
            100                 105                 110

Thr Asp Phe Thr Leu Thr Ile Ser Ser Leu Gln Pro Glu Asp Phe Ala
        115                 120                 125

Thr Tyr Tyr Cys Gln Gln Thr Val Val Ala Pro Pro Leu Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175
```

Val Cys Leu Leu Asn Asn Phe Tyr Pro Arg Glu Ala Lys Val Gln Trp
                180                 185                 190

Lys Val Asp Asn Ala Leu Gln Ser Gly Asn Ser Gln Glu Ser Val Thr
            195                 200                 205

Glu Gln Asp Ser Lys Asp Ser Thr Tyr Ser Leu Ser Ser Thr Leu Thr
210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys

<210> SEQ ID NO 133
<211> LENGTH: 774
<212> TYPE: DNA
<213> ORGANISM: Artificial Sequence
<220> FEATURE:
<223> OTHER INFORMATION: chemically synthesized

<400> SEQUENCE: 133
caaggccagt ctggccagtg caatatttgg ctcgtaggtg gtgattgcag gggctggcag      60
gggggctcga gcggtggcag cggtggctct ggtggtctga gcggccgttc cgataatcat     120
ggcggcggtt ctgacatcca gatgacccag tctccatcct ccctgtctgc atctgtagga     180
gacagagtca ccatcacttg ccgggcaagt cagagcatta gcagctattt aaattggtat     240
cagcagaaac cagggaaagc ccctaagctc ctgatctatg cggcatccag tttgcaaagt     300
ggggtcccat caaggttcag tggcagtgga tctgggacag atttcactct caccatcagc     360
agtctgcaac tgaagatttt gcaacttac tactgtcaac agacggttgt ggcgcctccg     420
ttattcggcc aagggaccaa ggtggaaatc aaacgtacgg tggctgcacc atctgtcttc     480
atcttcccgc catctgatga gcagttgaaa tctggaactg cctctgttgt gtgcctgctg     540
aataacttct atcccagaga ggccaaagta cagtggaagg tggataacgc cctccaatcg     600
ggtaactccc aggagagtgt cacagagcag gacagcaagg acagcaccta cagcctcagc     660
agcaccctga cgctgagcaa agcagactac gagaaacaca agtctacgc ctgcgaagtc      720 acccatcagg gcctgagctc gcccgtcaca aagagcttca cagggggaga gtgt            774

<210> SEQ ID NO 134
<211> LENGTH: 258
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (126)..(126)
<223> OTHER INFORMATION: X is any amino acid

<400> SEQUENCE: 134

Gln Gly Gln Ser Gly Gln Cys Asn Ile Trp Leu Val Gly Gly Asp Cys
1               5                   10                  15

Arg Gly Trp Gln Gly Gly Ser Ser Gly Gly Ser Gly Ser Gly Gly
            20                  25                  30

Leu Ser Gly Arg Ser Asp Asn His Gly Gly Gly Ser Asp Ile Gln Met
        35                  40                  45

Thr Gln Ser Pro Ser Ser Leu Ser Ala Ser Val Gly Asp Arg Val Thr
    50                  55                  60

Ile Thr Cys Arg Ala Ser Gln Ser Ile Ser Ser Tyr Leu Asn Trp Tyr
65                  70                  75                  80

Gln Gln Lys Pro Gly Lys Ala Pro Lys Leu Leu Ile Tyr Ala Ala Ser
                85                  90                  95

Ser Leu Gln Ser Gly Val Pro Ser Arg Phe Ser Gly Ser Gly Ser Gly
            100                 105                 110

Thr Asp Phe Thr Leu Thr Ile Ser Ser Leu Gln Pro Glu Xaa Phe Ala
        115                 120                 125

Thr Tyr Tyr Cys Gln Gln Thr Val Val Ala Pro Pro Leu Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys

<210> SEQ ID NO 135
<211> LENGTH: 774
<212> TYPE: DNA
<213> ORGANISM: Artificial Sequence
<220> FEATURE:
<223> OTHER INFORMATION: chemically synthesized

<400> SEQUENCE: 135
caaggccagt ctggccagtg caatatttgg ctcgtaggtg gtgattgcag gggctggcag     60
gggggctcga gcggtggcag cggtggctct ggtggctcac cactgactgg tcgttccggt    120
ggcggcggtt ctgacatcca gatgacccag tctccatcct ccctgtctgc atctgtagga    180
gacagagtca ccatcacttg ccgggcaagt cagagcatta gcagctattt aaattggtat    240
cagcagaaac cagggaaagc ccctaagctc ctgatctatg cggcatccag tttgcaaagt    300
ggggtcccat caaggttcag tggcagtgga tctgggacag atttcactct caccatcagc    360
agtctgcaac tgaagatttt gcaacttac tactgtcaac agacggttgt ggcgcctccg    420
ttattcggcc aagggaccaa ggtggaaatc aaacgtacgg tggctgcacc atctgtcttc    480
atcttcccgc catctgatga gcagttgaaa tctggaactg cctctgttgt gtgcctgctg    540
aataacttct atcccagaga ggccaaagta cagtggaagg tggataacgc cctccaatcg    600
ggtaactccc aggagagtgt cacagagcag gacagcaagg acagcaccta cagcctcagc    660
agcaccctga cgctgagcaa agcagactac gagaaacaca agtctacgc ctgcgaagtc    720
acccatcagg gcctgagctc gcccgtcaca aagagcttca caggggaga gtgt           774

<210> SEQ ID NO 136
<211> LENGTH: 258
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (91)..(91)
<223> OTHER INFORMATION: X is any amino acid

<400> SEQUENCE: 136

Gln Gly Gln Ser Gly Gln Cys Asn Ile Trp Leu Val Gly Gly Asp Cys
1               5                   10                  15

Arg Gly Trp Gln Gly Gly Ser Ser Gly Ser Gly Ser Gly Gly
            20                  25                  30

Ser Pro Leu Thr Gly Arg Ser Gly Gly Gly Ser Asp Ile Gln Met
        35                  40                  45

Thr Gln Ser Pro Ser Ser Leu Ser Ala Ser Val Gly Asp Arg Val Thr
50                  55                  60

Ile Thr Cys Arg Ala Ser Gln Ser Ile Ser Ser Tyr Leu Asn Trp Tyr
65                  70                  75                  80

Gln Gln Lys Pro Gly Lys Ala Pro Lys Leu Xaa Ile Tyr Ala Ala Ser
                85                  90                  95

Ser Leu Gln Ser Gly Val Pro Ser Arg Phe Ser Gly Ser Gly Ser Gly
            100                 105                 110

Thr Asp Phe Thr Leu Thr Ile Ser Arg Leu Gln Pro Glu Asp Phe Ala
        115                 120                 125

Thr Tyr Tyr Cys Gln Gln Thr Val Val Ala Pro Pro Leu Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys

<210> SEQ ID NO 137
<211> LENGTH: 774
<212> TYPE: DNA
<213> ORGANISM: Artificial Sequence
<220> FEATURE:
<223> OTHER INFORMATION: chemically synthesized

<400> SEQUENCE: 137
caaggccagt ctggccagtg caatatttgg ctcgtaggtg gtgattgcag gggctggcag      60 ggggctcga gcggtggcag cggtggctct ggtggctcag gtgaggctc gccactgggc      120 ctgggcggtt ctgacatcca gatgacccag tctccatcct ccctgtctgc atctgtagga      180
gacagagtca ccatcacttg ccgggcaagt cagagcatta gcagctattt aaattggtat      240
cagcagaaac cagggaaagc ccctaagctc ctgatctatg cggcatccag tttgcaaagt      300

-continued

```
ggggtcccat caaggttcag tgcagtgga tctgggacag atttcactct caccatcagc      360
agtctgcaac ctgaagattt tgcaacttac tactgtcaac agacggttgt ggcgcctccg      420
ttattcggcc aagggaccaa ggtggaaatc aaacgtacgg tggctgcacc atctgtcttc      480
atcttcccgc catctgatga gcagttgaaa tctggaactg cctctgttgt gtgcctgctg      540
aataacttct atcccagaga ggccaaagta cagtggaagg tggataacgc cctccaatcg      600
ggtaactccc aggagagtgt cacagagcag gacagcaagg acagcaccta cagcctcagc      660
agcaccctga cgctgagcaa agcagactac gagaaacaca agtctacgc ctgcgaagtc       720 acccatcagg gcctgagctc gcccgtcaca aagagcttca caggggaga gtgt             774
```

<210> SEQ ID NO 138
<211> LENGTH: 258
<212> TYPE: PRT
<213> ORGANISM: Artificial Sequence
<220> FEATURE:
<223> OTHER INFORMATION: chemically synthesized

<400> SEQUENCE: 138

```
Gln Gly Gln Ser Gly Gln Cys Asn Ile Trp Leu Val Gly Gly Asp Cys
1               5                   10                  15

Arg Gly Trp Gln Gly Gly Ser Ser Gly Ser Gly Gly Ser Gly Gly
            20                  25                  30

Ser Gly Gly Gly Ser Pro Leu Gly Leu Gly Gly Ser Asp Ile Gln Met
        35                  40                  45

Thr Gln Ser Pro Ser Ser Leu Ser Ala Ser Val Gly Asp Arg Val Thr
    50                  55                  60

Ile Thr Cys Arg Ala Ser Gln Ser Ile Ser Ser Tyr Leu Asn Trp Tyr
65                  70                  75                  80

Gln Gln Lys Pro Gly Lys Ala Pro Lys Leu Leu Ile Tyr Ala Ala Ser
                85                  90                  95

Ser Leu Gln Ser Gly Val Pro Ser Arg Phe Ser Gly Ser Gly Ser Gly
            100                 105                 110

Thr Asp Phe Thr Leu Thr Ile Ser Ser Leu Gln Pro Glu Asp Phe Ala
        115                 120                 125

Thr Tyr Tyr Cys Gln Gln Thr Val Val Ala Pro Pro Leu Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys
```

<210> SEQ ID NO 139
<211> LENGTH: 774

<212> TYPE: DNA
<213> ORGANISM: Artificial Sequence
<220> FEATURE:
<223> OTHER INFORMATION: chemically synthesized

<400> SEQUENCE: 139

```
caaggccagt ctggccagtg caatatttgg ctcgtaggtg gtgattgcag gggctggcag      60
gggggctcga gcggtggcag cagtggctct ggtggctcag gtggaggctc gggcggtggg     120
agcggcggtt ctgacatcca gatgacccag tctccatcct ccctgtctgc atctgtagga     180
gacagagtca ccatcacttg ccgggcaagt cagagcatta gcagctattt aaattggtat     240
cagcagaaac cagggaaagc ccctaagctc ctgatctatg cggcatccag tttgcaaagt     300
ggggtcccat caaggttcag tggcagtgga tctgggacag atttcactct caccatcagc     360
agtctgcaac tgaagatttt gcaacttac tactgtcaac agacggttgt ggcgcctccg      420
ttattcggcc aagggaccaa ggtggaaatc aaacgtacgg tggctgcacc atctgtcttc     480
atcttcccgc catctgatga gcagttgaaa tctggaactg cctctgttgt gtgcctgctg     540
aataacttct atcccagaga ggccaaagta cagtggaagg tggataacgc cctccaatcg     600
ggtaactccc aggagagtgt cacagagcag gacagcaagg acagcaccta cagcctcagc     660
agcaccctga cgctgagcaa agcagactac gagaaacaca agtctacgc ctgcgaagtc      720
acccatcagg gcctgagctc gcccgtcaca aagagcttca caggggaga gtgt            774
```

<210> SEQ ID NO 140
<211> LENGTH: 258
<212> TYPE: PRT
<213> ORGANISM: Artificial Sequence
<220> FEATURE:
<223> OTHER INFORMATION: chemically synthesized

<400> SEQUENCE: 140

```
Gln Gly Gln Ser Gly Gln Cys Asn Ile Trp Leu Val Gly Gly Asp Cys
1               5                   10                  15
Arg Gly Trp Gln Gly Gly Ser Ser Gly Gly Ser Ser Gly Ser Gly Gly
                20                  25                  30
Ser Gly Gly Gly Ser Gly Gly Ser Gly Gly Ser Asp Ile Gln Met
            35                  40                  45
Thr Gln Ser Pro Ser Ser Leu Ser Ala Ser Val Gly Asp Arg Val Thr
50                  55                  60
Ile Thr Cys Arg Ala Ser Gln Ser Ile Ser Ser Tyr Leu Asn Trp Tyr
65                  70                  75                  80
Gln Gln Lys Pro Gly Lys Ala Pro Lys Leu Leu Ile Tyr Ala Ala Ser
                85                  90                  95
Ser Leu Gln Ser Gly Val Pro Ser Arg Phe Ser Gly Ser Gly Ser Gly
            100                 105                 110
Thr Asp Phe Thr Leu Thr Ile Ser Ser Leu Gln Pro Glu Asp Phe Ala
        115                 120                 125
Thr Tyr Tyr Cys Gln Gln Thr Val Val Ala Pro Pro Leu Phe Gly Gln
    130                 135                 140
Gly Thr Lys Val Glu Ile Lys Arg Thr Val Ala Ala Pro Ser Val Phe
145                 150                 155                 160
Ile Phe Pro Pro Ser Asp Glu Gln Leu Lys Ser Gly Thr Ala Ser Val
                165                 170                 175
Val Cys Leu Leu Asn Asn Phe Tyr Pro Arg Glu Ala Lys Val Gln Trp
            180                 185                 190
```

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys

<210> SEQ ID NO 141
<211> LENGTH: 132
<212> TYPE: DNA
<213> ORGANISM: Artificial Sequence
<220> FEATURE:
<223> OTHER INFORMATION: chemically synthesized

<400> SEQUENCE: 141
caaggccagt ctggccagtg caatatttgg ctcgtaggtg gtgattgcag gggctggcag      60
gggggctcga gcggtggcag cggtggctct ggtggctcag ctggcttctc cctccccgca    120
ggtggcggtt ct                                                        132

<210> SEQ ID NO 142
<211> LENGTH: 44
<212> TYPE: PRT
<213> ORGANISM: Artificial Sequence
<220> FEATURE:
<223> OTHER INFORMATION: chemically synthesized

<400> SEQUENCE: 142

Gln Gly Gln Ser Gly Gln Cys Asn Ile Trp Leu Val Gly Gly Asp Cys
1               5                   10                  15

Arg Gly Trp Gln Gly Gly Ser Ser Gly Gly Ser Gly Gly Ser Gly Gly
            20                  25                  30

Ser Ala Gly Phe Ser Leu Pro Ala Gly Gly Gly Ser
        35                  40

<210> SEQ ID NO 143
<211> LENGTH: 132
<212> TYPE: DNA
<213> ORGANISM: Artificial Sequence
<220> FEATURE:
<223> OTHER INFORMATION: chemically synthesized

<400> SEQUENCE: 143
caaggccagt ctggccagtg caatatttgg ctcgtaggtg gtgattgcag gggctggcag      60
gggggctcga gcggtggcag cggtggctct ggtagcctgg cacctctggg tctgcaacgc    120
cgtggcggtt ct                                                        132

<210> SEQ ID NO 144
<211> LENGTH: 44
<212> TYPE: PRT
<213> ORGANISM: Artificial Sequence
<220> FEATURE:
<223> OTHER INFORMATION: chemically synthesized

<400> SEQUENCE: 144

Gln Gly Gln Ser Gly Gln Cys Asn Ile Trp Leu Val Gly Gly Asp Cys
1               5                   10                  15

Arg Gly Trp Gln Gly Gly Ser Ser Gly Gly Ser Gly Gly Ser Gly Ser

```
                20                  25                  30
Leu Ala Pro Leu Gly Leu Gln Arg Arg Gly Gly Ser
        35                  40

<210> SEQ ID NO 145
<211> LENGTH: 132
<212> TYPE: DNA
<213> ORGANISM: Artificial Sequence
<220> FEATURE:
<223> OTHER INFORMATION: chemically synthesized

<400> SEQUENCE: 145
caaggccagt ctggccagtg caatatttgg ctcgtaggtg gtgattgcag gggctggcag      60
gggggctcga gcggtggcag cggtggctct ggtggctcag gtggaccttt gggagtcaga     120
ggtggcggtt ct                                                         132

<210> SEQ ID NO 146
<211> LENGTH: 44
<212> TYPE: PRT
<213> ORGANISM: Artificial Sequence
<220> FEATURE:
<223> OTHER INFORMATION: chemically synthesized

<400> SEQUENCE: 146

Gln Gly Gln Ser Gly Gln Cys Asn Ile Trp Leu Val Gly Gly Asp Cys
1               5                  10                  15

Arg Gly Trp Gln Gly Gly Ser Ser Gly Gly Ser Gly Gly Ser Gly Gly
            20                  25                  30

Ser Gly Gly Pro Leu Gly Val Arg Gly Gly Ser
        35                  40

<210> SEQ ID NO 147
<211> LENGTH: 1347
<212> TYPE: DNA
<213> ORGANISM: Artificial Sequence
<220> FEATURE:
<223> OTHER INFORMATION: chemically synthesized

<400> SEQUENCE: 147
gaggtgcacc tgttggagtc tgggggaggc ttggtacagc ctgggggtc cctgagactc        60 tcctgtgcag cctctggatt cacctttagc agctatgcca tgagctgggt ccgccaggct     120
ccagggaagg ggctggagtg ggtgtcaagt attgacccgg aaggtcggca gacatattac     180
gcagactccg tgaagggccg gttcaccatc tccagagaca attccaagaa cacgctgtat     240
ctgcaaatga acagcctgag agccgaggac acggccgtat attactgtgc gaaagacatc     300
ggcggcaggt cggccttga ctactgggggc cagggaaccc tggtcaccgt ctcctcagct     360
agcaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactcacac atgcccaccg tgcccagcac ctgaactcct ggggggaccg     720
tcagtcttcc tcttcccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
```

```
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggaggagatg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaa                                       1347
```

<210> SEQ ID NO 148
<211> LENGTH: 449
<212> TYPE: PRT
<213> ORGANISM: Artificial Sequence
<220> FEATURE:
<223> OTHER INFORMATION: chemically synthesized

<400> SEQUENCE: 148

```
Glu Val His Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Pro Glu Gly Arg Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
```

```
            275                 280                 285
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 149
<211> LENGTH: 54
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (16)..(17)
<223> OTHER INFORMATION: n is a, t, c or g
<220> FEATURE:
<221> NAME/KEY: misc_feature
<222> LOCATION: (40)..(41)
<223> OTHER INFORMATION: n is a, t, c or g
<220> FEATURE:
<221> NAME/KEY: misc_feature
<222> LOCATION: (43)..(44)
<223> OTHER INFORMATION: n is a, t, c or g
<220> FEATURE:
<221> NAME/KEY: misc_feature
<222> LOCATION: (46)..(47)
<223> OTHER INFORMATION: n is a, t, c or g
<220> FEATURE:
<221> NAME/KEY: misc_feature
<222> LOCATION: (49)..(50)
<223> OTHER INFORMATION: n is a, t, c or g
<220> FEATURE:
<221> NAME/KEY: misc_feature
<222> LOCATION: (52)..(53)
<223> OTHER INFORMATION: n is a, t, c or g

<400> SEQUENCE: 149
tgcaatmtkt ggvbcnnkgg tggtgattgc cgcgggtggn nknnknnknn knnk        54

<210> SEQ ID NO 150
<211> LENGTH: 54
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (1)..(2)
<223> OTHER INFORMATION: n is a, t, c or g
<220> FEATURE:
<221> NAME/KEY: misc_feature
<222> LOCATION: (4)..(5)
<223> OTHER INFORMATION: n is a, t, c or g
<220> FEATURE:
<221> NAME/KEY: misc_feature
<222> LOCATION: (7)..(8)
<223> OTHER INFORMATION: n is a, t, c or g
<220> FEATURE:
<221> NAME/KEY: misc_feature
<222> LOCATION: (10)..(11)
<223> OTHER INFORMATION: n is a, t, c or g
<220> FEATURE:
<221> NAME/KEY: misc_feature
<222> LOCATION: (28)..(29)
<223> OTHER INFORMATION: n is a, t, c or g
<220> FEATURE:
<221> NAME/KEY: misc_feature
<222> LOCATION: (52)..(53)
<223> OTHER INFORMATION: n is a, t, c or g

<400> SEQUENCE: 150
nnknnknnkn nktgcaatmt ktggvbcnnk ggtggtgatt gccgcgggtg gnnk            54

<210> SEQ ID NO 151
<211> LENGTH: 48
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (16)..(17)
<223> OTHER INFORMATION: n is a, t, c or g
<220> FEATURE:
<221> NAME/KEY: misc_feature
<222> LOCATION: (34)..(35)
<223> OTHER INFORMATION: n is a, t, c or g
<220> FEATURE:
<221> NAME/KEY: misc_feature
<222> LOCATION: (37)..(38)
<223> OTHER INFORMATION: n is a, t, c or g
<220> FEATURE:
<221> NAME/KEY: misc_feature
<222> LOCATION: (40)..(41)
<223> OTHER INFORMATION: n is a, t, c or g
<220> FEATURE:
<221> NAME/KEY: misc_feature
<222> LOCATION: (43)..(44)
<223> OTHER INFORMATION: n is a, t, c or g
<220> FEATURE:
<221> NAME/KEY: misc_feature
<222> LOCATION: (46)..(47)
<223> OTHER INFORMATION: n is a, t, c or g

<400> SEQUENCE: 151
tgcaatmtkt ggvbcnnkgg tggtgattgc cgcnnknnkn nknnknnk              48

<210> SEQ ID NO 152
<211> LENGTH: 48
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (1)..(1)
<223> OTHER INFORMATION: n is a, t, c or g
<220> FEATURE:
<221> NAME/KEY: misc_feature
<222> LOCATION: (2)..(2)
<223> OTHER INFORMATION: n is a, c, g, or t
<220> FEATURE:

```
<221> NAME/KEY: misc_feature
<222> LOCATION: (4)..(5)
<223> OTHER INFORMATION: n is a, t, c or g
<220> FEATURE:
<221> NAME/KEY: misc_feature
<222> LOCATION: (7)..(8)
<223> OTHER INFORMATION: n is a, t, c or g
<220> FEATURE:
<221> NAME/KEY: misc_feature
<222> LOCATION: (10)..(11)
<223> OTHER INFORMATION: n is a, t, c or g
<220> FEATURE:
<221> NAME/KEY: misc_feature
<222> LOCATION: (28)..(29)
<223> OTHER INFORMATION: n is a, t, c or g
<220> FEATURE:
<221> NAME/KEY: misc_feature
<222> LOCATION: (46)..(47)
<223> OTHER INFORMATION: n is a, t, c or g

<400> SEQUENCE: 152
nnknnknnkn nktgcaatmt ktggvbcnnk ggtggtgatt gccgcnnk         48

<210> SEQ ID NO 153
<211> LENGTH: 20
<212> TYPE: PRT
<213> ORGANISM: Artificial Sequence
<220> FEATURE:
<223> OTHER INFORMATION: chemically synthesized

<400> SEQUENCE: 153

Gly Cys Asn Ile Trp Leu Asn Gly Gly Asp Cys Arg Gly Trp Val Asp
1               5                   10                  15

Pro Leu Gln Gly
            20

<210> SEQ ID NO 154
<211> LENGTH: 20
<212> TYPE: PRT
<213> ORGANISM: Artificial Sequence
<220> FEATURE:
<223> OTHER INFORMATION: chemically synthesized

<400> SEQUENCE: 154

Gly Cys Asn Ile Trp Leu Val Gly Gly Asp Cys Arg Gly Trp Ile Gly
1               5                   10                  15

Asp Thr Asn Gly
            20

<210> SEQ ID NO 155
<211> LENGTH: 20
<212> TYPE: PRT
<213> ORGANISM: Artificial Sequence
<220> FEATURE:
<223> OTHER INFORMATION: chemically synthesized

<400> SEQUENCE: 155

Gly Cys Asn Ile Trp Leu Val Gly Gly Asp Cys Arg Gly Trp Ile Glu
1               5                   10                  15

Asp Ser Asn Gly
            20

<210> SEQ ID NO 156
<211> LENGTH: 20
<212> TYPE: PRT
<213> ORGANISM: Artificial Sequence
<220> FEATURE:
<223> OTHER INFORMATION: chemically synthesized
```

```
<400> SEQUENCE: 156

Gly Cys Asn Ile Trp Ala Asn Gly Gly Asp Cys Arg Gly Trp Ile Asp
1               5                   10                  15

Asn Ile Asp Gly
            20

<210> SEQ ID NO 157
<211> LENGTH: 20
<212> TYPE: PRT
<213> ORGANISM: Artificial Sequence
<220> FEATURE:
<223> OTHER INFORMATION: chemically synthesized

<400> SEQUENCE: 157

Gly Cys Asn Ile Trp Leu Val Gly Gly Asp Cys Arg Gly Trp Leu Gly
1               5                   10                  15

Glu Ala Val Gly
            20

<210> SEQ ID NO 158
<211> LENGTH: 20
<212> TYPE: PRT
<213> ORGANISM: Artificial Sequence
<220> FEATURE:
<223> OTHER INFORMATION: chemically synthesized

<400> SEQUENCE: 158

Gly Cys Asn Ile Trp Leu Val Gly Gly Asp Cys Arg Gly Trp Leu Glu
1               5                   10                  15

Glu Ala Val Gly
            20

<210> SEQ ID NO 159
<211> LENGTH: 20
<212> TYPE: PRT
<213> ORGANISM: Artificial Sequence
<220> FEATURE:
<223> OTHER INFORMATION: chemically synthesized

<400> SEQUENCE: 159

Gly Gly Pro Ala Leu Cys Asn Ile Trp Leu Asn Gly Gly Asp Cys Arg
1               5                   10                  15

Gly Trp Ser Gly
            20

<210> SEQ ID NO 160
<211> LENGTH: 20
<212> TYPE: PRT
<213> ORGANISM: Artificial Sequence
<220> FEATURE:
<223> OTHER INFORMATION: chemically synthesized

<400> SEQUENCE: 160

Gly Ala Pro Val Phe Cys Asn Ile Trp Leu Asn Gly Gly Asp Cys Arg
1               5                   10                  15

Gly Trp Met Gly
            20

<210> SEQ ID NO 161
<211> LENGTH: 20
<212> TYPE: PRT
<213> ORGANISM: Artificial Sequence
<220> FEATURE:
```

```
<223> OTHER INFORMATION: chemically synthesized

<400> SEQUENCE: 161

Gly Gln Gln Gln Trp Cys Asn Ile Trp Ile Asn Gly Gly Asp Cys Arg
1               5                   10                  15

Gly Trp Asn Gly
            20

<210> SEQ ID NO 162
<211> LENGTH: 20
<212> TYPE: PRT
<213> ORGANISM: Artificial Sequence
<220> FEATURE:
<223> OTHER INFORMATION: chemically synthesized

<400> SEQUENCE: 162

Gly Lys Ser Glu Phe Cys Asn Ile Trp Leu Asn Gly Gly Asp Cys Arg
1               5                   10                  15

Gly Trp Ile Gly
            20

<210> SEQ ID NO 163
<211> LENGTH: 20
<212> TYPE: PRT
<213> ORGANISM: Artificial Sequence
<220> FEATURE:
<223> OTHER INFORMATION: chemically synthesized

<400> SEQUENCE: 163

Gly Thr Pro Gly Gly Cys Asn Ile Trp Ala Asn Gly Gly Asp Cys Arg
1               5                   10                  15

Gly Trp Glu Gly
            20

<210> SEQ ID NO 164
<211> LENGTH: 20
<212> TYPE: PRT
<213> ORGANISM: Artificial Sequence
<220> FEATURE:
<223> OTHER INFORMATION: chemically synthesized

<400> SEQUENCE: 164

Gly Ala Ser Gln Tyr Cys Asn Leu Trp Ile Asn Gly Gly Asp Cys Arg
1               5                   10                  15

Gly Trp Arg Gly
            20

<210> SEQ ID NO 165
<211> LENGTH: 18
<212> TYPE: PRT
<213> ORGANISM: Artificial Sequence
<220> FEATURE:
<223> OTHER INFORMATION: chemically synthesized

<400> SEQUENCE: 165

Gly Cys Asn Ile Trp Leu Val Gly Gly Asp Cys Arg Pro Trp Val Glu
1               5                   10                  15

Gly Gly

<210> SEQ ID NO 166
<211> LENGTH: 18
<212> TYPE: PRT
<213> ORGANISM: Artificial Sequence
<220> FEATURE:
```

<223> OTHER INFORMATION: chemically synthesized

<400> SEQUENCE: 166

Gly Cys Asn Ile Trp Ala Val Gly Gly Asp Cys Arg Pro Phe Val Asp
1               5                   10                  15

Gly Gly

<210> SEQ ID NO 167
<211> LENGTH: 18
<212> TYPE: PRT
<213> ORGANISM: Artificial Sequence
<220> FEATURE:
<223> OTHER INFORMATION: chemically synthesized

<400> SEQUENCE: 167

Gly Cys Asn Ile Trp Leu Asn Gly Gly Asp Cys Arg Ala Trp Val Asp
1               5                   10                  15

Thr Gly

<210> SEQ ID NO 168
<211> LENGTH: 18
<212> TYPE: PRT
<213> ORGANISM: Artificial Sequence
<220> FEATURE:
<223> OTHER INFORMATION: chemically synthesized

<400> SEQUENCE: 168

Gly Cys Asn Ile Trp Ile Val Gly Gly Asp Cys Arg Pro Phe Ile Asn
1               5                   10                  15

Asp Gly

<210> SEQ ID NO 169
<211> LENGTH: 18
<212> TYPE: PRT
<213> ORGANISM: Artificial Sequence
<220> FEATURE:
<223> OTHER INFORMATION: chemically synthesized

<400> SEQUENCE: 169

Gly Cys Asn Ile Trp Leu Asn Gly Gly Asp Cys Arg Pro Val Val Phe
1               5                   10                  15

Gly Gly

<210> SEQ ID NO 170
<211> LENGTH: 18
<212> TYPE: PRT
<213> ORGANISM: Artificial Sequence
<220> FEATURE:
<223> OTHER INFORMATION: chemically synthesized

<400> SEQUENCE: 170

Gly Cys Asn Ile Trp Leu Ser Gly Gly Asp Cys Arg Met Phe Met Asn
1               5                   10                  15

Glu Gly

<210> SEQ ID NO 171
<211> LENGTH: 18
<212> TYPE: PRT
<213> ORGANISM: Artificial Sequence
<220> FEATURE:
<223> OTHER INFORMATION: chemically synthesized

<400> SEQUENCE: 171

Gly Cys Asn Ile Trp Val Asn Gly Gly Asp Cys Arg Ser Phe Val Tyr
1               5                   10                  15

Ser Gly

<210> SEQ ID NO 172
<211> LENGTH: 18
<212> TYPE: PRT
<213> ORGANISM: Artificial Sequence
<220> FEATURE:
<223> OTHER INFORMATION: chemically synthesized

<400> SEQUENCE: 172

Gly Cys Asn Ile Trp Leu Asn Gly Gly Asp Cys Arg Gly Trp Glu Ala
1               5                   10                  15

Ser Gly

<210> SEQ ID NO 173
<211> LENGTH: 18
<212> TYPE: PRT
<213> ORGANISM: Artificial Sequence
<220> FEATURE:
<223> OTHER INFORMATION: chemically synthesized

<400> SEQUENCE: 173

Gly Cys Asn Ile Trp Ala His Gly Gly Asp Cys Arg Gly Phe Ile Glu
1               5                   10                  15

Pro Gly

<210> SEQ ID NO 174
<211> LENGTH: 18
<212> TYPE: PRT
<213> ORGANISM: Artificial Sequence
<220> FEATURE:
<223> OTHER INFORMATION: chemically synthesized

<400> SEQUENCE: 174

Gly Cys Asn Ile Trp Leu Asn Gly Gly Asp Cys Arg Thr Phe Val Ala
1               5                   10                  15

Ser Gly

<210> SEQ ID NO 175
<211> LENGTH: 18
<212> TYPE: PRT
<213> ORGANISM: Artificial Sequence
<220> FEATURE:
<223> OTHER INFORMATION: chemically synthesized

<400> SEQUENCE: 175

Gly Cys Asn Ile Trp Ala His Gly Gly Asp Cys Arg Gly Phe Ile Glu
1               5                   10                  15

Pro Gly

<210> SEQ ID NO 176
<211> LENGTH: 18
<212> TYPE: PRT
<213> ORGANISM: Artificial Sequence
<220> FEATURE:
<223> OTHER INFORMATION: chemically synthesized

<400> SEQUENCE: 176

Gly Phe Leu Glu Asn Cys Asn Ile Trp Leu Asn Gly Gly Asp Cys Arg
1               5                   10                  15

Thr Gly

<210> SEQ ID NO 177
<211> LENGTH: 18
<212> TYPE: PRT
<213> ORGANISM: Artificial Sequence
<220> FEATURE:
<223> OTHER INFORMATION: chemically synthesized

<400> SEQUENCE: 177

Gly Ile Tyr Glu Asn Cys Asn Ile Trp Leu Asn Gly Gly Asp Cys Arg
1               5                   10                  15

Met Gly

<210> SEQ ID NO 178
<211> LENGTH: 18
<212> TYPE: PRT
<213> ORGANISM: Artificial Sequence
<220> FEATURE:
<223> OTHER INFORMATION: chemically synthesized

<400> SEQUENCE: 178

Gly Ile Pro Asp Asn Cys Asn Ile Trp Ile Asn Gly Gly Asp Cys Arg
1               5                   10                  15

Tyr Gly

<210> SEQ ID NO 179
<211> LENGTH: 78
<212> TYPE: DNA
<213> ORGANISM: Artificial Sequence
<220> FEATURE:
<223> OTHER INFORMATION: chemically synthesized

<400> SEQUENCE: 179
caaggccagt ctggccaggg tcagcagcag tggtgcaata tttggatcaa tggtggtgat    60
tgccgcgggt ggaatggt                                                 78

<210> SEQ ID NO 180
<211> LENGTH: 26
<212> TYPE: PRT
<213> ORGANISM: Artificial Sequence
<220> FEATURE:
<223> OTHER INFORMATION: chemically synthesized

<400> SEQUENCE: 180

Gln Gly Gln Ser Gly Gln Gly Gln Gln Trp Cys Asn Ile Trp Ile
1               5                   10                  15

Asn Gly Gly Asp Cys Arg Gly Trp Asn Gly
                20                  25

<210> SEQ ID NO 181
<211> LENGTH: 147
<212> TYPE: DNA
<213> ORGANISM: Artificial Sequence
<220> FEATURE:
<223> OTHER INFORMATION: chemically synthesized

<400> SEQUENCE: 181
caaggccagt ctggccaggg tcagcagcag tggtgcaata tttggatcaa tggtggtgat    60
tgccgcgggt ggaatggtgg ctcgagcggt ggcagcggtg gctctggtgg tactggccgt   120
ggtccaagct gggttggcgg cggttct                                      147

<210> SEQ ID NO 182

```
<211> LENGTH: 49
<212> TYPE: PRT
<213> ORGANISM: Artificial Sequence
<220> FEATURE:
<223> OTHER INFORMATION: chemically synthesized

<400> SEQUENCE: 182

Gln Gly Gln Ser Gly Gln Gly Gln Gln Gln Trp Cys Asn Ile Trp Ile
1               5                   10                  15

Asn Gly Gly Asp Cys Arg Gly Trp Asn Gly Ser Ser Gly Gly Ser
            20                  25                  30

Gly Gly Ser Gly Gly Thr Gly Arg Gly Pro Ser Trp Val Gly Gly Gly
        35                  40                  45

Ser

<210> SEQ ID NO 183
<211> LENGTH: 147
<212> TYPE: DNA
<213> ORGANISM: Artificial Sequence
<220> FEATURE:
<223> OTHER INFORMATION: chemically synthesized

<400> SEQUENCE: 183
caaggccagt ctggccaggg tcagcagcag tggtgcaata tttggatcaa tggtggtgat      60
tgccgcgggt ggaatggtgg ctcgagcggt ggcagcggtg gctctggtgg tctgagcggc     120
cgttccgata atcatggcgg cggttct                                         147

<210> SEQ ID NO 184
<211> LENGTH: 49
<212> TYPE: PRT
<213> ORGANISM: Artificial Sequence
<220> FEATURE:
<223> OTHER INFORMATION: chemically synthesized

<400> SEQUENCE: 184

Gln Gly Gln Ser Gly Gln Gly Gln Gln Gln Trp Cys Asn Ile Trp Ile
1               5                   10                  15

Asn Gly Gly Asp Cys Arg Gly Trp Asn Gly Ser Ser Gly Gly Ser
            20                  25                  30

Gly Gly Ser Gly Gly Leu Ser Gly Arg Ser Asp Asn His Gly Gly Gly
        35                  40                  45

Ser

<210> SEQ ID NO 185
<211> LENGTH: 147
<212> TYPE: DNA
<213> ORGANISM: Artificial Sequence
<220> FEATURE:
<223> OTHER INFORMATION: chemically synthesized

<400> SEQUENCE: 185
caaggccagt ctggccaggg tcagcagcag tggtgcaata tttggatcaa tggtggtgat      60
tgccgcgggt ggaatggtgg ctcgagcggt ggcagcggtg gctctggtgg ctcaccactg     120
actggtcgtt ccggtggcgg cggttct                                         147

<210> SEQ ID NO 186
<211> LENGTH: 49
<212> TYPE: PRT
<213> ORGANISM: Artificial Sequence
<220> FEATURE:
<223> OTHER INFORMATION: chemically synthesized
```

<400> SEQUENCE: 186

Gln Gly Gln Ser Gly Gln Gly Gln Gln Trp Cys Asn Ile Trp Ile
1               5                   10                  15

Asn Gly Gly Asp Cys Arg Gly Trp Asn Gly Ser Ser Gly Gly Ser
            20                  25                  30

Gly Gly Ser Gly Gly Ser Pro Leu Thr Gly Arg Ser Gly Gly Gly
        35                  40                  45

Ser

<210> SEQ ID NO 187
<211> LENGTH: 147
<212> TYPE: DNA
<213> ORGANISM: Artificial Sequence
<220> FEATURE:
<223> OTHER INFORMATION: chemically synthesized

<400> SEQUENCE: 187
caaggccagt ctggccaggg tcagcagcag tggtgcaata tttggatcaa tggtggtgat    60
tgccgcgggt ggaatggtgg ctcgagcggt ggcagcggtg gctctggtgg ctcaggtgga   120
ggctcgccac tgggcctggg cggttct                                        147

<210> SEQ ID NO 188
<211> LENGTH: 49
<212> TYPE: PRT
<213> ORGANISM: Artificial Sequence
<220> FEATURE:
<223> OTHER INFORMATION: chemically synthesized

<400> SEQUENCE: 188

Gln Gly Gln Ser Gly Gln Gly Gln Gln Trp Cys Asn Ile Trp Ile
1               5                   10                  15

Asn Gly Gly Asp Cys Arg Gly Trp Asn Gly Ser Ser Gly Gly Ser
            20                  25                  30

Gly Gly Ser Gly Gly Ser Gly Gly Ser Pro Leu Gly Leu Gly Gly
        35                  40                  45

Ser

<210> SEQ ID NO 189
<211> LENGTH: 147
<212> TYPE: DNA
<213> ORGANISM: Artificial Sequence
<220> FEATURE:
<223> OTHER INFORMATION: chemically synthesized

<400> SEQUENCE: 189
caaggccagt ctggccaggg tcagcagcag tggtgcaata tttggatcaa tggtggtgat    60
tgccgcgggt ggaatggtgg ctcgagcggt ggcagcggtg gctctggtgg ctcagctggc   120 ttctcccctcc ccgcaggtgg cggttct                                       147

<210> SEQ ID NO 190
<211> LENGTH: 49
<212> TYPE: PRT
<213> ORGANISM: Artificial Sequence
<220> FEATURE:
<223> OTHER INFORMATION: chemically synthesized

<400> SEQUENCE: 190

Gln Gly Gln Ser Gly Gln Gly Gln Gln Trp Cys Asn Ile Trp Ile
1               5                   10                  15

Asn Gly Gly Asp Cys Arg Gly Trp Asn Gly Gly Ser Ser Gly Gly Ser
            20                  25                  30

Gly Gly Ser Gly Gly Ser Ala Gly Phe Ser Leu Pro Ala Gly Gly Gly
            35                  40                  45

Ser

<210> SEQ ID NO 191
<211> LENGTH: 147
<212> TYPE: DNA
<213> ORGANISM: Artificial Sequence
<220> FEATURE:
<223> OTHER INFORMATION: chemically synthesized

<400> SEQUENCE: 191
caaggccagt ctggccaggg tcagcagcag tggtgcaata tttggatcaa tggtggtgat    60
tgccgcgggt ggaatggtgg ctcgagcggt ggcagcggtg gctctggtag cctggcacct   120
ctgggtctgc aacgccgtgg cggttct                                       147

<210> SEQ ID NO 192
<211> LENGTH: 49
<212> TYPE: PRT
<213> ORGANISM: Artificial Sequence
<220> FEATURE:
<223> OTHER INFORMATION: chemically synthesized

<400> SEQUENCE: 192

Gln Gly Gln Ser Gly Gln Gly Gln Gln Gln Trp Cys Asn Ile Trp Ile
1               5                   10                  15

Asn Gly Gly Asp Cys Arg Gly Trp Asn Gly Gly Ser Ser Gly Gly Ser
            20                  25                  30

Gly Gly Ser Gly Ser Leu Ala Pro Leu Gly Leu Gln Arg Arg Gly Gly
            35                  40                  45

Ser

<210> SEQ ID NO 193
<211> LENGTH: 147
<212> TYPE: DNA
<213> ORGANISM: Artificial Sequence
<220> FEATURE:
<223> OTHER INFORMATION: chemically synthesized

<400> SEQUENCE: 193
caaggccagt ctggccaggg tcagcagcag tggtgcaata tttggatcaa tggtggtgat    60
tgccgcgggt ggaatggtgg ctcgagcggt ggcagcggtg gctctggtgg ctcaggtgga   120
cctttgggag tcagaggtgg cggttct                                       147

<210> SEQ ID NO 194
<211> LENGTH: 49
<212> TYPE: PRT
<213> ORGANISM: Artificial Sequence
<220> FEATURE:
<223> OTHER INFORMATION: chemically synthesized

<400> SEQUENCE: 194

Gln Gly Gln Ser Gly Gln Gly Gln Gln Gln Trp Cys Asn Ile Trp Ile
1               5                   10                  15

Asn Gly Gly Asp Cys Arg Gly Trp Asn Gly Gly Ser Ser Gly Gly Ser
            20                  25                  30

Gly Gly Ser Gly Gly Ser Gly Gly Pro Leu Gly Val Arg Gly Gly Gly

```
                     35                  40                  45

Ser

<210> SEQ ID NO 195
<211> LENGTH: 147
<212> TYPE: DNA
<213> ORGANISM: Artificial Sequence
<220> FEATURE:
<223> OTHER INFORMATION: chemically synthesized

<400> SEQUENCE: 195
caaggccagt ctggccaggg tcagcagcag tggtgcaata tttggatcaa tggtggtgat      60
tgccgcgggt ggaatggtgg ctcgagcggt ggcagcggtg gctctggtgg ctcaggtgga     120
ggctcgggcg gtgggagcgg cggttct                                         147

<210> SEQ ID NO 196
<211> LENGTH: 49
<212> TYPE: PRT
<213> ORGANISM: Artificial Sequence
<220> FEATURE:
<223> OTHER INFORMATION: chemically synthesized

<400> SEQUENCE: 196

Gln Gly Gln Ser Gly Gln Gly Gln Gln Trp Cys Asn Ile Trp Ile
1               5                   10                  15

Asn Gly Gly Asp Cys Arg Gly Trp Asn Gly Gly Ser Ser Gly Ser
            20                  25                  30

Gly Gly Ser Gly Gly Ser Gly Gly Gly Ser Gly Gly Ser Gly Gly
        35                  40                  45

Ser

<210> SEQ ID NO 197
<211> LENGTH: 11
<212> TYPE: PRT
<213> ORGANISM: Artificial Sequence
<220> FEATURE:
<223> OTHER INFORMATION: chemically synthesized

<400> SEQUENCE: 197

Arg Ala Ser Gln Ser Ile Ser Ser Leu Tyr Asn
1               5                   10

<210> SEQ ID NO 198
<211> LENGTH: 6
<212> TYPE: PRT
<213> ORGANISM: Artificial Sequence
<220> FEATURE:
<223> OTHER INFORMATION: chemically synthesized

<400> SEQUENCE: 198

Ala Ala Ser Leu Gln Ser
1               5

<210> SEQ ID NO 199
<211> LENGTH: 9
<212> TYPE: PRT
<213> ORGANISM: Artificial Sequence
<220> FEATURE:
<223> OTHER INFORMATION: chemically synthesized

<400> SEQUENCE: 199

Gln Gln Thr Val Val Ala Pro Leu Thr
1               5
```

<210> SEQ ID NO 200
<211> LENGTH: 5
<212> TYPE: PRT
<213> ORGANISM: Artificial Sequence
<220> FEATURE:
<223> OTHER INFORMATION: chemically synthesized

<400> SEQUENCE: 200

Ser Ala Tyr Met Ser
1               5

<210> SEQ ID NO 201
<211> LENGTH: 19
<212> TYPE: PRT
<213> ORGANISM: Artificial Sequence
<220> FEATURE:
<223> OTHER INFORMATION: chemically synthesized

<400> SEQUENCE: 201

Ser Ile Glu Gln Met Gly Gly Trp Gln Thr Tyr Tyr Ala Asp Ser Ser
1               5                   10                  15

Val Lys Gly

<210> SEQ ID NO 202
<211> LENGTH: 7
<212> TYPE: PRT
<213> ORGANISM: Artificial Sequence
<220> FEATURE:
<223> OTHER INFORMATION: chemically synthesized

<400> SEQUENCE: 202

Ser Ala Ala Ala Phe Asp Tyr
1               5

<210> SEQ ID NO 203
<211> LENGTH: 9
<212> TYPE: PRT
<213> ORGANISM: Artificial Sequence
<220> FEATURE:
<223> OTHER INFORMATION: chemically synthesized

<400> SEQUENCE: 203

Gln Gln Thr Val Val Ala Pro Leu Thr
1               5

<210> SEQ ID NO 204
<211> LENGTH: 19
<212> TYPE: PRT
<213> ORGANISM: Artificial Sequence
<220> FEATURE:
<223> OTHER INFORMATION: chemically synthesized

<400> SEQUENCE: 204

Ser Ile Glu Gln Met Gly Gly Trp Gln Thr Tyr Tyr Ala Asp Ser Ser
1               5                   10                  15

Val Lys Gly

<210> SEQ ID NO 205
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE

```
<222> LOCATION: (8)..(11)
<223> OTHER INFORMATION: X is any amino acid

<400> SEQUENCE: 205

Ser Ala Ala Ala Phe Asp Tyr Xaa Xaa Xaa Xaa
1               5                   10

<210> SEQ ID NO 206
<211> LENGTH: 7
<212> TYPE: PRT
<213> ORGANISM: Artificial Sequence
<220> FEATURE:
<223> OTHER INFORMATION: chemically synthesized

<400> SEQUENCE: 206

Ser Ala Ala Ala Phe Asp Tyr
1               5

<210> SEQ ID NO 207
<211> LENGTH: 14
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (8)..(14)
<223> OTHER INFORMATION: X is any amino acid

<400> SEQUENCE: 207

Ser Ala Ala Ala Phe Asp Tyr Xaa Xaa Xaa Xaa Xaa Xaa Xaa
1               5                   10

<210> SEQ ID NO 208
<211> LENGTH: 17
<212> TYPE: PRT
<213> ORGANISM: Artificial Sequence
<220> FEATURE:
<223> OTHER INFORMATION: chemically synthesized

<400> SEQUENCE: 208

Ser Ile Asp Pro Glu Gly Arg Gln Thr Tyr Tyr Ala Asp Ser Val Lys
1               5                   10                  15

Gly

<210> SEQ ID NO 209
<211> LENGTH: 10
<212> TYPE: PRT
<213> ORGANISM: Artificial Sequence
<220> FEATURE:
<223> OTHER INFORMATION: chemically synthesized

<400> SEQUENCE: 209

Asp Ile Gly Gly Arg Ser Ala Phe Asp Tyr
1               5                   10

<210> SEQ ID NO 210
<211> LENGTH: 9
<212> TYPE: PRT
<213> ORGANISM: Artificial Sequence
<220> FEATURE:
<223> OTHER INFORMATION: chemically synthesized

<400> SEQUENCE: 210

Arg Ala Ser Gln Ser Ile Ser Ser Tyr
1               5
```

<210> SEQ ID NO 211
<211> LENGTH: 7
<212> TYPE: PRT
<213> ORGANISM: Artificial Sequence
<220> FEATURE:
<223> OTHER INFORMATION: chemically synthesized

<400> SEQUENCE: 211

Ala Ala Ser Ser Leu Gln Ser
1               5

<210> SEQ ID NO 212
<211> LENGTH: 9
<212> TYPE: PRT
<213> ORGANISM: Artificial Sequence
<220> FEATURE:
<223> OTHER INFORMATION: chemically synthesized

<400> SEQUENCE: 212

Gln Gln Thr Val Val Ala Pro Pro Leu
1               5

<210> SEQ ID NO 213
<211> LENGTH: 8
<212> TYPE: PRT
<213> ORGANISM: Artificial Sequence
<220> FEATURE:
<223> OTHER INFORMATION: chemically synthesized

<400> SEQUENCE: 213

Leu Ser Gly Arg Ser Asp Asn His
1               5

<210> SEQ ID NO 214
<211> LENGTH: 8
<212> TYPE: PRT
<213> ORGANISM: Artificial Sequence
<220> FEATURE:
<223> OTHER INFORMATION: chemically synthesized

<400> SEQUENCE: 214

Thr Gly Arg Gly Pro Ser Trp Val
1               5

<210> SEQ ID NO 215
<211> LENGTH: 8
<212> TYPE: PRT
<213> ORGANISM: Artificial Sequence
<220> FEATURE:
<223> OTHER INFORMATION: chemically synthesized

<400> SEQUENCE: 215

Ser Ala Arg Gly Pro Ser Arg Trp
1               5

<210> SEQ ID NO 216
<211> LENGTH: 8
<212> TYPE: PRT
<213> ORGANISM: Artificial Sequence
<220> FEATURE:
<223> OTHER INFORMATION: chemically synthesized

<400> SEQUENCE: 216

Thr Ala Arg Gly Pro Ser Phe Lys
1               5

```
<210> SEQ ID NO 217
<211> LENGTH: 8
<212> TYPE: PRT
<213> ORGANISM: Artificial Sequence
<220> FEATURE:
<223> OTHER INFORMATION: chemically synthesized

<400> SEQUENCE: 217

Gly Gly Trp His Thr Gly Arg Asn
1               5

<210> SEQ ID NO 218
<211> LENGTH: 8
<212> TYPE: PRT
<213> ORGANISM: Artificial Sequence
<220> FEATURE:
<223> OTHER INFORMATION: chemically synthesized

<400> SEQUENCE: 218

His Thr Gly Arg Ser Gly Ala Leu
1               5

<210> SEQ ID NO 219
<211> LENGTH: 8
<212> TYPE: PRT
<213> ORGANISM: Artificial Sequence
<220> FEATURE:
<223> OTHER INFORMATION: chemically synthesized

<400> SEQUENCE: 219

Pro Leu Thr Gly Arg Ser Gly Gly
1               5

<210> SEQ ID NO 220
<211> LENGTH: 8
<212> TYPE: PRT
<213> ORGANISM: Artificial Sequence
<220> FEATURE:
<223> OTHER INFORMATION: chemically synthesized

<400> SEQUENCE: 220

Ala Ala Arg Gly Pro Ala Ile His
1               5

<210> SEQ ID NO 221
<211> LENGTH: 8
<212> TYPE: PRT
<213> ORGANISM: Artificial Sequence
<220> FEATURE:
<223> OTHER INFORMATION: chemically synthesized

<400> SEQUENCE: 221

Arg Gly Pro Ala Phe Asn Pro Met
1               5

<210> SEQ ID NO 222
<211> LENGTH: 8
<212> TYPE: PRT
<213> ORGANISM: Artificial Sequence
<220> FEATURE:
<223> OTHER INFORMATION: chemically synthesized

<400> SEQUENCE: 222

Ser Ser Arg Gly Pro Ala Tyr Leu
1               5

<210> SEQ ID NO 223
```

<211> LENGTH: 8
<212> TYPE: PRT
<213> ORGANISM: Artificial Sequence
<220> FEATURE:
<223> OTHER INFORMATION: chemically synthesized

<400> SEQUENCE: 223

Arg Gly Pro Ala Thr Pro Ile Met
1               5

<210> SEQ ID NO 224
<211> LENGTH: 4
<212> TYPE: PRT
<213> ORGANISM: Artificial Sequence
<220> FEATURE:
<223> OTHER INFORMATION: chemically synthesized

<400> SEQUENCE: 224

Arg Gly Pro Ala
1

<210> SEQ ID NO 225
<211> LENGTH: 10
<212> TYPE: PRT
<213> ORGANISM: Artificial Sequence
<220> FEATURE:
<223> OTHER INFORMATION: chemically synthesized

<400> SEQUENCE: 225

Gly Gly Gln Pro Ser Gly Met Trp Gly Trp
1               5                   10

<210> SEQ ID NO 226
<211> LENGTH: 10
<212> TYPE: PRT
<213> ORGANISM: Artificial Sequence
<220> FEATURE:
<223> OTHER INFORMATION: chemically synthesized

<400> SEQUENCE: 226

Phe Pro Arg Pro Leu Gly Ile Thr Gly Leu
1               5                   10

<210> SEQ ID NO 227
<211> LENGTH: 10
<212> TYPE: PRT
<213> ORGANISM: Artificial Sequence
<220> FEATURE:
<223> OTHER INFORMATION: chemically synthesized

<400> SEQUENCE: 227

Val His Met Pro Leu Gly Phe Leu Gly Pro
1               5                   10

<210> SEQ ID NO 228
<211> LENGTH: 8
<212> TYPE: PRT
<213> ORGANISM: Artificial Sequence
<220> FEATURE:
<223> OTHER INFORMATION: chemically synthesized

<400> SEQUENCE: 228

Ser Pro Leu Thr Gly Arg Ser Gly
1               5

<210> SEQ ID NO 229
<211> LENGTH: 8

```
<212> TYPE: PRT
<213> ORGANISM: Artificial Sequence
<220> FEATURE:
<223> OTHER INFORMATION: chemically synthesized

<400> SEQUENCE: 229

Ser Ala Gly Phe Ser Leu Pro Ala
1               5

<210> SEQ ID NO 230
<211> LENGTH: 9
<212> TYPE: PRT
<213> ORGANISM: Artificial Sequence
<220> FEATURE:
<223> OTHER INFORMATION: chemically synthesized

<400> SEQUENCE: 230

Leu Ala Pro Leu Gly Leu Gln Arg Arg
1               5

<210> SEQ ID NO 231
<211> LENGTH: 8
<212> TYPE: PRT
<213> ORGANISM: Artificial Sequence
<220> FEATURE:
<223> OTHER INFORMATION: chemically synthesized

<400> SEQUENCE: 231

Ser Gly Gly Pro Leu Gly Val Arg
1               5

<210> SEQ ID NO 232
<211> LENGTH: 4
<212> TYPE: PRT
<213> ORGANISM: Artificial Sequence
<220> FEATURE:
<223> OTHER INFORMATION: chemically synthesized

<400> SEQUENCE: 232

Pro Leu Gly Leu
1

<210> SEQ ID NO 233
<211> LENGTH: 6
<212> TYPE: PRT
<213> ORGANISM: Artificial Sequence
<220> FEATURE:
<223> OTHER INFORMATION: chemically synthesized

<400> SEQUENCE: 233

Gln Gly Gln Ser Gly Gln
1               5

<210> SEQ ID NO 234
<211> LENGTH: 21
<212> TYPE: PRT
<213> ORGANISM: Artificial Sequence
<220> FEATURE:
<223> OTHER INFORMATION: chemically synthesized

<400> SEQUENCE: 234

Gln Gly Gln Ser Gly Gln Cys Asn Ile Trp Leu Val Gly Gly Asp Cys
1               5                   10                  15

Arg Gly Trp Gln Gly
            20
```

```
<210> SEQ ID NO 235
<211> LENGTH: 8
<212> TYPE: PRT
<213> ORGANISM: Artificial Sequence
<220> FEATURE:
<223> OTHER INFORMATION: chemically synthesized

<400> SEQUENCE: 235

Pro Arg Phe Lys Ile Ile Gly Gly
1               5

<210> SEQ ID NO 236
<211> LENGTH: 8
<212> TYPE: PRT
<213> ORGANISM: Artificial Sequence
<220> FEATURE:
<223> OTHER INFORMATION: chemically synthesized

<400> SEQUENCE: 236

Pro Arg Phe Arg Ile Ile Gly Gly
1               5

<210> SEQ ID NO 237
<211> LENGTH: 9
<212> TYPE: PRT
<213> ORGANISM: Artificial Sequence
<220> FEATURE:
<223> OTHER INFORMATION: chemically synthesized

<400> SEQUENCE: 237

Ser Ser Arg His Arg Arg Ala Leu Asp
1               5

<210> SEQ ID NO 238
<211> LENGTH: 14
<212> TYPE: PRT
<213> ORGANISM: Artificial Sequence
<220> FEATURE:
<223> OTHER INFORMATION: chemically synthesized

<400> SEQUENCE: 238

Arg Lys Ser Ser Ile Ile Ile Arg Met Arg Asp Val Val Leu
1               5                   10

<210> SEQ ID NO 239
<211> LENGTH: 15
<212> TYPE: PRT
<213> ORGANISM: Artificial Sequence
<220> FEATURE:
<223> OTHER INFORMATION: chemically synthesized

<400> SEQUENCE: 239

Ser Ser Ser Phe Asp Lys Gly Lys Tyr Lys Lys Gly Asp Asp Ala
1               5                   10                  15

<210> SEQ ID NO 240
<211> LENGTH: 15
<212> TYPE: PRT
<213> ORGANISM: Artificial Sequence
<220> FEATURE:
<223> OTHER INFORMATION: chemically synthesized

<400> SEQUENCE: 240

Ser Ser Ser Phe Asp Lys Gly Lys Tyr Lys Arg Gly Asp Asp Ala
1               5                   10                  15

<210> SEQ ID NO 241
```

```
<211> LENGTH: 4
<212> TYPE: PRT
<213> ORGANISM: Artificial Sequence
<220> FEATURE:
<223> OTHER INFORMATION: chemically synthesized

<400> SEQUENCE: 241

Ile Glu Gly Arg
1

<210> SEQ ID NO 242
<211> LENGTH: 4
<212> TYPE: PRT
<213> ORGANISM: Artificial Sequence
<220> FEATURE:
<223> OTHER INFORMATION: chemically synthesized

<400> SEQUENCE: 242

Ile Asp Gly Arg
1

<210> SEQ ID NO 243
<211> LENGTH: 7
<212> TYPE: PRT
<213> ORGANISM: Artificial Sequence
<220> FEATURE:
<223> OTHER INFORMATION: chemically synthesized

<400> SEQUENCE: 243

Gly Gly Ser Ile Asp Gly Arg
1               5

<210> SEQ ID NO 244
<211> LENGTH: 6
<212> TYPE: PRT
<213> ORGANISM: Artificial Sequence
<220> FEATURE:
<223> OTHER INFORMATION: chemically synthesized

<400> SEQUENCE: 244

Pro Leu Gly Leu Trp Ala
1               5

<210> SEQ ID NO 245
<211> LENGTH: 8
<212> TYPE: PRT
<213> ORGANISM: Artificial Sequence
<220> FEATURE:
<223> OTHER INFORMATION: chemically synthesized

<400> SEQUENCE: 245

Gly Pro Gln Gly Ile Ala Gly Gln
1               5

<210> SEQ ID NO 246
<211> LENGTH: 8
<212> TYPE: PRT
<213> ORGANISM: Artificial Sequence
<220> FEATURE:
<223> OTHER INFORMATION: chemically synthesized

<400> SEQUENCE: 246

Gly Pro Gln Gly Leu Leu Gly Ala
1               5

<210> SEQ ID NO 247
<211> LENGTH: 5
```

```
<212> TYPE: PRT
<213> ORGANISM: Artificial Sequence
<220> FEATURE:
<223> OTHER INFORMATION: chemically synthesized

<400> SEQUENCE: 247

Gly Ile Ala Gly Gln
1               5

<210> SEQ ID NO 248
<211> LENGTH: 8
<212> TYPE: PRT
<213> ORGANISM: Artificial Sequence
<220> FEATURE:
<223> OTHER INFORMATION: chemically synthesized

<400> SEQUENCE: 248

Gly Pro Leu Gly Ile Ala Gly Ile
1               5

<210> SEQ ID NO 249
<211> LENGTH: 8
<212> TYPE: PRT
<213> ORGANISM: Artificial Sequence
<220> FEATURE:
<223> OTHER INFORMATION: chemically synthesized

<400> SEQUENCE: 249

Gly Pro Glu Gly Leu Arg Val Gly
1               5

<210> SEQ ID NO 250
<211> LENGTH: 8
<212> TYPE: PRT
<213> ORGANISM: Artificial Sequence
<220> FEATURE:
<223> OTHER INFORMATION: chemically synthesized

<400> SEQUENCE: 250

Tyr Gly Ala Gly Leu Gly Val Val
1               5

<210> SEQ ID NO 251
<211> LENGTH: 8
<212> TYPE: PRT
<213> ORGANISM: Artificial Sequence
<220> FEATURE:
<223> OTHER INFORMATION: chemically synthesized

<400> SEQUENCE: 251

Ala Gly Leu Gly Val Val Glu Arg
1               5

<210> SEQ ID NO 252
<211> LENGTH: 8
<212> TYPE: PRT
<213> ORGANISM: Artificial Sequence
<220> FEATURE:
<223> OTHER INFORMATION: chemically synthesized

<400> SEQUENCE: 252

Ala Gly Leu Gly Ile Ser Ser Thr
1               5

<210> SEQ ID NO 253
<211> LENGTH: 8
<212> TYPE: PRT
```

```
<213> ORGANISM: Artificial Sequence
<220> FEATURE:
<223> OTHER INFORMATION: chemically synthesized

<400> SEQUENCE: 253

Glu Pro Gln Ala Leu Ala Met Ser
1               5

<210> SEQ ID NO 254
<211> LENGTH: 8
<212> TYPE: PRT
<213> ORGANISM: Artificial Sequence
<220> FEATURE:
<223> OTHER INFORMATION: chemically synthesized

<400> SEQUENCE: 254

Gln Ala Leu Ala Met Ser Ala Ile
1               5

<210> SEQ ID NO 255
<211> LENGTH: 8
<212> TYPE: PRT
<213> ORGANISM: Artificial Sequence
<220> FEATURE:
<223> OTHER INFORMATION: chemically synthesized

<400> SEQUENCE: 255

Ala Ala Tyr His Leu Val Ser Gln
1               5

<210> SEQ ID NO 256
<211> LENGTH: 8
<212> TYPE: PRT
<213> ORGANISM: Artificial Sequence
<220> FEATURE:
<223> OTHER INFORMATION: chemically synthesized

<400> SEQUENCE: 256

Met Asp Ala Phe Leu Glu Ser Ser
1               5

<210> SEQ ID NO 257
<211> LENGTH: 8
<212> TYPE: PRT
<213> ORGANISM: Artificial Sequence
<220> FEATURE:
<223> OTHER INFORMATION: chemically synthesized

<400> SEQUENCE: 257

Glu Ser Leu Pro Val Val Ala Val
1               5

<210> SEQ ID NO 258
<211> LENGTH: 8
<212> TYPE: PRT
<213> ORGANISM: Artificial Sequence
<220> FEATURE:
<223> OTHER INFORMATION: chemically synthesized

<400> SEQUENCE: 258

Ser Ala Pro Ala Val Glu Ser Glu
1               5

<210> SEQ ID NO 259
<211> LENGTH: 8
<212> TYPE: PRT
<213> ORGANISM: Artificial Sequence
```

```
<220> FEATURE:
<223> OTHER INFORMATION: chemically synthesized

<400> SEQUENCE: 259

Asp Val Ala Gln Phe Val Leu Thr
1               5

<210> SEQ ID NO 260
<211> LENGTH: 8
<212> TYPE: PRT
<213> ORGANISM: Artificial Sequence
<220> FEATURE:
<223> OTHER INFORMATION: chemically synthesized

<400> SEQUENCE: 260

Val Ala Gln Phe Val Leu Thr Glu
1               5

<210> SEQ ID NO 261
<211> LENGTH: 8
<212> TYPE: PRT
<213> ORGANISM: Artificial Sequence
<220> FEATURE:
<223> OTHER INFORMATION: chemically synthesized

<400> SEQUENCE: 261

Ala Gln Phe Val Leu Thr Glu Gly
1               5

<210> SEQ ID NO 262
<211> LENGTH: 8
<212> TYPE: PRT
<213> ORGANISM: Artificial Sequence
<220> FEATURE:
<223> OTHER INFORMATION: chemically synthesized

<400> SEQUENCE: 262

Pro Val Gln Pro Ile Gly Pro Gln
1               5

<210> SEQ ID NO 263
<211> LENGTH: 263
<212> TYPE: PRT
<213> ORGANISM: Artificial Sequence
<220> FEATURE:
<223> OTHER INFORMATION: chemically synthesized

<400> SEQUENCE: 263

Gln Gly Gln Ser Gly Gln Gly Gln Gln Trp Cys Asn Ile Trp Ile
1               5                   10                  15

Asn Gly Gly Asp Cys Arg Gly Trp Asn Gly Ser Ser Gly Gly Ser
            20                  25                  30

Gly Gly Ser Gly Gly Thr Gly Arg Gly Pro Ser Trp Val Gly Gly Gly
        35                  40                  45

Ser Asp Ile Gln Met Thr Gln Ser Pro Ser Ser Leu Ser Ala Ser Val
    50                  55                  60

Gly Asp Arg Val Thr Ile Thr Cys Arg Ala Ser Gln Ser Ile Ser Ser
65                  70                  75                  80

Tyr Leu Asn Trp Tyr Gln Gln Lys Pro Gly Lys Ala Pro Lys Leu Leu
                85                  90                  95

Ile Tyr Ala Ala Ser Ser Leu Gln Ser Gly Val Pro Ser Arg Phe Ser
            100                 105                 110

Gly Ser Gly Ser Gly Thr Asp Phe Thr Leu Thr Ile Ser Ser Leu Gln
```

```
            115                 120                 125
Pro Glu Asp Phe Ala Thr Tyr Tyr Cys Gln Gln Thr Val Val Ala Pro
    130                 135                 140

Pro Leu Phe Gly Gln Gly Thr Lys Val Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260

<210> SEQ ID NO 264
<211> LENGTH: 789
<212> TYPE: DNA
<213> ORGANISM: Artificial Sequence
<220> FEATURE:
<223> OTHER INFORMATION: chemically synthesized

<400> SEQUENCE: 264
caaggccagt ctggccaggg tcagcagcag tggtgcaata tttggatcaa tggtggtgat      60
tgccgcgggt ggaatggtgg ctcgagcggt ggcagcggtg gctctggtgg tactggccgt     120
ggtccaagct gggttggcgg cggttctgac atccagatga cccagtctcc atcctccctg     180
tctgcatctg taggagacag agtcaccatc acttgccggg caagtcagag cattagcagc     240
tatttaaatt ggtatcagca gaaaccaggg aaagccccta agctcctgat ctatgcggca     300
tccagtttgc aaagtggggt cccatcaagg ttcagtggca gtggatctgg gacagatttc     360
actctcacca tcagcagtct gcaacctgaa gattttgcaa cttactactg tcaacagacg     420
gttgtggcgc ctccgttatt cggccaaggg accaaggtgg aaatcaaacg tacggtggct     480
gcaccatctg tcttcatctt cccgccatct gatgagcagt tgaaatctgg aactgcctct     540
gttgtgtgcc tgctgaataa cttctatccc agagaggcca agtacagtg gaaggtggat     600 aacgccctcc aatcgggtaa ctcccaggag agtgtcacag agcaggacag caaggacagc     660
acctacagcc tcagcagcac cctgacgctg agcaaagcag actacgagaa acacaaagtc     720
tacgcctgcg aagtcaccca tcagggcctg agctcgcccg tcacaaagag cttcaacagg     780
ggagagtgt                                                            789

<210> SEQ ID NO 265
<211> LENGTH: 263
<212> TYPE: PRT
<213> ORGANISM: Artificial Sequence
<220> FEATURE:
<223> OTHER INFORMATION: chemically synthesized

<400> SEQUENCE: 265

Gln Gly Gln Ser Gly Gln Gly Gln Gln Gln Trp Cys Asn Ile Trp Ile
1               5                   10                  15
```

Asn Gly Gly Asp Cys Arg Gly Trp Asn Gly Ser Gly Gly Ser
            20                  25                  30

Gly Gly Ser Gly Gly Leu Ser Gly Arg Ser Asp Asn His Gly Gly Gly
        35                  40                  45

Ser Asp Ile Gln Met Thr Gln Ser Pro Ser Ser Leu Ser Ala Ser Val
50                  55                  60

Gly Asp Arg Val Thr Ile Thr Cys Arg Ala Ser Gln Ser Ile Ser Ser
65                  70                  75                  80

Tyr Leu Asn Trp Tyr Gln Gln Lys Pro Gly Lys Ala Pro Lys Leu Leu
                85                  90                  95

Ile Tyr Ala Ala Ser Ser Leu Gln Ser Gly Val Pro Ser Arg Phe Ser
            100                 105                 110

Gly Ser Gly Ser Gly Thr Asp Phe Thr Leu Thr Ile Ser Ser Leu Gln
        115                 120                 125

Pro Glu Asp Phe Ala Thr Tyr Tyr Cys Gln Gln Thr Val Val Ala Pro
    130                 135                 140

Pro Leu Phe Gly Gln Gly Thr Lys Val Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260

<210> SEQ ID NO 266
<211> LENGTH: 789
<212> TYPE: DNA
<213> ORGANISM: Artificial Sequence
<220> FEATURE:
<223> OTHER INFORMATION: chemically synthesized

<400> SEQUENCE: 266
caaggccagt ctggccaggg tcagcagcag tggtgcaata tttggatcaa tggtggtgat      60
tgccgcgggt ggaatggtgg ctcgagcggt ggcagcggtg gctctggtgg tctgagcggc     120
cgttccgata tcatggcggc cggttctgac atccagatga cccagtctcc atcctccctg     180
tctgcatctg taggagacag agtcaccatc acttgccggg caagtcagag cattagcagc     240
tatttaaatt ggtatcagca gaaaccaggg aaagccccta agctcctgat ctatgcggca     300
tccagtttgc aaagtggggt cccatcaagg ttcagtggca gtggatctgg gacagatttc     360
actctcacca tcagcagtct gcaacctgaa gattttgcaa cttactactg tcaacagacg     420
gttgtggcgc tccgttattc ggccaaggga accaaggtgg aaatcaaacg tacggtggct     480
gcaccatctg tcttcatctt cccgccatct gatgagcagt tgaaatctgg aactgcctct     540
gttgtgtgcc tgctgaataa cttctatccc agagaggcca agtacagtg gaaggtggat     600

```
aacgccctcc aatcgggtaa ctcccaggag agtgtcacag agcaggacag caaggacagc    660
acctacagcc tcagcagcac cctgacgctg agcaaagcag actacgagaa acacaaagtc    720
tacgcctgcg aagtcaccca tcagggcctg agctcgcccg tcacaaagag cttcaacagg    780
ggagagtgt                                                             789
```

<210> SEQ ID NO 267
<211> LENGTH: 263
<212> TYPE: PRT
<213> ORGANISM: Artificial Sequence
<220> FEATURE:
<223> OTHER INFORMATION: chemically synthesized

<400> SEQUENCE: 267

```
Gln Gly Gln Ser Gly Gln Gly Gln Gln Gln Trp Cys Asn Ile Trp Ile
1               5                   10                  15

Asn Gly Gly Asp Cys Arg Gly Trp Asn Gly Ser Ser Gly Gly Ser
            20                  25                  30

Gly Gly Ser Gly Gly Ser Pro Leu Thr Gly Arg Ser Gly Gly Gly
        35                  40                  45

Ser Asp Ile Gln Met Thr Gln Ser Pro Ser Ser Leu Ser Ala Ser Val
50                  55                  60

Gly Asp Arg Val Thr Ile Thr Cys Arg Ala Ser Gln Ser Ile Ser Ser
65                  70                  75                  80

Tyr Leu Asn Trp Tyr Gln Gln Lys Pro Gly Lys Ala Pro Lys Leu Leu
                85                  90                  95

Ile Tyr Ala Ala Ser Ser Leu Gln Ser Gly Val Pro Ser Arg Phe Ser
            100                 105                 110

Gly Ser Gly Ser Gly Thr Asp Phe Thr Leu Thr Ile Ser Ser Leu Gln
        115                 120                 125

Pro Glu Asp Phe Ala Thr Tyr Tyr Cys Gln Gln Thr Val Val Ala Pro
130                 135                 140

Pro Leu Phe Gly Gln Gly Thr Lys Val Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260
```

<210> SEQ ID NO 268
<211> LENGTH: 789
<212> TYPE: DNA
<213> ORGANISM: Artificial Sequence
<220> FEATURE:
<223> OTHER INFORMATION: chemically synthesized

<400> SEQUENCE: 268

```
caaggccagt ctggccaggg tcagcagcag tggtgcaata tttggatcaa tggtggtgat    60
tgccgcgggt ggaatggtgg ctcgagcggt ggcagcggtg gctctggtgg ctcaccactg   120
actggtcgtt ccggtggcgg cggttctgac atccagatga cccagtctcc atcctccctg   180
tctgcatctg taggagacag agtcaccatc acttgccggg caagtcagag cattagcagc   240
tatttaaatt ggtatcagca gaaaccaggg aaagccccta agctcctgat ctatgcggca   300
tccagtttgc aaagtggggt cccatcaagg ttcagtggca gtggatctgg gacagatttc   360
actctcacca tcagcagtct gcaacctgaa gattttgcaa cttactactg tcaacagacg   420
gttgtggcgc ctccgttatt cggccaaggg accaaggtgg aaatcaaacg tacggtggct   480
gcaccatctg tcttcatctt cccgccatct gatgagcagt tgaaatctgg aactgcctct   540
gttgtgtgcc tgctgaataa cttctatccc agagaggcca agtacagtg gaaggtggat   600
aacgccctcc aatcgggtaa ctcccaggag agtgtcacag agcaggacag caaggacagc   660
acctacagcc tcagcagcac cctgacgctg agcaaagcag actacgagaa acacaaagtc   720
tacgcctgcg aagtcaccca tcagggcctg agctcgcccg tcacaaagag cttcaacagg   780
ggagagtgt                                                          789

<210> SEQ ID NO 269
<211> LENGTH: 263
<212> TYPE: PRT
<213> ORGANISM: Artificial Sequence
<220> FEATURE:
<223> OTHER INFORMATION: chemically synthesized

<400> SEQUENCE: 269

Gln Gly Gln Ser Gly Gln Gly Gln Gln Trp Cys Asn Ile Trp Ile
1               5                   10                  15

Asn Gly Gly Asp Cys Arg Gly Trp Asn Gly Gly Ser Ser Gly Gly Ser
            20                  25                  30

Gly Gly Ser Gly Gly Ser Gly Gly Gly Ser Pro Leu Gly Leu Gly Gly
        35                  40                  45

Ser Asp Ile Gln Met Thr Gln Ser Pro Ser Ser Leu Ser Ala Ser Val
    50                  55                  60

Gly Asp Arg Val Thr Ile Thr Cys Arg Ala Ser Gln Ser Ile Ser Ser
65              70                  75                  80

Tyr Leu Asn Trp Tyr Gln Gln Lys Pro Gly Lys Ala Pro Lys Leu Leu
                85                  90                  95

Ile Tyr Ala Ala Ser Ser Leu Gln Ser Gly Val Pro Ser Arg Phe Ser
            100                 105                 110

Gly Ser Gly Ser Gly Thr Asp Phe Thr Leu Thr Ile Ser Ser Leu Gln
        115                 120                 125

Pro Glu Asp Phe Ala Thr Tyr Tyr Cys Gln Gln Thr Val Val Ala Pro
    130                 135                 140

Pro Leu Phe Gly Gln Gly Thr Lys Val Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220
```

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
            245                 250                 255

Ser Phe Asn Arg Gly Glu Cys
        260

<210> SEQ ID NO 270
<211> LENGTH: 789
<212> TYPE: DNA
<213> ORGANISM: Artificial Sequence
<220> FEATURE:
<223> OTHER INFORMATION: chemically synthesized

<400> SEQUENCE: 270
caaggccagt ctggccaggg tcagcagcag tggtgcaata tttggatcaa tggtggtgat      60
tgccgcgggt ggaatggtgg ctcgagcggt ggcagcggtg gctctggtgg ctcaggtgga     120
ggctcgccac tgggcctggg cggttctgac atccagatga cccagtctcc atcctccctg     180
tctgcatctg taggagacag agtcaccatc acttgccggg caagtcagag cattagcagc     240
tatttaaatt ggtatcagca gaaaccaggg aaagccccta agctcctgat ctatgcggca     300
tccagtttgc aaagtggggt cccatcaagg ttcagtggca gtggatctgg gacagatttc     360
actctcacca tcagcagtct gcaacctgaa gattttgcaa cttactactg tcaacagacg     420
gttgtggcgc tccgttatt cggccaaggg accaaggtgg aaatcaaacg tacggtggct     480
gcaccatctg tcttcatctt cccgccatct gatgagcagt tgaaatctgg aactgcctct     540
gttgtgtgcc tgctgaataa cttctatccc agagaggcca agtacagtg gaaggtggat     600 aacgccctcc aatcgggtaa ctcccaggag agtgtcacag agcaggacag caaggacagc     660
acctacagcc tcagcagcac cctgacgctg agcaaagcag actacgagaa acacaaagtc     720
tacgcctgcg aagtcaccca tcagggcctg agctcgcccg tcacaaagag cttcaacagg     780
ggagagtgt                                                             789

<210> SEQ ID NO 271
<211> LENGTH: 263
<212> TYPE: PRT
<213> ORGANISM: Artificial Sequence
<220> FEATURE:
<223> OTHER INFORMATION: chemically synthesized

<400> SEQUENCE: 271

Gln Gly Gln Ser Gly Gln Gly Gln Gln Gln Trp Cys Asn Ile Trp Ile
1               5                   10                  15

Asn Gly Gly Asp Cys Arg Gly Trp Asn Gly Gly Ser Ser Gly Gly Ser
            20                  25                  30

Gly Gly Ser Gly Gly Ser Ala Gly Phe Ser Leu Pro Ala Gly Gly
        35                  40                  45

Ser Asp Ile Gln Met Thr Gln Ser Pro Ser Ser Leu Ser Ala Ser Val
    50                  55                  60

Gly Asp Arg Val Thr Ile Thr Cys Arg Ala Ser Gln Ser Ile Ser Ser
65                  70                  75                  80

Tyr Leu Asn Trp Tyr Gln Gln Lys Pro Gly Lys Ala Pro Lys Leu Leu
                85                  90                  95

Ile Tyr Ala Ala Ser Ser Leu Gln Ser Gly Val Pro Ser Arg Phe Ser
            100                 105                 110

Gly Ser Gly Ser Gly Thr Asp Phe Thr Leu Thr Ile Ser Ser Leu Gln
            115                 120                 125

Pro Glu Asp Phe Ala Thr Tyr Tyr Cys Gln Gln Thr Val Val Ala Pro
        130                 135                 140

Pro Leu Phe Gly Gln Gly Thr Lys Val Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
                260

<210> SEQ ID NO 272
<211> LENGTH: 789
<212> TYPE: DNA
<213> ORGANISM: Artificial Sequence
<220> FEATURE:
<223> OTHER INFORMATION: chemically synthesized

<400> SEQUENCE: 272
caaggccagt ctggccaggg tcagcagcag tggtgcaata tttggatcaa tggtggtgat      60
tgccgcgggt ggaatggtgg ctcgagcggt ggcagcggtg gctctggtgg ctcagctggc     120
ttctcccctcc ccgcaggtgg cggttctgac atccagatga cccagtctcc atcctccctg    180
tctgcatctg taggagacag agtcaccatc acttgccggg caagtcagag cattagcagc     240
tatttaaatt ggtatcagca gaaaccaggg aaagccccta agctcctgat ctatgcggca     300
tccagtttgc aaagtggggt cccatcaagg ttcagtggca gtggatctgg gacagatttc     360
actctcacca tcagcagtct gcaacctgaa gattttgcaa cttactactg tcaacagacg     420
gttgtggcgc tcccgttatt cggccaaggg accaaggtgg aaatcaaacg tacggtggct     480
gcaccatctg tcttcatctt cccgccatct gatgagcagt tgaaatctgg aactgcctct     540
gttgtgtgcc tgctgaataa cttctatccc agagaggcca agtacagtg gaaggtggat      600
aacgccctcc aatcgggtaa ctcccaggag agtgtcacag agcaggacag caaggacagc     660
acctacagcc tcagcagcac cctgacgctg agcaaagcag actacgagaa acacaaagtc     720
tacgcctgcg aagtcaccca tcagggcctg agctcgcccg tcacaaagag cttcaacagg     780
ggagagtgt                                                              789

<210> SEQ ID NO 273
<211> LENGTH: 263
<212> TYPE: PRT
<213> ORGANISM: Artificial Sequence
<220> FEATURE:
<223> OTHER INFORMATION: chemically synthesized

<400> SEQUENCE: 273

Gln Gly Gln Ser Gly Gln Gly Gln Gln Gln Trp Cys Asn Ile Trp Ile

```
              1               5               10              15
Asn Gly Gly Asp Cys Arg Gly Trp Asn Gly Gly Ser Ser Gly Gly Ser
                20                  25                  30
Gly Gly Ser Gly Ser Leu Ala Pro Leu Gly Leu Gln Arg Arg Gly Gly
                35                  40                  45
Ser Asp Ile Gln Met Thr Gln Ser Pro Ser Ser Leu Ser Ala Ser Val
                50                  55                  60
Gly Asp Arg Val Thr Ile Thr Cys Arg Ala Ser Gln Ser Ile Ser Ser
 65                  70                  75                  80
Tyr Leu Asn Trp Tyr Gln Gln Lys Pro Gly Lys Ala Pro Lys Leu Leu
                    85                  90                  95
Ile Tyr Ala Ala Ser Ser Leu Gln Ser Gly Val Pro Ser Arg Phe Ser
                100                 105                 110
Gly Ser Gly Ser Gly Thr Asp Phe Thr Leu Thr Ile Ser Ser Leu Gln
                115                 120                 125
Pro Glu Asp Phe Ala Thr Tyr Tyr Cys Gln Gln Thr Val Val Ala Pro
            130                 135                 140
Pro Leu Phe Gly Gln Gly Thr Lys Val Glu Ile Lys Arg Thr Val Ala
145                 150                 155                 160
Ala Pro Ser Val Phe Ile Phe Pro Pro Ser Asp Glu Gln Leu Lys Ser
                165                 170                 175
Gly Thr Ala Ser Val Val Cys Leu Leu Asn Asn Phe Tyr Pro Arg Glu
                180                 185                 190
Ala Lys Val Gln Trp Lys Val Asp Asn Ala Leu Gln Ser Gly Asn Ser
                195                 200                 205
Gln Glu Ser Val Thr Glu Gln Asp Ser Lys Asp Ser Thr Tyr Ser Leu
            210                 215                 220
Ser Ser Thr Leu Thr Leu Ser Lys Ala Asp Tyr Glu Lys His Lys Val
225                 230                 235                 240
Tyr Ala Cys Glu Val Thr His Gln Gly Leu Ser Ser Pro Val Thr Lys
                245                 250                 255
Ser Phe Asn Arg Gly Glu Cys
                260

<210> SEQ ID NO 274
<211> LENGTH: 789
<212> TYPE: DNA
<213> ORGANISM: Artificial Sequence
<220> FEATURE:
<223> OTHER INFORMATION: chemically synthesized

<400> SEQUENCE: 274
caaggccagt ctggccaggg tcagcagcag tggtgcaata tttggatcaa tggtggtgat      60
tgccgcgggt ggaatggtgg ctcgagcggt ggcagcggtg gctctggtag cctggcacct     120
ctgggtctgc aacgccgtgg cggttctgac atccagatga cccagtctcc atcctccctg     180
tctgcatctg taggagacag agtcaccatc acttgccggg caagtcagag cattagcagc     240
tatttaaatt ggtatcagca gaaaccaggg aaagccccta agctcctgat ctatgcggca     300
tccagtttgc aaagtggggt cccatcaagg ttcagtggca gtggatctgg gacagatttc     360
actctcacca tcagcagtct gcaacctgaa gattttgcaa cttactactg tcaacagacg     420
gttgtggcgc ctccgttatt cggccaaggg accaaggtgg aaatcaaacg tacggtggct     480
gcaccatctg tcttcatctt cccgccatct gatgagcagt tgaaatctgg aactgcctct     540
gttgtgtgcc tgctgaataa cttctatccc agagaggcca agtacagtgg aaggtggat     600
```

```
aacgccctcc aatcgggtaa ctcccaggag agtgtcacag agcaggacag caaggacagc    660
acctacagcc tcagcagcac cctgacgctg agcaaagcag actacgagaa acacaaagtc    720
tacgcctgcg aagtcaccca tcagggcctg agctcgcccg tcacaaagag cttcaacagg    780
ggagagtgt                                                           789
```

<210> SEQ ID NO 275
<211> LENGTH: 263
<212> TYPE: PRT
<213> ORGANISM: Artificial Sequence
<220> FEATURE:
<223> OTHER INFORMATION: chemically synthesized

<400> SEQUENCE: 275

```
Gln Gly Gln Ser Gly Gln Gly Gln Gln Gln Trp Cys Asn Ile Trp Ile
 1               5                   10                  15

Asn Gly Gly Asp Cys Arg Gly Trp Asn Gly Ser Ser Gly Gly Ser
            20                  25                  30

Gly Gly Ser Gly Gly Ser Gly Gly Pro Leu Gly Val Arg Gly Gly Gly
         35                  40                  45

Ser Asp Ile Gln Met Thr Gln Ser Pro Ser Ser Leu Ser Ala Ser Val
     50                  55                  60

Gly Asp Arg Val Thr Ile Thr Cys Arg Ala Ser Gln Ser Ile Ser Ser
 65                  70                  75                  80

Tyr Leu Asn Trp Tyr Gln Gln Lys Pro Gly Lys Ala Pro Lys Leu Leu
                 85                  90                  95

Ile Tyr Ala Ala Ser Ser Leu Gln Ser Gly Val Pro Ser Arg Phe Ser
            100                 105                 110

Gly Ser Gly Ser Gly Thr Asp Phe Thr Leu Thr Ile Ser Ser Leu Gln
         115                 120                 125

Pro Glu Asp Phe Ala Thr Tyr Tyr Cys Gln Gln Thr Val Val Ala Pro
    130                 135                 140

Pro Leu Phe Gly Gln Gly Thr Lys Val Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260
```

<210> SEQ ID NO 276
<211> LENGTH: 789
<212> TYPE: DNA
<213> ORGANISM: Artificial Sequence
<220> FEATURE:
<223> OTHER INFORMATION: chemically synthesized

<400> SEQUENCE: 276

```
caaggccagt ctggccaggg tcagcagcag tggtgcaata tttggatcaa tggtggtgat    60
tgccgcgggt ggaatggtgg ctcgagcggt ggcagcggtg gctctggtgg ctcaggtgga   120
cctttgggag tcagaggtgg cggttctgac atccagatga cccagtctcc atcctccctg   180
tctgcatctg taggagacag agtcaccatc acttgccggg caagtcagag cattagcagc   240
tatttaaatt ggtatcagca gaaaccaggg aaagccccta agctcctgat ctatgcggca   300
tccagtttgc aaagtggggt cccatcaagg ttcagtggca gtggatctgg gacagatttc   360
actctcacca tcagcagtct gcaacctgaa gattttgcaa cttactactg tcaacagacg   420
gttgtggcgc tccgttatt cggccaaggg accaaggtgg aaatcaaacg tacggtggct   480
gcaccatctg tcttcatctt cccgccatct gatgagcagt tgaaatctgg aactgcctct   540
gttgtgtgcc tgctgaataa cttctatccc agagaggcca agtacagtg aaggtggat    600
aacgccctcc aatcgggtaa ctcccaggag agtgtcacag agcaggacag caaggacagc   660
acctacagcc tcagcagcac cctgacgctg agcaaagcag actacgagaa acacaaagtc   720
tacgcctgcg aagtcaccca tcagggcctg agctcgcccg tcacaaagag cttcaacagg   780
ggagagtgt                                                            789

<210> SEQ ID NO 277
<211> LENGTH: 0
<212> TYPE: DNA
<213> ORGANISM: Artificial Sequence
<220> FEATURE:
<223> OTHER INFORMATION: chemically synthesized

<400> SEQUENCE: 277

000

<210> SEQ ID NO 278
<211> LENGTH: 263
<212> TYPE: PRT
<213> ORGANISM: Artificial Sequence
<220> FEATURE:
<223> OTHER INFORMATION: chemically synthesized

<400> SEQUENCE: 278

Gln Gly Gln Ser Gly Gln Gly Gln Gln Trp Cys Asn Ile Trp Ile
1               5                   10                  15

Asn Gly Gly Asp Cys Arg Gly Trp Asn Gly Ser Gly Gly Ser
            20                  25                  30

Gly Gly Ser Gly Gly Ser Gly Gly Gly Ser Gly Gly Gly Ser Gly Gly
        35                  40                  45

Ser Asp Ile Gln Met Thr Gln Ser Pro Ser Ser Leu Ser Ala Ser Val
    50                  55                  60

Gly Asp Arg Val Thr Ile Thr Cys Arg Ala Ser Gln Ser Ile Ser Ser
65                  70                  75                  80

Tyr Leu Asn Trp Tyr Gln Gln Lys Pro Gly Lys Ala Pro Lys Leu Leu
                85                  90                  95

Ile Tyr Ala Ala Ser Ser Leu Gln Ser Gly Val Pro Ser Arg Phe Ser
            100                 105                 110

Gly Ser Gly Ser Gly Thr Asp Phe Thr Leu Thr Ile Ser Ser Leu Gln
        115                 120                 125

Pro Glu Asp Phe Ala Thr Tyr Tyr Cys Gln Gln Thr Val Val Ala Pro
    130                 135                 140

Pro Leu Phe Gly Gln Gly Thr Lys Val Glu Ile Lys Arg Thr Val Ala
```

```
145                 150                 155                 160
Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
                180                 185                 190

Ala Lys Val Gln Trp Lys Val Asp Asn Ala Leu Gln Ser Gly Asn Ser
            195                 200                 205

Gln Glu Ser Val Thr Glu Gln Asp Ser Lys Asp Ser Thr Tyr Ser Leu
        210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260

<210> SEQ ID NO 279
<211> LENGTH: 789
<212> TYPE: DNA
<213> ORGANISM: Artificial Sequence
<220> FEATURE:
<223> OTHER INFORMATION: chemically synthesized

<400> SEQUENCE: 279
caaggccagt ctggccaggg tcagcagcag tggtgcaata tttggatcaa tggtggtgat        60
tgccgcgggt ggaatggtgg ctcgagcggt ggcagcggtg gctctggtgg ctcaggtgga       120
ggctcgggcg gtgggagcgg cggttctgac atccagatga cccagtctcc atcctccctg       180
tctgcatctg taggagacag agtcaccatc acttgccggg caagtcagag cattagcagc       240
tatttaaatt ggtatcagca gaaaccaggg aaagccccta agctcctgat ctatgcggca       300
tccagtttgc aaagtggggt cccatcaagg ttcagtggca gtggatctgg gacagatttc       360
actctcacca tcagcagtct gcaacctgaa gattttgcaa cttactactg tcaacagacg       420
gttgtggcgc tccgttatt cggccaaggg accaaggtgg aaatcaaacg tacggtggct       480
gcaccatctg tcttcatctt cccgccatct gatgagcagt tgaaatctgg aactgcctct       540
gttgtgtgcc tgctgaataa cttctatccc agagaggcca agtacagtg gaaggtggat       600 aacgccctcc aatcgggtaa ctcccaggag agtgtcacag agcaggacag caaggacagc       660
acctacagcc tcagcagcac cctgacgctg agcaaagcag actacgagaa acacaaagtc       720
tacgcctgcg aagtcaccca tcagggcctg agctcgcccg tcacaaagag cttcaacagg       780
ggagagtgt                                                               789
```